(12) United States Patent
Clare et al.

(10) Patent No.: US 12,016,864 B2
(45) Date of Patent: Jun. 25, 2024

(54) LOX ENZYME INHIBITING METHODS AND COMPOSITIONS

(71) Applicant: ANOVIA BIOSCIENCES, INC., New York, NY (US)

(72) Inventors: Michael Clare, Skokie, IL (US); Juan Du, Beijing (CN); Xiang Li, Beijing (CN); Ronggang Liu, Berwyn, PA (US)

(73) Assignee: Anovia Biosciences, Inc., New York, NY (US)

( * ) Notice: Subject to any disclaimer, the term of this patent is extended or adjusted under 35 U.S.C. 154(b) by 0 days.

(21) Appl. No.: 18/265,422

(22) PCT Filed: Oct. 28, 2022

(86) PCT No.: PCT/US2022/048180
§ 371 (c)(1),
(2) Date: Jun. 5, 2023

(87) PCT Pub. No.: WO2023/076567
PCT Pub. Date: May 4, 2023

(65) Prior Publication Data
US 2023/0390299 A1  Dec. 7, 2023

Related U.S. Application Data

(60) Provisional application No. 63/273,090, filed on Oct. 28, 2021.

(51) Int. Cl.
*A61K 31/541*  (2006.01)
*A61K 31/40*  (2006.01)
*A61K 31/5377*  (2006.01)

(52) U.S. Cl.
CPC ............ *A61K 31/541* (2013.01); *A61K 31/40* (2013.01); *A61K 31/5377* (2013.01)

(58) Field of Classification Search
CPC ... A61K 31/541; A61K 31/40; A61K 31/5377
See application file for complete search history.

(56) References Cited

FOREIGN PATENT DOCUMENTS

| | | | |
|---|---|---|---|
| WO | 2017/003862 A1 | 1/2017 | |
| WO | 2017/141049 A1 | 8/2017 | |
| WO | WO2017/141049 A1 * | 8/2017 | ........... C07D 333/34 |
| WO | 2021/216592 A1 | 10/2021 | |

OTHER PUBLICATIONS

PubChem SID 308221703 Deposit Date: Jan. 30, 3026, pp. 1-5; p. 2.
PubChem SID 348802764 Deposit Date: Dec. 18, 2017, pp. 1-6; p. 2.
Leo Leung et al., Anti-metastatic Inhibitors of Lysyl Oxidate (LOX): Design and Structure-Activity Relationships. Journal of Medicinal Chemistry, 2019, vol. 62, pp. 5863-5884.

* cited by examiner

*Primary Examiner* — Joseph R Kosack
*Assistant Examiner* — David M Shim
(74) *Attorney, Agent, or Firm* — Ballard Spahr LLP

(57) ABSTRACT

This invention relates to LOX enzyme-inhibiting compounds in accordance with Formula I or Formula II, or a pharmaceutically acceptable salt or hydrate thereof:

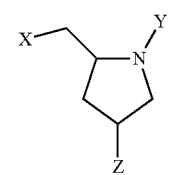

I

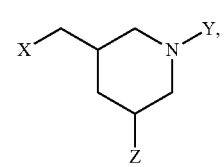

II and pharmaceutical compositions comprising the compounds. Such compounds and compositions can be useful in treating a variety of conditions, diseases, and disorders including, but not limited to, fibrotic disorders, proliferative disorders, cardiovascular disorders, acute and chronic inflammatory disorders, primary and metastatic cancer, pulmonary conditions, ocular diseases, and neurological and neuropsychiatric conditions. This abstract is intended as a scanning tool for purposes of searching in the particular art and is not intended to be limiting of the present invention.

20 Claims, No Drawings

LOX ENZYME INHIBITING METHODS AND COMPOSITIONS

CROSS-REFERENCE TO RELATED APPLICATIONS

This Application is a U.S. National Phase of International Application No. PCT/US2022/048180, filed on Oct. 28, 2022, which claims the benefit of U.S. Application No. 63/273,090, filed on Oct. 28, 2021, the contents of which are incorporated herein by reference in their entireties.

STATEMENT REGARDING FEDERALLY SPONSORED RESEARCH

This invention was made with government support under grant number 1R43HL147651-01A1 awarded by the National Institutes of Health (NIH). The government has certain rights in the invention.

BACKGROUND

Prototypic LOX (protein-6-lysine-oxidase; EC 1.4.3.13) is a copper and quinone-cofactor containing amine oxidase, which is expressed in various cell types such as basal and suprabasal keratinocytes, fibroblasts, adipocytes, osteoblasts, smooth muscle cells, and endothelial cells. The most well known function of LOX is the initiation of the cross-linking of collagens and elastins. More specifically, LOX catalyzes oxidative deamination of the primary amines of lysine and hydroxylysine in proteins such as collagen and tropoelastin to generate peptidyl aminoadipic-δ-semialdehyde, an aldehyde that spontaneously condenses to form inter- and intra-chain cross-links (Lucero and Kagan 2006). Such modifications of structural components of the extracellular matrix (ECM) stabilize fibrous deposits and contribute to tissue strength and integrity in the connective tissue. Other proteins have been reported as substrates for oxidation by LOX, such as basic fibroblast growth factor, PDGFR-β and other globular proteins with basic isoelectric points such histones H1, H2, and H3 (Kagan and Li 2003, Li, Nugent et al. 2003, Lucero and Kagan 2006, Lucero, Ravid et al. 2008).

The LOX mRNA is translated to a pre-pro-protein (pre-pro-LOX), 48 kDa), followed by incorporation of copper, cleavage of 21 amino acids, glycosylation of the N-terminus, and tertiary folding, to form the inactive LOX pro-protein (pro-LOX, 50 kDa). Pro-LOX is then secreted out of the cell and cleaved to a mature active form by procollagen C-proteinases (bone morphogenetic protein 1, BMP-1) and mammalian tolloid-like protein (mTLL-1) (Uzel, Scott et al. 2001) to become LOX pro-peptide (PP-LOX, 18 kDa) and the 32-kDa mature active LOX enzyme (Lucero and Kagan 2006). The catalytic domain contains a lysine-tyrosylquinone (LTQ) cofactor. LTQ is formed by post-translational oxidation of a catalytic site tyrosine (Tyr349), which then condenses onto a lysine, also within the catalytic site (Lys314), to form a stable covalent modification that is an essential part of the catalytic mechanism (Lucero and Kagan 2006, Kagan and Li 2003).

LOX is part of a protein family which consists of five enzymes, LOX, LOX-like 1 [LOXL1], LOX-like 2 [LOXL2], LOX-like 3 [LOXL3] and LOX-like 4 [LOXL4]), all containing a highly conserved C-terminal region containing the copper binding domain, residues for lysine tryosylquinone (LTQ), cofactor formation, and a cytokine receptor-like (CRL) domain. Although the C-terminal regions of the members of this family are conserved, the N-terminal portions are variable. Accordingly, this family is divided into two groups based on the N-terminal similarities. LOX and LOXL1 have N-terminals with pro-sequences, which confer their secretion as inactive pro-enzymes, whereas LOXL2, LOXL3, and LOXL4 contain scavenger receptor cysteine-rich (SRCR) domains.

LOX enzymes play a crucial role in maintaining ECM stability, by initiating and regulating the crosslinking of collagens and elastin within the ECM. The function of these enzymes is key to maintaining the normal tensile and elastic features of connective tissue of many organ systems within the body and as such is required for the structural integrity of many tissues. LOX expression decreases during ageing indicating that its activity is especially important during development. Inappropriate expression of these enzymes has been observed in a number of human diseases (many involving a fibrotic response), in particular primary and metastatic cancer. LOX family members are reported to have both intracellular and extracellular functions.

LOX was first proposed to be a tumor suppressor gene owing to its inhibitory effects on oncogenic HRAS-mediated transformation. There is now compelling evidence that the 18-kDa LOX-PP can suppress the neoplastic transformation of normal rat kidney fibroblasts and is capable of suppressing transformation and xenograft tumor formation of mammary epithelial cells that express HRAS or HER2 (Min et al. 2007, Sato et al 2011). Currently, evidence only exists to support tumor suppressive roles for LOX-PP, which adds extra complexity to the role of this family member in tumorigenesis.

Alteration in LOX and LOX-like (e.g., LOXL1, LOXL2, LOXL3, or LOXL4) enzyme activity is implicated in many diseases and disorders including but not limited to inflammation and acute and chronic inflammatory diseases, fibrosis of distinct organs and fibrotic disorders, cancer promotion and progression, and cardiovascular diseases.

LOX and LOX-like enzymes are implicated in fibrotic diseases, such as liver fibrosis (Siegel et al., 1978; Carter et al., 1982; Wakasaki et al., 1990; Murawaki et al., 1991; Mesarwi et al., 2015, Liu et al., 2016, Kumar et al., 2018), lung fibrosis (Counts et al., 1981; Almassian et al., 1991; Cheng et al., 2014; Tijn, et al., 2017, Aumiller et al., 2017, Lu et al., 2018), kidney fibrosis (Goto et al., 2005, Cosgrove et al., 2018, Stangenberg, et al., 2018, Saifi et al., 2020), cardiac fibrosis (Lopez et al., 2009, Yang et al., 2016, Lu et al., 2019), myelofibrosis (Papadantonakis et al, 2012, Tadmor et al., 2013, Leiva, et al., 2017, Abbonante et al., 2017, Leiva et al., 2019) and scleroderma, and can contribute to atherosclerosis (Kagan et al., 1981; Ovchinnikova et al., 2014). Decreased LOX activity is involved in disorders such as Menkes disease (Vulpe et al., 1993; Kim et al., 2015), osteoporosis, and cutis laxa (Sasaki et al., 2016).

In the United States, heart failure (HF) is a major public health problem and the leading cause of morbidity and mortality, resulting in 800,000 hospitalizations and 80,000 deaths per year [REF]. About one million people are newly diagnosed with HF every year, and >6 million people in the US are now afflicted with this disease, with annual treatment cost exceeding $30 billion. The HF epidemic is worsening. In 10 years (by 2030), >8 million adults in the US (near 3% of the adult population) are projected to be afflicted with HF, and the treatment cost will rise to $70 billion. Despite the huge socioeconomic expenses, the 1- and 5-year mortality rates of HF remain high at 30% and 50%, respectively. Such persistently high mortality of HF reflects inadequacy of current medical therapies and calls for new mechanistic paradigms for treatment. The LOX enzyme family plays also a role in cardiac function and disease. Fibrosis impairs myocardial relaxation and causes diastolic dysfunction, increasing the probability of heart failure (HF) development. HF is associated with substantial morbidity and mortality. Cardiac fibrosis also impedes propagation of the cardiac impulse, leading to arrhythmias such as atrial fibrillation (AF). AF is the most common sustained arrhythmia and is associated with adverse outcomes such as stroke, HF, and death. LOXL2 expression is increased in the cardiac interstitium and correlates with collagen cross-linking and cardiac dysfunction in failing human hearts. LOXL2 is also increased in the serum of HF-patients, correlating with biomarkers of HF, collagen cross-linking, and cardiac dysfunction (Yang et al., 2016; Al-u'datt, et al., 2019). As discussed in the detailed description of the invention, LOXL2 inhibition may prove beneficial in the treatment or prevention of cardiovascular conditions, including hypertensive heart disease, pressure overload, myocardial ischemia, heart failure, cardiac hypertrophy, and atherosclerosis.

LOX is associated with the amyloid-beta (Aβ) related pathological hallmarks (such as cerebral amyloid angiopathy and senile plaques) of both Alzheimer's disease (AD) and hereditary cerebral hemorrhage with amyloidosis of the Dutch type (HCHWA-D) pathogenesis (Wilhelmus, Bol et al. 2013). LOX activity is increased in the hippocampal samples of AD and also in non-Alzheimer's dementia (Gilad, Kagan et al. 2005). LOX is increased at the site of brain injury (Gilad, Kagan et al. 2001) and spinal cord injury and its inhibition lead to accelerated functional recovery in an unilateral spinal cord dissection model (Gilad and Gilad 2001). Increased LOX is associated with pathological progression of ALS, where it is a potential biomarker (Li et al., 2004). Genomic analyses identified the enzyme LOX as the most highly regulated lithium-responsive astroglial gene and as a common factor and potential surrogate biomarker in bipolar disease, schizophrenia and AD (Rivera, Butt, 2019).

LOX inhibition may be beneficial in the treatment of various ocular conditions. Inhibition of LOX and/or LOXL2 prevents neovascularization and fibrosis following laser-induced choroidal neovascularization (Van Bergen, et al., 2015). Therefore, targeting LOX and LOX-like proteins can be useful in the treatment of conditions characterized by neovascularization, such as age-related macular degeneration, diabetic retinopathy, and retinopathy of prematurity.

Another medical condition that may benefit from ECM remodeling factors-based therapeutics is IBD-associated fibrosis, considered an irreversible self-propagating process, currently treated mainly by mechanical means (e.g., surgical resection or balloon dilation). As increase in matrix stiffness seems to be an early event in tissue fibrosis, targeting collagen cross-linking enzymes, such as the LOX family, may be of therapeutic significance (de Bruyn, et al., 2018). LOX is implicated in inflammatory conditions and may be useful in the treatment of other conditions such as acute respiratory distress syndrome (ARDS) (Mambetsariev, Tian et al. 2014).

In recent years, fibrosis has been recognized as a crucial player in adipose tissue dysfunction in obesity. LOX is the main LOX family enzyme expressed in human adipose tissue and its expression is strongly upregulated in samples from obese patients. BAPN, a pan-LOX inhibitor, reduces body weight gain, improves the metabolic profile in diet-induced obesity in rats (Miana, Galan et al. 2015), and reduces local adipose tissue inflammation (Halberg, Khan et al. 2009). BAPN has also been shown to reduce leptin pro-fibrotic effects and ameliorates cardiovascular remodeling in diet-induced obesity in rats.

LOX is upregulated in endometriosis and may be implicated in the establishment and progression of endometriotic lesions (Ruiz, Dutil et al. 2011; Dentillo, Meola et al. 2010).

Aberrant expression and activity of LOX and LOX-like enzymes has been reported in several cancer types (reviewed by Barker et al., 2012 and Amendola et al., 2019). For example, a functional role of LOX proteins has been described in breast (Erler et al., 2006; Kirschmann et al, 2002; Salvador et al., 2017), colorectal (Kim et al., 2009; Baker et al., 2011; Baker et al., 2013), pancreatic (Miller et al., 2015), prostate (Lapointe et al., 2004), and ovarian (Cheon et al., 2014; Chang et al., 2007) cancers, in head and neck squamous cell carcinoma (Le et al., 2009; Gorogh et al., 2015; Albinger-Hegyi et al., 2010), renal cells carcinoma (Hase et al., 2014), uveal melanoma (Abourbih et al., 2010), and squamous cell skin carcinoma (Martin et al., 2015). The precise contribution to each LOX protein however still remains to be fully elucidated. Of note, while LOX and LOXL2 are involved in similar extra-cellular processes, it appears that they have distinct roles.

LOX enzymes represent exciting targets for the treatment of fibrotic disorders, proliferative disorders, cardiovascular diseases, acute and chronic inflammatory disorders, primary and metastatic cancer, pulmonary conditions, ocular diseases, or neurological and neuropsychiatric conditions. Targeting LOX proteins with small molecule inhibitors is very challenging owing to the lack of crystal structures useful for drug design for any of the isoforms (except LOXL2) and the high degree of homology of the catalytic domain and difficulties associated with isolating several of the enzymes in an active form, particularly LOX, LOXL1, and LOXL4.

A number of small molecule LOX inhibitors are known (reviewed by Hajdii et al, 2018). However, in general these compounds are either non-selective (e.g., the prototypical pan-LOX inhibitor BAPN and copper chelator molecules, such as D-penicillamin), lack potency, or are unsuitable for use in patients. More recently a variety of LOX protein inhibitors have been described. For example, LOX inhibitors containing hydrazine and hydrazide groups (Burke et al, 2017); LOXL2 inhibitors: derivatives of haloallylamine (Chang et al, 2017, Stangenberg et al, 2018, Schilter et al, 2019), pyridines (Rowbottom et al, 2016a; Rowbottom et al, 2016b), pyrimidines (Rowbottom & Hutchinson, 2017a) chromenones (Rowbottom & Hutchinson, 2017b), and 2-Aminomethylene-5-sulfonylthiazole (Tang et al., 2017; Smithen et al., 2019; Springer et al, 2017). LOXL2/3 inhibitors PAT-1251 and PXS-5153A, pan-LOX inhibitor PXS-5505A, and the LOXL2-selective inhibitor PXS-4878A are in early clinical development.

There is, therefore, a need for new LOX inhibitors.

SUMMARY

Provided are compounds, pharmaceutical compositions, and methods of treating or preventing diseases associated with aberrant LOX family enzyme expression, particularly fibrotic disorders, including more specifically proliferative disorders, chronic and acute inflammatory disorders, cardiovascular diseases, primary or metastatic cancer, ocular diseases, pulmonary conditions, neurological and neuropsychiatric conditions, or other diseases and medical conditions for which inhibiting one or more enzyme of the family of lysyl oxidases (LOX) provides a therapeutic effect.

In a particular embodiment, provided are LOX enzyme-inhibiting compounds in accordance with Formula I or Formula II, or a pharmaceutically acceptable salt and/or hydrate thereof:

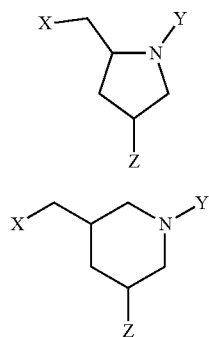

wherein: X is independently selected from —OR$^1$, —SO$_2$R$^1$, or —C(═O)R$^1$; Y is independently selected from —C(═O)R$^2$ or —SO$_2$R$^2$; Z is independently selected from —R$^3$, —CH$_2$—R$^3$, —SO$_2$R$^3$, —C(═O)R$^3$, and —OR$^3$; R$^1$ is phenyl or heteroaryl containing 1 to 2 heteroatom(s) each independently selected from N, O, and S, wherein said phenyl or heteroaryl is substituted with —CR$^4$R$^5$NH$_2$ and optionally halogen or lower alkyl, where R$^4$ and R$^5$ are independently H or lower alkyl or R$^4$ and R$^5$ form a (C$_1$-C$_8$) cycloalkyl or (C$_1$-C$_8$) hetero-cycloalkyl; R$^2$ is substituted or unsubstituted phenyl, substituted or unsubstituted benzyl, substituted or unsubstituted heteroaryl containing 1 to 2 heteroatom(s) each independently selected from N, O, and S, (C$_1$-C$_8$) alkyl, (C$_1$-C$_8$) cycloalkyl, mono-, di-, or trihalo (C$_1$-C$_4$)alkyl, or —NR$^6$R$^7$, where R$^6$ and R$^7$ are independently selected from H and lower alkyl or where R$^6$ and R$^7$ form together a (C$_3$-C$_6$) hetero-cycloalkyl, wherein the (C$_3$-C$_6$) hetero-cycloalkyl optionally contains besides the nitrogen one additional heteroatom selected from N, O, and S, wherein N is substituted or unsubstituted, wherein the substituent is lower alkyl or —SO$_2$R$^8$ or —OR$^8$, and wherein S is unsubstituted or forms sulfonyl, wherein said substituted phenyl, benzyl, or heteroaryl has at least one substituent being halogen, mono-, di- or trihalo(C$_1$-C$_4$)alkyl, —SO$_2$R$^8$, or —OR$^8$, where R$^8$ is lower alkyl, cyano, lower alkyl, or —SO$_2$NR$^9$R$^{10}$, where R$^9$ and R$^{10}$ are independently selected from H and lower alkyl; R$^3$ is unsubstituted or substituted phenyl, substituted or unsubstituted benzyl, substituted or unsubstituted heteroaryl containing 1 to 2 heteroatom(s) each independently selected from N, O, and S, mono-, di-, or trihalo(C$_1$-C$_4$)alkyl, (C$_1$-C$_8$) cycloalkyl, (C$_1$-C$_8$) alkyl, or —NR$^{11}$R$^{12}$, where R$^{11}$ and R$^{12}$ are independently selected from H and lower alkyl or where R$^{11}$ and R$^{12}$ form together a (C$_3$-C$_6$) hetero-cycloalkyl, wherein the (C$_3$-C$_6$) hetero-cycloalkyl optionally contains besides the nitrogen one additional heteroatom selected from N, O, and S, wherein N is optionally substituted with a lower alkyl or —SO$_2$R$^{13}$ or —OR$^{13}$, and wherein S is unsubstituted or forms sulfonyl, wherein said substituted phenyl, benzyl, or heteroaryl has at least one substituent being halogen, mono-, di- or trihalo(C$_1$-C$_4$)alkyl, —SO$_2$R$^{14}$, or —OR$^{14}$ where R$^{14}$ is lower alkyl, cyano, lower alkyl, or —SO$_2$NR$^{15}$R$^{16}$, where R$^{15}$ and R$^{16}$ are independently selected from H and lower alkyl; or a tautomer or stereoisomer thereof.

Also provided herein are methods of treating or preventing a disease associated with aberrant LOX family enzyme expression for which inhibiting one or more enzyme of the family of lysyl oxidases provides a therapeutic effect, comprising administering to a subject in need thereof an effective amount of a lysyl oxidase (LOX) enzyme-inhibiting compound or a pharmaceutically acceptable salt and/or hydrate thereof as described herein.

Also provided herein are pharmaceutical compositions comprising a LOX enzyme-inhibiting compound described herein and a pharmaceutically acceptable carrier.

Also provided are methods of synthesizing the LOX enzyme inhibiting compounds described herein.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

The term "heteroatom" means O, S or N, selected on an independent basis.

"Halogen" and "halo" refer to fluorine, chlorine, bromine and iodine.

The term "lower alkyl" refers to methyl, ethyl, propyl, butyl and their various branched isomers.

When any variable (e.g. aryl, heterocycle, R', etc.) occurs more than one time in any constituent, its definition on each occurrence is independent at every other occurrence.

The nomenclature "$C_x$-$C_y$", for example, "$C_1$-$C_6$", species corresponds to the number of carbon atoms of a hydrocarbon. For example, $C_1$-$C_6$ indicates a hydrocarbon containing 1, 2, 3, 4, 5, or 6 carbon atoms.

"Alkyl" refers to a saturated hydrocarbon chain. Such hydrocarbon chains may be branched or linear. Unless specified otherwise, "Alkyl" groups may be substituted by one or more substituents selected from halogen, amido, aryl, or $C_1$-$C_4$ alkoxy. Nonlimiting examples include methyl, trifluoromethyl, ethyl, propyl, butyl, pentyl, 1-methylbutyl, 1-ethylpropyl, 3-methylpentyl, octyl and the like.

"Cycloalkyl" refers to a saturated or unsaturated cyclic hydrocarbon radical, including bridged, fused, or spiro cyclic compounds, preferably having 3 to 8 carbon atoms. Non-limiting examples of "$C_3$-$C_i$ cycloalkyl" groups according to the present invention are cyclopropyl, cyclopentyl, cyclohexyl and the like. In some embodiments, the cycloalkyl has 3 to 8 carbon atoms. In some embodiments, the cycloalkyl has 3 to 6 carbon atoms.

The term "aryl" refers to a moiety derived from an aromatic ring or polycyclic ring, such as phenyl, naphthyl, or quinolinyl. An aryl can be a $C_3$-$C_i$ aryl.

The term "heteroaryl" refers to an aromatic moiety having at least one heteroatom as part of the aromatic ring. A heteroaryl can be a $C_3$-$C_{10}$ aryl. Non-limiting examples of "$C_3$-$C_{10}$ heteroaryl" groups according to the present invention are thiophenyl, thiazolyl, pyridinyl, pyrimidinyl, imidazolyl, pyrrolyl, oxazolyl, and the like.

The term "alkoxy" refers to an alkyl singularly bonded to an oxygen, thus R—O—.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric/chiral centers and may thus occur as racemates, racemic mixtures, single enantiomers, diastereomeric mixtures, and individual diastereomers.

All configurational isomers of the compounds of the present invention are contemplated, either in admixture or in pure or substantially pure form. "Substantially pure" is at least 90%, at least 95%, at least 98% or at least 99%. The definition of compounds of the present invention embraces both cis (Z) and trans (E) alkene isomers, as well as cis and trans isomers of cyclic hydrocarbon or heterocyclo rings.

The term "LOX family enzymes", "LOX enzymes", or "LOX and LOX-like enzymes" refers, except indicated otherwise, to the protein family of lysyl oxidases, which consist of five enzymes: LOX, LOXL1, LOXL2, LOXL3, and LOXL4.

The term "LOX", "prototypic LOX", or "LOX enzyme" refers to the prototypic member of the LOX enzyme family: LOX, protein-6-lysine-oxidase; EC 1.4.3.13.

The term "LOX enzyme-inhibiting compound(s)" refers to compounds of this invention, which inhibit one or more LOX enzymes.

In embodiments, provided are compounds that selectively or specifically inhibit one or more of the LOX enzymes. A compound with an $IC_{50}$ below or equal to 500 nM in LOX, LOXL2, and LOXL3 activity assays, for example, specifically, as described in the Examples 1 and 2 below, is an unselective, pan-LOX enzyme inhibitor. A compound with an $IC_{50}$ below or equal to 500 nM in a LOXL2 activity assay and greater than 30 µM in both LOX and LOXL3 assays, for example, specifically, as described in the Examples below, is a specific LOXL2 inhibitor. A compound with an $IC_{50}$ below or equal to 500 nM in the LOXL2 assay and greater than 30 µM in LOX and an IC 50 which is at least 10-fold greater in the LOXL3 assay than the LOXL2 assay, for example, as described in the Examples below, is a selective LOXL2 inhibitor. A compound with an $IC_{50}$ below or equal to 500 nM in the LOXL2 assay and an $IC_{50}$, which is at least 10-fold greater in the LOX and LOXL3 activity assays than the LOXL2 assay, for example, as described in the Examples below, is a selective LOXL2 inhibitor. A compound with an $IC_{50}$ below or equal to 500 nM in a LOX activity assay and greater than 30 µM in LOXL2 and LOXL3 activity assays, for example, specifically, as described in the Examples below, is a specific inhibitor of prototypic LOX. A compound with an $IC_{50}$ below or equal to 500 nM in the LOX assay and an $IC_{50}$, which is at least 10-fold greater in the LOXL2 and LOXL3 activity assays than the LOX assay, for example, as described in the Examples below, is a selective inhibitor of prototypic LOX. A compound with an $IC_{50}$ below or equal to 500 nM in both the LOXL2 and LOXL3 activity assay and greater than 30 µM in the LOX assay, for example, specifically as described in the Examples below, is a dual (specific) LOXL2/LOXL3 inhibitor. A compound with an $IC_{50}$ below or equal to 500 nM in both the LOXL2 and LOXL3 activity assay and an $IC_{50}$, which is at least 10-fold greater in the LOX activity assay than the LOXL2 and LOXL3 activity assays, for example, specifically as described in the Examples below, is a dual (selective) LOXL2/LOXL3 inhibitor. A compound with an $IC_{50}$ below or equal to 500 nM in the LOXL3 assay and greater than µM in the LOX and LOXL2 assay, for example, specifically, as described in the Examples below, is a specific LOXL3 inhibitor. A compound with an $IC_{50}$ below or equal to 500 nM in the LOXL3 assay and an $IC_{50}$, which is at least 10-fold greater in the LOX and LOXL2 activity assays than the LOXL3 assay, for example, specifically, as described in the Examples below, is a selective LOXL3 inhibitor.

In general, specific inhibitors are compounds with an $IC_{50}$ below or equal to 500 nM in only one of the LOX, LOXL1, LOXL2, LOXL3, and LOXL4 activity assays, as described in the Examples below, and greater than 30 µM in the activity assays of the other LOX family enzymes. Dual-specific inhibitors are compounds with an $IC_{50}$ below or equal to 500 nM in two of the LOX, LOXL1, LOXL2, LOXL3, and LOXL4 activity assays, as described in the Examples below, and greater than 30 µM in the activity assays of the other LOX family enzymes. Any compound with an $IC_{50}$ below or equal to 500 nM in only one of the LOX, LOXL1, LOXL2, LOXL3, and LOXL4 activity assays, as described in the Examples below, and an $IC_{50}$, which is 10-fold greater in the other LOX enzyme activity assays, is deemed a selective inhibitor. Dual-selective inhibitors are compounds with an $IC_{50}$ below or equal to 500 nM in two of the LOX, LOXL1, LOXL2, LOXL3, and LOXL4 activity assays, as described in the Examples below, and an $IC_{50}$, which is 10-fold greater in the other LOX enzyme activity assays.

It will be understood that, as used herein, references to the compounds disclosed herein are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamme, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "mammal" "mammalian" or "mammals" includes humans, as well as animals, such as dogs, cats, horses, pigs and cattle.

The term "patient" refers to a living organism suffering from or prone to a condition that can be prevented or treated by administration of an active agent as described herein, and includes both humans and animals. In one embodiment, the patient is a human patient.

As used herein, "individual" (as in the subject of the treatment) means a mammal. Mammals include, for example, humans; non-human primates, e.g., apes and monkeys; and non-primates, e.g., dogs, cats, rats, mice, cattle, horses, sheep, and goats. Non-mammals include, for example, fish and birds.

The term "disease" or "disorder" are used interchangeably, and are used to refer to diseases or conditions wherein lack of or reduced amounts of a specific gene product, e.g., a lysosomal storage enzyme, plays a role in the disease such that a therapeutically beneficial effect can be achieved by supplementing, e.g., to at least 1% of normal levels.

Without being bound by theory, the administration of compounds according to the invention in an "effective amount" or "therapeutically effective amount" provides a concentration of the compound that functions as an inhibitor of one or more LOX enzymes sufficient to inhibit the effect of one or more LOX enzymes.

"Treating" or "treatment" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

"Prevent" or "preventing" a disease state includes: preventing the disease state, i.e. causing the clinical symptoms of the disease state not to develop in a subject that may be exposed to or predisposed to the disease state, but does not yet experience or display symptoms of the disease states.

All patents, patent applications and publications cited herein, whether supra or infra, are hereby incorporated by reference in their entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating or preventing a disease associated with aberrant LOX family enzyme expression such as, for example, fibrotic disorders, proliferative disorders, cardiovascular diseases, acute and chronic inflammatory disorders, primary and metastatic cancer, pulmonary conditions, ocular diseases, and neurological and neuropsychiatric conditions.

In one aspect, the compounds of the invention are useful in treating a disorder in a mammal. In a further aspect, the compounds of the invention are useful in treating a disorder in a human.

In one aspect, the compounds of the invention are useful in the treatment of fibrotic disorders, as further described herein.

In one aspect, the compounds of the invention are useful in the treatment of a primary or metastatic cancer, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

The derivatives of 1,3,5-tri-substituted piperidine and 1,2,4-tri-substituted pyrrolidine described herein are preferably inhibitors of one or more of the LOX proteins selected from LOX, LOXL1, LOXL2, LOXL3, or LOXL4, and are useful in the treatment or prevention or reduction in the likelihood of fibrotic disorders, cardiovascular diseases, acute or chronic inflammatory disorders, primary and metastatic cancer, pulmonary conditions, ocular diseases, or neurological and neuropsychiatric conditions or diseases in which one or more LOX proteins are involved. The compounds of the invention can be characterized by their activity to inhibit one or more of the enzyme family of lysyl oxidases.

In some embodiments, the compounds of Formula I, Formula Ia, Formula Ib, Formula II, Formula IIa, Formula IIb, or Table 1 are effective to inhibit one or more of the LOX enzymes, as determined using an assay which determines the inhibitory concentration ($IC_{50}$) for the conversion of primary amine substrates to aldehydes as described herein, with a $IC_{50}$ superior or equal to 30 µM. In preferred embodiments, the $IC_{50}$ as so determined is superior or equal to 1 μM. In an embodiment, the $IC_{50}$ as so determined is superior or equal to 500 nM.

The ability of compounds within the scope of this disclosure to inhibit the activity of one or more LOX enzymes may be determined by methods known to those in the art for measuring LOX enzymes inhibition. One method for measuring LOX activity uses a fluorometric assay (kit from Abcam). This assay measures the release of hydrogen peroxide ($H_2O_2$) by the substrate upon transformation of the primary amine to the reactive aldehyde. In turn, $H_2O_2$ is detected using a red fluorescence substrate for HRP-coupled reactions. Using this assay, preferred compounds of the invention have an $IC_{50}$ superior or equal to 30 μM. In increasingly preferred embodiments, the $IC_{50}$ as so determined is superior or equal to 1 μM. In a more preferred embodiment, the $IC_{50}$ as so determined is superior or equal to 500 nM.

In some embodiments, the compounds disclosed herein or a pharmaceutically acceptable salt and/or hydrate thereof, may be used in the selective or specific inhibition of LOX, LOXL1, LOXL2, LOXL3, or LOXL4. In other embodiments, it may be advantageous to selectively or specifically inhibit two or more enzymes of the LOX family. Accordingly, in another embodiment, the compounds disclosed herein or pharmaceutically acceptable salt and/or hydrate thereof, may be used in the selective inhibition of two or more members of the LOX family selected from LOX, LOXL1, LOXL2, LOXL3, or LOXL4. In one embodiment, a compound of Formula I, Formula Ia, or Formula Ib selectively or specifically inhibits LOXL2. In another embodiment, a compound of Formula II, Formula IIa, or Formula IIb inhibits selectively or specifically LOXL2. In another embodiment, provided is a compound of Formula I, which selectively or specifically inhibits LOX. In another embodiment, provided is a compound of Formula II, which selectively or specifically inhibits LOX.

Other embodiments are prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, 4$^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Prodrugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with this disclosure can, for example, be produced by replacing appropriate functionalities present in the compounds disclosed herein with certain moieties known to those skilled in the art as "pro-moieties" as described, for example, in Design of Prodrugs by H. Bundgaard (Elsevier, 1985), incorporated by reference in its entirety.

Some non-limiting examples of prodrugs in accordance with this disclosure include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

1. Structure

In one aspect, disclosed are LOX enzyme-inhibiting compounds in accordance with Formula I or Formula II, or a pharmaceutically acceptable salt or hydrate thereof:

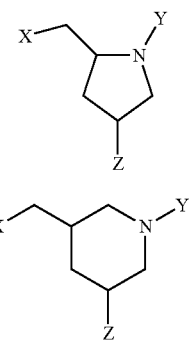

wherein: X is independently selected from —OR$^1$, —SO$_2$R$^1$, and —C(=O)R$^1$; Y is independently selected from —SO$_2$R$^2$ and —C(=O)R$^2$; Z is independently selected from —R$^3$, —CH$_2$—R$^3$, —SO$_2$R$^3$, —C(=O)R$^3$, and —OR$^3$; R$^1$ is phenyl or heteroaryl containing 1 to 2 heteroatom(s) each independently selected from N, O, and S, wherein said phenyl or heteroaryl is substituted with —CR$^4$R$^5$NH$_2$, and optionally, halogen or lower alkyl, where R$^4$ and R$^5$ are independently H or lower alkyl or R$^4$ and R$^5$ form a (C$_1$-C$_8$) cycloalkyl or (C$_1$-C$_8$) hetero-cycloalkyl; R$^2$ is substituted or unsubstituted phenyl, substituted or unsubstituted benzyl, substituted or unsubstituted heteroaryl containing 1 to 2 heteroatom(s) each independently selected from N, O, and S, (C$_1$-C$_8$) alkyl, (C$_1$-C$_8$) cycloalkyl, mono-, di-, or trihalo(C$_1$-C$_4$)alkyl, or —NR$^6$R$^7$, where R$^6$ and R$^7$ are independently selected from H and lower alkyl or where R$^6$ and R$^7$ form together a (C$_3$-C$_6$) hetero-cycloalkyl, wherein the (C$_3$-C$_6$) hetero-cycloalkyl optionally contains besides the nitrogen one additional heteroatom selected from N, O, and S, wherein N is optionally substituted with lower alkyl, —SO₂R⁸, or —OR⁸, and wherein S is unsubstituted or forms sulfonyl, wherein said substituted phenyl, benzyl, or heteroaryl has at least one substituent being halogen, mono-, di-, or trihalo($C_1$-$C_4$)alkyl, —SO₂R⁸, or —OR⁸, where R⁸ is lower alkyl, cyano, lower alkyl, or —SO₂NR⁹R¹⁰, and where R⁹ and R¹⁰ are independently selected from H and lower alkyl; R³ is unsubstituted or substituted phenyl, substituted or unsubstituted benzyl, substituted or unsubstituted heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, or —NR¹¹R¹², where R¹¹ and R¹² are independently selected from H and lower alkyl or where R¹¹ and R¹² form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —SO₂R¹³, or —OR¹³, and wherein S is unsubstituted or forms sulfonyl, wherein said substituted phenyl, benzyl, or heteroaryl has at least one substituent being halogen, mono-, di-, or trihalo($C_1$-$C_4$) alkyl, —SO₂R¹⁴, or —OR', where R¹⁴ is lower alkyl, cyano, lower alkyl, or —SO₂NR¹⁵R¹⁶, and where R¹⁵ and R¹⁶ are independently selected from H and lower alkyl, or a tautomer or stereoisomer thereof.

In further aspects, R⁴ and R⁵ are both hydrogen.

In further aspects, R¹ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted with —CR⁴R⁵NH₂, and optionally, halogen or lower alkyl, and where R⁴ and R⁵ are independently H or lower alkyl or R⁴ and R⁵ form a ($C_1$-$C_8$) cycloalkyl or ($C_1$-$C_8$)hetero-cycloalkyl.

In further aspects, X is —SO₂R¹.

In further aspects, Z is independently selected from —R³, —CH₂—R³, —SO₂R³, —C(=O)R³, and —OR³.

In further aspects, R³ is unsubstituted or substituted phenyl or unsubstituted or substituted 4-, 5-, or 6-membered heteroaryl containing 1 to 2 heteroatom(s) each independently selected from N, O, S, wherein said substituted phenyl or 4-, 5-, or 6-membered heteroaryl has at least one substituent being halogen, cyano, methoxy, methylsulfonyl, or dimethylaminosulfonyl. In still further aspects, R³ is halogen, trifluoromethyl, cyclohexyl, dimethylaminosulfonyl, methylsulfonyl, methoxy, cyano, or lower alkyl. In yet further aspects, R³ is —NR⁶R⁷, where R⁶ and R⁷ form together a ($C_3$-$C_6$) hetero-cycloalkyl, and wherein the ($C_3$-$C_6$) hetero-cycloalkyl is piperidinyl, piperazinyl, 4-methylpiperazin-1-yl, 4-(methylsulfonyl)piperazinyl, 4-morpholinyl, or 1,1-dioxidothiomorpholinyl.

In further aspects, Y is —C(=O)R², and R² is selected from:

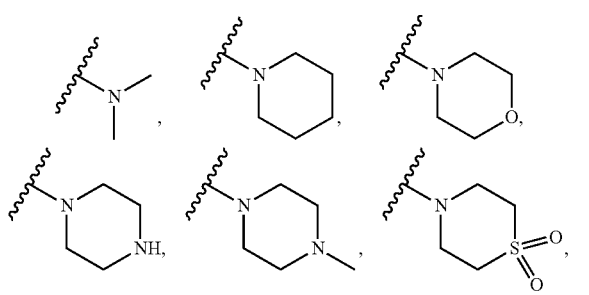

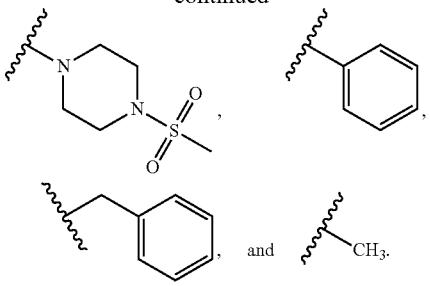

In further aspects, X is independently selected from —OW and —SO₂R¹, where R¹ is phenyl, where said phenyl is substituted with —CR⁴R⁵NH₂, and optionally, halogen or lower alkyl, and where R⁴ and R⁵ are independently H or lower alkyl or R⁴ and R⁵ form a cycloalkyl or hetero-cycloalkyl.

In further aspects, Y is —SO₂R², and R² is selected from:

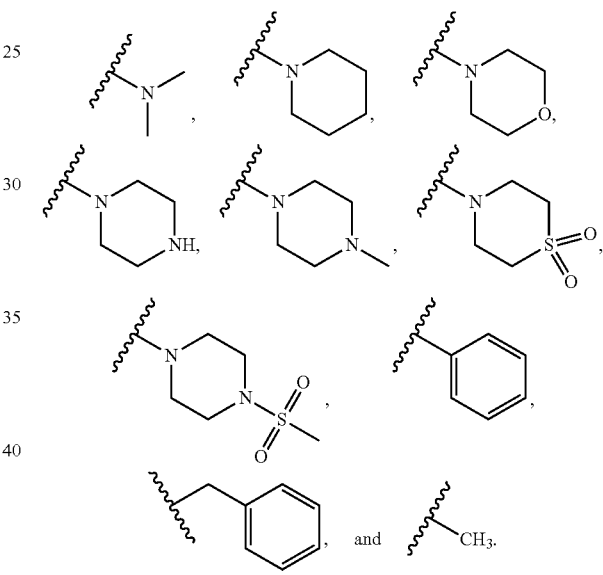

In further aspects, X is independently selected from —OR¹ and —SO₂R¹, where R¹ is phenyl, where said phenyl is substituted with —CR⁴R⁵NH₂, and optionally, halogen or lower alkyl, and where R⁴ and R⁵ are independently H or lower alkyl or R⁴ and R⁵ form a cycloalkyl or hetero-cycloalkyl.

In further aspects, R² is:

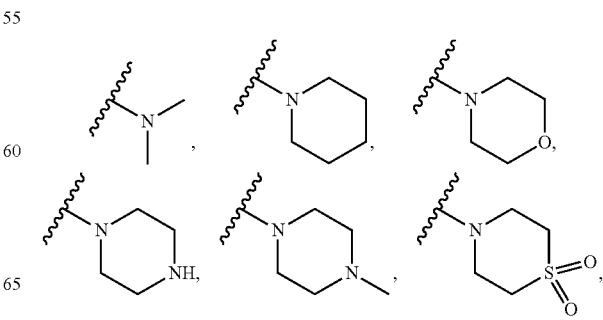

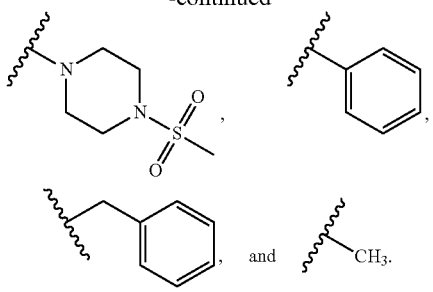

In further aspects, the compound is one of cis-4-((2-(((4-(Aminomethyl)pyridin-2-yl)sulfonyl)methyl)-4-phenylpyrrolidin-1-yl)sulfonyl)thiomorpholine 1,1-dioxide; 4-(((2S,4R)-2-(((4-(aminomethyl)pyridin-2-yl)sulfonyl)methyl)-4-phenylpyrrolidin-1-yl)sulfonyl)thiomorpholine 1,1-dioxide; 4-(((2R,4S)-2-(((4-(aminomethyl)pyridin-2-yl)sulfonyl)methyl)-4-phenylpyrrolidin-1-yl)sulfonyl)thiomorpholine 1,1-dioxide; cis-(2-(((4-(2-fluorophenyl)-1-(morpholinosulfonyl)pyrrolidin-2-yl)methyl)sulfonyl)pyridin-4-yl)methanamine; cis-(4-(((1-(Methylsulfonyl)-4-phenylpyrrolidin-2-yl)methyl)sulfonyl)phenyl)methanamine; cis-(3-(((1-(Methylsulfonyl)-4-phenylpyrrolidin-2-yl)methyl)sulfonyl)phenyl)methanamine; cis-(2-(((4-(2-Fluorophenyl)-1-(morpholinosulfonyl)pyrrolidin-2-yl)methyl)sulfonyl)pyridin-4-yl)methanamine; cis-(24(4-(4-Fluorophenyl)-1-(morpholinosulfonyl)pyrrolidin-2-yl)methyl)sulfonyl)pyridin-4-yl)methanamine; cis-4-((2-(((4-(Aminomethyl)pyridin-2-yl)sulfonyl)methyl)-4-(2-fluorophenyl)pyrrolidin-1-yl)sulfonyl)thiomorpholine 1,1-dioxide; cis-4-((2-(((4-(Aminomethyl)pyridin-2-yl)sulfonyl)methyl)-4-(4-fluorophenyl)pyrrolidin-1-yl)sulfonyl)thiomorpholine 1,1-dioxide; cis-(54(4-(2-Fluorophenyl)-1-(morpholinosulfonyl)pyrrolidin-2-yl)methyl)sulfonyl)thiophen-2-yl)methanamine; cis-(5-(((4-(4-Fluorophenyl)-1-(morpholinosulfonyl)pyrrolidin-2-yl)methyl)sulfonyl)thiophen-2-yl)methanamine; cis-4-((2-(((5-(Aminomethyl)thiophen-2-yl)sulfonyl)methyl)-4-(2-fluorophenyl)pyrrolidin-1-yl)sulfonyl)thiomorpholine 1,1-dioxide; cis-4-((2-(((5-(Aminomethyl)thiophen-2-yl)sulfonyl)methyl)-4-(4-fluorophenyl)pyrrolidin-1-yl)sulfonyl)thiomorpholine 1,1-dioxide; cis-(2-((4-(2-Fluorophenyl)-1-(morpholinosulfonyl)pyrrolidin-2-yl)methoxy)pyridin-4-yl)methanamine; cis-(2-((4-(4-Fluorophenyl)-1-(morpholinosulfonyl)pyrrolidin-2-yl)methoxy)pyridin-4-yl)methanamine; cis-4-((2-(((4-(Aminomethyl)pyridin-2-yl)oxy)methyl)-4-(2-fluorophenyl)pyrrolidin-1-yl)sulfonyl)thiomorpholine 1,1-dioxide; cis-4-((2-(((4-(Aminomethyl)pyridin-2-yl)oxy)methyl)-4-(4-fluorophenyl)pyrrolidin-1-yl)sulfonyl)thiomorpholine 1,1-dioxide; cis-(344-(2-Fluorophenyl)-1-(morpholinosulfonyl)pyrrolidin-2-yl)methoxy)phenyl)methanamine; cis-(3-((4-(4-Fluorophenyl)-1-(morpholinosulfonyl)pyrrolidin-2-yl)methoxy)phenyl)methanamine; cis-4-((2-((3-(Aminomethyl)phenoxy)methyl)-4-(2-fluorophenyl)pyrrolidin-1-yl)sulfonyl)thiomorpholine 1,1-dioxide; cis-4-((2-((3-(Aminomethyl)phenoxy)methyl)-4-(4-fluorophenyl)pyrrolidin-1-yl)sulfonyl)thiomorpholine 1,1-dioxide; (3-((((2S,4R)-1-(methylsulfonyl)-4-phenylpyrrolidin-2-yl)methyl)sulfonyl)phenyl)methanamine; (3-((((2R,4S)-1-(methylsulfonyl)-4-phenylpyrrolidin-2-yl)methyl)sulfonyl)phenyl)methanamine; cis-2-(((1-(Morpholinosulfonyl)-5-phenylpiperidin-3-yl)methyl)sulfonyl)pyridin-4-yl)methanamine; cis-(2-((1-(Morpholinosulfonyl)-5-phenylpiperidin-3-yl)methoxy)pyridin-4-yl)methanamine; cis-(3-((1-(Morpholinosulfonyl)-5-phenylpiperidin-3-yl)methoxy)phenyl)methanamine; and cis-(5-(((1-(Morpholinosulfonyl)-5-phenylpiperidin-3-yl)methyl)sulfonyl)thiophen-2-yl)methanamine, or a pharmaceutically acceptable salt or hydrate thereof and/or stereoisomer or racemic mixture thereof.

In various aspects, the compound has a structure represented by a formula:

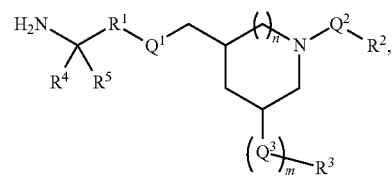

wherein: n is 0 or 1; m is 0 or 1; $Q^1$ is selected from —O—, —$SO_2$—, and —C(O)—; $Q^2$ is selected from —$SO_2$— and —C(O)—; $Q^3$, when present, is selected from —$CH_2$—, —$SO_2$—, —C(O)—, and —O—; $R^1$ is selected from phenyl and heteroaryl containing 1 to 2 heteroatoms independently selected from N, O, and S, and is substituted with 0, 1, 2, or 3 additional groups independently selected from halogen and C1-C4 alkyl; $R^2$ is selected from C1-C4 alkyl, C1-C4 haloalkyl, and —$NR^6R^7$; $R^6$ and $R^7$ are covalently bonded and, together with the intermediate atoms, comprise a C3-C6 heterocycloalkyl containing 0 or 1 additional heteroatom selected from N, O, and S; wherein the additional N, when present, is unsubstituted or substituted C1-C4 alkyl or —$SO_2R^8$; wherein $R^8$, when present, is C1-C4 alkyl; and wherein the additional S, when present, is unsubstituted or forms a sulfonyl group; $R^3$ is selected from C1-C4 haloalkyl, C3-C8 cycloalkyl, phenyl and heteroaryl containing 1 to 2 heteroatoms independently selected from N, O, and S, and wherein the C3-C8 cycloalkyl, phenyl, and heteroaryl, when present, are substituted with 0, 1, 2, or 3 groups independently selected from halogen, —CN, C1-C4 alkyl, C1-C4 haloalkyl, C1-C4 alkoxy, —$SO_2R^{14}$, and —$SO_2NR^{15}R^{16}$; wherein $R^{14}$, when present, is C1-C4 alkyl; wherein $R^{15}$ and $R^{16}$, when present, are independently selected from H and C1-C4 alkyl; and $R^4$ and $R^5$ are independently selected from H and C1-C4 alkyl, or a pharmaceutically acceptable salt thereof.

In various aspects, the compound has a structure represented by a formula:

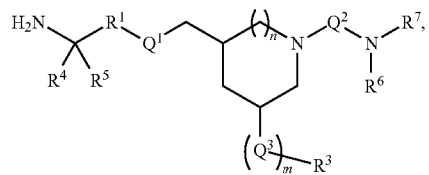

wherein: n is 0 or 1; m is 0 or 1; $Q^1$ is selected from —O—, —$SO_2$—, and —C(O)—; $Q^2$ is selected from —$SO_2$— and —C(O)—; $Q^3$, when present, is selected from —$CH_2$—, —$SO_2$—, —C(O)—, and —O—; $R^1$ is selected from phenyl and heteroaryl containing 1 to 2 heteroatoms independently selected from N, O, and S, and is substituted with 0, 1, 2, or 3 additional groups independently selected from halogen and C1-C4 alkyl; $R^3$ is selected from phenyl and heteroaryl containing 1 to 2 heteroatoms independently selected from N, O, and S, and is substituted with 0, 1, 2, or 3 groups independently selected from halogen, —CN, C1-C4 alkyl, C1-C4 haloalkyl, C1-C4 alkoxy, —SO$_2$R$^{14}$, and —SO$_2$NR$^{15}$R$^{16}$; wherein R$^{14}$, when present, is C1-C4 alkyl; wherein R$^{15}$ and R$^{16}$, when present, are independently selected from H and C1-C4 alkyl; R$^4$ and R$^5$ are independently selected from H and C1-C4 alkyl; R$^6$ and R$^7$ are covalently bonded and, together with the intermediate atoms, comprise a C3-C6 heterocycloalkyl containing 0 or 1 additional heteroatom selected from N, O, and S; wherein the additional N, when present, is unsubstituted or substituted C1-C4 alkyl or —SO$_2$R$^8$; wherein R$^8$, when present, is C1-C4 alkyl; and wherein the additional S, when present, is unsubstituted or forms a sulfonyl group, or a pharmaceutically acceptable salt thereof.

In a further aspect, n is 0. In a still further aspect, n is 1.

In a further aspect, m is 0.

In a further aspect, Q$^1$ is selected from —O— and —SO$_2$—. In a still further aspect, Q$^2$ is —SO$_2$—.

In a further aspect, R$^1$ is selected from phenyl and heteroaryl containing 1 to 2 heteroatoms independently selected from N, O, and S, and is substituted with 0 additional groups. In a still further aspect, R$^1$ is phenyl substituted with 0, 1, 2, or 3 additional groups independently selected from halogen and C1-C4 alkyl. In yet a further aspect, R$^1$ is phenyl substituted with 0 additional groups. In an even further aspect, R$^1$ is heteroaryl substituted with 0, 1, 2, or 3 additional groups independently selected from halogen and C1-C4 alkyl. In a still further aspect, R$^1$ is pyridinyl or thiophenyl. In yet a further aspect, R$^1$ is heteroaryl substituted with 0 additional groups.

In a further aspect, R$^3$ is C1-C4 haloalkyl. In a still further aspect, R$^3$ is —CF$_3$.

In a further aspect, R$^3$ is C3-C8 cycloalkyl substituted with 0, 1, 2, or 3 groups independently selected from halogen, —CN, C1-C4 alkyl, C1-C4 haloalkyl, C1-C4 alkoxy, —SO$_2$R$^{14}$, —SO$_2$NR$^{15}$R$^{16}$. In a still further aspect, R$^3$ is unsubstituted C3-C8 cycloalkyl. In yet a further aspect, R$^3$ is cyclohexyl substituted with 0, 1, 2, or 3 groups independently selected from halogen, —CN, C1-C4 alkyl, C1-C4 haloalkyl, C1-C4 alkoxy, —SO$_2$R$^{14}$, —SO$_2$NR$^{15}$R$^{16}$. In an even further aspect, R$^3$ is unsubstituted cyclohexyl.

In a further aspect, R$^3$ is phenyl substituted with 0, 1, 2, or 3 groups independently selected from halogen, —CN, C1-C4 alkyl, C1-C4 haloalkyl, C1-C4 alkoxy, —SO$_2$R$^{14}$, —SO$_2$NR$^{15}$R$^{16}$. In a still further aspect, R$^3$ is unsubstituted phenyl.

In a further aspect, R$^3$ is heteroaryl containing 1 to 2 heteroatoms independently selected from N, O, and S, and is substituted with 0, 1, 2, or 3 groups independently selected from halogen, —CN, C1-C4 alkyl, C1-C4 haloalkyl, C1-C4 alkoxy, —SO$_2$R$^{14}$, and —SO$_2$NR$^{15}$R$^{16}$. In an even further aspect, R$^3$ is unsubstituted heteroaryl.

In a further aspect, each of R$^4$ and R$^5$ is H.

In a further aspect, R$^6$ and R$^7$ are covalently bonded and, together with the intermediate atoms, comprise a C3-C6 heterocycloalkyl having a structure selected from:

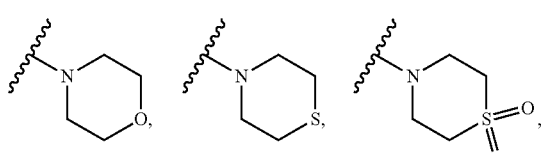

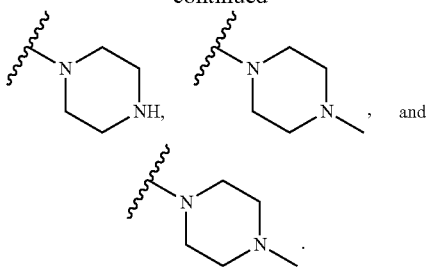

In a further aspect, the compound has a structure represented by a formula:

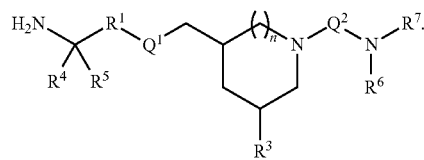

In a further aspect, the compound has a structure represented by a formula selected from:

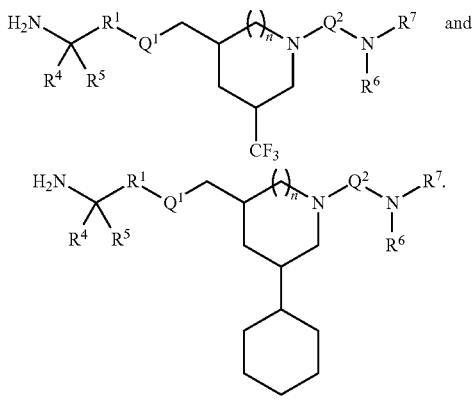

In a further aspect, the compound has a structure represented by a formula:

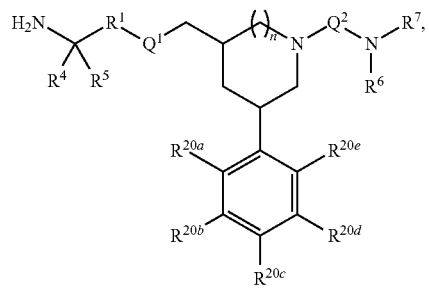

wherein each of R$^{20a}$, R$^{20b}$, R$^{20c}$, R$^{20d}$, and R$^{20e}$ independently selected from H, halogen, —CN, C1-C4 alkyl, C1-C4 haloalkyl, C1-C4 alkoxy, —SO$_2$R$^{14}$, and —SO$_2$NR$^{15}$R$^{16}$.

In a further aspect, the compound has a structure represented by a formula:

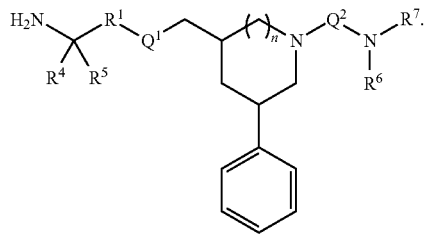

In a further aspect, the compound has a structure represented by a formula:

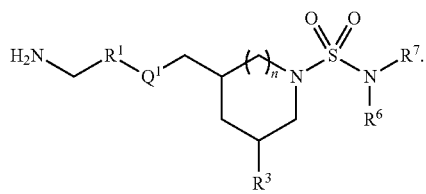

In a further aspect, the compound has a structure represented by a formula:

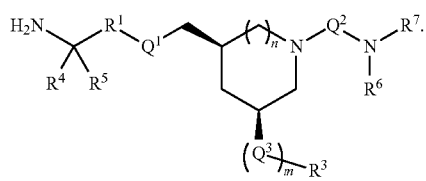

In a further aspect, compound has a structure represented by a formula:

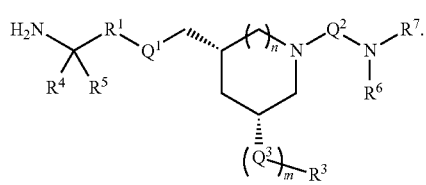

In a further aspect, the compound has a structure represented by a formula:

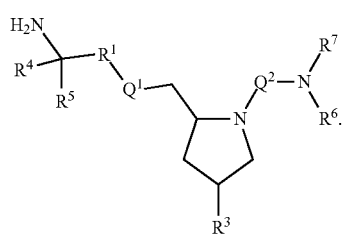

In a further aspect, the compound has a structure represented by a formula selected from:

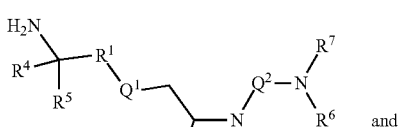

and

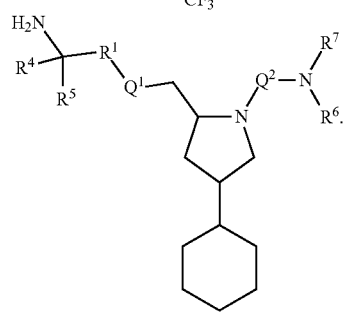

In a further aspect, the compound has a structure represented by a formula:

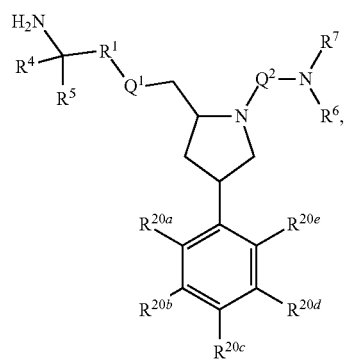

wherein each of $R^{20a}$, $R^{20b}$, $R^{20c}$, $R^{20d}$, and $R^{20e}$ is independently selected from H, halogen, —CN, C1-C4 alkyl, C1-C4 haloalkyl, C1-C4 alkoxy, —SO$_2$R$^{14}$, and —SO$_2$NR$^{15}$R$^{16}$.

In a further aspect, the compound has a structure represented by a formula:

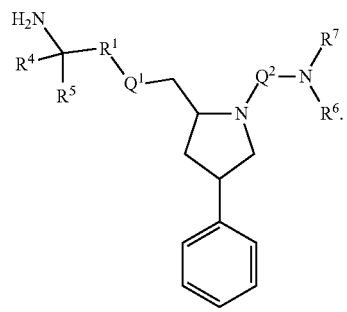

In a further aspect, the compound has a structure represented by a formula:

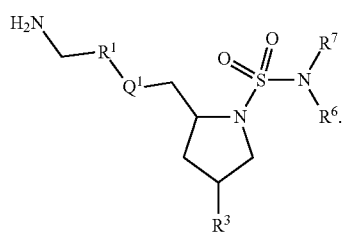
In a further aspect, the compound has a structure represented by a formula:
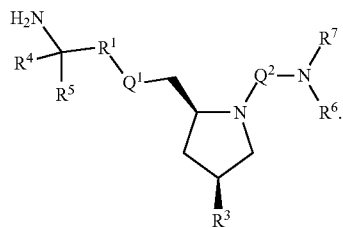
In a further aspect, the compound has a structure represented by a formula:
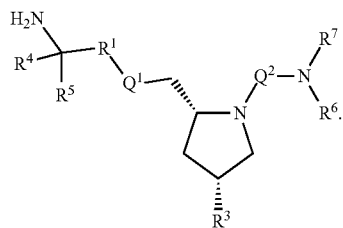
In a further aspect, the compound is selected from:
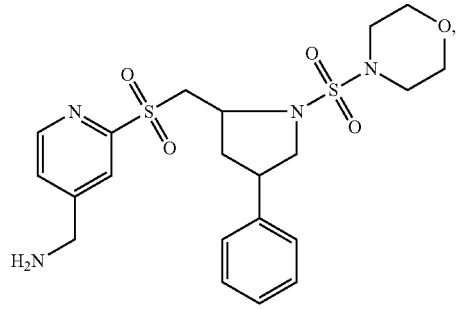
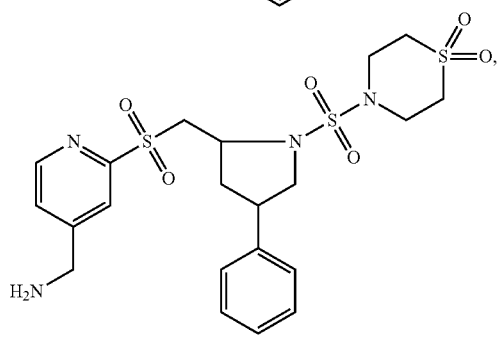
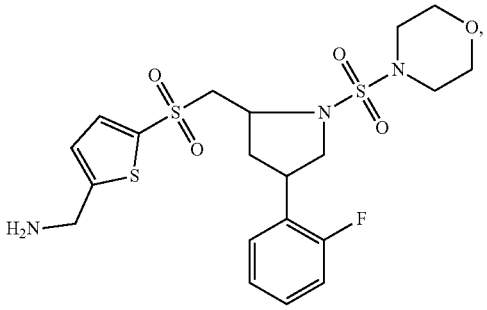
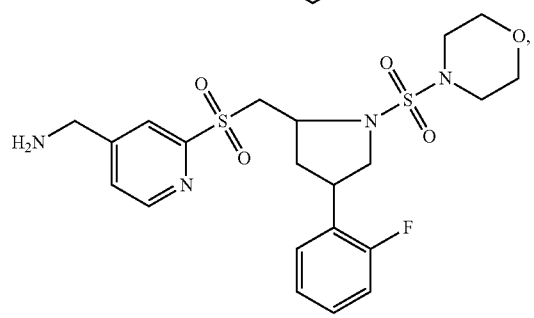
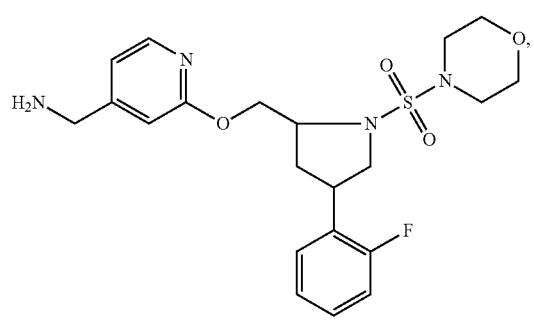
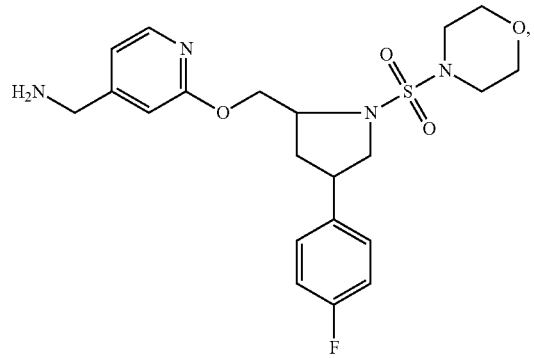
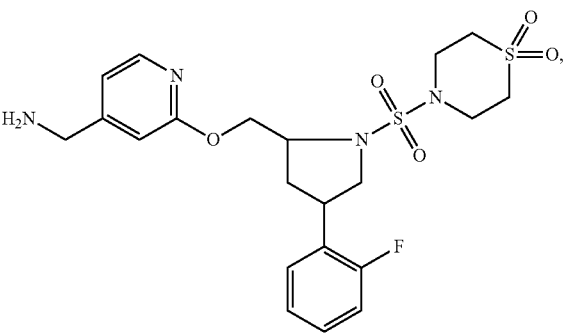

-continued
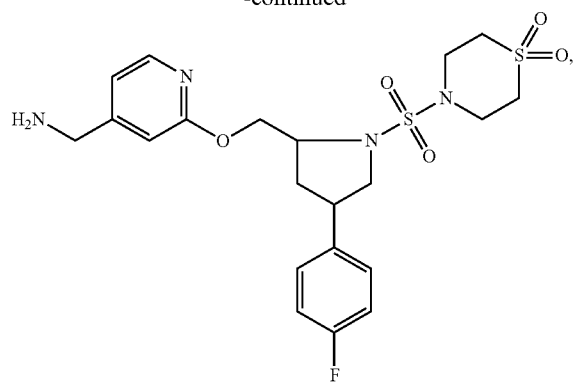
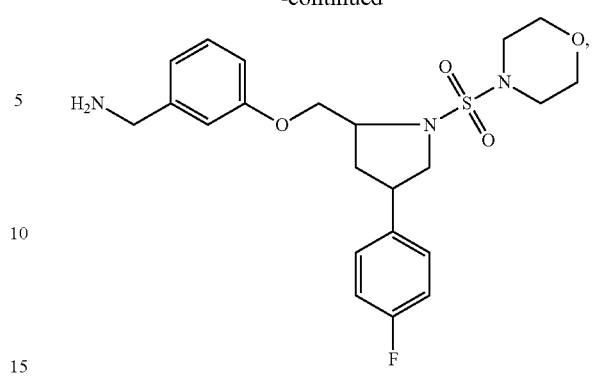
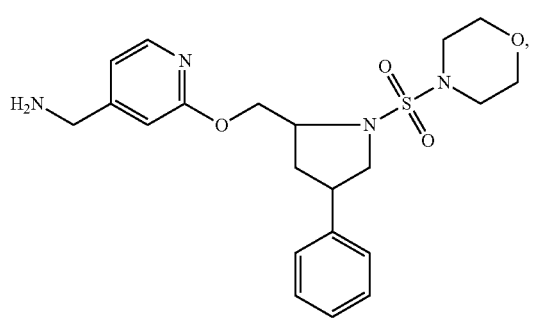
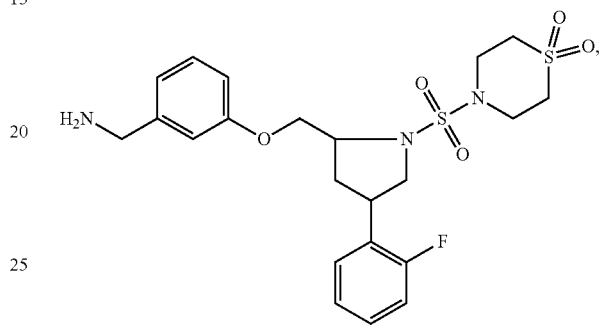
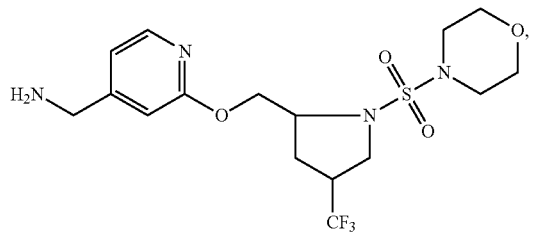
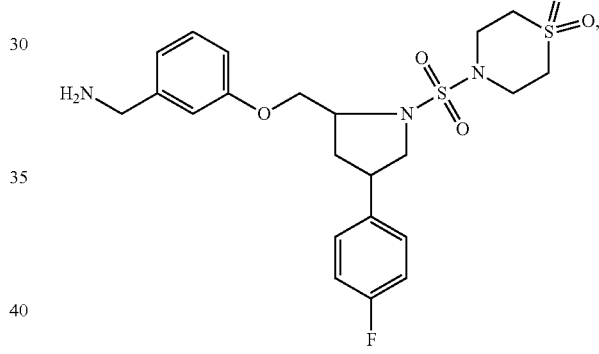
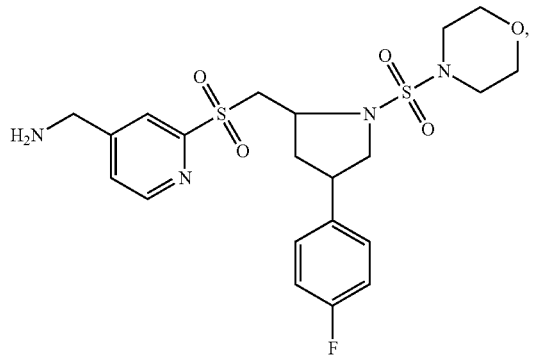
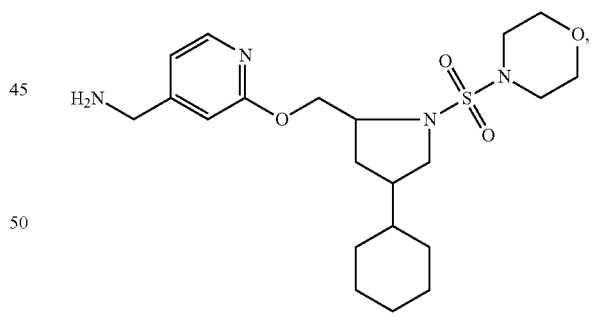
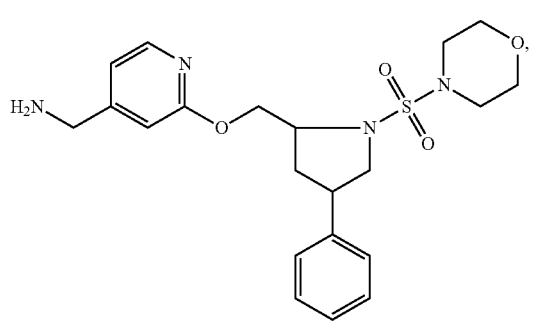
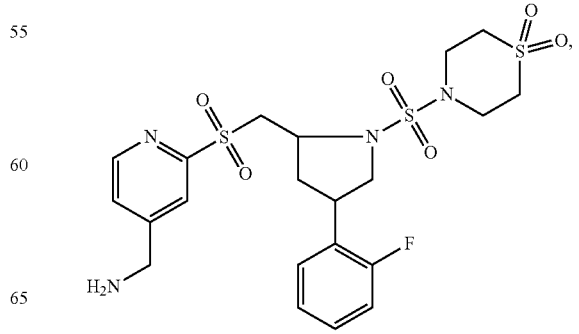

-continued
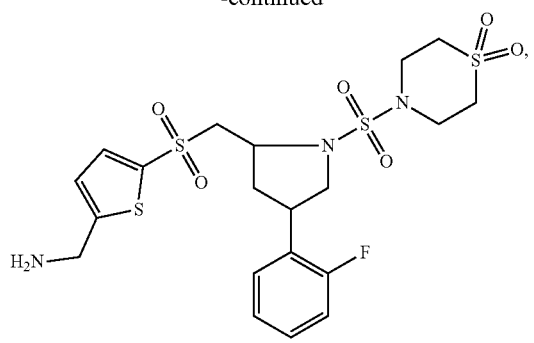
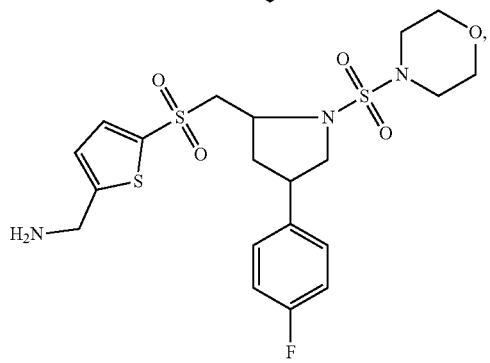
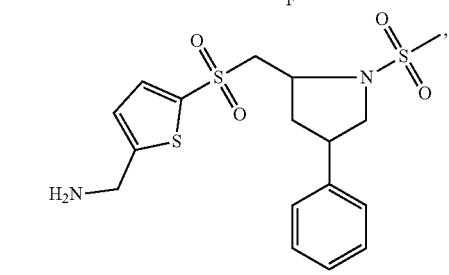
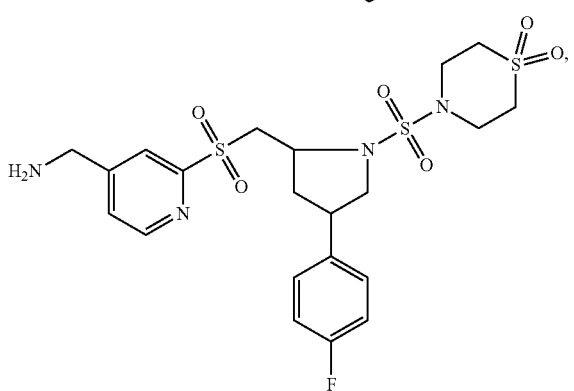
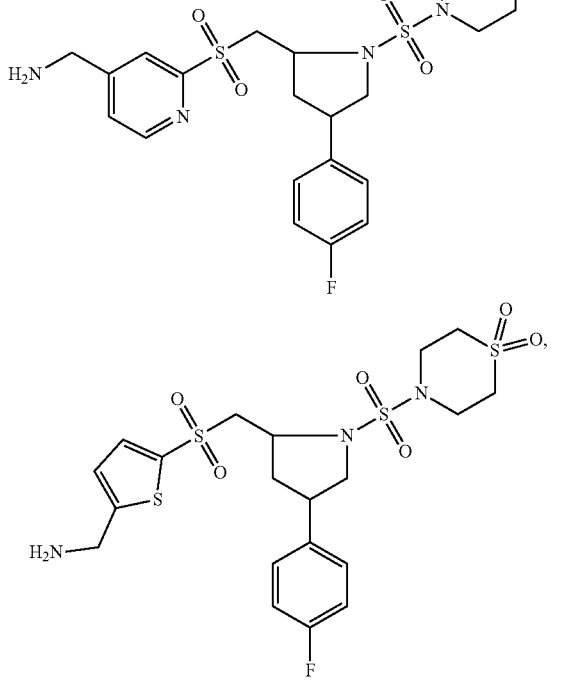
-continued
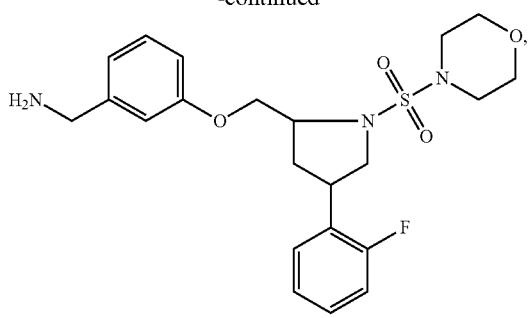
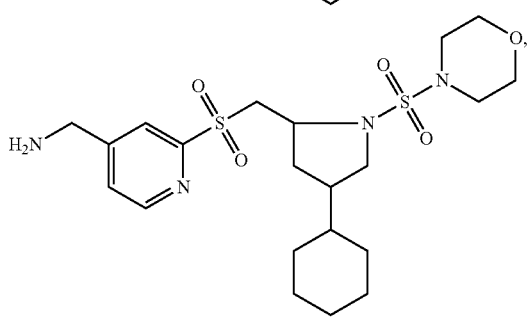
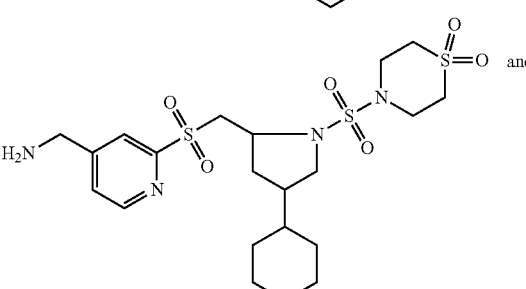 and
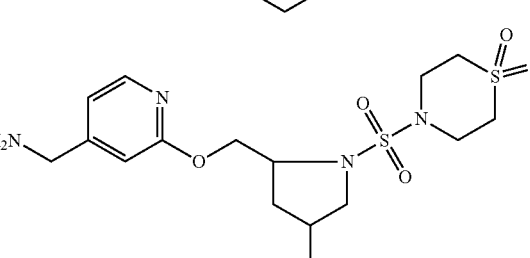
or a pharmaceutically acceptable salt thereof.
In a further aspect, the compound is selected from:
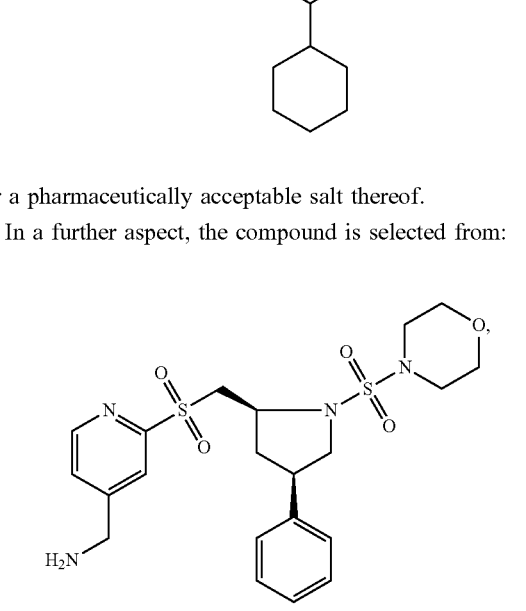

-continued
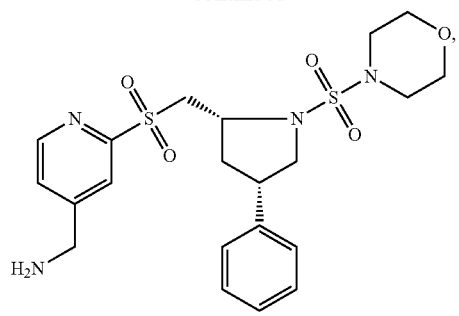
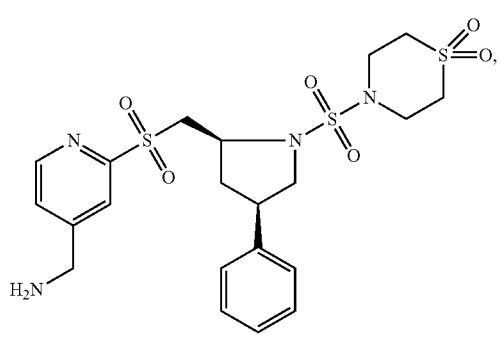
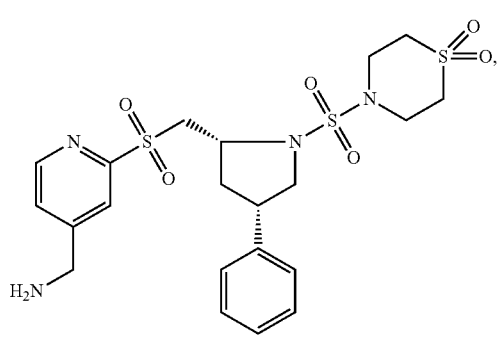
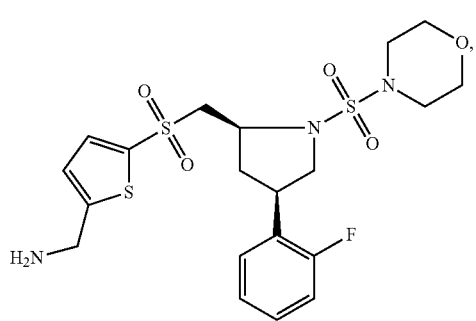
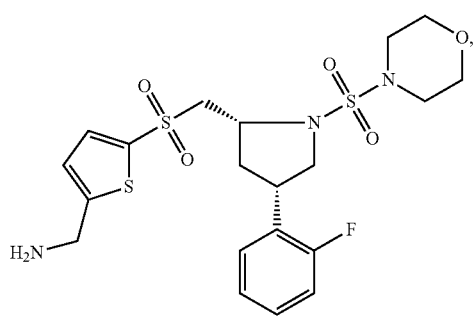
-continued
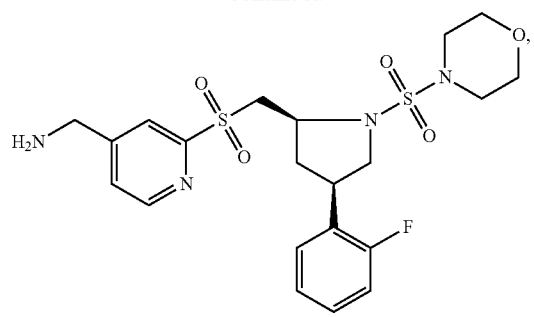
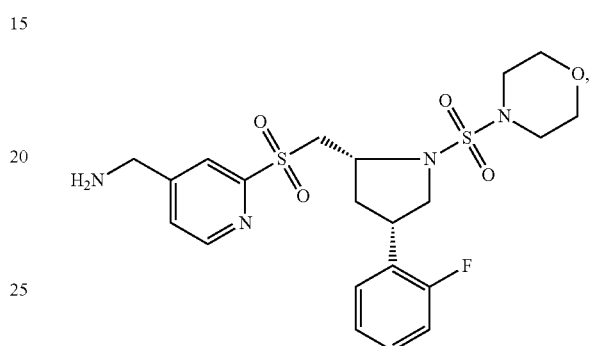
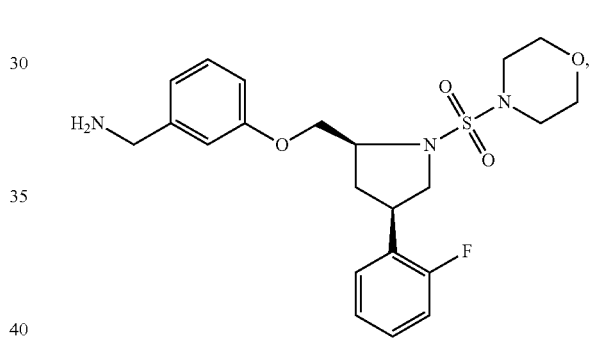
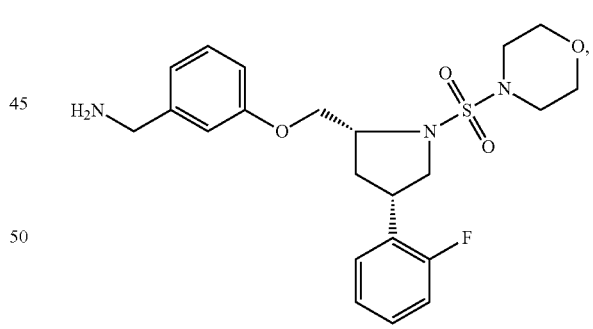
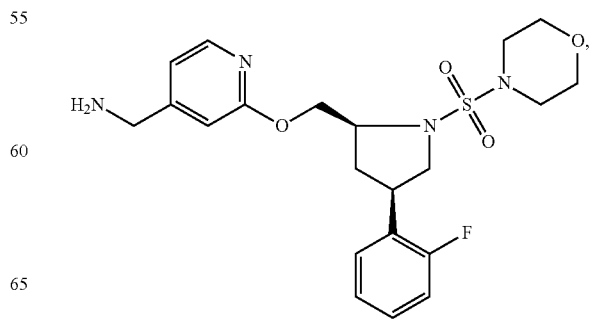

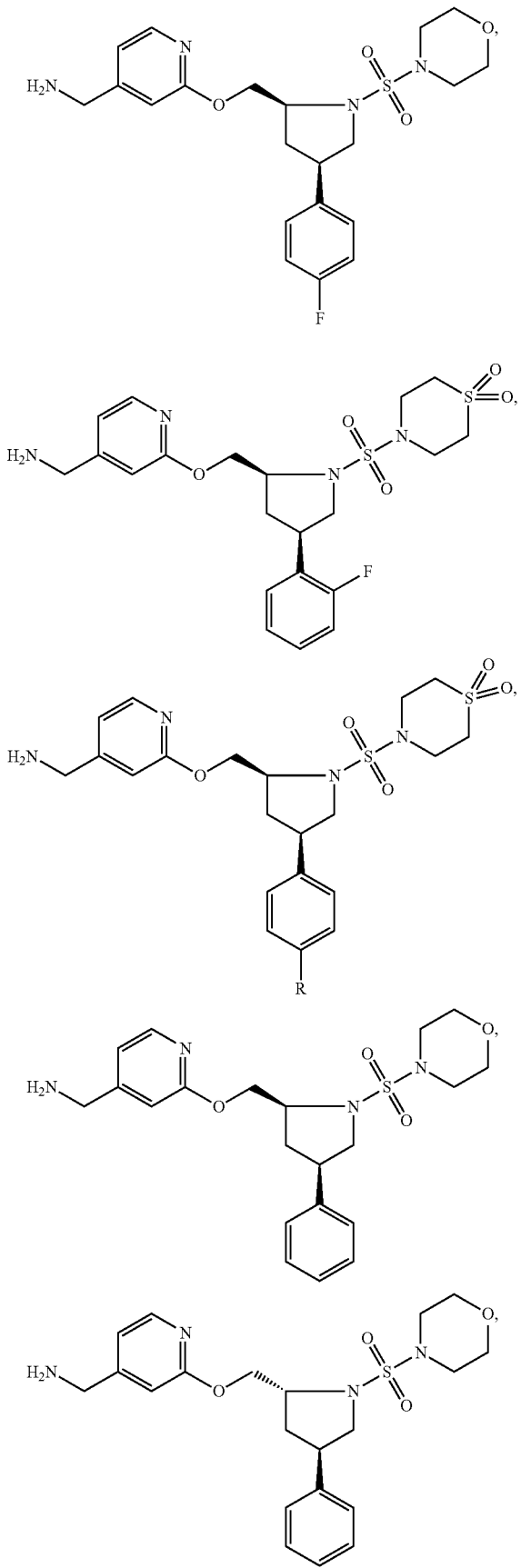
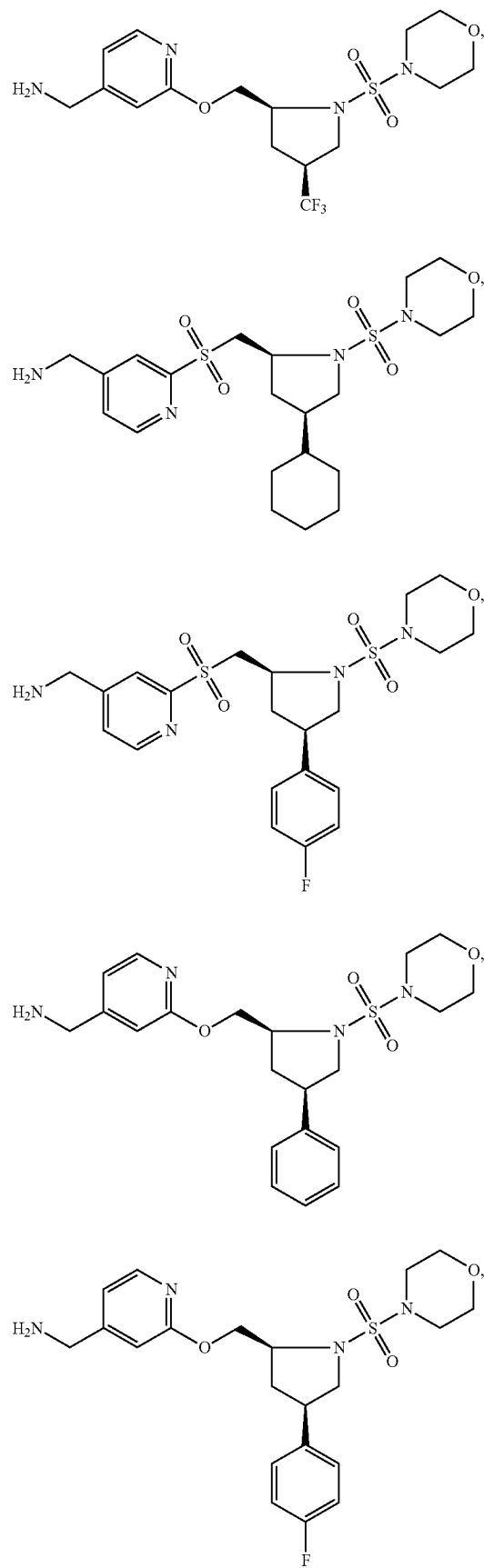

-continued
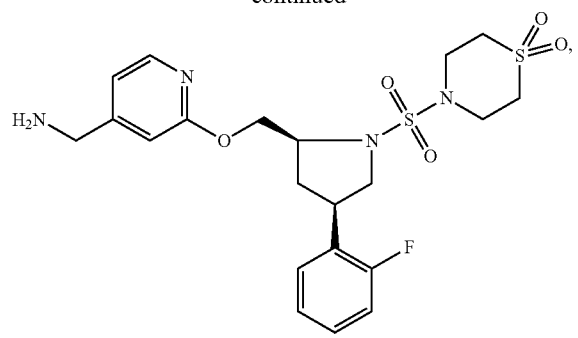
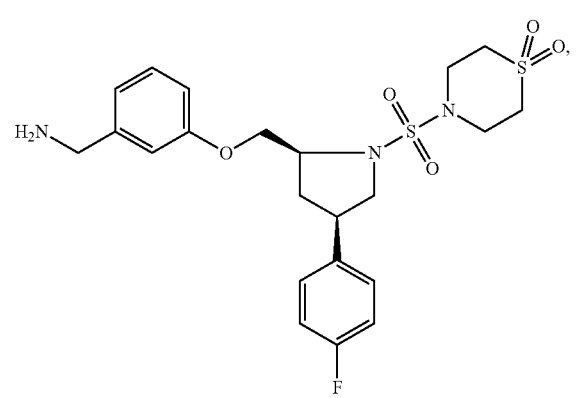
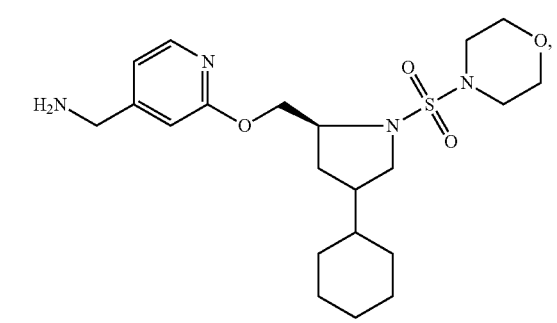
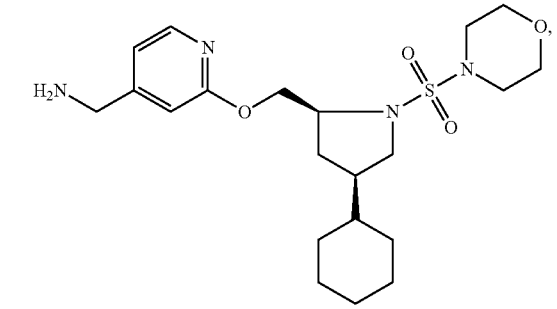
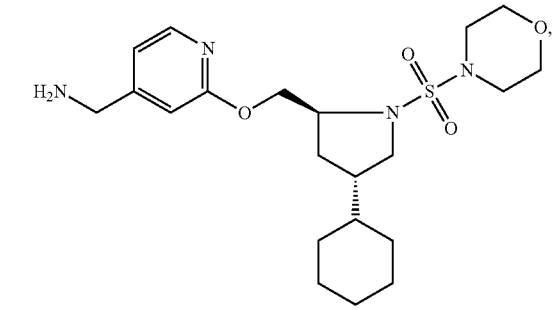
-continued
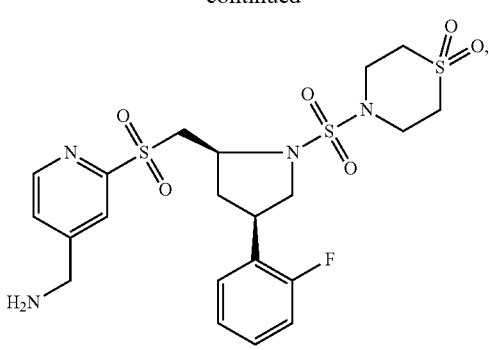
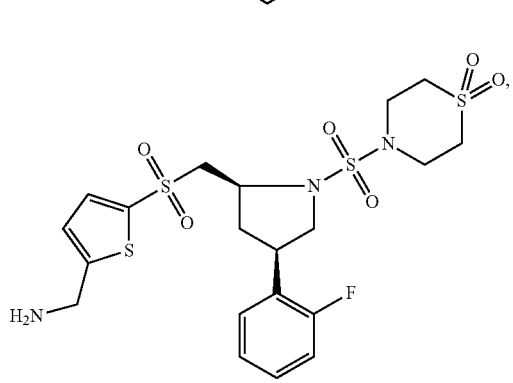
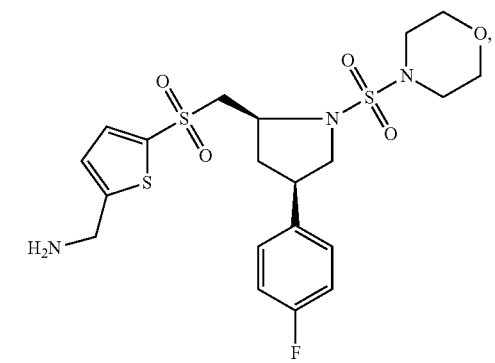
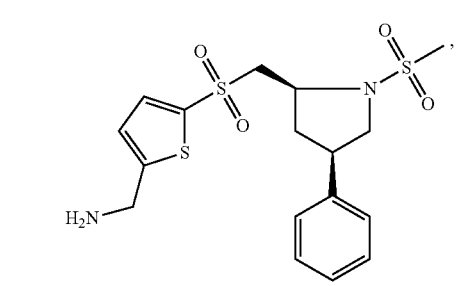
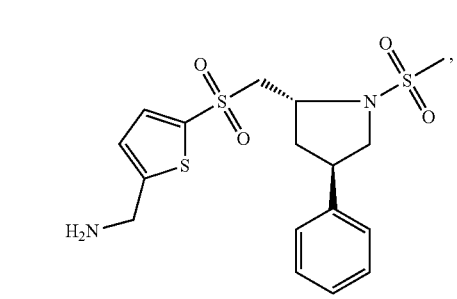

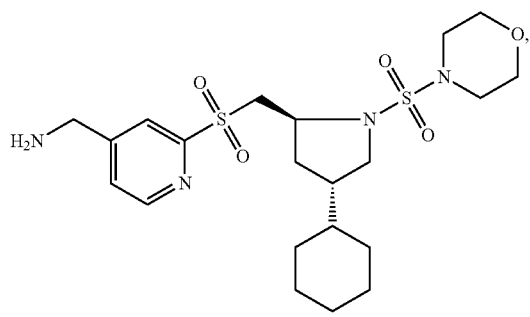 [SMILES: NCc1ccnc(S(=O)(=O)C[C@@H]2CC(C3CCCCC3)CN2S(=O)(=O)N2CCOCC2)c1]
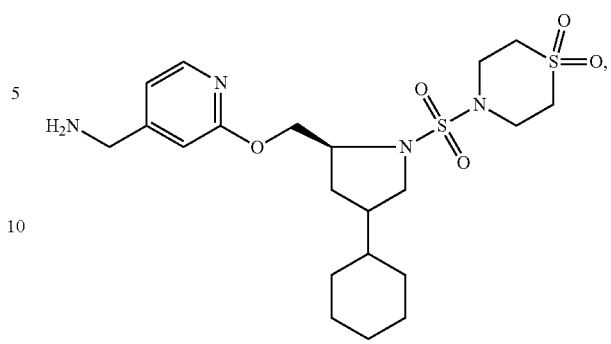
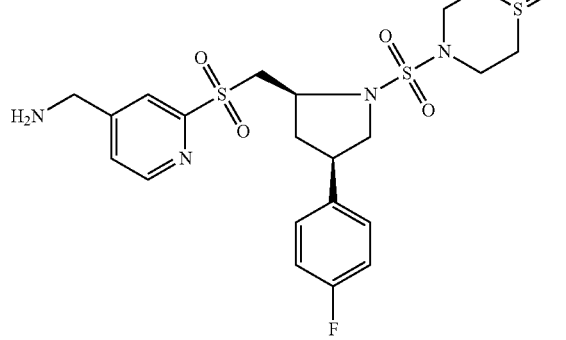
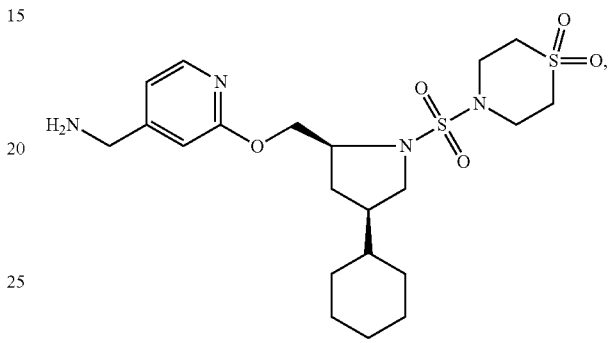
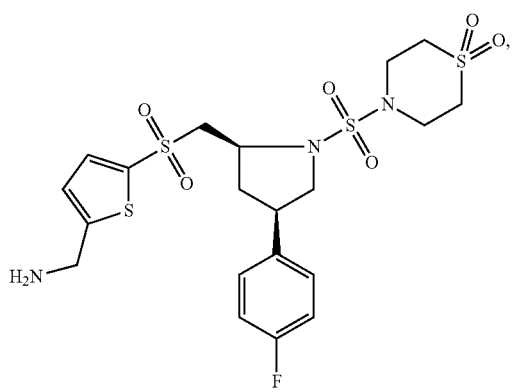
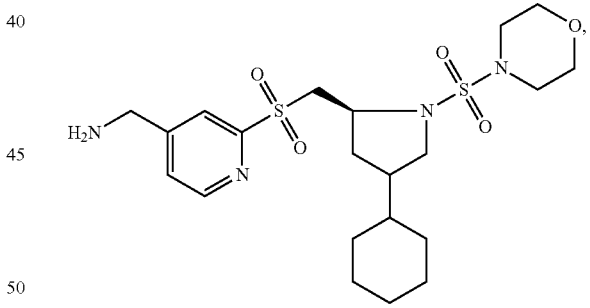
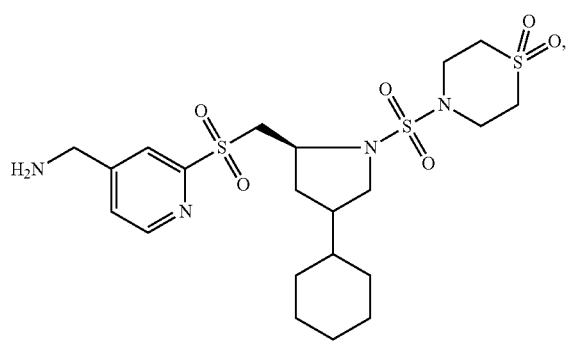
or a pharmaceutically acceptable salt thereof.
In a further aspect, the compound has a structure represented by a formula:
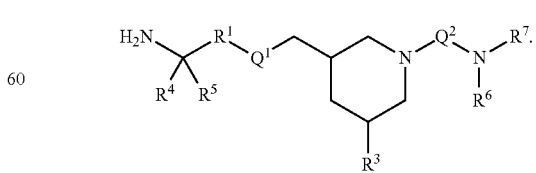
In a further aspect, the compound has a structure represented by a formula selected from:

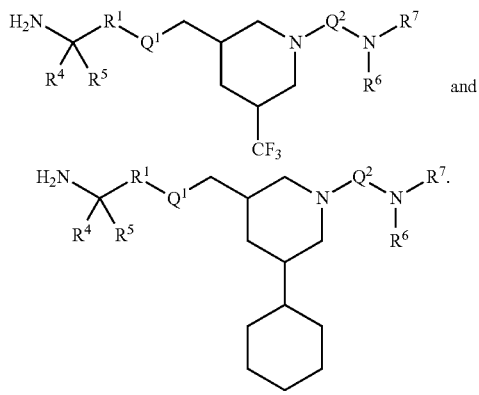

and

In a further aspect, the compound has a structure represented by a formula:

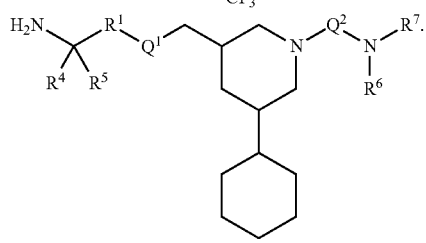

wherein each of $R^{20a}$, $R^{20b}$, $R^{20c}$, $R^{20d}$, and $R^{20e}$ is independently selected from H, halogen, —CN, C1-C4 alkyl, C1-C4 haloalkyl, C1-C4 alkoxy, —SO$_2$R$^{14}$, and —SO$_2$NR$^{15}$R$^{16}$.

In a further aspect, the compound has a structure represented by a formula:

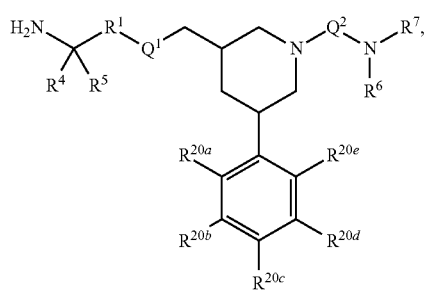

In a further aspect, the compound has a structure represented by a formula:

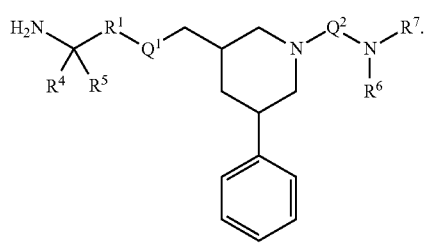

In a further aspect, the compound has a structure represented by a formula:

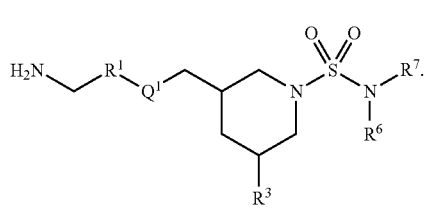

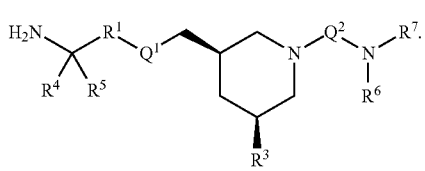

In a further aspect, the compound has a structure represented by a formula:

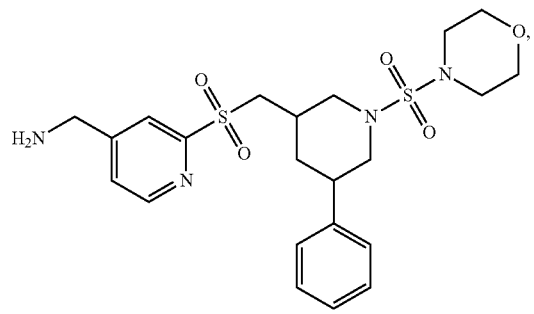

In a further aspect, the compound is selected from:

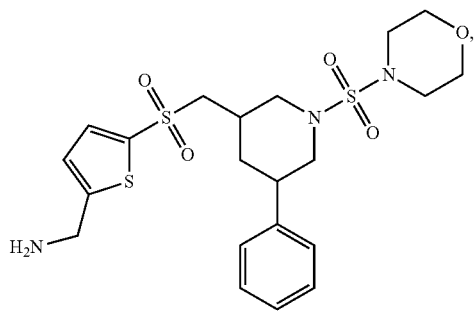

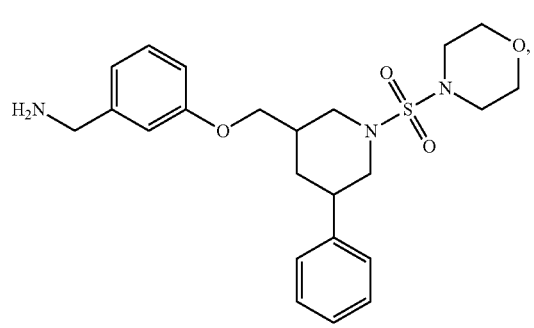

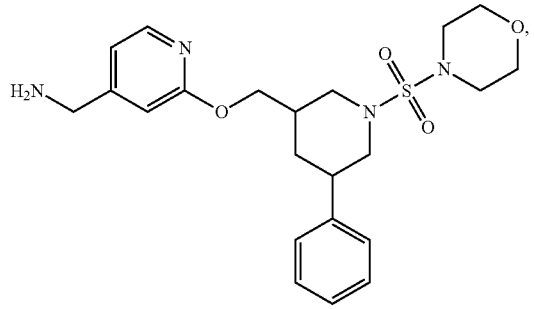
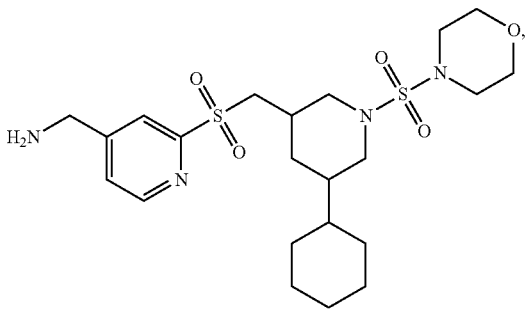
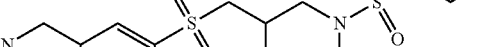
or a pharmaceutically acceptable salt thereof.

In a further aspect, the compound is selected from:
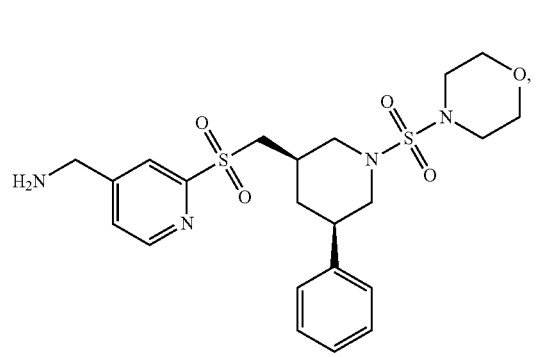
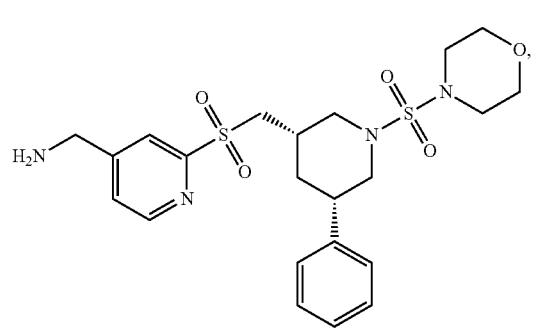
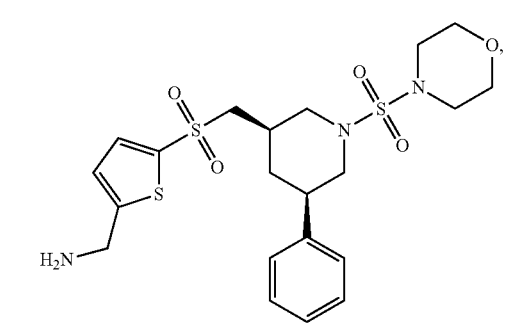
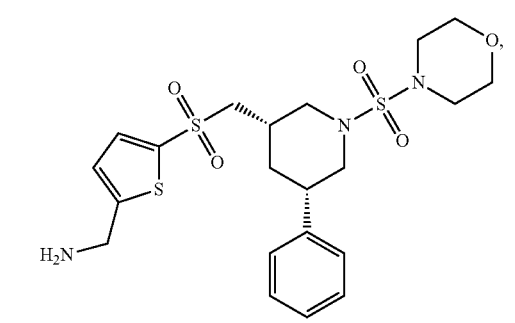
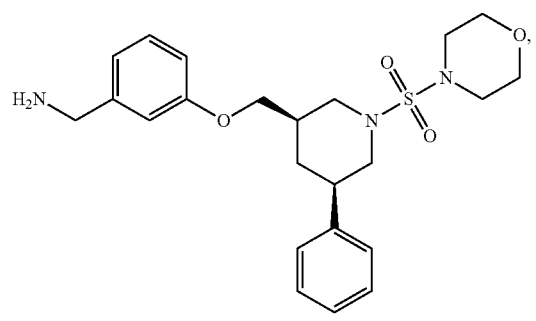
-continued
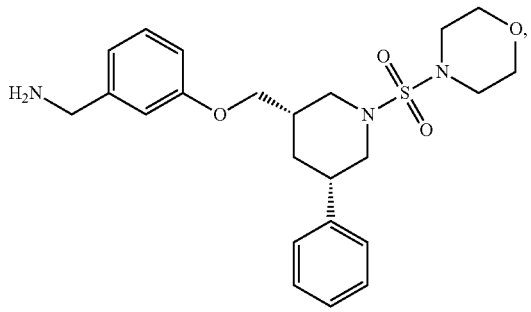
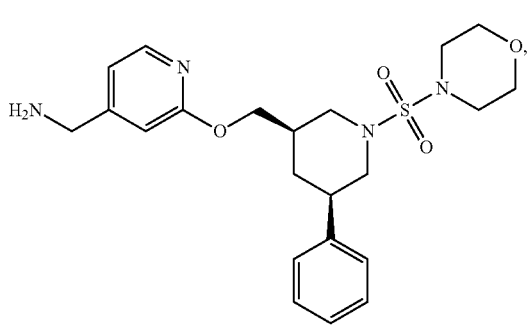
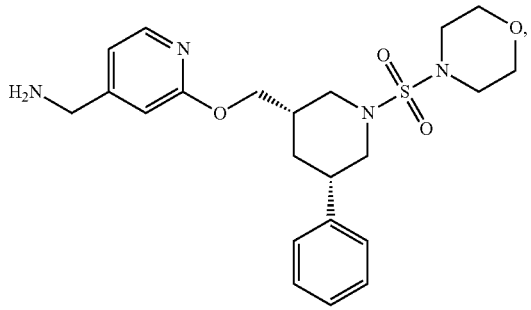
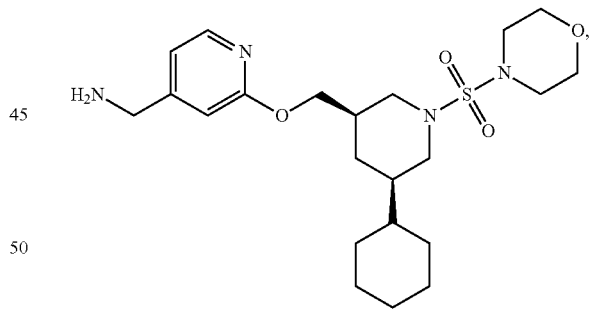
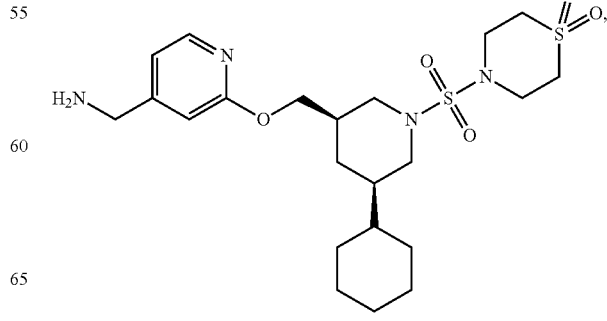

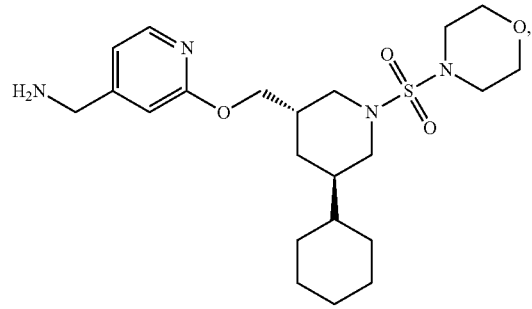
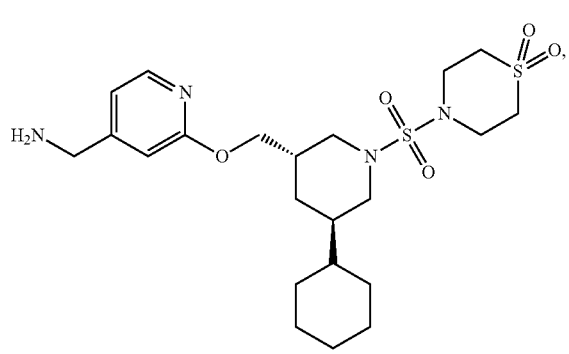
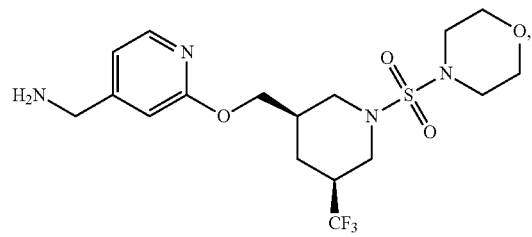
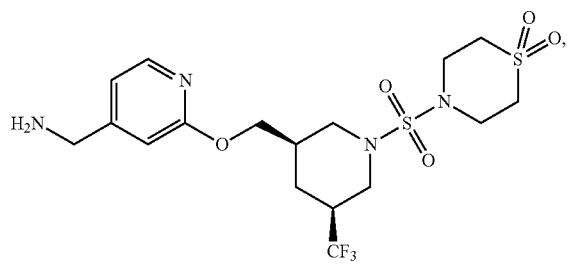
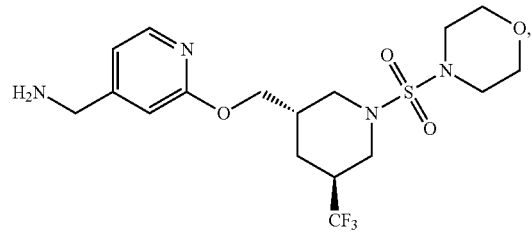
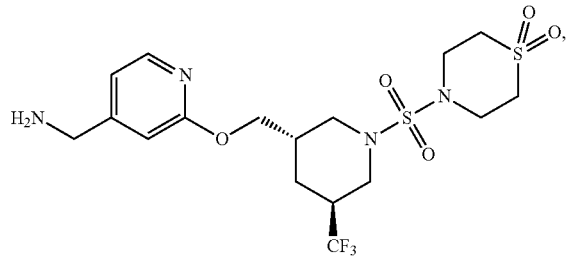
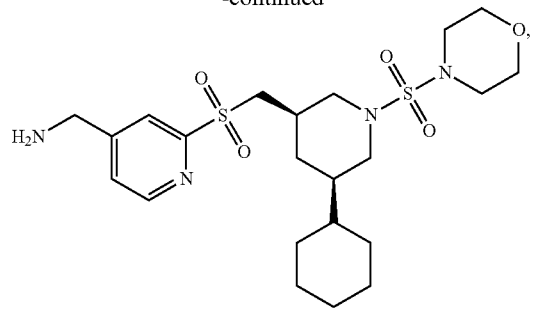
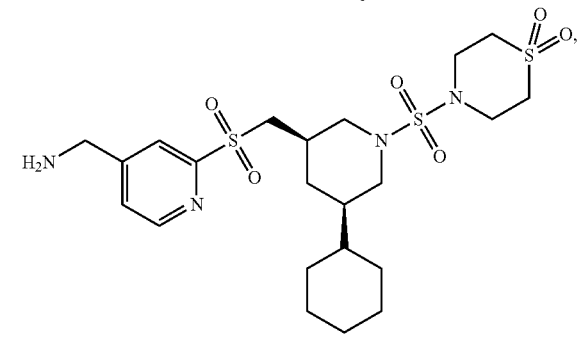
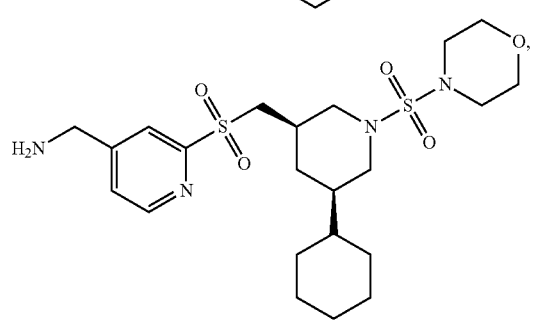
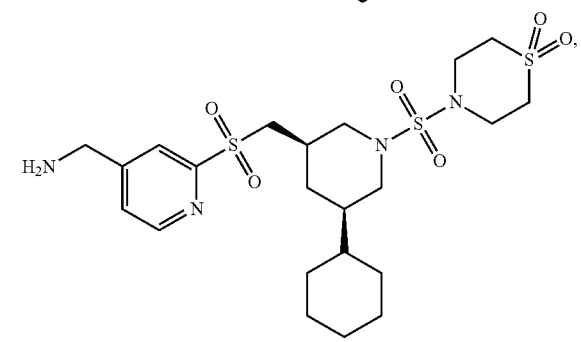
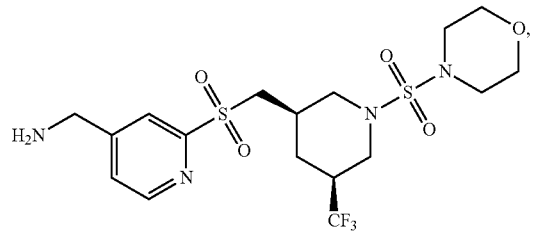
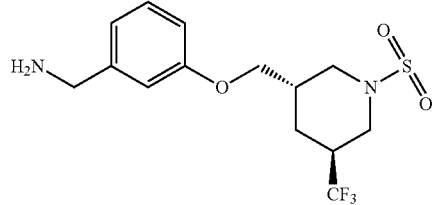

-continued

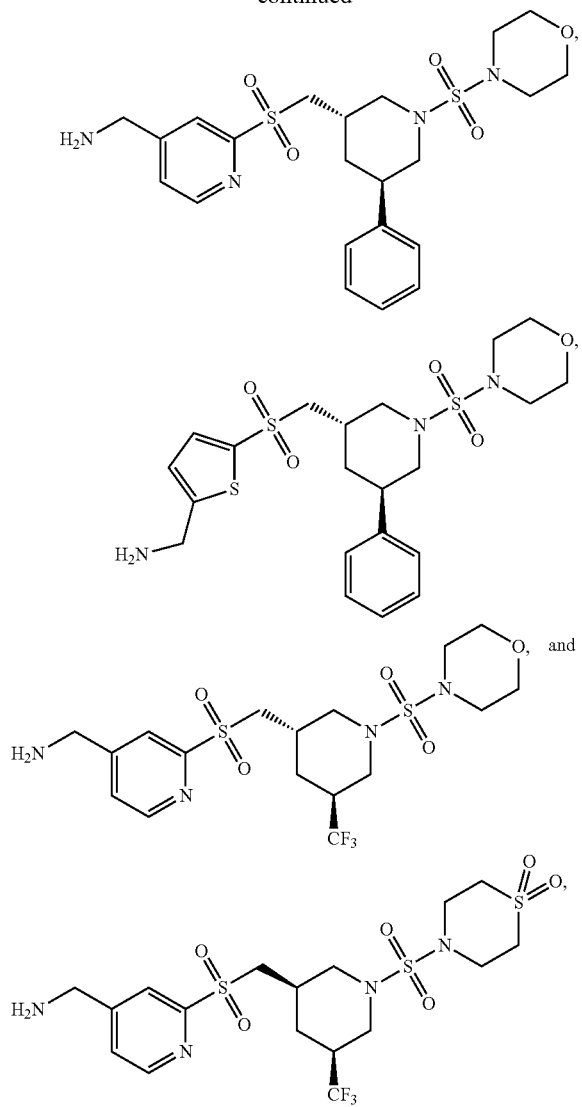

or a pharmaceutically acceptable salt thereof.

C. METHODS OF TREATING OR PREVENTING DISEASES ASSOCIATED WITH ABERRANT LOX FAMILY ENZYME EXPRESSION

The provided are methods of treating or preventing diseases associated with aberrant LOX family enzyme expression, particularly fibrotic disorders, including more specifically proliferative disorders, chronic and acute inflammatory disorders, cardiovascular diseases, primary or metastatic cancer, ocular diseases, pulmonary conditions, neurological ad neuropsychiatric conditions, or other diseases and medical conditions for which inhibiting one or more enzyme of the family of lysyl oxidases provides a therapeutic effect in a subject in need thereof by administering to the subject a LOX enzyme-inhibiting compound described herein, particularly a therapeutically effective amount of a pharmaceutical composition comprising the LOX enzyme-inhibiting compound disclosed herein.

One aspect of this disclosure it a method of treating, managing, ameliorating the symptoms of or preventing fibrotic disorders, proliferative disorders, inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit in a subject in need thereof by administering to the subject a LOX enzyme-inhibiting compound described herein, particularly a therapeutically effective amount of a pharmaceutical composition comprising the LOX enzyme-inhibiting compound disclosed herein.

Another aspect of this disclosure is a method of treating and preventing diseases associated with fibrosis, or treating symptoms associated with fibrotic diseases, and in particular such disorders for which inhibiting one or more LOX enzymes provides a therapeutic effect in a subject in need thereof by administering to the subject a LOX enzyme-inhibiting compound described herein, particularly a therapeutically effective amount of a pharmaceutical composition comprising the LOX enzyme-inhibiting compound disclosed herein. Without being bound by theory, the therapeutic effect provided is achieved by inhibiting oxidative deamination of lysine and hydroxylysine residues by LOX enzymes. Accordingly, embodiments herein include methods of treating and/or preventing a disease for which inhibiting of oxidative deamination of lysine and hydroxylysine residues in, for example but not limited to, collagen and elastin, provides a beneficial therapeutic effect by administering to a subject in need thereof a LOX enzyme-inhibiting compound described herein.

Embodiments herein include compounds of Formula I and methods of inhibiting one or more LOX enzymes in a subject in need thereof by administering to said subject an effective amount of LOX enzyme-inhibiting compound in accordance with Formula I, Formula II, or a pharmaceutically acceptable salt or hydrate thereof. Formula I and Formula II are as follows:

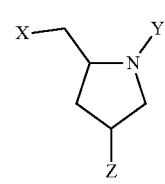

I

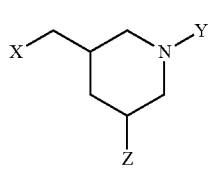

II wherein: X is independently selected from —C(=O)R$^1$, —OR$^1$, and —SO$_2$R$^1$; Y is independently selected from —C(=O)R$^2$ and —SO$_2$R$^2$; Z is independently selected from —R$^3$, —CH$_2$—R$^3$, —SO$_2$R$^3$, —C(=O)R$^3$, and —OR$^3$; R$^1$ is phenyl or heteroaryl containing 1 to 2 heteroatom(s) each independently selected from N, O, and S, wherein said phenyl or heteroaryl is substituted with —CR$^4$R$^5$NH$_2$ and optionally halogen or lower alkyl, where R$^4$ and R$^5$ are independently H or lower alkyl or R$^4$ and R$^5$ form a (C$_1$-C$_8$) cycloalkyl or (C$_1$-C$_8$) hetero-cycloalkyl; R$^2$ is substituted or unsubstituted phenyl, substituted or unsubstituted benzyl, substituted or unsubstituted heteroaryl containing 1 to 2 heteroatom(s) each independently selected from N, O, and S, (C$_1$-C$_8$) alkyl, (C$_1$-C$_8$) cycloalkyl, mono-, di-, or trihalo($C_1$-$C_4$)alkyl, or —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is substituted or unsubstituted, wherein substituent is lower alkyl or —$SO_2R^8$ or —$OR^8$, and wherein S is unsubstituted or forms sulfonyl, wherein said substituted phenyl, benzyl, or heteroaryl has at least one substituent being halogen, mono-, di- or trihalo($C_1$-$C_4$)alkyl, —$SO_2R^8$, or —$OR^8$, where $R^8$ is lower alkyl, cyano, lower alkyl, or —$SO_2NR^9R^{10}$, where $R^9$ and $R^{10}$ are independently selected from H and lower alkyl; $R^3$ is unsubstituted or substituted phenyl, substituted or unsubstituted benzyl, substituted or unsubstituted heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, or —$NR^{11}R^{12}$, where Ru and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with a lower alkyl, —$SO_2R^{13}$, or —$OR^{13}$, and wherein S is unsubstituted or forms sulfonyl, wherein said substituted phenyl, benzyl, or heteroaryl has at least one substituent being halogen, mono-, di-, or trihalo($C_1$-$C_4$)alkyl, —$SO_2R^{14}$, or —$OR^{14}$, where $R^{14}$ is lower alkyl, cyano, lower alkyl, or —$SO_2NR^{15}R^{16}$, where $R^{15}$ and $R^{16}$ are independently selected from H and lower alkyl; including a tautomer, stereoisomer, or racemic mixture thereof.

In particular embodiments, X is —$OR^1$, —$SO_2R^1$, or —$C(=O)R^1$, where $R^1$ is phenyl or heteroaryl, wherein said phenyl or heteroaryl is substituted with —$CR^4R^5NH_2$ and optionally a halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiment, $R^4$ and $R^5$ are both hydrogen. In embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl.

In preferred embodiments, X is —$SO_2R^1$, where $R^1$ is phenyl or 4-, 5-, or 6-membered heteroaryl, wherein said phenyl or 4-, 5-, or 6-membered heteroaryl is substituted with methylamine, and optionally, a halogen or lower alkyl. In preferred embodiments, $R^1$ is phenyl, thiophen-2-yl, pyridin-4-yl, pyridin-2-yl, thiazol-2-yl, or pyrimidin-2-yl, wherein phenyl, thiophen-2-yl, pyridin-4-yl, pyridin-2-yl, thiazol-2-yl, or pyrimidin-2-yl is substituted with —$CR^4R^5NH_2$, and optionally, halogen or lower alkyl, where $R^4$ and $R^5$ are both hydrogen.

In embodiments, Y is selected from —C=$OR^2$ and —$SO_2R^2$.

In some embodiments, $R^2$ is lower alkyl, but preferably methyl or $NR^6R^7$, where $R^6$ and $R^7$ are independently selected from H and lower alkyl. In other embodiments, $R^2$ is $NR^6R^7$, where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^8$, or —$OR^8$, where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, or 1,1-dioxidothiomorpholinyl. In some embodiments, $R^2$ is unsubstituted or substituted phenyl or unsubstituted or substituted benzyl, wherein substituted phenyl or benzyl is substituted with lower alkyl, halogen, mono-, di-, or trihalo($C_1$-$C_4$) alkyl, cyano, —$OR^9$, —$SO_2R^9$, or —$SO_2NR^9R^{10}$, where $R^9$ and $R^{10}$ are independently selected from H and lower alkyl.

In embodiments, Z is independently selected from —$R^3$, —$CH_2$—$R^3$, —$SO_2R^3$, —$C(=O)R^3$, and —$OR^3$.

In some embodiments, $R^3$ is mono-, di-, or tri-halo($C_1$-$C_4$)alkyl, ($C_3$-$C_6$) cycloalkyl, lower alkyl, or —$NR^{11}R^{12}$, where $R^{11}$ and $R^{12}$ are independently selected from lower alkyl. In some embodiments, $R^3$ is —$NR^{11}R^{12}$, where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^{13}$, or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, or 1,1-dioxidothiomorpholinyl. In some embodiments, $R^3$ is unsubstituted or substituted phenyl, unsubstituted or substituted benzyl, or unsubstituted or substituted heteroaryl containing 1 to 2 heteroatom(s) each independently selected from N, O, and S, wherein said substituted phenyl, benzyl, or heteroaryl has at least one substituent being halogen, mono-, di-, or tri-halo($C_1$-$C_4$)alkyl, —$SO_2R^{14}$, or —$OR^{14}$, where $R^{14}$ is lower alkyl, cyano, lower alkyl, or —$SO_2NR^{15}R^{16}$, where $R^{15}$ and $R^{16}$ are independently selected from H and lower alkyl.

In preferred embodiments, $R^3$ is substituted or unsubstituted phenyl, unsubstituted or substituted pyrimidin-2-yl, unsubstituted or substituted pyridin-4-yl, methoxy, halogen, cyclohexyl, methylsulfonyl, dimethylaminosulfonyl, or trifluoromethyl, wherein said phenyl, pyrimidin-2-yl, or pyridine-4-yl is substituted with halogen, cyano, lower alkyl, or methylsulfonyl. In some embodiments, when V is nitrogen, Z is methyl, methylcarbonyl, or unsubstituted or substituted benzyl or unsubstituted or substituted benzoyl, wherein said substituted benzyl or benzoyl is substituted with lower alkyl, methoxy, halogen, cyano, dimethylaminosulfonyl, or methylsulfonyl.

Some embodiments include compounds of Formula Ia or IIa and methods of inhibiting one or more LOX enzymes in a subject in need thereof by administering to said subject an effective amount of a LOX enzyme-inhibiting compound in accordance with Formula Ia or IIa, or a pharmaceutically acceptable salt or hydrate thereof. Formula Ia and IIa are as follows:

Ia

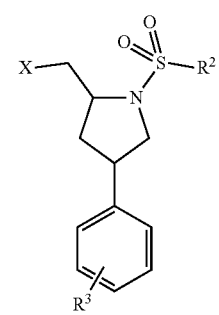

-continued

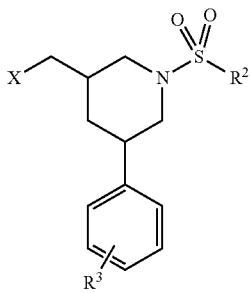

IIa wherein: X is independently selected from —C=OR$^1$, +OR$^1$, or —SO$_2$R$^1$; R$^1$ is phenyl or heteroaryl containing 1 to 2 heteroatom(s) each independently selected from N, O, and S, wherein said phenyl or heteroaryl is substituted with —CR$^4$R$^5$NH$_2$ and optionally halogen or lower alkyl, where R$^4$ and R$^5$ are independently H or lower alkyl or R$^4$ and R$^5$ form a (C$_1$-C$_8$) cycloalkyl or (C$_1$-C$_8$) hetero-cycloalkyl; R$^2$ is substituted or unsubstituted phenyl, substituted or unsubstituted benzyl, substituted or unsubstituted heteroaryl containing 1 to 2 heteroatom(s) each independently selected from N, O, and S, (C$_1$-C$_8$) alkyl, (C$_1$-C$_8$) cycloalkyl, mono-, di-, or trihalo(C$_1$-C$_4$)alkyl, or —NR$^6$R$^7$, where R$^6$ and R$^7$ are independently selected from H and lower alkyl or where R$^6$ and R$^7$ form together a (C$_3$-C$_6$) hetero-cycloalkyl, wherein the (C$_3$-C$_6$) hetero-cycloalkyl optionally contains besides the nitrogen one additional heteroatom selected from N, O, and S, wherein N is substituted or unsubstituted, wherein substituent is lower alkyl, —SO$_2$R$^8$, or —OR$^1$, and wherein S is unsubstituted or forms sulfonyl, wherein said substituted phenyl, benzyl, or heteroaryl has at least one substituent being halogen, mono-, di-, or trihalo(C$_1$-C$_4$) alkyl, —SO$_2$R$^8$, or —OR$^8$, where R$^8$ is lower alkyl, cyano, lower alkyl, or —SO$_2$NR$^9$R$^{10}$, where R$^9$ and R$^{10}$ are independently selected from H and lower alkyl; R$^3$ is halogen, mono-, di-, or trihalo(C$_1$-C$_4$)alkyl, —SO$_2$R$^{11}$, or —OR$^{11}$, where R$^{11}$ is lower alkyl, cyano, lower alkyl, or —SO$_2$NR$^{12}$R$^{13}$, where R$^{12}$ and R$^{13}$ are independently selected from H and lower alkyl; including a tautomer, stereoisomer or racemic mixture thereof.

In embodiments, X is selected from —C=OR$^1$, —OR$^1$, and —SO$_2$R$^1$.

In particular embodiments, X is —SO$_2$R$^1$, where R$^1$ is phenyl or heteroaryl, wherein said phenyl or heteroaryl is substituted with —CR$^4$R$^5$NH$_2$, and optionally, a halogen or lower alkyl, where R$^4$ and R$^5$ are independently H or lower alkyl or R$^4$ and R$^5$ form a (C$_1$-C$_8$) cycloalkyl or (C$_1$-C$_8$) hetero-cycloalkyl. In preferred embodiment, R$^4$ and R$^5$ are both hydrogen. In embodiments, R$^4$ and R$^5$ are independently H or methyl or R$^4$ and R$^5$ form cyclohexyl, 1,1-dioxidotetrahydro-2H-thiopyran-4-yl, or tetrahydropyran-4-yl.

In preferred embodiments, X is —SO$_2$R$^1$, where R$^1$ is phenyl or 4-, 5-, or 6-membered heteroaryl, wherein said phenyl or 4-, 5-, or 6-membered heteroaryl is substituted with methylamine, and optionally, a halogen or lower alkyl. In preferred embodiments, R$^1$ is phenyl, thiophen-2-yl, pyridin-4-yl, pyridin-2-yl, thiazol-2-yl, or pyrimidin-2-yl, wherein phenyl, thiophen-2-yl, pyridin-4-yl, pyridin-2-yl, thiazol-2-yl, or pyrimidin-2-yl is substituted with —CR$^4$R$^5$NH$_2$, and optionally, halogen or lower alkyl, where R$^4$ and R$^5$ are both hydrogen.

In some embodiments, R$^2$ is lower alkyl, but preferably methyl, or NR$^6$R$^7$ where R$^6$ and R$^7$ are independently selected from H or lower alkyl. In other embodiments, R$^2$ is NR$^6$R$^7$, where R$^6$ and R$^7$ form together a (C$_3$-C$_6$) hetero-cycloalkyl, wherein the (C$_3$-C$_6$) hetero-cycloalkyl optionally contains besides the nitrogen one additional heteroatom selected from N, O, and S, wherein N is optionally substituted with lower alkyl, —SO$_2$R$^8$, or —OR$^1$, where R$^8$ is lower alkyl, and wherein S is unsubstituted or forms sulfonyl. In preferred embodiments, R$^6$ and R$^7$ form together a (C$_3$-C$_6$) hetero-cycloalkyl, wherein the (C$_3$-C$_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, R$^2$ is unsubstituted or substituted phenyl or unsubstituted or substituted benzyl, wherein substituted phenyl or benzyl is substituted with lower alkyl, halogen, mono-, di-, or trihalo(C$_1$-C$_4$)alkyl, cyano, —OR$^9$, —SO$_2$R$^9$, or —SO$_2$NR$^9$R$^{10}$, where R$^9$ and R$^{10}$ are independently selected from H and lower alkyl.

In some embodiments, R$^3$ is halogen, mono-, di-, or tri-halo(C$_1$-C$_4$)alkyl, —SO$_2$R$^{11}$, or —OR$^{11}$, where R$^{11}$ is lower alkyl, cyano, lower alkyl, or —SO$_2$NR$^{12}$R$^{13}$, where R$^{12}$ and R$^{13}$ are independently selected from H and lower alkyl. In particular embodiments, R$^3$ is halogen, preferably —F or —Cl, or cyano.

Embodiments include compounds of Formula Ib or Formula IIb and methods of inhibiting one or more LOX enzymes in a subject by administering such Formula Ib or Formula IIb compound. These methods comprise administering to a subject in need thereof an effective amount of a LOX enzyme-inhibiting compound in accordance with Formula Ib or Formula IIb or a pharmaceutically acceptable salt or hydrate thereof. Formula Ib and Formula IIb are as follows:

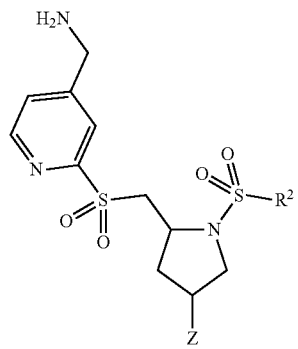

Ib

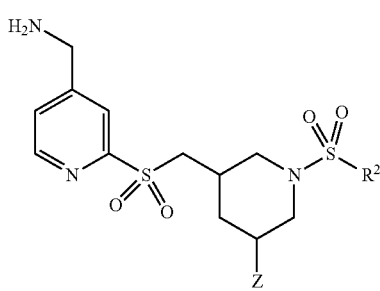

IIB wherein: Z is independently selected from —$R^3$, —$CH_2$—$R^3$, —$SO_2R^3$, —C(=O)$R^3$, and —$OR^3$; $R^2$ is substituted or unsubstituted phenyl, substituted or unsubstituted benzyl, substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, or —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^8$, or —$OR^8$, and wherein S is unsubstituted or forms sulfonyl, wherein said substituted phenyl, benzyl, or 4, 5, or 6-membered heteroaryl has at least one substituent being halogen, mono-, di-, or trihalo($C_1$-$C_4$)alkyl, —$SO_2R^8$, or —$OR^1$, where $R^8$ is lower alkyl, cyano, lower alkyl, or —$SO_2NR^9R^{10}$, where $R^9$ and $R^{10}$ are independently selected from H and lower alkyl; $R^3$ is unsubstituted or substituted phenyl, unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^{13}$, or —$OR^{13}$, and wherein S is unsubstituted or forms sulfonyl, wherein said substituted phenyl or 4-, 5-, or 6-membered heteroaryl has at least one substituent being halogen, mono-, di- or trihalo ($C_1$-$C_4$)alkyl, —$SO_2R^{14}$, or —$OR^{14}$, where $R^{14}$ is lower alkyl, cyano, lower alkyl, or —$SO_2NR^{15}R^{16}$, where $R^{15}$ and $R^{16}$ are independently selected from H and lower alkyl; including a tautomer, stereoisomer or racemic mixture thereof.

In some embodiments, $R^2$ is lower alkyl or $NR^6R^7$, where $R^6$ and $R^7$ are independently selected from H and lower alkyl. In preferred embodiments, $R^2$ is $NR^6R^7$, where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^8$, or —$OR^8$, where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidin-1-yl, piperazin-1-yl, 4-methylpiperazin-1-yl, 4-(methylsulfonyl) piperazin-1-yl, 4-morpholinyl, or 1,1-dioxidothiomorpholinyl.

In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di-, or trihalo($C_1$-$C_4$)alkyl, —$SO_2R^8$, or —$OR^1$, where $R^8$ is lower alkyl, cyano, lower alkyl, or —$SO_2NR^9R^{10}$, where $R^9$ and $R^{10}$ are independently selected from H and lower alkyl.

In some embodiments, Z is selected from —$R^3$, —$SO_2R^3$, and —$OR^3$. In some embodiments, $R^3$ is unsubstituted or substituted phenyl or substituted or unsubstituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di-, or trihalo ($C_1$-$C_4$)alkyl, —$SO_2R^{14}$, or —$OR^{14}$, where $R^{14}$ is lower alkyl, cyano, lower alkyl, or —$SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, —$SO_2R^{13}$, or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, or 1,1-dioxidothiomorpholinyl. In preferred embodiments, $R^3$ is substituted or unsubstituted phenyl, substituted or unsubstituted pyrimidin-2-yl, substituted or unsubstituted pyridin-4-yl, methoxy, halogen, cyclohexyl, methylsulfonyl, dimethylaminosulfonyl, or trifluoromethyl, wherein said phenyl, pyrimidin-2-yl, or pyridin-4-yl is substituted with halogen, cyano, lower alkyl, or methylsulfonyl.

Specific compounds within the scope of Formula I and II are provided below in Table 1. Provided are the compounds listed Table 1, as well as pharmaceutically acceptable salts and hydrates thereof, and also provided are stereoisomers of the depicted compounds and racemic mixtures of the stereoisomers, and pharmaceutically acceptable salts and hydrates thereof. Also provided are methods of treatment or prevention of a disease or disorder associated with LOX enzymes in a subject in need thereof comprising administering one or more of the following compounds, including pharmaceutically acceptable salts, hydrates, stereoisomers, and racemic mixtures thereof, to the subject in need thereof.

TABLE 1

| IUPAC Name | Structure |
|---|---|
| cis-4-((2-(((4-(Aminomethyl)pyridin-2-yl)sulfonyl)methyl)-4-phenylpyrrolidin-1-yl)sulfonyl)thiomorpholine 1,1-dioxide 2,2,2-trifluoroacetate | 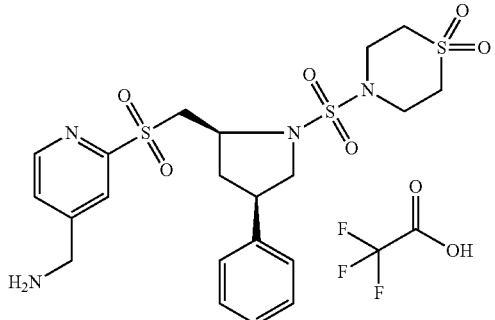<br>cis racemic |
| 4-(((2S,4R)-2-(((4-(aminomethyl)pyridin-2-yl)sulfonyl)methyl)-4-phenylpyrrolidin-1-yl)sulfonyl)thiomorpholine 1,1-dioxide 2,2,2-trifluoroacetate | 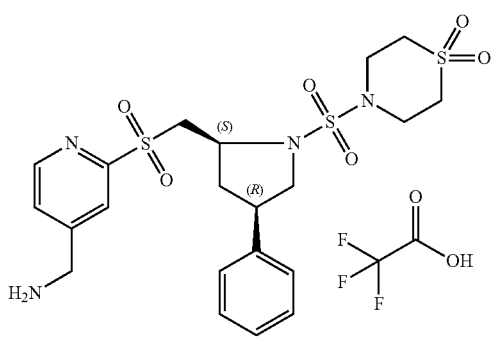 |
| 4-(((2R,4S)-2-(((4-(aminomethyl)pyridin-2-yl)sulfonyl)methyl)-4-phenylpyrrolidin-1-yl)sulfonyl)thiomorpholine 1,1-dioxide 2,2,2-trifluoroacetate | 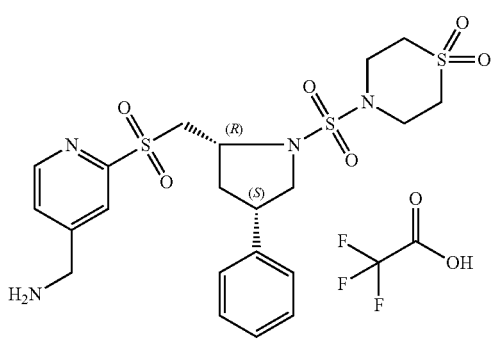 |
| (2-((((2S)-4-cyclohexyl-1-(morpholinosulfonyl)pyrrolidin-2-yl)methyl)sulfonyl)pyridin-4-yl)methanamine 2,2,2-trifluoroacetate | 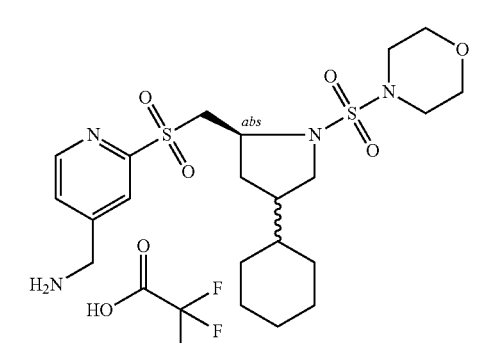 |

TABLE 1-continued

| IUPAC Name | Structure |
|---|---|
| cis-(4-(((1-(Methylsulfonyl)-4-phenylpyrrolidin-2-yl)methyl)sulfonyl)phenyl)methanamine 2,2,2-trifluoroacetate | 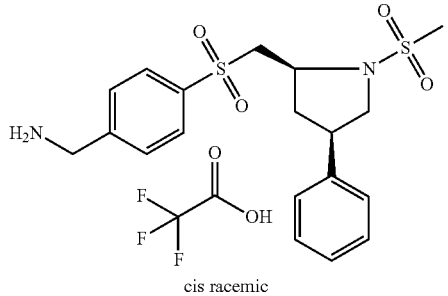  cis racemic |
| cis-(3-(((1-(Methylsulfonyl)-4-phenylpyrrolidin-2-yl)methyl)sulfonyl)phenyl)methanamine 2,2,2-trifluoroacetate | 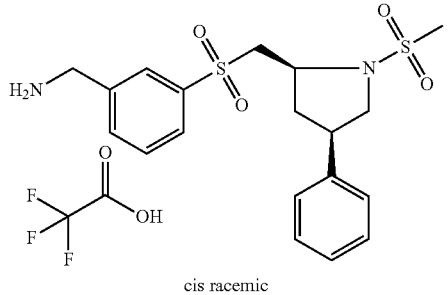  cis racemic |
| cis-(2-(((4-(2-Fluorophenyl)-1-(morpholinosulfonyl)pyrrolidin-2-yl)methyl)sulfonyl)pyridin-4-yl)methanamine 2,2,2-trifluoroacetate | 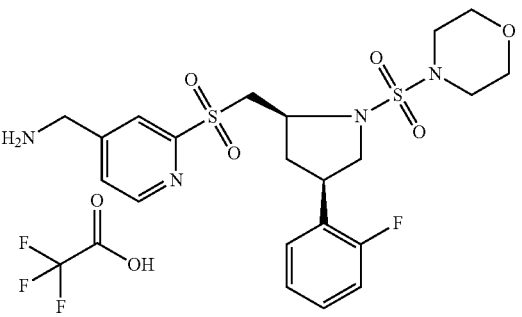  cis racemic |
| cis-(2-(((4-(4-Fluorophenyl)-1-(morpholinosulfonyl)pyrrolidin-2-yl)methyl)sulfonyl)pyridin-4-yl)methanamine | 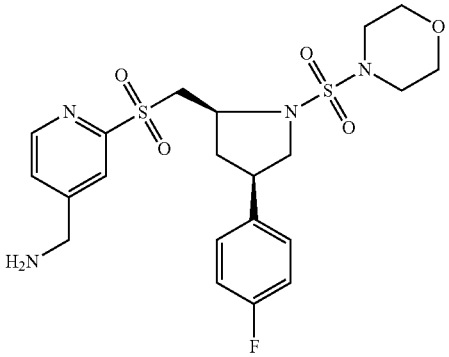  cis racemic |

TABLE 1-continued

| IUPAC Name | Structure |
|---|---|
| cis-4-((2-(((4-(Aminomethyl)pyridin-2-yl)sulfonyl)methyl)-4-(2-fluorophenyl)pyrrolidin-1-yl)sulfonyl)thiomorpholine 1,1-dioxide | 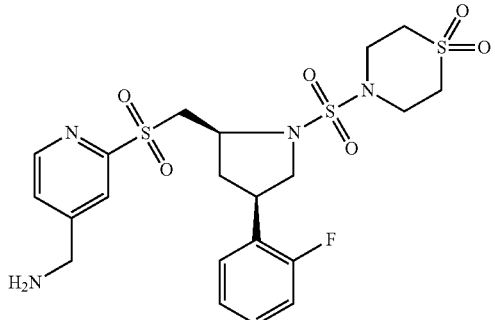<br>cis racemic |
| cis-4-((2-(((4-(Aminomethyl)pyridin-2-yl)sulfonyl)methyl)-4-(4-fluorophenyl)pyrrolidin-1-yl)sulfonyl)thiomorpholine 1,1-dioxide | 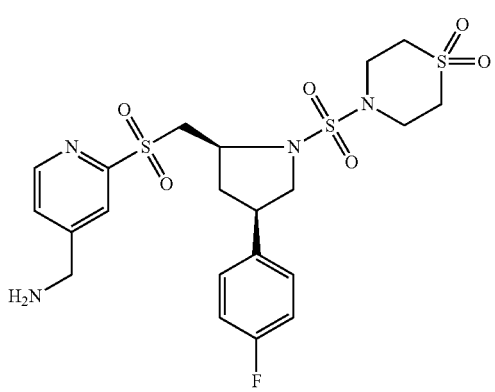<br>cis racemic |
| cis-(5-(((4-(2-Fluorophenyl)-1-(morpholinosulfonyl)pyrrolidin-2-yl)methyl)sulfonyl)thiophen-2-yl)methanamine | 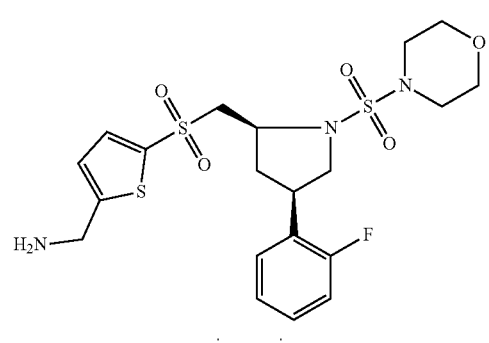<br>cis racemic |
| cis-(5-(((4-(4-Fluorophenyl)-1-(morpholinosulfonyl)pyrrolidin-2-yl)methyl)sulfonyl)thiophen-2-yl)methanamine | 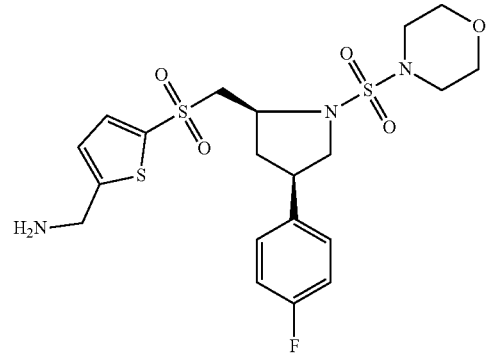<br>cis racemic |

TABLE 1-continued

| IUPAC Name | Structure |
|---|---|
| cis-4-((2-(((5-(Aminomethyl)thiophen-2-yl)sulfonyl)methyl)-4-(2-fluorophenyl)pyrrolidin-1-yl)sulfonyl)thiomorpholine 1,1-dioxide | 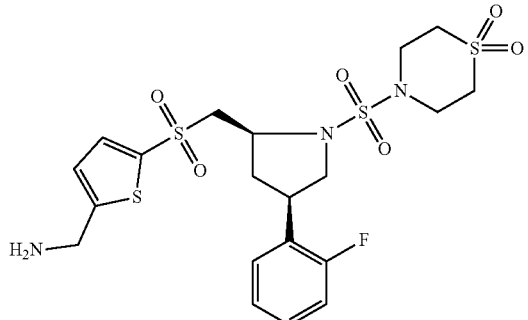<br>cis racemic |
| cis-4-((2-(((5-(Aminomethyl)thiophen-2-yl)sulfonyl)methyl)-4-(4-fluorophenyl)pyrrolidin-1-yl)sulfonyl)thiomorpholine 1,1-dioxide | 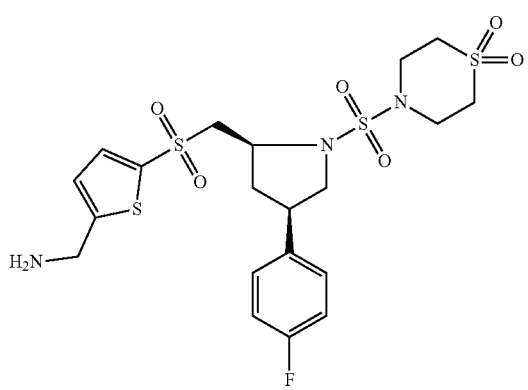<br>cis racemic |
| cis-(2-((4-(2-Fluorophenyl)-1-(morpholinosulfonyl)pyrrolidin-2-yl)methoxy)pyridin-4-yl)methanamine | 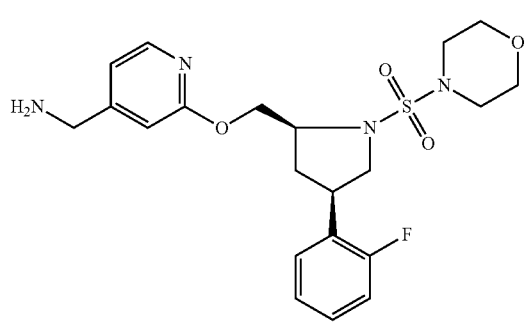<br>cis racemic |
| cis-(2-((4-(4-Fluorophenyl)-1-(morpholinosulfonyl)pyrrolidin-2-yl)methoxy)pyridin-4-yl)methanamine | 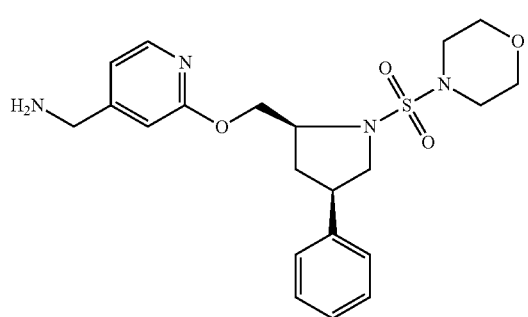<br>cis racemic |

TABLE 1-continued

| IUPAC Name | Structure |
|---|---|
| cis-4-((2-(((4-(Aminomethyl)pyridin-2-yl)oxy)methyl)-4-(2-fluorophenyl)pyrrolidin-1-yl)sulfonyl)thiomorpholine 1,1-dioxide | cis racemic |
| cis-4-((2-(((4-(Aminomethyl)pyridin-2-yl)oxy)methyl)-4-(4-fluorophenyl)pyrrolidin-1-yl)sulfonyl)thiomorpholine 1,1-dioxide | cis racemic |
| cis-(3-((4-(2-Fluorophenyl)-1-(morpholinosulfonyl)pyrrolidin-2-yl)methoxy)phenyl)methanamine | cis racemic |
| cis-(3-((4-(4-Fluorophenyl)-1-(morpholinosulfonyl)pyrrolidin-2-yl)methoxy)phenyl)methanamine | cis racemic |

TABLE 1-continued

| IUPAC Name | Structure |
|---|---|
| cis-4-((2-((3-(Aminomethyl)phenoxy)methyl)-4-(2-fluorophenyl)pyrrolidin-1-yl)sulfonyl)thiomorpholine 1,1-dioxide | 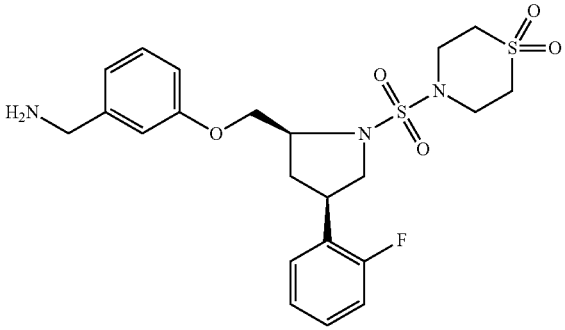<br>cis racemic |
| cis-4-((2-((3-(Aminomethyl)phenoxy)methyl)-4-(4-fluorophenyl)pyrrolidin-1-yl)sulfonyl)thiomorpholine 1,1-dioxide | 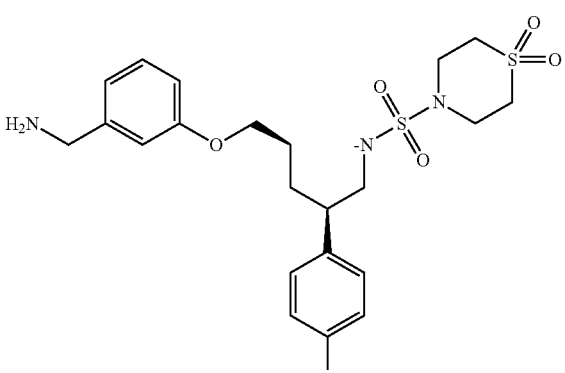<br>cis racemic |
| (3-((((2S,4R)-1-(methylsulfonyl)-4-phenylpyrrolidin-2-yl)methyl)sulfonyl)phenyl)methanamine 2,2,2-trifluoroacetate | 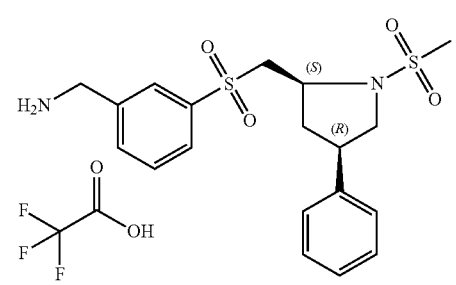<br>unconfirmed |
| (3-((((2R,4S)-1-(methylsulfonyl)-4-phenylpyrrolidin-2-yl)methyl)sulfonyl)phenyl)methanamine 2,2,2-trifluoroacetate | 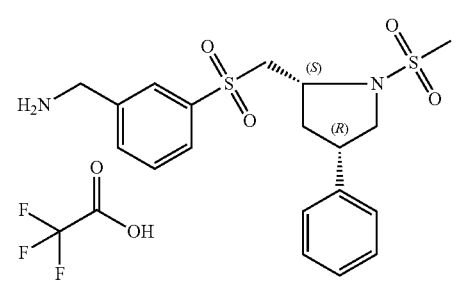<br>unconfirmed |

TABLE 1-continued

| IUPAC Name | Structure |
|---|---|
| cis-(2-(((1-(Morpholinosulfonyl)-5-phenylpiperidin-3-yl)methyl)sulfonyl)pyridin-4-yl)methanamine | 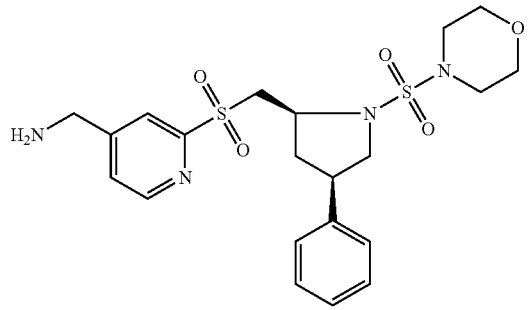<br>cis racemic |
| cis-(2-((1-(Morpholinosulfonyl)-5-phenylpiperidin-3-yl)methoxy)pyridin-4-yl)methanamine | 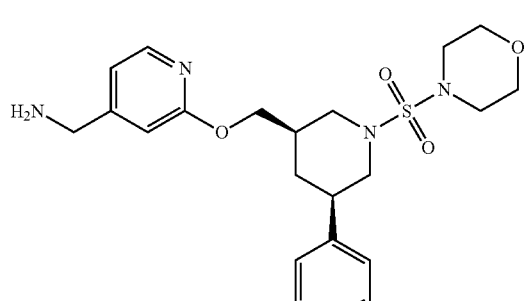<br>cis racemic |
| cis-(3-((1-(Morpholinosulfonyl)-5-phenylpiperidin-3-yl)methoxy)phenyl)methanamine | 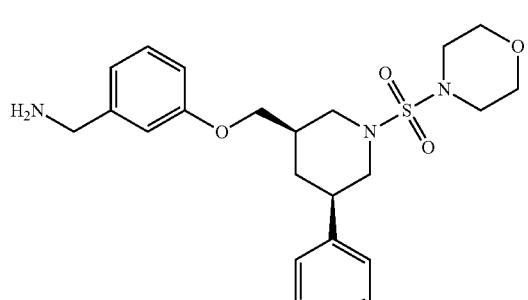<br>cis racemic |
| cis-(5-(((1-(Morpholinosulfonyl)-5-phenylpiperidin-3-yl)methyl)sulfonyl)thiophen-2-yl)methanamine | 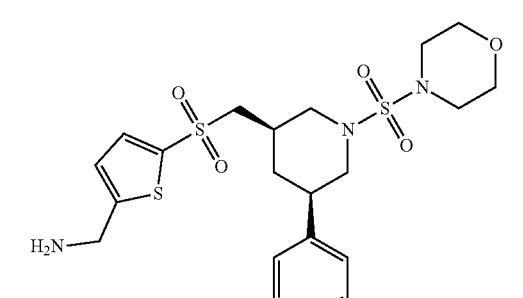<br>cis racemic |

TABLE 1-continued

| IUPAC Name | Structure |
|---|---|
| cis-(2-((1-(Morpholinosulfonyl)-5-(trifluoromethyl)piperidin-3-yl)methoxy)pyridin-4-yl)methanamine 2,2,2-trifluoroacetate | 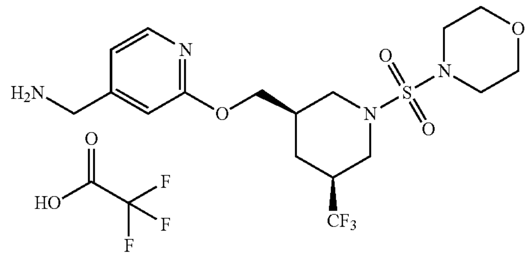 |
| trans-(2-((1-(Morpholinosulfonyl)-5-phenylpiperidin-3-yl)methoxy)pyridin-4-yl)methanamine 2,2,2-trifluoroacetate | 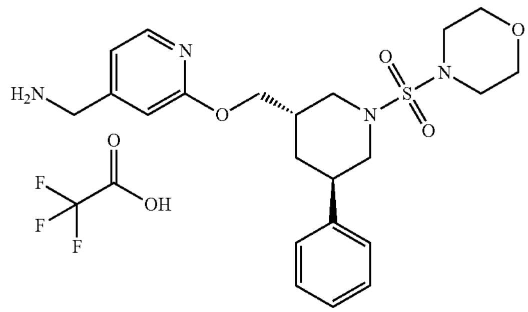 |
| cis-(5-(((1-(Methylsulfonyl)-4-phenylpyrrolidin-2-yl)methyl)sulfonyl)thiophen-2-yl)methanamine 2,2,2-trifluoroacetate | cis racemic |
| trans-(3-((1-(Morpholinosulfonyl)-5-phenylpiperidin-3-yl)methoxy)phenyl)methanamine 2,2,2-trifluoroacetate | 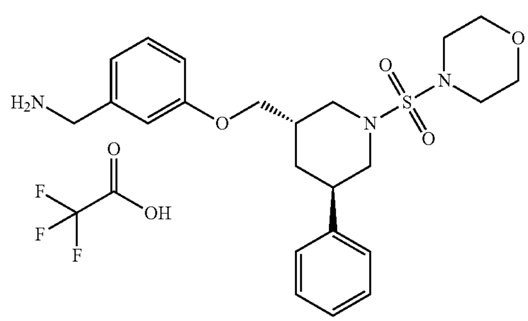 |
| cis-(2-((5-Cyclohexyl-1-(morpholinosulfonyl)piperidin-3-yl)methoxy)pyridin-4-yl)methanamine 2,2,2-trifluoroacetate | cis racemic |

TABLE 1-continued

| IUPAC Name | Structure |
|---|---|
| trans-(2-((5-Cyclohexyl-1-(morpholinosulfonyl)piperidin-3-yl)methoxy)pyridin-4-yl)methanamine | 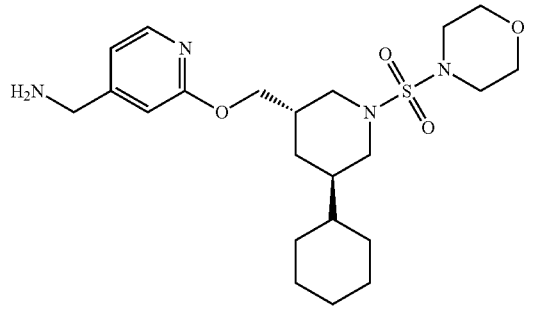<br>trans racemic |
| cis-4-((3-(((4-(Aminomethyl)pyridin-2-yl)oxy)methyl)-5-cyclohexylpiperidin-1-yl)sulfonyl)thiomorpholine 1,1-dioxide 2,2,2-trifluoroacetate | 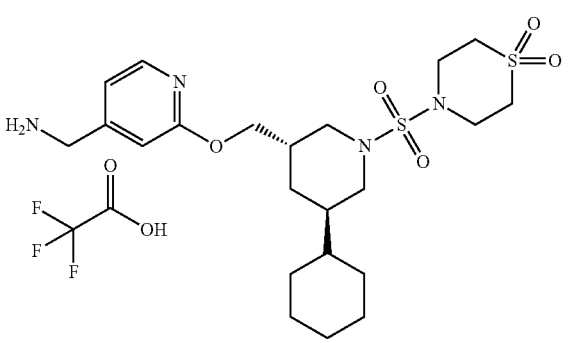<br>cis racemic |
| trans-4-((3-(((4-(Aminomethyl)pyridin-2-yl)oxy)methyl)-5-cyclohexylpiperidin-1-yl)sulfonyl)thiomorpholine 1,1-dioxide 2,2,2-trifluoroacetate | 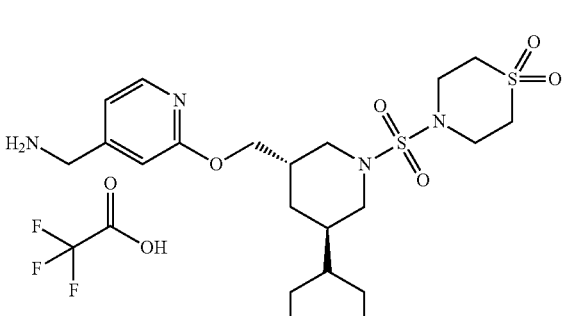<br>trans racemic |
| trans-(2-((1-(Morpholinosulfonyl)-5-(trifluoromethyl)piperidin-3-yl)methoxy)pyridin-4-yl)methanamine 2,2,2-trifluoroacetate | 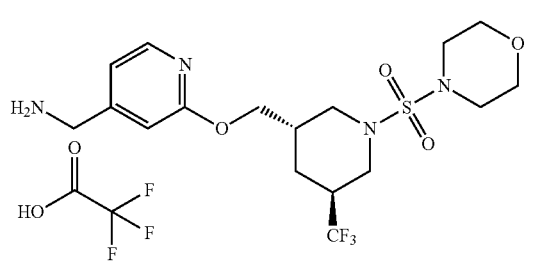<br>trans racemic |

TABLE 1-continued

| IUPAC Name | Structure |
|---|---|
| cis-4-((3-(((4-(Aminomethyl)pyridin-2-yl)oxy)methyl)-5-(trifluoromethyl)piperidin-1-yl)sulfonyl)thiomorpholine 1,1-dioxide 2,2,2-trifluoroacetate | 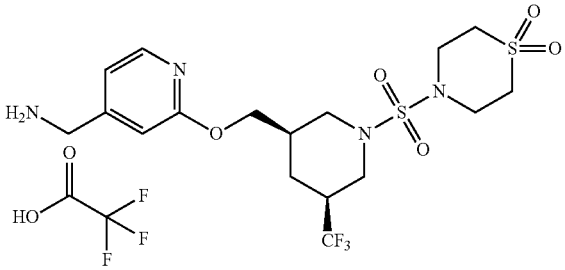<br>cis racemic |
| trans-4-((3-(((4-(Aminomethyl)pyridin-2-yl)oxy)methyl)-5-(trifluoromethyl)piperidin-1-yl)sulfonyl)thiomorpholine 1,1-dioxide 2,2,2-trifluoroacetate | 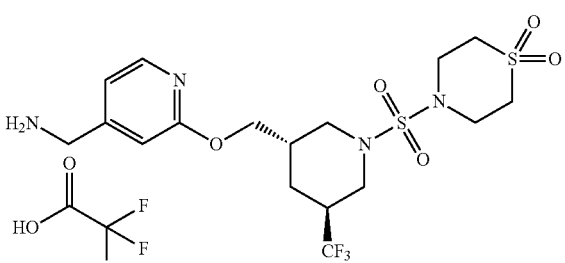<br>trans racemic |
| (2-(((2S)-4-cyclohexyl-1-(morpholinosulfonyl)pyrrolidin-2-yl)methoxy)pyridin-4-yl)methanamine 2,2,2-trifluoroacetate | 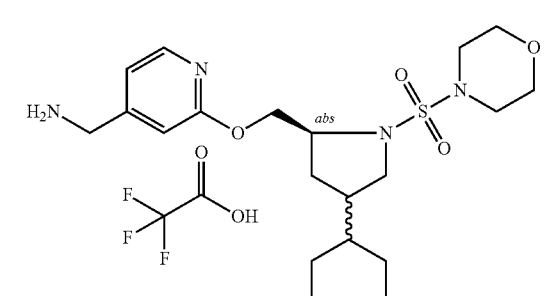 |
| (2-(((2S,4R)-4-cyclohexyl-1-(morpholinosulfonyl)pyrrolidin-2-yl)methoxy)pyridin-4-yl)methanamine 2,2,2-trifluoroacetate | 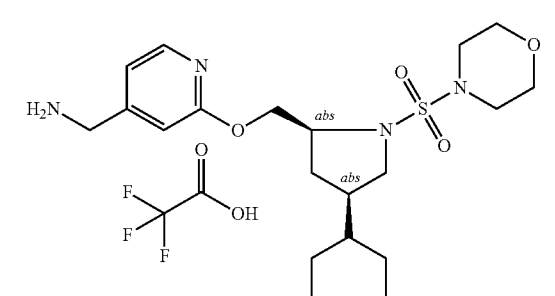 |
| (2-(((2S,4S)-4-cyclohexyl-1-(morpholinosulfonyl)pyrrolidin-2-yl)methoxy)pyridin-4-yl)methanamine 2,2,2-trifluoroacetate | 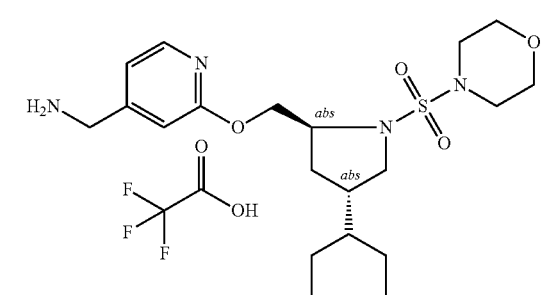 |

TABLE 1-continued

| IUPAC Name | Structure |
|---|---|
| trans-(5-(((1-(Methylsulfonyl)-4-phenylpyrrolidin-2-yl)methyl)sulfonyl)thiophen-2-yl)methanamine 2,2,2-trifluoroacetate | 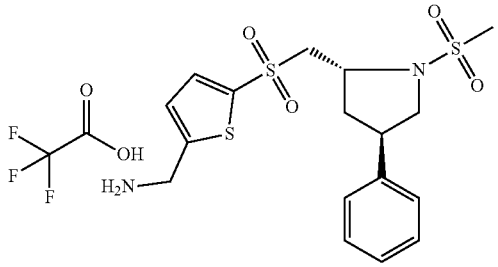<br>trans racemic |
| trans-(2-(((1-(Morpholinosulfonyl)-5-phenylpiperidin-3-yl)methyl)sulfonyl)pyridin-4-yl)methanamine 2,2,2-trifluoroacetate | 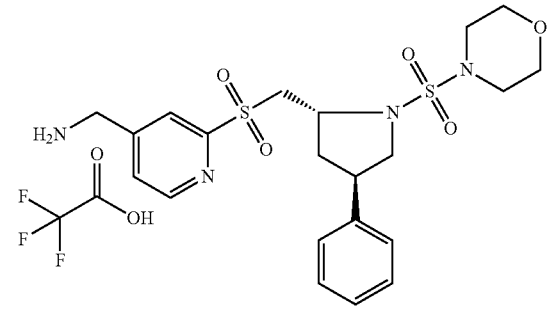<br>trans racemic |
| trans-(5-(((1-(Morpholinosulfonyl)-5-phenylpiperidin-3-yl)methyl)sulfonyl)thiophen-2-yl)methanamine 2,2,2-trifluoroacetate | 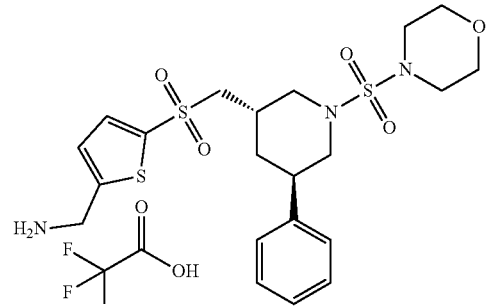 |
| cis-(2-(((5-Cyclohexyl-1-(morpholinosulfonyl)piperidin-3-yl)methyl)sulfonyl)pyridin-4-yl)methanamine 2,2,2-trifluoroacetate | 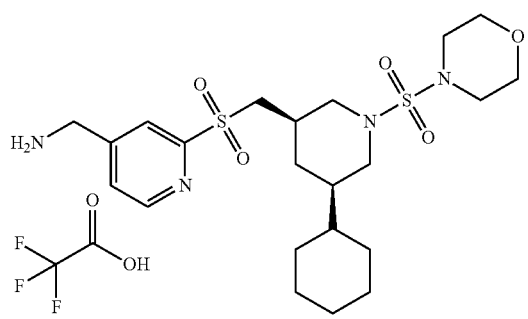 |

TABLE 1-continued

| IUPAC Name | Structure |
|---|---|
| trans-(2-(((5-Cyclohexyl-1-(morpholinosulfonyl)piperidin-3-yl)methyl)sulfonyl)pyridin-4-yl)methanamine 2,2,2-trifluoroacetate | 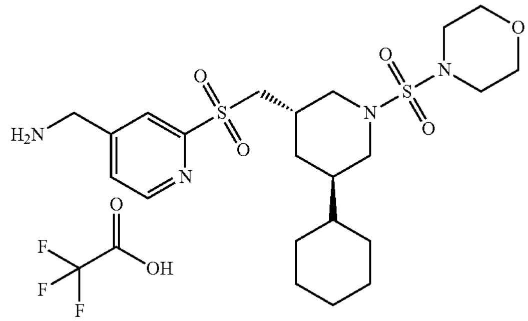 |
| cis-4-((3-(((4-(Aminomethyl)pyridin-2-yl)sulfonyl)methyl)-5-cyclohexylpiperidin-1-yl)sulfonyl)thiomorpholine 1,1-dioxide 2,2,2-trifluoroacetate | 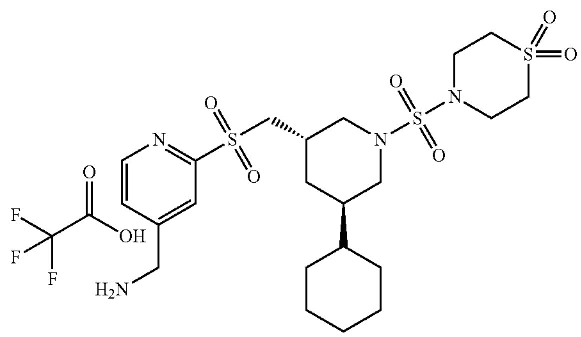 |
| trans-4-((3-(((4-(Aminomethyl)pyridin-2-yl)sulfonyl)methyl)-5-cyclohexylpiperidin-1-yl)sulfonyl)thiomorpholine 1,1-dioxide 2,2,2-trifluoroacetate | 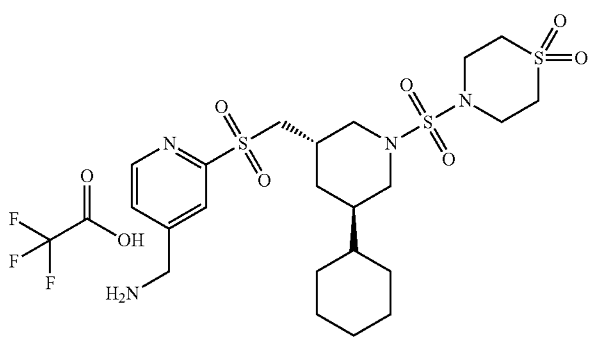 |
| cis-(2-(((1-(Morpholinosulfonyl)-5-(trifluoromethyl)piperidin-3-yl)methyl)sulfonyl)pyridin-4-yl)methanamine formate | 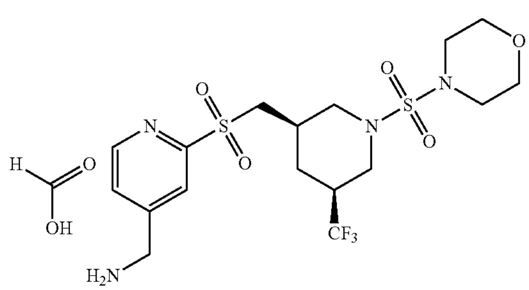 |
| trans-(2-(((1-(Morpholinosulfonyl)-5-(trifluoromethyl)piperidin-3-yl)methyl)sulfonyl)pyridin-4-yl)methanamine formate | 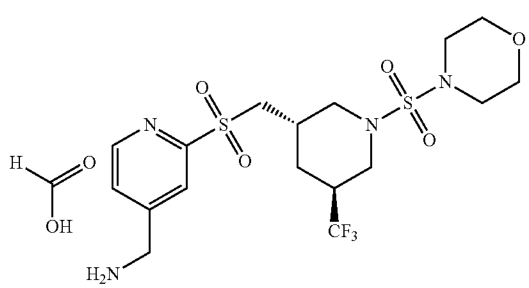 |

TABLE 1-continued

| IUPAC Name | Structure |
|---|---|
| (2-((((2S,4S)-4-cyclohexyl-1-(morpholinosulfonyl)pyrrolidin-2-yl)methyl)sulfonyl)pyridin-4-yl)methanamine | 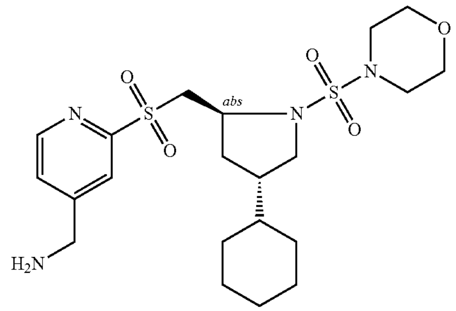 [SMILES: NCc1ccnc(S(=O)(=O)C[C@@H]2C[C@@H](C3CCCCC3)CN2S(=O)(=O)N2CCOCC2)c1] |
| (2-((((2S,4R)-4-cyclohexyl-1-(morpholinosulfonyl)pyrrolidin-2-yl)methyl)sulfonyl)pyridin-4-yl)methanamine | 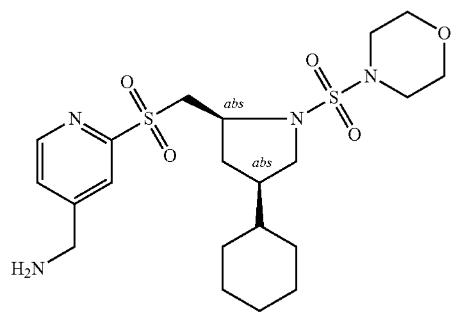 |
| cis-(2-(((1-(morpholinosulfonyl)-4-phenylpyrrolidin-2-yl)methyl)sulfonyl)pyridin-4-yl)methanamine 2,2,2-trifluoroacetate | cis racemic |
| (2-((((2R,4S)-1-(morpholinosulfonyl)-4-phenylpyrrolidin-2-yl)methyl)sulfonyl)pyridin-4-yl)methanamine | unconfirmed |

TABLE 1-continued

| IUPAC Name | Structure |
|---|---|
| (2-((((2S,4R)-1-(morpholinosulfonyl)-4-phenylpyrrolidin-2-yl)methyl)sulfonyl)pyridin-4-yl)methanamine | 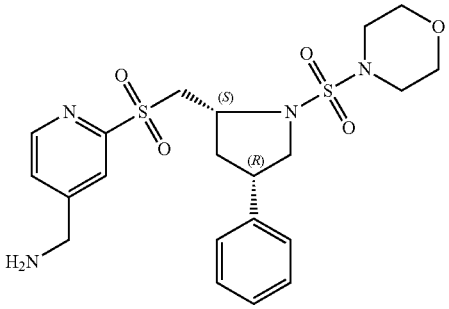<br>unconfirmed |
| cis-4-(((3R,5S)-3-(((4-(aminomethyl)pyridin-2-yl)sulfonyl)methyl)-5-(trifluoromethyl)piperidin-1-yl)sulfonyl)thiomorpholine 1,1-dioxide 2,2,2-trifluoroacetate | 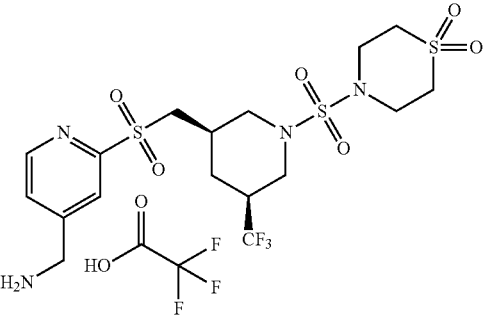<br>cis racemic |
| 4-(((2S)-2-(((4-(aminomethyl)pyridin-2-yl)sulfonyl)methyl)-4-cyclohexylpyrrolidin-1-yl)sulfonyl)thiomorpholine 1,1-dioxide formate | 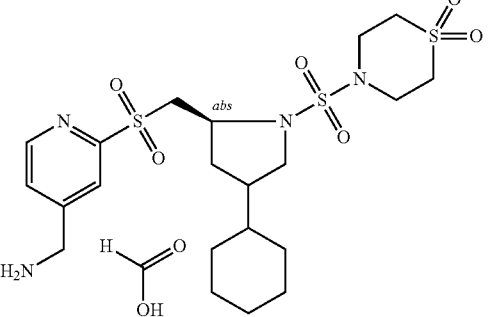 |
| 4-(((2S,4R)-2-(((4-(aminomethyl)pyridin-2-yl)oxy)methyl)-4-cyclohexylpyrrolidin-1-yl)sulfonyl)thiomorpholine 1,1-dioxide | 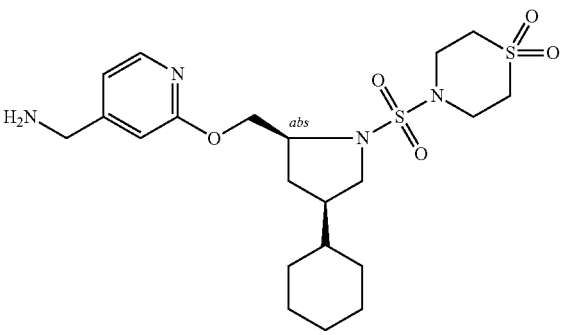<br>unconfirmed |

TABLE 1-continued

| IUPAC Name | Structure |
|---|---|
| 4-(((2S,4S)-2-(((4-(aminomethyl)pyridin-2-yl)oxy)methyl)-4-cyclohexylpyrrolidin-1-yl)sulfonyl)thiomorpholine 1,1-dioxide | unconfirmed |
| 4-(((2S)-2-(((4-(aminomethyl)pyridin-2-yl)oxy)methyl)-4-cyclohexylpyrrolidin-1-yl)sulfonyl)thiomorpholine 1,1-dioxide 2,2,2-trifluoroacetate | 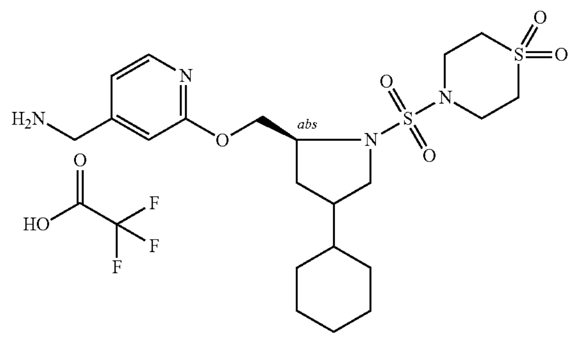 |

While the above compound structures refer to racemic, the present disclosure is not limited to such. The present disclosure covers compounds of any form, including racemic mixtures or enantiomerically pure or substantially pure forms of any stereoisomer.

Also provided are methods of synthesizing compounds of Formula I, Formula Ia, Formula Ib, Formula II, Formula IIa, Formula IIb, or Table 1 according to the synthetic methods described in Example 1, including synthetic scheme 1 or synthetic method A.

A compound or compounds (including pharmaceutical salts and hydrates thereof, stereoisomers and racemic mixtures thereof, of Formula I, Formula Ia, Formula Ib, Formula II, Formula IIa, Formula IIb, or Table 1 can be provided in a pharmaceutical composition. The composition can further comprise a pharmaceutically acceptable carrier as described herein. Pharmaceutical compositions can comprise one or more compounds described herein in combination with a second therapeutic agent that is effective for the treatment of the indication. Such pharmaceutical compositions can be administered in methods described herein.

Methods can also comprise administration of a compound(s) of the invention in combination with an additional therapeutic agent.

Methods comprise the use of LOX enzyme-inhibiting compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, for treating, managing, ameliorating the symptoms of or preventing fibrotic disorders, proliferative disorders, inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit.

In some embodiments, the method comprises administering an effective amount of LOX-inhibiting compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, to a subject suffering from any of the conditions listed in Tables 2, 3, and 4.

In one embodiment, the method of the invention comprises administering an effective amount of LOX-inhibiting compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, in combination with one or more of the agents described below to a subject in need thereof.

In particular, exemplary embodiments of the invention include methods of treating, managing, ameliorating the symptoms of or preventing fibrotic disorders, which include, but are not limited to, fibrotic conditions affecting the liver (e.g., NASH, cirrhosis), lung (e.g., idiopathic pulmonary fibrosis), kidney (e.g., chronic kidney disease), heart (e.g., myocardial infarction, sarcoidosis, myocarditis, cardiomyopathy), bone marrow (e.g., myeloproliferative neoplasms, MDS, AML), skin (e.g., scleroderma), and gut (e.g., IBD, Crohn's) by administering compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, to a subject in need thereof.

LOX family enzymes may have distinct roles in diseases as described herein. Accordingly the selective inhibition of any of the LOX enzymes or selective inhibition of a specific combination of any of the LOX enzymes (e.g., LOXL2/ LOX or LOXL2/LOXL3) may be advantageous. In one embodiment, the compounds disclosed herein including, pharmaceutically acceptable salts or hydrates thereof, or stereoisomers or racemic mixtures thereof, may be used in the selective or specific inhibition of LOX, LOXL1, LOXL2, LOXL3, or LOXL4. In other embodiments, it may be advantageous to inhibit two or more enzymes of the LOX family. Accordingly in another embodiment, the compounds disclosed herein, including pharmaceutically acceptable salts or hydrates thereof, or stereoisomers or racemic mixtures thereof, may be used in the selective inhibition of two or more members of the LOX family selected from LOX, LOXL1, LOXL2, LOXL3, or LOXL4.

Targeting cardiac tissue fibrosis is orthogonal to existing therapeutic strategies. Given the social and economic impact of HF, there remains an urgent need for novel, complementary medical therapies to improve HF clinical outcomes. Such therapeutic gap can be filled by using LOXL2-selective or LOXL2-specific inhibitors to reduce cardiac tissue fibrosis and relieve the constraint of fibrosis on heart pump function. LOXL2-targeting therapy is expected to provide clinical benefits on top of the standard of care.

Consequently, a particular method comprises the use of LOXL2-selective or LOXL2-specific inhibitor of Formula I or Formula II, and preferably Formula Ib, including pharmaceutically acceptable salts or hydrates thereof, or stereoisomers or racemic mixtures thereof, for treating, managing, ameliorating the symptoms of or preventing cardiovascular diseases or fibrotic disorders affecting the heart or other diseases or medical conditions for which selectively or specifically inhibiting LOXL2 provides a therapeutic benefit. In a preferred embodiment, the fibrotic disorder of the heart or cardiovascular diseases is heart failure (HF). In one embodiment, the method comprises administering an effective amount of LOXL2-selective or LOXL2-specific inhibitor of Formula I, preferably Formula Ib, or Formula II, including pharmaceutically acceptable salts or hydrates thereof, or stereoisomers or racemic mixtures thereof, in combination with guideline-directed medical therapy for HF including but not limited to one or more of the agents selected from angiotensin-converting-enzyme inhibitors, β-blocker, angiotensin receptor blocker, digoxins, diuretics, nitrates, hydralazines, or mineralcorticoid receptor antagonists (Virani et al., 2020) to a subject suffering from HF.

A particular method comprises also the use of a compound of Formula I, which selectively or specifically inhibits LOX for treating, managing, ameliorating the symptoms of or preventing fibrotic disorders affecting the bone marrow or other diseases or medical conditions for which selectively or specifically inhibiting LOX provides a therapeutic benefit. In a preferred embodiment, the fibrotic disorder of the bone marrow is primary myelofibrosis (MF), polycythemia vera (PV), essential thrombocythemia (ET), post-PV MF, or post-ET MF. In one embodiment, the method comprises administering an effective amount of a compound of Formula I, including pharmaceutically acceptable salts or hydrates thereof, or stereoisomers or racemic mixtures thereof, which selectively or specifically inhibits LOX in combination with one or more of the agents selected from Janus kinase inhibitors (e.g. ruxolitinib, fedratinib), hydroxyurea, aspirin, anagrelide, and interferon therapy to a subject suffering from primary MF, PV, ET, post-PV MF, or post-ET MF or other bone marrow disorders presenting with bone marrow fibrosis.

A particular method comprises also the use of LOX enzyme-inhibiting compounds of Formula I, Formula Ia, Formula Ib, Formula II, Formula IIa, or Formula IIb, including pharmaceutically acceptable salts or hydrates thereof, or stereoisomers or racemic mixtures thereof, for treating, managing, ameliorating the symptoms of or preventing primary or metastatic cancer or other diseases or medical conditions for which dual inhibition of LOX and LOXL2 (and optionally LOXL3 and/or LOXL4) provides a therapeutic benefit. In a preferred embodiment, the cancer is primary or metastatic breast cancer. In one embodiment, the breast cancer is estrogen-receptor negative breast cancer or inflammatory breast cancer. In one embodiment, the method comprises administering an effective amount of LOX enzyme-inhibiting compounds of Formula I or Formula II, including pharmaceutically acceptable salts or hydrates thereof, or stereoisomers or racemic mixtures thereof, in combination with one or more of chemotherapeutic agents described below and/or radiation therapy to a subject suffering from primary or metastatic cancer.

As discussed above, the LOX enzyme-inhibiting compounds of the invention can be used for treating, managing, ameliorating the symptoms of or preventing fibrotic disorders, proliferative disorders, acute or chronic inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit.

The disease of medical condition mediated by LOX, LOXL1, LOXL2, LOXL3, and/or LOXL4 may be any of the diseases or medical conditions listed in Tables 2, 3, and 4.

a. Fibrotic Indications

LOX family enzymes are implicated in fibrotic diseases. In some embodiments, the compounds of the invention or a pharmaceutically acceptable salt or hydrate thereof are used in the treatment of a fibrotic disorder. In some embodiments, the fibrotic disorder is characterized by excess fibrosis, for example an excess of fibrous connective tissue in a tissue or organ. In some embodiments, the excess of fibrous connective tissue is triggered by a reparative or reactive process or in response to injury (e.g., scarring or healing) or excess fibrotic tissue arising from a single cell line (e.g., fibroma). In some embodiments, compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, are used in the treatment of a fibrotic disorder selected from any one of the diseases listed in Tables 2, 3, and 4 infra. In preferred embodiments, the fibrotic disorder is a fibrotic condition affecting the lungs, liver, kidney, heart, vascular system, mediastinum, bone, brain, nervous system, retroperitoneum, skin, GI tract, connective tissue, and eye.

TABLE 2

| Organ | Disorders |
|---|---|
| Lung | Idiopathic pulmonary fibrosis, cystic fibrosis, pulmonary fibrosis secondary to cystic fibrosis, chronic obstructive pulmonary disease, diffuse parenchymal lung disease, pulmonary hypertension, |

TABLE 2-continued

| Organ | Disorders |
|---|---|
| | emphysema, thromboembolic disease, coal worker's progressive massive fibrosis, cryptogenic fibrosing alveolitis, chronic fibrosing interstitial pneumonia, interstitial lung disease, chronic asthma |
| Liver | Liver fibrosis, cirrhosis, Wilson's disease, portal hypertension, liver fibrosis/cirrhosis due to non-alcoholic steatohepatitis (NASH), HIV and/or Hepatitis B or C- infection or primary sclerosing cholangitis, compensated liver cirrhosis due to NASH, non-alcoholic fatty liver disease, primary biliary cirrhosis, biliary cirrhosis or autoimmune hepatitis |
| Eye | Subretinal fibrosis, epiretinal fibrosis, ocular fibrosis following surgery or pseudoexfoliation syndrome glaucoma |
| Retroperitoneum | Retroperitoneal fibrosis |
| Mediastinum | Mediastinal fibrosis |
| Heart | Endomyocardial fibrosis, old myocardial infarction, atrial fibrosis hypertensive heart disease, hypertension and fibrosis associated with hypertension, pressure overload, myocardial ischemia, (congestive) heart failure, myocarditis, sarcoidosis, cardiomyopathy (e.g., hypertrophic cardiomyopathy), valvular disease, arrhythmia, cardiac hypertrophy, and atherosclerosis, restenosis (e.g., coronary, carotid, and cerebral lesions) |
| Skin | Scleroderma, hypertrophic scar, systemic sclerosis, nephrogenic systemic fibrosis, keloid formation and scarring |
| Kidney | Chronic kidney disease, cystic fibrosis, nephrogenic systemic fibrosis, renal anemia, diabetic nephropathy, vesicoureteral reflux, tubulointerstitial renal fibrosis; glomerulonephritis or glomerular nephritis, including focal segmental glomerulosclerosis and membranous glomerulonephritis or mesangiocapillary glomerular nephritis |
| Brain, Nervous System | Glial scar, amyloid-beta related diseases (e.g., Alzheimers) |
| Bone marrow | (Primary) myelofibrosis, polycythemia vera (PV), essential thrombocythemia (ET), post-PV MF, post-ET MF, myelodysplastic syndrome (MDS), chronic myelogenous leukemia, acute megakaryocytic leukemia |
| Breast | Fibrocystic breast disease |
| Gut | Inflammatory bowel disease, ulcerative colitis, Crohn's disease, intestinal fibrosis, enteropathies |
| Joint | Arthrofibrosis, capsuliti |
| Pancreas | Pancreatic fibrosis, cystic fibrosis, chronic pancreatitis, duct obstruction |
| Female/ Reproductive Organs | Endometriosis, uterine fibroids |

In some embodiments, the fibrotic indication is bone marrow fibrosis, for example primary myelofibrosis (MF), polycythemia vera (PV), or essential thrombocythemia (ET). Among the preferred fibrotic indications is treating, managing, ameliorating the symptoms of or preventing progression of blood disorders associated with myeloproliferative neoplasms, for example progression of PV and/or ET to post-PV/ET-MF myelofibrosis, preferably when co-administered with JAK inhibitor Jakafi® or fedratinib. In some embodiments, a LOX-specific or LOX-selective inhibitor is used in the treatment of are primary myelofibrosis (MF), polycythemia vera (PV), essential thrombocythemia (ET), post-ET MF, or post-PV MF. In another embodiment, a pan-LOX inhibitor is used in the treatment of bone marrow fibrosis, for example primary myelofibrosis (MF), polycythemia vera (PV), essential thrombocythemia (ET), post-ET MF, or post-PV MF.

Among the preferred indications are fibrotic conditions affecting the heart, in particular, cardiac interstitial fibrosis and heart failure (HF). In some embodiments, a LOXL2-selective or LOXL2-specific inhibitor of Formula I or Formula II, and preferably Formula Ib, is used for treating, managing, ameliorating the symptoms of or preventing cardiovascular diseases or fibrotic disorders affecting the heart, in particular HF, or other diseases or medical conditions for which selectively or specifically inhibiting LOXL2 provides a therapeutic benefit.

b. Cancer

LOX enzymes play a critical role in primary cancer and metastasis [reviewed by Barker, Cox, et al. 2012].

As such, in some embodiments, the method of use of compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, is the treatment of a cancer, which may be metastatic or non-metastatic cancer, and which may further be a solid tumor or a hematological cancer selected from Table 3 infra. For example, in some embodiments, the primary or metastatic cancer includes, but is not limited to, head and neck cancer, breast cancer, colorectal cancer, lung cancer, liver cancer, prostate cancer, brain cancer, renal cancer, esophageal and laryngeal cancer, or skin cancer.

In some embodiments, the cancer is a carcinoma, including for example tumors derived from stratified squamous epithelia (squamous cell carcinomas), tumors arising within organs or glands (adenocarcinomas), and tumors developing in the basal cell (basal cell carcinomas). In other embodiments, the cancer is a sarcoma, including for example tumors arising within fat, muscle, blood vessels, deep skin tissues, nerves, bones, and cartilage. In other embodiments, the cancer is has mixed histology, including for example adenosquamous carcinoma, mixed mesodermal tumor, carcinosarcoma or teratocarcinoma.

TABLE 3

| Organ | Disorders |
|---|---|
| Lung | Non-small cell lung cancer (e.g., adenocarcinoma, squamous cell carcinoma, and large cell carcinoma), small cell lung carcinoma, bronchogenic carcinoma, and bronchioloalveolar carcinoma |
| Liver | Hepatocellular carcinoma (HCC), cirrhotic HCC, liver and bile duct carcinoma (for example cholangiocarcinoma and hemangioma) |
| Skin, glandular structures | Melanoma, uveal melanoma, retinoblastoma, basal cell carcinoma, eccrine carcinoma, sebaceous gland carcinoma, papillary carcinoma, papillary adenocarcinoma, cystadenocarcinoma |
| Brain/Nervous System | Glioblastoma, astrocytoma, glioma, and medulloblastoma, craniopharyngioma, ependymoma, pinealoma, hemangioblastoma, acoustic neuroma, oligodendroglioma, meningioma, neuroblastoma and schwannoma |
| Head/neck, thyroid | Oral and oropharyngeal carcinoma (e.g., squamous cell carcinomas), esophageal carcinoma (e.g., esophageal adenocarcinoma and squamous cell carcinoma), laryngeal carcinoma (e.g., larynx squamous cell carcinoma), nasopharyngeal carcinoma, head and neck cancer (e.g., squamous cell carcinomas), thyroid cancer (e.g., anaplastic thyroid cancer) |
| Bone/Blood | Myelogenous and granulocytic leukemia, lymphatic, lymphocytic, and lymphoblastic leukemia; myeloproliferative neoplasm (e.g., polycythemia vera and erythremia; myelofibrosis, and essential thrombocythemia), myelodysplastic syndrome, myeloma, multiple myeloma, lymphomas (e.g., hodgkin and non-hodgkin lymphomas), osteosarcoma and osteogenic sarcoma |
| Breast | ER-negative breast cancer, basal-like breast carcinoma, ductal carcinoma (in situ), lobular carcinoma, inflammatory breast cancer, clear cell carcinoma, mucinous carcinoma, medullary carcinoma |
| GI tract | Colorectal cancer (e.g., colon carcinoma and rectal carcinoma), anal carcinoma, stomach carcinoma (e.g., stomach adenocarcinoma, gastrointestinal stromal tumor), gastric carcinoma |
| Pancreas | Pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors |
| Ovary, Uterus | Ovarian epithelial carcinoma or surface epithelial-stromal tumor (e.g., serous tumor, endometrioid tumor and mucinous cystadenocarcinoma, sex-cord-stromal tumor), cervical carcinoma, uterine carcinoma (e.g., endometrial adenocarcinoma, uterine papillary serous carcinoma, uterine clear-cell carcinoma, uterine sarcomas and leiomyosarcomas, mixed mullerian tumors), germ cell tumors, choriocarcinoma |
| Prostate, Testicles | Prostate carcinoma, germ cell tumors, ductal carcinoma in situ, choriocarcinoma, seminoma, embryonal carcinoma, testicular carcinoma, germ cell tumor of the testicles (e.g., seminoma, teratoma, embryonal carcinoma) |
| Bladder, Kidneys | Bladder carcinoma (e.g., transitional cell carcinoma), kidney carcinoma (e.g., renal cell carcinoma, clear cell carcinoma and Wilm's tumor) |
| Connective tissue (fat, muscle, blood vessels, deep skin tissues, nerves, bones, and cartilage) | Mesothelial sarcoma and mesothelioma, fibrosarcoma, angiosarcoma and hemangioendothelioma, liposarcoma, myxosarcoma, chordoma, endotheliosarcoma, lymphangiosarcoma, lymphangioendotheliosarcoma, synovioma, chondrosarcoma, leiomyosarcoma, rhabdomyosarcoma, Ewing's sarcoma, mesenchymous and mixed mesodermal tumor and other soft tissue sarcomas |
| Other | Signet ring cell carcinoma, neuroendocrine tumors, adrenocortical carcinoma, medullary carcinoma, epithelial carcinoma, sarcomatoid carcinoma |

In some embodiments, the method of use of the compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, is to improve the delivery of chemotherapeutic drugs and/or the therapeutic efficacy of chemotherapeutics in a subject with primary or metastatic cancer. In other embodiments, the method of use of the compounds disclosed herein is to prevent or reduce metastatic spread of the primary tumor to distant sites. In specific embodiments, the method of use of the compounds of this invention is to prevent or reduce the metastatic spread of primary breast cancer, for example ER-negative breast cancer, to the bone. In specific embodiments, the method of use of the compounds disclosed herein is to prevent or reduce the metastatic spread of primary cancers upon surgical resection of the tumor. In some embodiments, the method of use of the compounds disclosed herein is to inhibit or treat the growth of fibrous or connective tissue which may occur around a neoplasm, causing dense fibrosis around the tumor, or scar tissue (adhesions), for example within the abdomen after abdominal surgery.

c. Other Indications

TABLE 4

| Organ Ocular | Disorders |
|---|---|
| Pulmonary (including inflammatory conditions) | Acute respiratory distress syndrome (ARDS), acute lung injury, endotoxin-induced lung injury, pulmonary inflammation, chronic obstructive pulmonary disease and systemic cachexia, primary alveolar proteinosis, bronchopulmonary dysplasia. |
| Acute and chronic inflammatory conditions | Inflammatory bowel disease, Crohn's disease, ulcerative colitis, psoriasis, eczema, allergic rhinitis, allergic conjunctivitis, sarcoidosis, rheumatoid arthritis, osteoarthritis, psoriatic arthritis, Reiter's syndrome, traumatic arthritis, rubella arthritis, acute synovitis, gouty arthritis and spondylitis, diabetes, systemic cachexia, gout, endotoxemia, toxic shock syndrome, a bone resorption disease, osteoporosis, reperfusion injury, graft versus host reaction, allograft rejection, sepsis, septic shock, endotoxic shock, Gram negative sepsis, glomerulonephritis, restenosis, vasculitis, thrombosis, polymyositis, systemic lupus or interstitial nephritis. |
| Neurological, Neuropsychiatric | Alzheimer's disease, hereditary cerebral hemorrhage with amyloidosis of the Dutch type (HCHWA-D), non-Alzheimer's dementia, bipolar disorder, nerve damage and spinal cord injury. |
| Cardiovascular | Atherosclerosis, prevention of fibrotic atrial remodelling, old myocardial infarction; congestive heart failure, cardiomyopathy, hypertensive heart disease, (pulmonary) hypertension, restenosis (e.g., coronary, carotid, and cerebral lesions), and heart disease associated with cardiac ischemic events. |
| Skin (genetic) | Keratinization disorder is selected from among Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, pityriasis rubra pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome. |
| Viral Infections | Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus or cytomegalovirus. |
| Other | Obesity, parasitic infection (e.g., schistosomiasis), Chlamydia infection. |

In particularly desirable embodiments, the LOX enzyme-inhibiting compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, are useful for treating any of the cardiovascular diseases listed in Tables 2 and 4. Accordingly, a method for treating cardiovascular diseases comprises administering to a patient in need thereof a LOX-enzyme inhibiting compound described hereinabove.

The compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, are useful in methods for the prevention, treatment, control, amelioration, or reduction of risk of the diseases, disorders and conditions noted herein.

D. COMBINATION THERAPIES

The compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, are further useful in a method for treating, managing, ameliorating the symptoms of or preventing aforementioned diseases, disorders and conditions in combination with other agents. In many instances, the combination of the drugs together is safer or more effective than either drug alone; the compounds of the present invention and the other active ingredients may often be used in lower doses than when each is used singly. The drug(s) in the combination may be administered contemporaneously or sequentially (i.e., one preceding or following the other, at any appropriate time interval). When administered contemporaneously, the drugs may be administered separately, or a single dosage form may contain both active agents.

Accordingly, the subject compounds may be used in combination with other agents, which are known to be beneficial in the subject indications, or other drugs that affect receptors or enzymes that either increase the efficacy, safety, convenience, or reduce unwanted side effects or toxicity of the compounds of the present invention. It will be appreciated that any of the drugs listed herein may be in the form of a pharmaceutically acceptable salt.

The compounds are useful in combination with standard cancer therapies. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds and encompass anti-neoplastic/anti-proliferative agents, cytotoxic agents, cytostatic agents, anti-invasion agents, anti-angiogenic agents, and inhibitors of growth factor functions. Non-limiting examples of chemotherapeutic agents include alkylating agents, nitrosoureas, antimetabolites, antitumor antibiotics, plant (vinca) alkaloids, and steroid hormones. In addition, the compounds disclosed herein are useful in combination with gene therapy approaches, immunotherapy approaches, targeted therapies, and chimeric antigen receptors, anticancer vaccines and arginase inhibitors.

The compounds of Formula I, Formula Ia, Formula Ib, Formula II, Formula IIa, Formula IIb, or Table 1 are useful in combination with one or more additional chemotherapeutics selected from the group of alkylating agents, antimetabolites, natural products and their derivatives, microtubule affecting agents, hormone modulators and steroids, metal complexes, urea compounds and hydrazines, immunosuppressants, proteasome inhibitors, kinase inhibitors, anti-apoptotic inhibitors, DNA repair inhibitors, HDAC inhibitors, DNA demethylating agents, anti-angiogenic agents, interferon therapy, growth factor antibodies and growth factor receptor antibodies, immunotherapies, gene therapy, and/or radiotherapy:

In a particularly preferred embodiment, the subject compound is employed in combination with Janus kinase inhibitors ruxolitinib or fedratinib. In other embodiments, the LOX-enzyme inhibiting compound is administered in combination with urea compounds, for example hydroxyurea, and hydrazines, aspirin, anagrelide, or interferon therapy to a subject suffering from primary MF, PV, ET, post-PV MF, or post-ET MF or other bone marrow disorders presenting with bone marrow fibrosis.

In another embodiment, the subject compound may be employed in combination with a neuroleptic or antipsychotic agent, or pharmaceutically acceptable salts thereof, including but not limited to anticholinergics such as biperiden and trihexyphenidyl (benzhexol) hydrochloride, other COMT inhibitors such as entacapone, MOA-B inhibitors, antioxidants, Ala adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In a particularly preferred embodiment, the LOX-inhibiting compound of the invention is administered in combination with heart medication including but not limited to anticoagulants, antiplatelet agents and dual antiplatelet therapy, angiotensin-converting enzyme inhibitors, angiotensin II receptor blockers, angiotensin receptor-neprilysin inhibitors, n-blockers, calcium channel blockers, diuretics, nitrates, and cholesterol-lowering medications.

In a particularly preferred embodiment, the LOX-inhibiting compound of the invention is administered in combination with to other anti-fibrotic drugs, for example nintedanib, pirfenidone, TGF-β inhibitors (e.g., AVID200), LSD1 inhibitors (e.g., IMG-2789), pamrevlumab (FG-3019), pentraxin 2 (PRM-151), GLPG-1690, PHI-4050, AD-214, AD-114, endothelin receptor antagonist (e.g., bosentan, ambrisentan), MMP inhibitors or antibodies (e.g., Marimastat), integrin inhibitors (PLN-74809, IDL-2965), or angiotensin receptor blocker.

E. FORMULATION AND ADMINISTRATION

The invention provides a method for administering a LOX enzyme-inhibiting compound of Formula I, Formula Ia, Formula Ib, Formula II, Formula IIa, Formula IIb, or Table 1, including pharmaceutically acceptable salts or hydrates thereof, or stereoisomers or racemic mixtures thereof, to a patient suffering from a condition, or prone to a condition, that is responsive to treatment or prevention with the compound. The method comprises administering, e.g., orally, transdermally, or parenterally, a therapeutically effective amount of the compound, preferably provided as part of a pharmaceutical preparation.

In some embodiments, a prodrug of the LOX enzyme-inhibiting compound is administered.

The invention also provides pharmaceutical preparations comprising a LOX enzyme-inhibiting compound in combination with a pharmaceutical excipient.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds disclosed herein may be administered by oral, parenteral injection or infusion (e.g., intramuscular, intraperitoneal, intravenous, intraarterial, intrathecal, ICV, or intracisternal injection or infusion), subcutaneous injection or implant, by inhalation spray, other transmucosal delivery (e.g., nasal, vaginal, rectal, or sublingual delivery) or topical routes of administration. A preferred administration is oral administration or topical routes of administration. The compounds may be formulated, alone or together, in suitable dosage unit formulations containing conventional pharmaceutically acceptable carriers, adjuvants and vehicles appropriate for each route of administration.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include, but are not limited to, water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer including, but not limited to, citric acid, sodium chloride, potassium chloride, sodium sulfate, potassium nitrate, sodium phosphate monobasic, sodium phosphate dibasic, and combinations thereof.

A surfactant may be present as an excipient. Exemplary surfactants include, but are not limited to, polysorbates such as Tween 20 and Tween 80 and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), and fatty acids and fatty esters.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

For pressurized compositions, the liquid carrier can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically, as a solution, cream, or lotion, by formulation with pharmaceutically acceptable vehicles containing the active compound. The compositions can be in a form suitable for use in transdermal devices.

The compositions of this invention may be orally administered, in formulations such as capsules, tablets, powders or granules, or as suspensions or solutions in water or non-aqueous media. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The amount of the compound in the composition will vary depending on a number of factors but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the LOX enzyme-inhibiting compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", 21st ed., Williams & Williams, (2005), the "Physician's Desk Reference", 67th ed., PDR Network, Montvale, N.J. (2013), and Kibbe, A. H., "Handbook of Pharmaceutical Excipients", 7th Edition, Pharmaceutical Press, Washington, D.C., 2012.

The dose of the compounds of Formula I, Formula Ia, Formula Ib, Formula II, Formula IIa, Formula IIb, or Table 1, including pharmaceutically acceptable salts or hydrates thereof, or stereoisomers or racemic mixtures thereof, to be administered, both unit dosage and dosing schedule, will vary depend upon the age, weight, and general condition of the subject, as well as the desired therapeutic effect, the route of administration, and the duration of the treatment. The compounds of the invention are administered to the patient in therapeutically effective amounts. Methods are known to those skilled in the art to adjust the dose to obtain maximal benefit. Generally, dosage levels of between 0.001 to 10 mg/kg of body weight daily are administered to the patient. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. The compounds may be administered on a regimen of 1 to 4 times per day, such as once or twice per day.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. LOXL2/LOXL3 Inhibition Assay Procedures

The ability of compounds to inhibit one or more of the lysyl oxidases LOXL2 and/or LOXL3 was determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by the specific LOX family enzyme present in the sample. Hydrogen peroxide is in turn detected using a red fluorescence substrate for HRP-coupled reactions (Amplex Red Enzyme Assays, Thermo Scientific Fisher). This leads to increase in fluorescence that can be easily detected at Ex/Em=540/590 nm in a fluorescence microplate reader.

Recombinant human LOXL2 (lysyl oxidase like 2) and recombinant human LOXL3 (lysyl oxidase like 3) were purchased from R&D systems and assays were performed in 1.2 M urea, 50 mM sodium borate buffer pH 8.0, and 10 mM CaCl. The final concentrations in the LOXL2 and LOXL3 assays are shown in Table 5 below.

TABLE 5

|  | LOXL3 | LOXL2 |
| --- | --- | --- |
| Protein (nM) | 150 | 130 |
| Cadaverine (mM) | 1 | 2.5 |
| Amplex Red (µM) | 20 | 20 |
| HPR U/mL | 1 | 1 |

5 µl of freshly prepared reaction buffer were delivered to reaction wells. Compounds were resuspended in 100% DMSO at 10 mM and delivered into buffer using acoustic technology (Echo550; nanoliter range). A 3× solution of LOXL2 or LOXL3 in reaction buffer was prepared ("enzyme solution") and 5 µL of enzyme solution was added into the reaction wells. Buffer only was added to column 1 for no protein control. Reactions were incubated for 30 minutes at 37° C. A 3× mixture of cadaverine, Amplex Red, and HRP ("Substrate/Detection Mix") was prepared and subsequently 5 µL of the mixture added to each reaction well. Progress of reactions was monitored for 60 minutes at 37° C. using Clariostar plate reader (ex 530-12, ems 600-40). For all activity assays, pan-LOX inhibitor CCT365623 (Tang et al, 2017) and LOXL2/LOXL3 inhibitor PAT-1251 (PharmaKea) were included as standards.

For the data analysis, the slope of the linear portion of the progress curve was calculated using Clariostar software. Typical analysis interval was between 8-30 min, but varied between experiments. The background-subtracted signals (No protein wells are considered as background) were converted to % activity relative to DMSO controls. Data was analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) were included as standards.

Activity data are shown in Table 8.

2. LOX Inhibition Assay Procedures

The ability of compounds to inhibit prototypic LOX was determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by prototypic LOX enzyme present in the sample. Hydrogen peroxide was in turn detected using a red fluorescence substrate for HRP-coupled reactions (Amplex Red Enzyme Assays, Thermo Scientific Fisher). This lead to an increase in fluorescence that can be easily detected at Ex/Em=540/590 nm in a fluorescence microplate Bovine lysyl oxidase (LOX) was extracted by adapting the methodology from [Kagan et al. 1979 and Borel et al. 2001.] from bovine tendon: Frozen adult bovine tendon was placed in room temperature water to defrost, and then membranes were removed and the remaining tissue cut into 1 cm pieces. The material was first passed through a course mesh meat grinder, and this mince was passed through a fine mesh grinder. The mince was homogenized in 10 v/w of buffer (16 mM sodium phosphate buffer pH 7.8, 400 mM NaCl) using a Waring blender. The homogenate was centrifuged at 15,000×g for 15 min at 4° C. After centrifugation, the supernatant was discarded and the pellets resuspended in 10 volumes of the same buffer. The mixture was blended again and centrifuged with the same settings. This time the pellets were blended in 3 volumes of extraction buffer (16 mM sodium phosphate buffer pH 7.8) and left to incubate at 4° C. for 2 h. After this time, the slurry was centrifuged with the same settings as described above. The supernatant was used in an ultrafiltration step to remove large proteins by size exclusion through a 30 kDalton filter (EMD Millipore). The filtrate was mixed with DEAE Sephadex (GE Healthcare), or passed over a MonoQ FPLC column. After two washes, one in 16 mM sodium phosphate buffer pH 7.8, 380 mM NaCl, and another in 16 mM sodium phosphate buffer pH 7.8, the proteins were eluted with 16 mM sodium phosphate pH 7.8, 10 µM $CuSO_4$, and 4 M urea. Fractions containing Lox activity were collected and stored frozen at −70° C.

Final concentration in the LOX assay is shown in Table 6 below and performed in a total volume of 15 vil.

TABLE 6

|  | LOX |
| --- | --- |
| Protein (µl) | 1 |
| Cadaverine (mM) | 5 |
| Amplex Red (µM) | 20 |
| HPR U/mL | 10 |

7 µl of freshly prepared reaction buffer were delivered to reaction wells. Compounds were resuspended in 100% DMSO at 10 mM and delivered into buffer using acoustic technology (Echo550; nanoliter range). A 2.85× solution of LOX protein in reaction buffer was prepared ("LOX solution") and 7 µl of LOX solution was added into the reaction wells. Buffer only was added to column 1 for no protein control. Reactions were incubated for 30 minutes at 37° C. A 3.33× mixture of cadaverine, Amplex Red, and HRP ("Substrate/Detection Mix") was prepared and subsequently 6 µL of the mixture was added to each reaction well. Progress of reactions was monitored for 120 minutes at 37°

C. using Clariostar plate reader (ex530-12, ems 600-40). For all activity assays, pan-LOX inhibitor CCT365623 (Tang et al, 2017) and LOXL2/LOXL3 inhibitor PAT-1251 (PharmaKea) were included as standards.

The slope of the linear portion of the progress curve was calculated using Clariostar software. Typical analysis interval was between 20-50 min, but varied between experiments. The background subtracted signals (No protein wells were considered as background) were converted to % activity relative to DMSO controls. Data was analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) were included as standards.

Activity data are shown in Table 8.

3. LOXL1/4 Inhibition Assay Procedures

The ability of compounds to inhibit human LOX, LOXL1 and/or LOXL4 is determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by the lysyl oxidase enzyme present in the sample. Hydrogen peroxide is in turn detected using a red fluorescence substrate for HRP-coupled reactions (Amplex Red Enzyme Assays, Thermo Scientific Fisher). This leads to increase in fluorescence that can be easily detected at Ex/Em=540/590 nm in a fluorescence microplate reader.

Recombinant human LOX, recombinant human and/or bovine LOXL1 (lysyl oxidase like 1), and recombinant human and/or bovine LOXL4 (lysyl oxidase like 4) are used for activity assays and assays are performed in 1.2 M urea, 50 mM sodium borate buffer pH 8.0, and 10 mM CaCl.

Final concentration in the LOX, LOXL1, and LOXL4 assays can be as shown in Table 7 and are performed in a total volume of 15 vil.

TABLE 7

|  | LOX | LOXL1 | LOXL4 |
|---|---|---|---|
| Protein (µl) | 1-5 | 1-5 | 1-5 |
| Cadaverine (mM) | 1-10 | 1-10 | 1-10 |
| Amplex Red (µM) | 5-20 | 5-20 | 5-20 |
| HPR U/mL | 5-10 | 5-10 | 5-10 |

1-5 µl of freshly prepared reaction buffer is delivered to reaction wells. Compounds are resuspended in 100% DMSO at 10 mM and delivered into buffer using acoustic technology (Echo550; nanoliter range). A 3× solution of LOX, LOXL1, or LOXL4 in reaction buffer is prepared ("enzyme solution") and 1-5 µL of enzyme solution is added into the reaction wells. Buffer only is added to column 1 for no protein control. Reactions are incubated for 30 minutes at 37° C. A 3× mixture of cadaverine, Amplex Red, and HRP ("Substrate/Detection Mix) is prepared and subsequently 5 µL of the mixture is added to each reaction well. Progress of reactions is monitored for 120 minutes at 37° C. using Clariostar plate reader (ex 530-12, ems 600-40).

Slope of the linear portion of the progress curve is calculated using Clariostar software. Typical analysis interval is between 8-30 min, but may vary between experiments. The background subtracted signals (No protein wells are considered as background) are converted to % activity relative to DMSO controls. Data is analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) are included as standards.

4. Activity Data of Selected Compounds

As the data herein indicate, compounds of Formula I were found effective as LOX enzyme inhibitors at low concentrations. $IC_{50}$ values for exemplary compounds of Formula I, Formula Ia, Formula Ib, Formula II, Formula IIa, Formula IIb, or Table 1, are provided in Table 8 below. Any compound with an $IC_{50}$ below or equal to 500 nM in all LOX, LOXL2, and LOXL3 assays, as described above, is deemed a pan-LOX inhibitor. Any compound with an $IC_{50}$ below or equal to 500 nM in the LOXL2 assay and greater than 30 µM in both the LOX and LOXL3 assay, as described above, is deemed a LOXL2 inhibitor. Any compound with an $IC_{50}$ below or equal to 500 nM in the LOX assay and greater than 30 µM in the LOXL2/LOXL3 assays, as described above, is deemed a LOX inhibitor. Any compound with an $IC_{50}$ below or equal to 500 nM in both the LOXL2 and LOXL3 assay and greater than 30 µM in the LOX assay, as described above, is deemed a dual LOXL2/LOXL3 inhibitor. Any compound with an $IC_{50}$ below or equal to 500 nM in the LOXL3 assay and greater than 30 µM in the LOX and LOXL2 assay, as described above, is deemed a LOXL3 inhibitor. Any compound with an $IC_{50}$ below or equal to 500 nM in the LOXL2 assay and greater than 30 µM µM in LOX and an $IC_{50}$ which is 10-fold greater in the LOXL3 assay than the LOXL2 assay, as described above, is deemed a LOXL2-selective inhibitor.

As the data herein indicate, a broad variety of compounds of Formula I were found effective as LOX enzyme inhibitors at low concentrations. $IC_{50}$ values for exemplary compounds of Formula I (see below for compound names and structures) are provided in Table 8 infra. Any compound with an $IC_{50}$ superior or equal to 10 µM in this assay, as described above, is deemed a LOX enzyme-inhibiting compound. In the table below, a three plus signs (+++) are associated with an $IC_{50}$ of less than or equal to 500 nM; two plus signs (++) is associated with an $IC_{50}$ of from 500 nM to less than 1 µM; and a single plus sign (+) is associated with an $IC_{50}$ of equal or greater than 1 µM and less than or equal to 30 µM.

TABLE 8

| Example | Activity Range LOX | Activity Range LOXL2 | Activity Range LOXL3 |
|---|---|---|---|
| 26 | + | +++ | nd |
| 27 | + | +++ | nd |
| 195 | + | +++ | +++ |
| 195A | + | +++ | +++ |
| 195B | + | +++ | +++ |
| 196 | + | +++ | +++ |
| 196A | ++ | +++ | +++ |
| 196B | ++ | +++ | +++ |
| 203 | + | +++ | nd |
| 204 | + | +++ | nd |
| 205 | Nd | +++ | nd |
| 206 | + | +++ | nd |
| 207 | +++ | +++ | nd |
| 208 | +++ | +++ | nd |
| 209 | Nd | +++ | nd |
| 210 | + | +++ | nd |
| 211 | Nd | +++ | nd |
| 212 | + | +++ | nd |
| 213 | Nd | +++ | nd |
| 214 | Inactive | +++ | nd |
| 215 | Nd | ++ | nd |
| 216 | Inactive | ++ | nd |

TABLE 8-continued

| Example | Activity Range LOX | Activity Range LOXL2 | Activity Range LOXL3 |
|---|---|---|---|
| 217 | Nd | ++ | nd |
| 218 | + | +++ | nd |
| 219 | Nd | +++ | nd |
| 219T | Nd | +++ | nd |
| 220 | Nd | +++ | nd |
| 220T | Nd | ++ | nd |
| 221 | Nd | +++ | nd |
| 221T | Nd | +++ | nd |
| 222 | Nd | +++ | nd |
| 222T | Nd | +++ | nd |
| 223 | Nd | +++ | nd |
| 223T | Nd | +++ | nd |
| 230 | Nd | +++ | nd |
| 230T | Nd | +++ | nd |
| 231 | Nd | +++ | nd |
| 231T | Nd | +++ | nd |
| 234 | Nd | +++ | nd |
| 234T | Nd | +++ | nd |
| 235 | Nd | +++ | ++ |
| 235T | Nd | +++ | nd |
| 239 | Nd | +++ | +++ |
| 239RAC | Nd | +++ | nd |
| 239T | Nd | +++ | +++ |

5. Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

a. Intermediate 26: 4-((2-(bromomethyl)-4-phenylpyrrolidin-1-yl)sulfonyl)morpholine

SCHEME 1

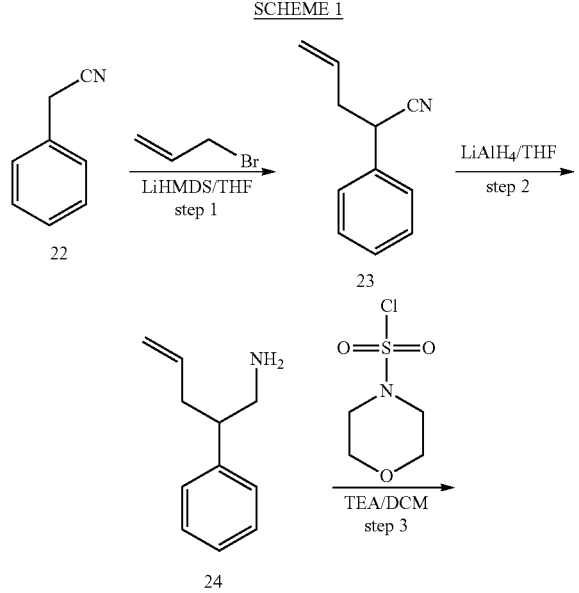

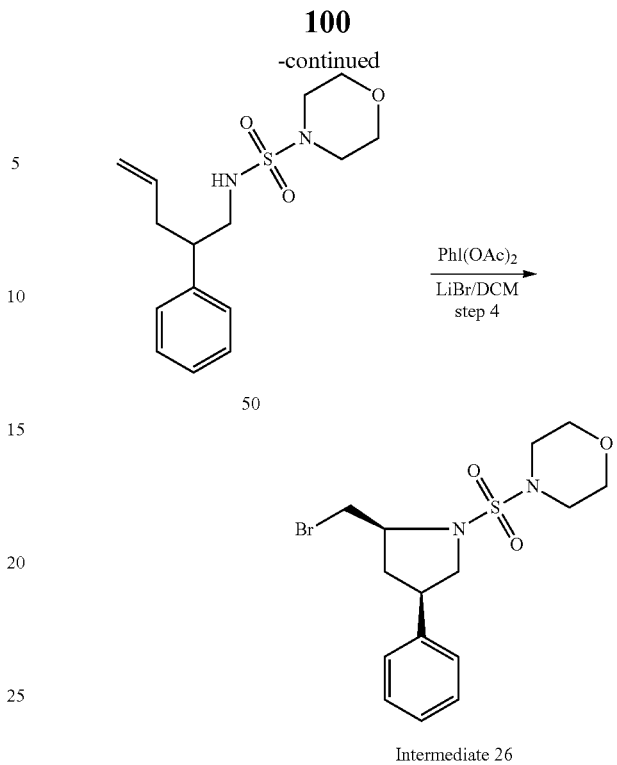

Intermediate 26

Step 1: 2-Phenylpent-4-enenitrile. To a stirred solution of 2-phenylacetonitrile (10 g, 85.4 mmol, 1.0 equiv) in THF (100 mL) was added LiHMDS in THF (1M, 86 mL, 86 mmol, 1.01 equiv) dropwise at −78° C. under nitrogen atmosphere. The resulting mixture was stirred for 1 h at −78° C. under nitrogen atmosphere. To above mixture was added 3-bromoprop-1-ene (10.8 g, 89.6 mmol, 1.05 equiv) dropwise at −78° C. The resulting mixture was stirred for 16 h at rt. The reaction was quenched with $H_2O$ (200 mL) and extracted with EtOAc (3×300 mL). The combined organic layers were dried over anhydrous $Na_2SO_4$ and concentrated under vacuum. The residue was eluted from silica gel with PE/EtOAc (20:1) to afford the title compound (12 g, 89%) as yellow oil. MS-ESI: 156 (M−1).

Step 2: 2-Phenylpent-4-en-1-amine. To a stirred solution of 2-phenylpent-4-enenitrile (12 g, 76.3 mmol, 1.0 equiv) in THF (200 mL) was added $LiAlH_4$ (3.48 g, 91.6 mmol, 1.2 equiv) in portions at 0° C. under nitrogen atmosphere. The resulting mixture was stirred for 16 h at rt under nitrogen atmosphere. The reaction was quenched with MeOH (10 mL) at 0° C. The resulting mixture was concentrated under vacuum. The residue was eluted from silica gel with MeOH/DCM (1:20) to afford the title compound (5.15 g, 33%) as brown oil. MS-ESI: 162 (M+1).

Step 3: N-(2-Phenylpent-4-en-1-yl)morpholine-4-sulfonamide. To a stirred solution of 2-phenylpent-4-en-1-amine (4.0 g, 24.8 mmol, 1.0 equiv) in DCM (40 mL) were added morpholine-4-sulfonyl chloride (5.07 g, 27.3 mmol, 1.1 equiv) and TEA (5.02 g, 49.6 mmol, 2.0 equiv) in portions at rt. The resulting mixture was stirred for 2 h at rt. The reaction was quenched with water (20 mL) and extracted with DCM (3×40 mL). The combined organic layers were dried with anhydrous $Na_2SO_4$ and concentrated under vacuum. The residue was eluted from silica gel with PE/EA (3:1) to afford the title compound (6.1 g, 63%) as yellow oil. MS-ESI: 311 (M+1).

Step 4: cis-4-((2-(Bromomethyl)-4-phenylpyrrolidin-1-yl)sulfonyl)morpholine. To a stirred solution of N-(2-phenylpent-4-en-1-yl)morpholine-4-sulfonamide (1.89 g, 6.09 mmol, 1.0 equiv) in DCM (244 mL) were added (acetyloxy)(phenyl)-lambda3-iodanyl acetate (2.16 g, 6.70 mmol, 1.1 equiv) and LiBr (1.06 g, 12.2 mmol, 2.0 equiv) in portions at rt. The resulting mixture was stirred for 16 h at rt. The resulting mixture was concentrated under vacuum. The residue was eluted from silica gel with PE/EA (3:1) to afford the title compound (1.98 g, 83%) as a white solid. MS-ESI: 389/342 (M+1).

The intermediate in Table 9 was prepared using the similar procedures for converting compound 22 to intermediate 26 shown in Scheme 1 from appropriated starting materials.

TABLE 9

| Intermediate # | Structure | IUPAC Name | Exact Mass [M + H]+ |
|---|---|---|---|
| Intermediate 27 | 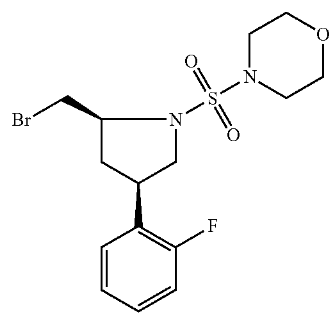 [SMILES: O=S(=O)(N1CCOCC1)N1C[C@@H](c2ccccc2F)C[C@H]1CBr] | cis-4-((2-(bromomethyl)-4-(2-fluorophenyl)pyrrolidin-1-yl)sulfonyl)morpholine | 407/409 |
| Intermediate 28 | 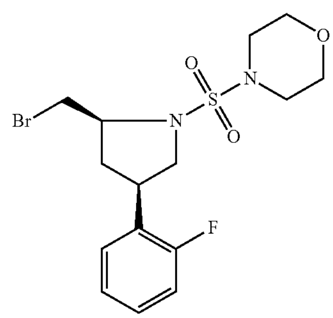 [SMILES: O=S(=O)(N1CCOCC1)N1C[C@@H](c2ccccc2F)C[C@H]1CBr] | cis-4-((2-(bromomethyl)-4-(2-fluorophenyl)pyrrolidin-1-yl)sulfonyl)morpholine | 407/409 |
| Intermediate 29 | 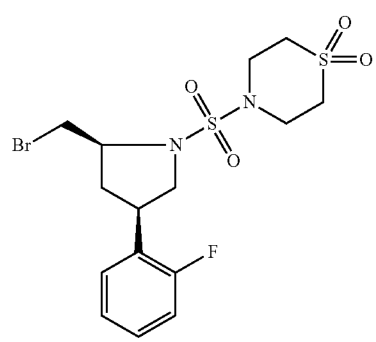 [SMILES: O=S1(=O)CCN(S(=O)(=O)N2C[C@@H](c3ccccc3F)C[C@H]2CBr)CC1] | cis-4-((2-(bromomethyl)-4-(2-fluorophenyl)pyrrolidin-1-yl)sulfonyl)thiomorpholine 1,1-dioxide | 455/457 |
| Intermediate 30 | 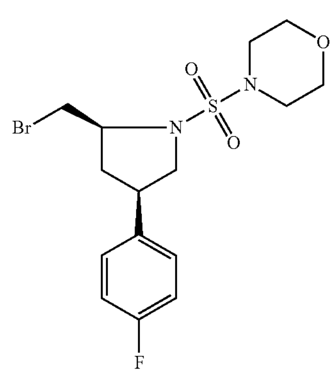 [SMILES: O=S(=O)(N1CCOCC1)N1C[C@@H](c2ccc(F)cc2)C[C@H]1CBr] | cis-4-((2-(bromomethyl)-4-(4-fluorophenyl)pyrrolidin-1-yl)sulfonyl)morpholine | 407/409 |

TABLE 9-continued

| Intermediate # | Structure | IUPAC Name | Exact Mass [M + H]+ |
|---|---|---|---|
| Intermediate 31 | 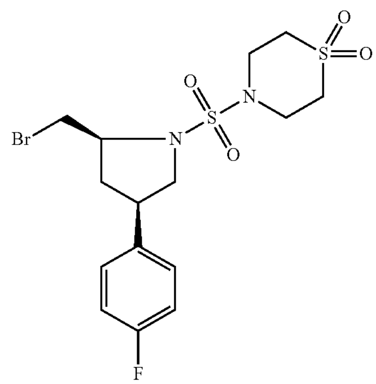 [SMILES: O=S1(=O)CCN(S(=O)(=O)N2C[C@@H](c3ccc(F)cc3)C[C@H]2CBr)CC1] | cis-4-((2-(bromomethyl)-4-(4-fluorophenyl)pyrrolidin-1-yl)sulfonyl)thiomorpholine 1,1-dioxide | 455/457 |
| Intermediate 32 | 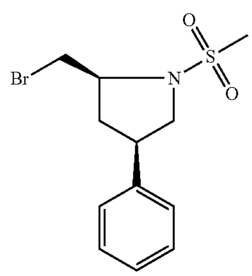 [SMILES: CS(=O)(=O)N1C[C@@H](c2ccccc2)C[C@H]1CBr] | cis-2-(bromomethyl)-1-(methylsulfonyl)-4-phenylpyrrolidine | 318/320 |
| Intermediate 33 | 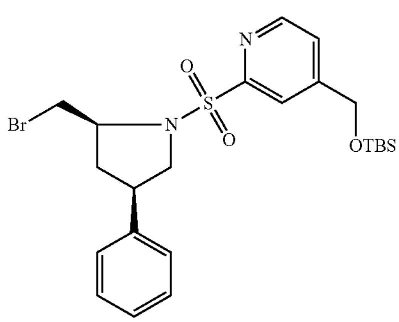 [SMILES: CC(C)(C)[Si](C)(C)OCc1ccnc(S(=O)(=O)N2C[C@@H](c3ccccc3)C[C@H]2CBr)c1] | cis-2-((2-(bromomethyl)-4-phenylpyrrolidin-1-yl)sulfonyl)-4-(((tert-butyldimethylsilyl)oxy)methyl)pyridine | 525/527 |
| Intermediate 34 | | trans-2-((2-(bromomethyl)-4-phenylpyrrolidin-1-yl)sulfonyl)-4-(((tert-butyldimethylsilyl)oxy)methyl)pyridine | 525/527 | b. Intermediate 35:
1-(Morpholinosulfonyl)-5-phenylpiperidin-3-yl 4-methylbenzenesulfonate

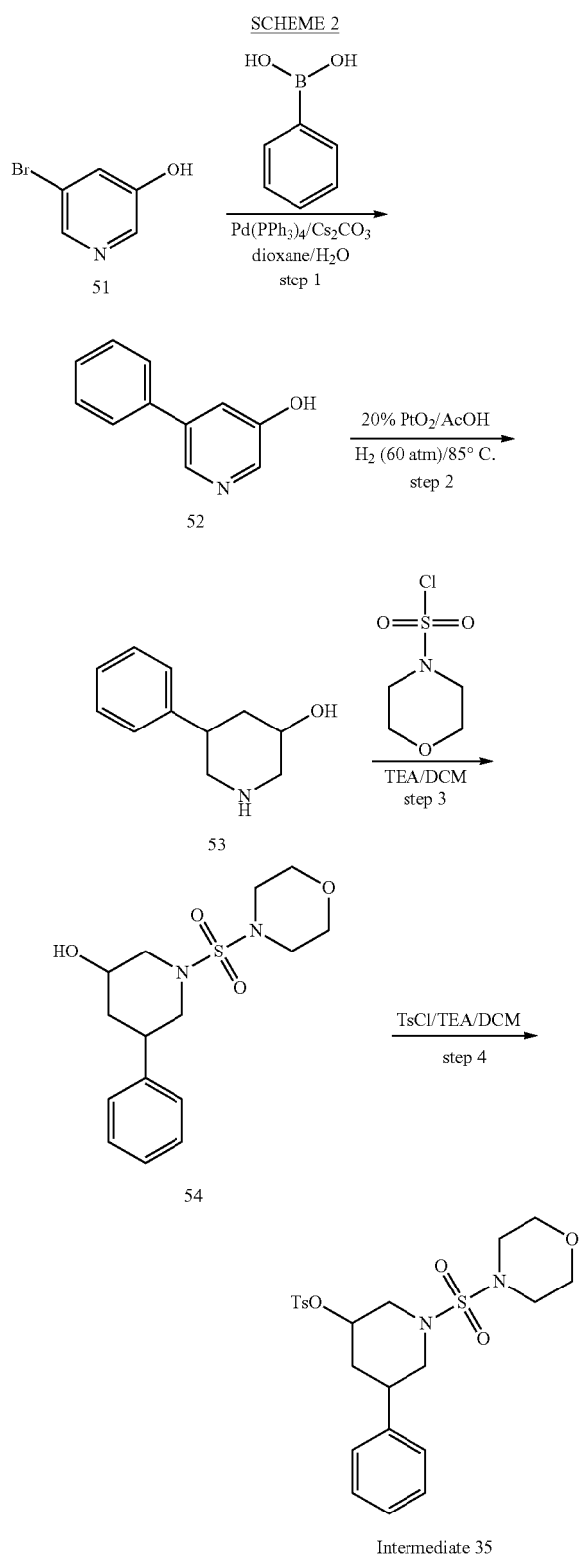

Intermediate 35

Step 1: 5-Phenylpyridin-3-ol. To a stirred solution of 5-bromopyridin-3-ol (5.0 g, 29.1 mmol, 1.0 equiv) and phenylboronic acid (3.90 g, 31.96 mmol, 1.1 equiv) in dioxane (200 mL) and $H_2O$ (20 mL) were added $Pd(PPh_3)_4$ (3.32 g, 2.9 mmol, 0.1 equiv) and $Cs_2CO_3$ (18.7 g, 58.1 mmol, 2.0 equiv) at rt. The resulting mixture was stirred overnight at 100° C. under nitrogen atmosphere. The reaction mixture was quenched with $H_2O$ (200 mL) and extracted with EtOAc (3×200 mL). The combined organic layers were dried with anhydrous $Na_2SO_4$ and concentrated under vacuum. The residue was eluted from silica gel with PE/EtOAc (1:1) to afford the title compound (3.9 g, 78%) as an off-white solid. MS-ESI: 172 (M+1).

Step 2: 5-Phenylpiperidin-3-ol. To a solution of 5-phenylpyridin-3-ol (3.9 g, 22.7 mmol, 1 equiv) in 30 mL AcOH was added $PtO_2$ (0.39 g) under nitrogen atmosphere. The resulting mixture was stirred for 5 h at 85° C. under hydrogen atmosphere at 60 atm. The resulting mixture was filtered and the filter cake was washed with MeOH (3×200 mL). The filtrate was concentrated under vacuum. The mixture was adjusted to pH 8 with sat. $Na_2CO_3$ (aq.). The resulting mixture was extracted with DCM (3×500 mL). The combined organic layers were dried with anhydrous $Na_2SO_4$ and concentrated under vacuum. This resulted in 4.0 g (crude) of the title compound as brown oil. MS-ESI: 178 (M+1).

Step 3: 1-(Morpholinosulfonyl)-5-phenylpiperidin-3-ol. To a stirred solution of 5-phenylpiperidin-3-ol (4.0 g, crude) in DCM (50 mL) were added morpholine-4-sulfonyl chloride (4.16 g, 22.7 mmol, 1.0 equiv) and TEA (6.81 g, 67.4 mmol, 3.0 equiv). The resulting mixture was stirred overnight at rt. The mixture was concentrated under vacuum. The residue was purified by Prep-TLC (PE/EtOAc 1:1) to afford the title compound (2.5 g, 33.4% over two steps) as brown oil. MS-ESI: 327 (M+1).

Step 4: 1-(Morpholinosulfonyl)-5-phenylpiperidin-3-yl 4-methylbenzenesulfonate. To a stirred solution of 1-(morpholinosulfonyl)-5-phenylpiperidin-3-ol of (1.2 g, 3.67 mmol, 1.0 equiv) in DCM (20 mL) were added TsCl (0.77 g, 4.04 mmol, 1.1 equiv) and TEA (0.74 g, 7.35 mmol, 2.0 equiv). The resulting mixture was stirred overnight at rt. The resulting mixture was concentrated under vacuum. The residue was eluted from silica gel with PE/EtOAc (1:1) to afford the title compound (480 mg, 40%) as yellow oil. MS-ESI: 481 (M+1).

The intermediate in Table 10 below was prepared using the similar procedures for converting compound 51 to intermediate 35 shown in Scheme 2 from appropriated starting materials.

TABLE 10

| Intermediate # | Structure | IUPAC Name | Exact Mass [M + H]+ |
|---|---|---|---|
| Intermediate 36 | 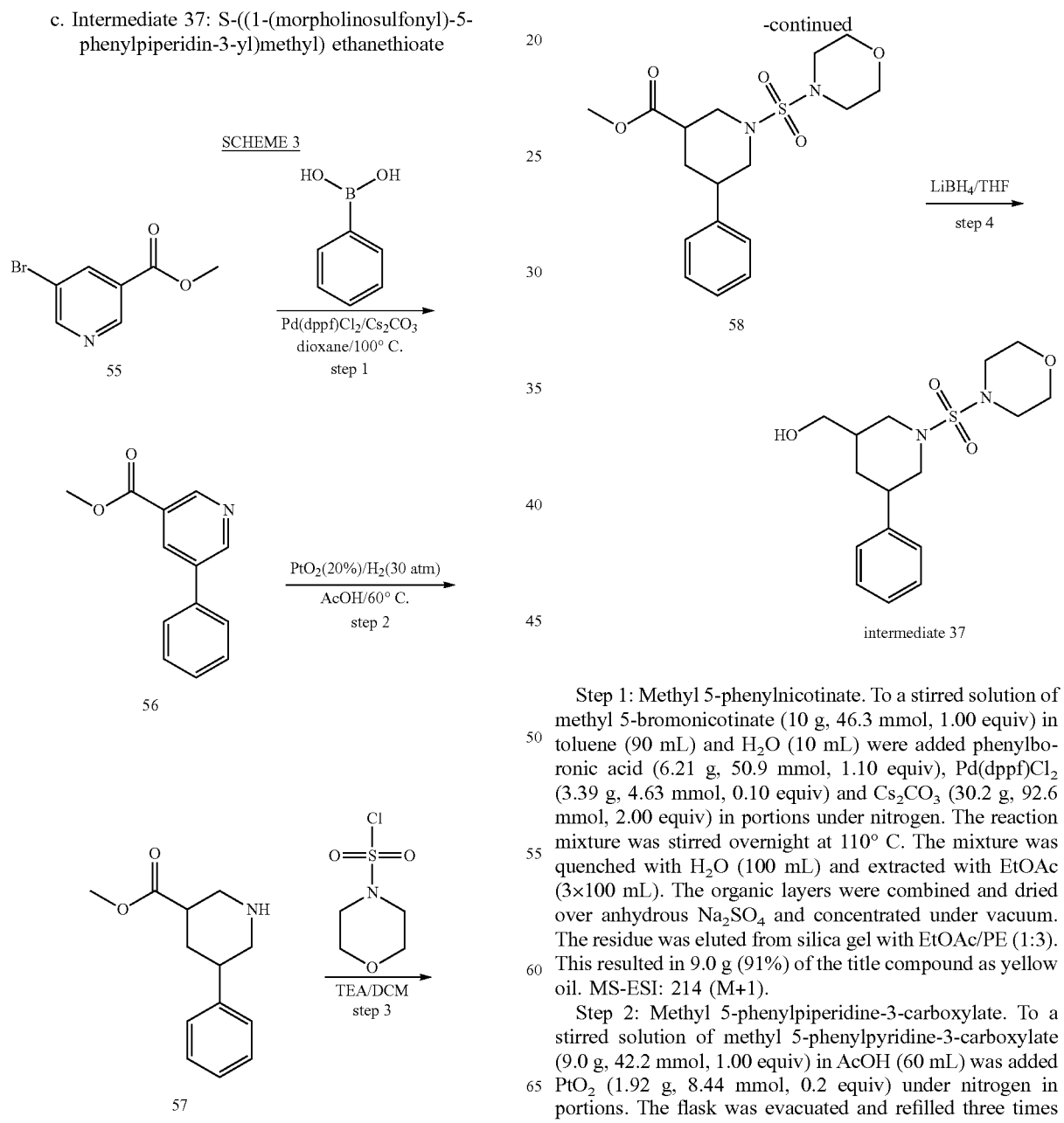 | 5-Cyclohexyl-1-(morpholinosulfonyl)piperidin-3-yl 4-methylbenzenesulfonate | 487 | c. Intermediate 37: S-((1-(morpholinosulfonyl)-5-phenylpiperidin-3-yl)methyl) ethanethioate Step 1: Methyl 5-phenylnicotinate. To a stirred solution of methyl 5-bromonicotinate (10 g, 46.3 mmol, 1.00 equiv) in toluene (90 mL) and H₂O (10 mL) were added phenylboronic acid (6.21 g, 50.9 mmol, 1.10 equiv), Pd(dppf)Cl₂ (3.39 g, 4.63 mmol, 0.10 equiv) and Cs₂CO₃ (30.2 g, 92.6 mmol, 2.00 equiv) in portions under nitrogen. The reaction mixture was stirred overnight at 110° C. The mixture was quenched with H₂O (100 mL) and extracted with EtOAc (3×100 mL). The organic layers were combined and dried over anhydrous Na₂SO₄ and concentrated under vacuum. The residue was eluted from silica gel with EtOAc/PE (1:3). This resulted in 9.0 g (91%) of the title compound as yellow oil. MS-ESI: 214 (M+1).

Step 2: Methyl 5-phenylpiperidine-3-carboxylate. To a stirred solution of methyl 5-phenylpyridine-3-carboxylate (9.0 g, 42.2 mmol, 1.00 equiv) in AcOH (60 mL) was added PtO₂ (1.92 g, 8.44 mmol, 0.2 equiv) under nitrogen in portions. The flask was evacuated and refilled three times with hydrogen. The mixture was stirred for 3 h at 60° C.

under hydrogen atmosphere with 30 atm. The mixture filtered through a celite pad and the filtrate was concentrated under vacuum. This resulted in 9.0 g (crude) of the title compound as dark brown oil. MS-ESI: 220 (M+1).

Step 3: Methyl 1-(morpholinosulfonyl)-5-phenylpiperidine-3-carboxylate. To a stirred solution of methyl 5-phenylpiperidine-3-carboxylate (9.0 g, crude) in DCM (100 mL) were added morpholine-4-sulfonyl chloride (8.45 g, 46.4 mmol, 1.1 equiv) and TEA (8.52 g, 84.4 mmol, 2.0 equiv) in portions at rt. The resulting mixture was stirred for 2 h at rt. The reaction was quenched with water (100 mL) and extracted with DCM (3×100 mL). The combined organic layers were dried with anhydrous $Na_2SO_4$ and concentrated under vacuum. The residue was eluted from silica gel with PE/EtOAc (3:1) to afford the title compound (4.1 g, 26.4%, over two steps) as yellow oil. MS-ESI: 369 (M+1).

Step 4: ((3R)-1-(morpholinosulfonyl)-5-phenylpiperidin-3-yl)methanol. To a stirred solution of methyl 1-(morpholinosulfonyl)-5-phenylpiperidine-3-carboxylate (450 mg, 1.221 mmol, 1 equiv) in THF (15 mL) were added $LiBH_4$ (133 mg, 6.12 mmol, 5 equiv) at room temperature. The resulting mixture was stirred for 16 h at room temperature. The reaction was quenched with MeOH at room temperature. The resulting mixture was concentrated under vacuum. The residue was purified by Prep-TLC (PE/EtOAc 1:1) to afford the title compound (340 mg, 75%) as a white solid. MS-ESI: 341 (M+1).

The intermediate in Table 11 below was prepared using the similar procedures for converting compound 55 to intermediate 37 shown in Scheme 3 from appropriated starting materials.

TABLE 11

| Intermediate # | Structure | IUPAC Name | Exact Mass [M + H]$^+$ |
|---|---|---|---|
| Intermediate 38 | 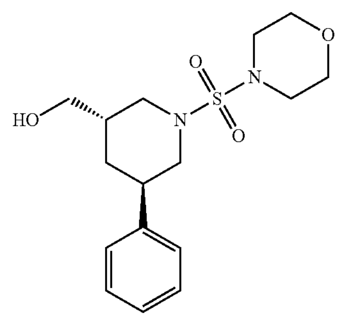 [SMILES: O=S(=O)(N1CCOCC1)N1C[C@@H](CO)C[C@H](c2ccccc2)C1] | trans-(1-(morpholinosulfonyl)-5-phenylpiperidin-3-yl)methanol | 341 |
| Intermediate 39 | 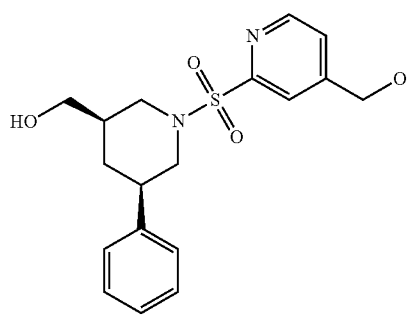 [SMILES: O=S(=O)(c1cc(CO)ccn1)N1C[C@H](CO)C[C@H](c2ccccc2)C1] | cis-(1-((4-(((tert-butyldimethylsilyl)oxy)methyl)pyridin-2-yl)sulfonyl)-5-phenylpiperidin-3-yl)methanol | 477 |
| Intermediate 40 | 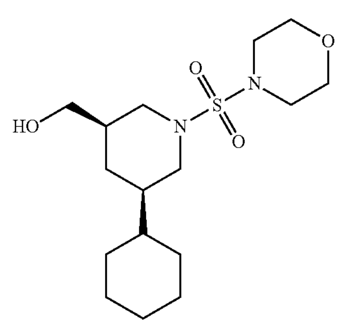 [SMILES: O=S(=O)(N1CCOCC1)N1C[C@H](CO)C[C@H](C2CCCCC2)C1] | cis-(cis-5-cyclohexyl-1-(morpholinosulfonyl)piperidin-3-yl)methanol | 347 |

TABLE 11-continued

| Intermediate # | Structure | IUPAC Name | Exact Mass [M + H]+ |
|---|---|---|---|
| Intermediate 41 | 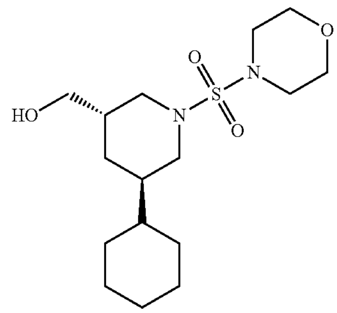 [SMILES: O=S(=O)(N1CCOCC1)N1C[C@@H](CO)C[C@H](C2CCCCC2)C1] | trans-(5-cyclohexyl-1-(morpholinosulfonyl)piperidin-3-yl)methanol | 347 |
| Intermediate 42 | 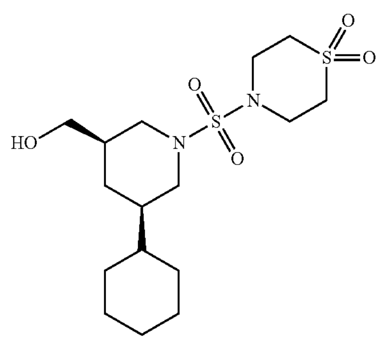 [SMILES: O=S1(=O)CCN(S(=O)(=O)N2C[C@H](CO)C[C@H](C3CCCCC3)C2)CC1] | cis-4-((3-cyclohexyl-5-(hydroxymethyl)piperidin-1-yl)sulfonyl)thiomorpholine 1,1-dioxide | 395 |
| Intermediate 43 | | trans-4-((3-cyclohexyl-5-(hydroxymethyl)piperidin-1-yl)sulfonyl)thiomorpholine 1,1-dioxide | 395 | d. Intermediate 44: (1-(morpholinosulfonyl)-5-(trifluoromethyl)piperidin-3-yl)methanol

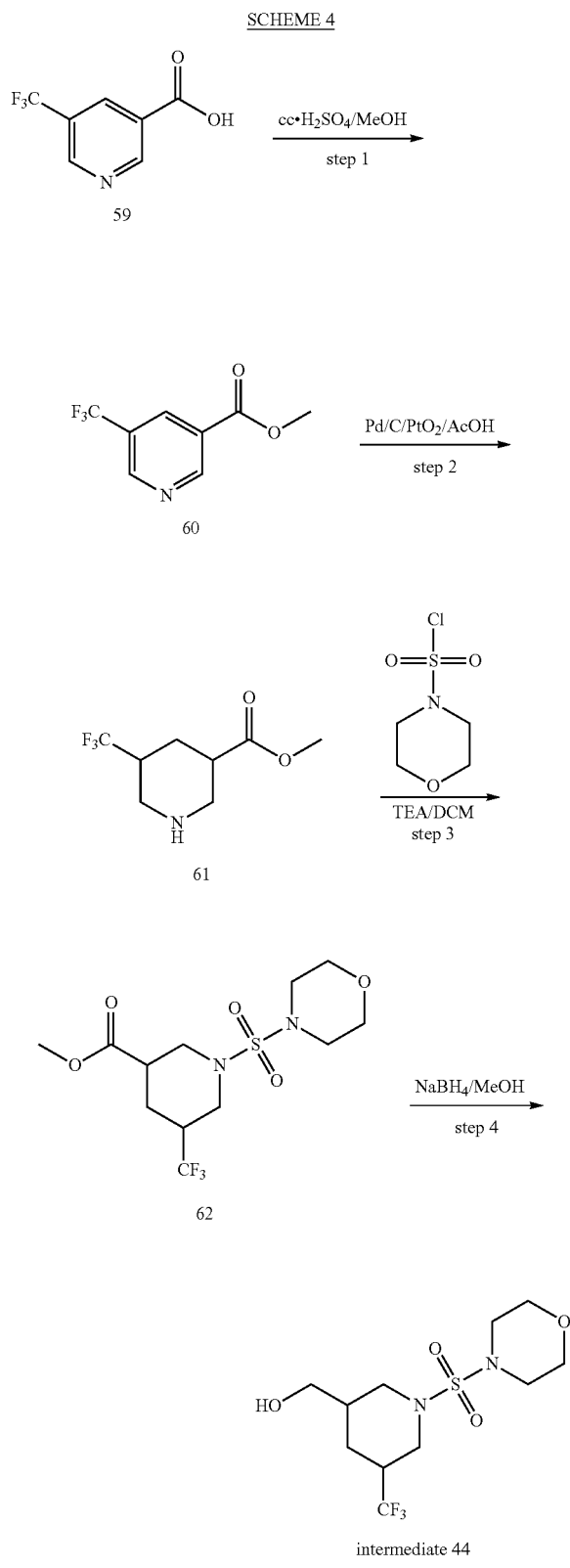

Step 1: Methyl 5-(trifluoromethyl)nicotinate. A solution of 5-(trifluoromethyl)nicotinic acid (20.0 g, 105 mmol, 1 equiv) and $H_2SO_4$ (13.9 mL, 262 mmol, 2.5 equiv) in MeOH (200 mL) was stirred overnight at 80° C. The resulting mixture was diluted with water (200 mL). The mixture was basified to pH 9 with saturated $NaHCO_3$ (aq.). The resulting mixture was extracted with DCM (3×300 mL). The combined organic layers were washed with brine (2×100 mL) and dried over anhydrous $Na_2SO_4$. After filtration, the filtrate was concentrated under reduced pressure to afford the title compound (20 g, 93.1%) as a light yellow solid. MS-ESI: 206 (M+1).

Step 2: Methyl 5-(trifluoromethyl)piperidine-3-carboxylate. A solution of methyl 5-(trifluoromethyl)nicotinate (8.0 g, 39 mmol, 1 equiv), $PtO_2$ (1.59 g, 7.02 mmol, 0.18 equiv) and Pd/C (10% wt., 3.98 g, 37.4 mmol, 0.96 equiv) in AcOH (100 mL) was stirred overnight at 80° C. under hydrogen atmosphere (60 atm). The resulting mixture was filtered and the filter cake was washed with MeOH (2×100 mL). The filtrate was concentrated under reduced pressure. The residue was basified to pH 9 with saturated $NaHCO_3$ (aq.). The resulting mixture was extracted with DCM/MeOH (10/1, 5×100 mL). The combined organic layers were washed with brine (2×500 mL) and dried over anhydrous $Na_2SO_4$. After filtration, the filtrate was concentrated under vacuum to afford the title compound (8.0 g, crude) as a light yellow oil. MS-ESI: 212 (M+1).

Step 3: Methyl 1-(morpholinosulfonyl)-5-(trifluoromethyl)piperidine-3-carboxylate. To a stirred solution of methyl 5-(trifluoromethyl)piperidine-3-carboxylate (5.6 g, crude) and morpholine-4-sulfonyl chloride (5.91 g, 31.8 mmol, 1.2 equiv) in DCM (60 mL) was added TEA (8.05 g, 79.5 mmol, 3 equiv) dropwise at room temperature. The resulting mixture was stirred for 3 h at room temperature. The resulting mixture was diluted with water (100 mL). The resulting mixture was extracted with DCM (2×100 mL). The combined organic layers were washed with brine (2×50 mL) and dried over anhydrous $Na_2SO_4$. After filtration, the filtrate was concentrated under vacuum. The residue was eluted from silica gel with PE/EtOAc (5:1) to afford the title compound (4.5 g, 47%) as light yellow oil. MS-ESI: 361 (M+1).

Step 4: (1-(Morpholinosulfonyl)-5-(trifluoromethyl)piperidin-3-yl)methanol. To a stirred solution of methyl 1-(morpholinosulfonyl)-5-(trifluoromethyl)piperidine-3-carboxylate (4.3 g, 11.9 mmol, 1 equiv) in MeOH (100 mL) was added $NaBH_4$ (9.03 g, 239 mmol, 20 equiv) in portions at room temperature. The resulting mixture was stirred overnight at room temperature. The reaction was quenched with sat. $NH_4C_1$ (aq.) (100 mL) at 0° C. The resulting mixture was concentrated under reduced pressure. The resulting mixture was extracted with EtOAc (2×100 mL). The combined organic layers were washed with brine (2×50 mL) and dried over anhydrous $Na_2SO_4$. After filtration, the filtrate was concentrated under reduced pressure to afford the title compound (4.0 g, 80%). MS-ESI: 333 (M+1).

The intermediate in Table 12 below was prepared using the similar procedures for converting compound 59 to intermediate 44 shown in Scheme 7 from appropriated starting materials

TABLE 12

| Intermediate # | Structure | IUPAC Name | Exact Mass [M + H]⁺ |
|---|---|---|---|
| Intermediate 45 | | 4-((3-(hydroxymethyl)-5-(trifluoromethyl)piperidin-1-yl)sulfonyl)thiomorpholine 1,1-dioxide | 381 | e. Intermediate 46: S-((1-(morpholinosulfonyl)-5-(trifluoromethyl)piperidin-3-yl)methyl) ethanethioate

SCHEME 5

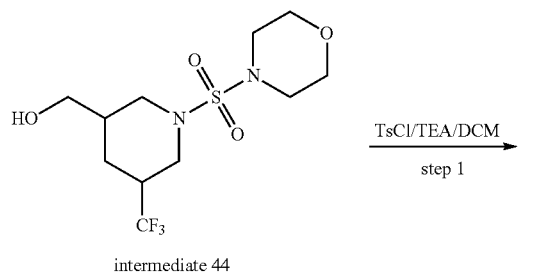

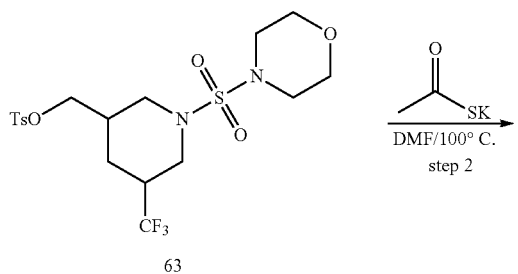

-continued

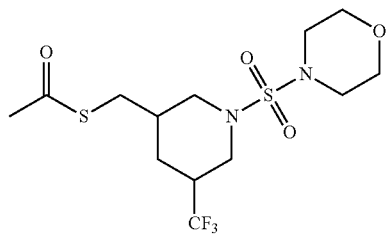

intermediate 46

Step 1: (1-(Morpholinosulfonyl)-5-(trifluoromethyl)piperidin-3-yl)methyl 4-methylbenzenesulfonate. To a stirred solution of (1-(morpholinosulfonyl)-5-(trifluoromethyl)piperidin-3-yl)methanol (4.0 g, 12 mmol, 1 equiv) and TsCl (3.44 g, 18 mmol, 1.5 equiv) in DCM (40 mL) was added TEA (5.02 mL, 36.1 mmol, 3 equiv) dropwise at room temperature. The resulting mixture was stirred overnight at room temperature. The resulting mixture was diluted with $H_2O$ (50 mL). The resulting mixture was extracted with DCM (2×100 mL). The combined organic layers were washed with brine (2×50 mL) and dried over anhydrous $Na_2SO_4$. After filtration, the filtrate was concentrated under vacuum. The residue was eluted from silica gel with PE/EtOAc (5:1) to afford the title compound (4.0 g, 68%) as a light yellow solid. MS-ESI: 487 (M+1).

Step 2: S-(((1-(morpholinosulfonyl)-5-(trifluoromethyl)piperidin-3-yl)methyl ethanethioate. To a stirred solution of (1-(morpholinosulfonyl)-5-(trifluoromethyl)piperidin-3-yl)methyl 4-methylbenzenesulfonate (2.0 g, 4.1 mmol, 1 equiv) in DMF (20 mL) was added potassium ethanethioate (0.94 g, 8.2 mmol, 2 equiv) at room temperature. The mixture was stirred for 3 h at 100° C. The resulting mixture was diluted with $H_2O$ (50 mL). The resulting mixture was extracted with EtOAc (2×100 mL). The combined organic layers were washed with brine (2×50 mL) and dried over anhydrous $Na_2SO_4$. After filtration, the filtrate was concentrated under vacuum to afford the title compound (1.4 g, 69%) as brown oil. MS-ESI: 391 (M+1).

The intermediate in Table 13 was prepared using the similar procedures for converting intermediate 44 to intermediate 46 shown in Scheme 5 from appropriated starting materials.

TABLE 13

| Intermediate # | Structure | IUPAC Name | Exact Mass [M + H]+ |
|---|---|---|---|
| Intermediate 58 | 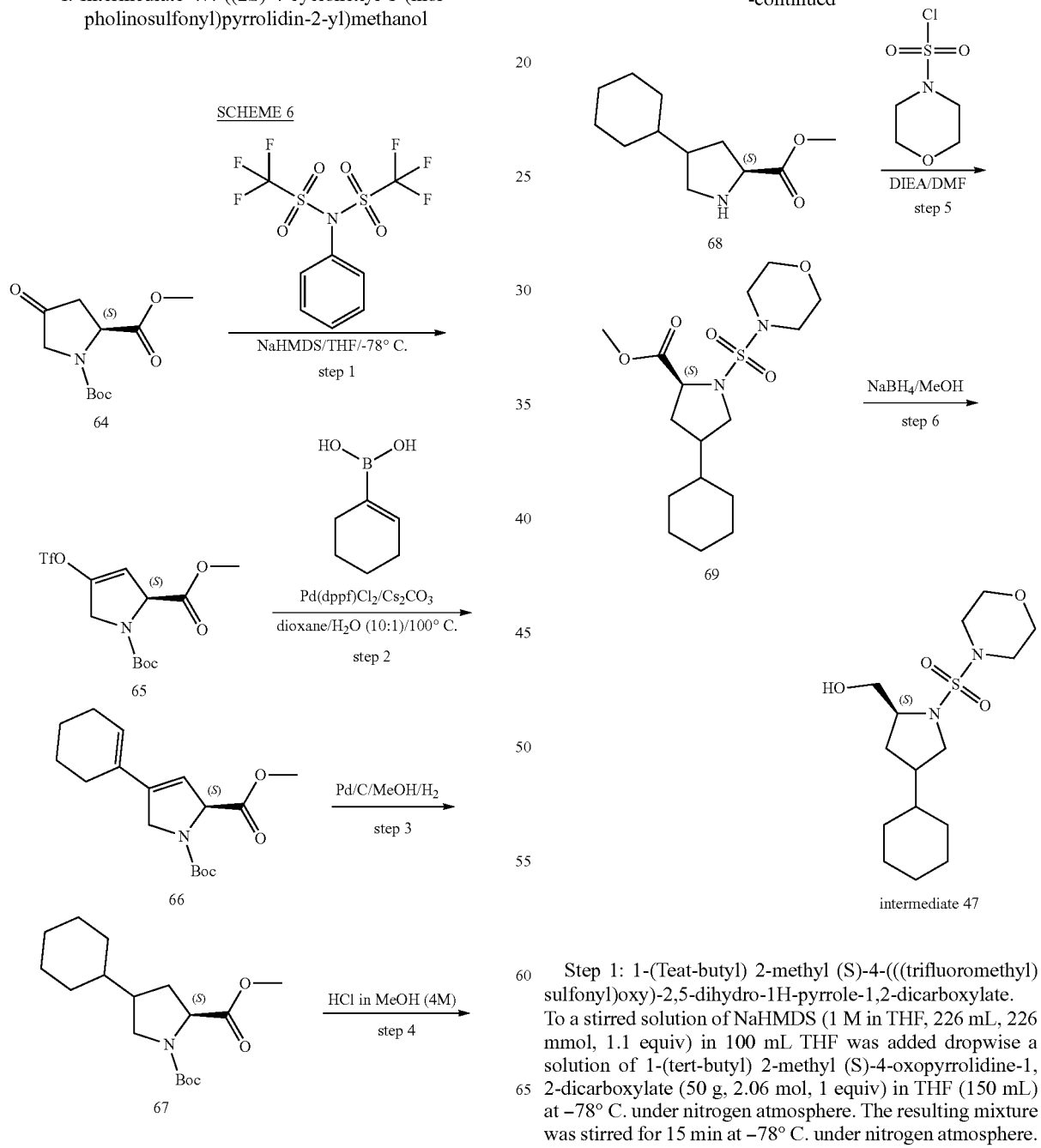 | S-((1-(((1,1-dioxidothiomorpholino)sulfonyl)-5-(trifluoromethyl)piperidin-3-yl)methyl) ethanethioate | 439 | f. Intermediate 47: ((2S)-4-cyclohexyl-1-(morpholinosulfonyl)pyrrolidin-2-yl)methanol Step 1: 1-(Teat-butyl) 2-methyl (S)-4-(((trifluoromethyl)sulfonyl)oxy)-2,5-dihydro-1H-pyrrole-1,2-dicarboxylate.

To a stirred solution of NaHMDS (1 M in THF, 226 mL, 226 mmol, 1.1 equiv) in 100 mL THF was added dropwise a solution of 1-(tert-butyl) 2-methyl (S)-4-oxopyrrolidine-1,2-dicarboxylate (50 g, 2.06 mol, 1 equiv) in THF (150 mL) at −78° C. under nitrogen atmosphere. The resulting mixture was stirred for 15 min at −78° C. under nitrogen atmosphere.

To the above mixture was added a solution of 1,1,1-trifluoro-N-phenyl-N-((trifluoromethyl)sulfonyl)methanesulfonamide (73.4 g, 206 mmol, 1 equiv) in THF (250 mL) dropwise at −78° C. The resulting mixture was stirred for additional 3 h at −78° C. The reaction was quenched with sat. NH₄Cl (aq.) at 0° C. The resulting mixture was extracted with EtOAc (2×1 L). The combined organic layers were dried over anhydrous Na₂SO₄. After filtration, the filtrate was concentrated under vacuum. The residue was eluted from silica gel with PE/EtOAc (5:1) to afford the title compound (70 g, 90%) as light yellow oil. MS-ESI: 376 (M+1).

Step 2: 1-(Teat-butyl) 2-methyl (S)-4-(cyclohex-1-en-1-yl)-2,5-dihydro-1H-pyrrole-1,2-dicarboxylate. To a stirred solution of 1-(tert-butyl) 2-methyl (S)-4-(((trifluoromethyl)sulfonyl)oxy)-2,5-dihydro-1H-pyrrole-1,2-dicarboxylate (27 g, 71.9 mmol, 1 equiv) and cyclohex-1-en-1-ylboronic acid (10.9 g, 86.3 mmol, 1.2 equiv) in dioxane (270 mL) and water (27 mL) were added Pd(dppf)Cl₂ (2.63 g, 3.60 mmol, 0.05 equiv) and Cs₂CO₃ (46.9 g, 144 mmol, 2 equiv) at room temperature. The resulting mixture was stirred overnight at 100° C. under nitrogen atmosphere. The mixture was allowed to cool down to room temperature. The residue was eluted from silica gel with PE/EtOAc (3:1) to afford the title compound (10 g, 45.2%) as yellow oil. MS-ESI: 308 (M+1).

Step 3: 1-(Teat-butyl) 2-methyl (2S)-4-cyclohexylpyrrolidine-1,2-dicarboxylate. To a stirred solution of 1-(tert-butyl) 2-methyl (S)-4-(cyclohex-1-en-1-yl)-2,5-dihydro-1H-pyrrole-1,2-dicarboxylate (10 g, 32.5 mmol, 1 equiv) in 100 mL MeOH was added Pd/C (10% wt., 1.00 g) at room temperature under nitrogen atmosphere. The resulting mixture was stirred overnight at room temperature under hydrogen atmosphere. The resulting mixture was filtered and the filtrate was concentrated under vacuum to afford the title compound (10 g, crude) as black oil. MS-ESI: 312 (M+1).

Step 4: Methyl (2S)-4-cyclohexylpyrrolidine-2-carboxylate. A mixture of 1-(tert-butyl) 2-methyl (2S)-4-cyclohexylpyrrolidine-1,2-dicarboxylate (10 g, crude) in HCl (gas) in 1,4-dioxane (4 M, 40 mL) was stirred overnight at room temperature. The mixture was basified to pH 9 with saturated Na₂CO₃ (aq.). The resulting mixture was extracted with EtOAc (2×300 mL). The combined organic layers were dried over anhydrous Na₂SO₄. After filtration, the filtrate was concentrated under vacuum to afford the title compound (9 g, crude) as brown oil. MS-ESI: 212 (M+1).

Step 5: Methyl (2S)-4-cyclohexyl-1-(morpholinosulfonyl)pyrrolidine-2-carboxylate. To a stirred mixture of methyl (2S)-4-cyclohexylpyrrolidine-2-carboxylate (1.5 g, crude) and TEA (2.16 g, 21.3 mmol, 3 equiv) in DCM (20 mL) was added morpholine-4-sulfonyl chloride (3.95 g, 21.3 mmol, 3 equiv) in portions at room temperature. The resulting mixture was stirred overnight at room temperature. The resulting mixture was concentrated under vacuum. The residue was eluted from silica gel with PE/EtOAc (1:1) to afford the title compound (1.59 g, 61.9%) as light yellow oil. MS-ESI: 361 (M+1).

Step 6: ((2S)-4-cyclohexyl-1-(morpholinosulfonyl)pyrrolidin-2-yl)methanol. To a stirred solution of methyl (2S)-4-cyclohexyl-1-(morpholinosulfonyl)pyrrolidine-2-carboxylate (1.5 g, 4.16 mmol, 1 equiv) in MeOH (15 mL) was added NaBH₄ (0.79 g, 20.8 mmol, 5 equiv) in portions at 0° C. The resulting mixture was stirred overnight at room temperature. The reaction was quenched with sat. NH₄C₁ (aq.) at 0° C. The resulting mixture was extracted with DCM (2×500 mL) and dried over anhydrous Na₂SO₄. After filtration, the filtrate was concentrated under vacuum to afford the title compound (1.06 g, 76.6%) as yellow oil. MS-ESI: 333 (M+1).

The intermediate in Table 14 was prepared using the similar procedures for converting compound 64 to intermediate 47 shown in Scheme 6 from appropriated starting materials.

TABLE 14

| Intermediate # | Structure | IUPAC Name | Exact Mass [M + H]⁺ |
|---|---|---|---|
| Intermediate 48 | | 4-(((2S)-4-cyclohexyl-2-(hydroxymethyl)pyrrolidin-1-yl)sulfonyl)thiomorpholine 1,1-dioxide | 381 | g. Synthesis of pH-AOV-0195 (Method A)

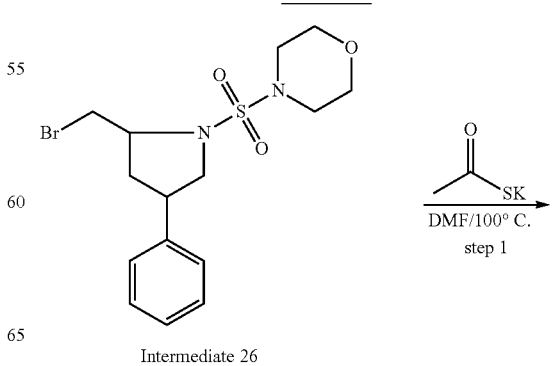

SCHEME 7

Intermediate 26 step 1

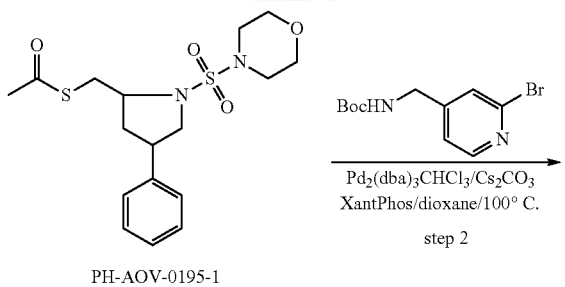

PH-AOV-0195-1

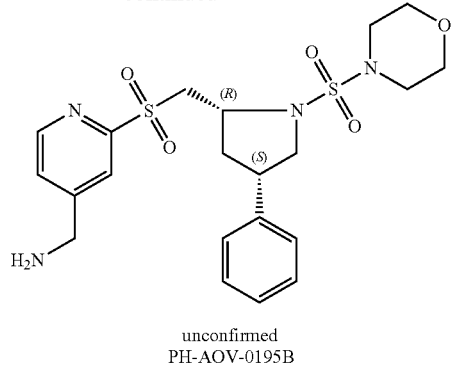

unconfirmed
PH-AOV-0195B

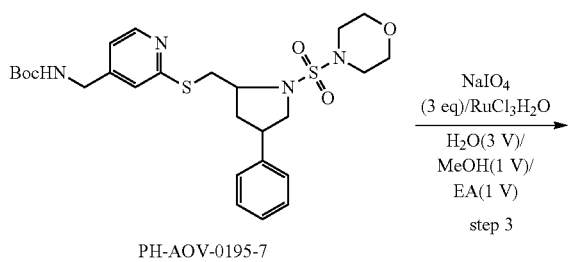

PH-AOV-0195-7

Step 1: S-((1-(morpholinosulfonyl)-4-phenylpyrrolidin-2-yl)methyl) ethanethioate. To a stirred solution of 4-((2-(bromomethyl)-4-phenylpyrrolidin-1-yl)sulfonyl)morpholine (1.96 g, 5.03 mmol, 1.0 equiv) in DMF (15 mL) was added potassium ethanethioate (0.86 g, 7.55 mmol, 1.5 equiv) one portion. The resulting mixture was stirred for 16 h at 100° C. The resulting mixture was diluted with $H_2O$ (100 mL) and extracted with EtOAc (3×100 mL). The combined organic layers were dried over anhydrous $Na_2SO_4$ and concentrated under vacuum to afford the title compound (2.1 g, crude) as brown oil. MS-ESI: 385 (M+1).

Step 2: Teat-butyl ((2-(((1-(morpholinosulfonyl)-4-phenylpyrrolidin-2-yl)methyl)thio)pyridin-4-yl)methyl)carbamate. To a stirred solution of S-((1-(morpholinosulfonyl)-4-phenylpyrrolidin-2-yl)methyl) ethanethioate (900 mg, 2.34 mmol, 1.0 equiv) in dioxane (20 mL) were added tert-butyl ((2-bromopyridin-4-yl)methyl)carbamate (0.74 g, 2.57 mmol, 1.1 equiv), $Pd_2(dba)_3$ (215 mg, 0.23 mmol, 0.1 equiv), $Cs_2CO_3$ (1.91 g, 5.85 mmol, 2.5 equiv) and XantPhos (0.14 g, 0.23 mmol, 0.1 equiv). The resulting mixture was stirred for 16 h at 100° C. under nitrogen atmosphere. The reaction was quenched with $H_2O$ (50 mL) and extracted with EtOAc (5×50 mL). The combined organic layers were dried over anhydrous $Na_2SO_4$ and concentrated under vacuum. The residue was eluted from silica gel with PE/EA (1:1) to afford the title compound (1.1 g, 85.6%) as brown oil. MS-ESI: 549 (M+1).

Step 3: Teat-butyl ((2-(((1-(morpholinosulfonyl)-4-phenylpyrrolidin-2-yl)methyl)sulfonyl)pyridin-4-yl)methyl) carbamate. To a stirred mixture of tert-butyl ((2-(((1-(morpholinosulfonyl)-4-phenylpyrrolidin-2-yl)methyl)thio)pyridin-4-yl)methyl)carbamate (800 mg, 1.46 mmol, 1.0 equiv) in ethyl acetate (2 mL), MeOH (2 mL) and $H_2O$ (2 mL) were added $RuCl_3 \cdot H_2O$ (32.9 mg, 0.15 mmol, 0.10 equiv) in $H_2O$ (2 mL) and $NaIO_4$ (935 mg, 4.37 mmol, 3.0 equiv) in $H_2O$ (2 mL) dropwise at 0° C. The resulting mixture was stirred for 2 h at 0° C. The reaction was quenched with $H_2O$ (10 mL) at 0° C. and extracted with EtOAc (5×50 mL). The combined organic layers were dried over anhydrous $Na_2SO_4$ and concentrated under vacuum. The residue was purified by Prep-TLC (PE/EA 1:2) to afford the title compound (300 mg, 35.4%) as a yellow solid. MS-ESI: 581 (M+1).

Step 4: Cis-(2-(((1-(Morpholinosulfonyl)-4-phenylpyrrolidin-2-yl)methyl)sulfonyl)pyridin-4-yl)methanamine 2,2,2-trifluoroacetate. To a stirred solution of tert-butyl ((2-(((1-(morpholinosulfonyl)-4-phenylpyrrolidin-2-yl)methyl)sulfonyl)pyridin-4-yl)methyl)carbamate (300 mg, 0.52 mmol, 1 equiv) in DCM (5 mL) was added TFA (0.5 mL) dropwise at 0° C. The resulting mixture was stirred for 1 h at rt. The resulting mixture was concentrated under vacuum. The crude product was purified by Prep-HPLC with the following conditions (Xselect CSH C18 OBD Column 30*150 mm 5 um; Mobile Phase A: Water (0.05% TFA), Mobile Phase B: ACN; Flow rate: 60 mL/min; Gradient: 23% B to 34% B in 7 min, Wave Length: 220 nm; RT1 (min): 6.47) to afford the title compound (150 mg, 48.8%) as a light yellow solid. MS-ESI: 481 (M+1). $^1$H NMR (400 MHz, MeOD-$d_4$) δ 8.87 (d, J=4.8 Hz, 1H), 8.26 (s, 1H), 7.77 (dd, J=4.8, 1.6 Hz, 1H), 7.37-7.25 (m, 5H), 4.39-4.16 (m, 4H), 3.86-3.81 (m, 2H), 3.80-3.71 (m, 4H), 3.31-3.17 (m, 6H), 2.81-2.68 (m, 1H), 2.29-2.15 (m, 1H).

Step 5: (2-((((2S,4R)-1-(morpholinosulfonyl)-4-phenylpyrrolidin-2-yl)methyl)sulfonyl)pyridin-4-yl)methanamine and (2-((((2R,4S)-1-(morpholinosulfonyl)-4-phenylpyrrolidin-2-yl)methyl)sulfonyl)pyridin-4-yl)methanamine. Cis-(2-(((1-(morpholinosulfonyl)-4-phenylpyrrolidin-2-yl)methyl)sulfonyl)pyridin-4-yl)methanamine 2,2,2-trifluoroacetate (120 mg, 0.202 mmol, 1 equiv) was separated with the following conditions: CHIRAL ART Cellulose-SB, 2*25 cm, 5 um; Mobile Phase A: Hex (0.2% DEA), Mobile Phase B: EtOH:DCM=1:1; Flow rate: 20 mL/min; Gradient: 40% B to 40% B in 17 min; Wave Length: 220/254 nm; RT1 (min): 8.82; RT2 (min): 14.47; Sample Solvent: EtOH:DCM=1:1; Injection Volume: 0.55 mL; Number Of Runs: 4 to afford (2-((((2S,4R)-1-(morpholinosulfonyl)-4-phenylpyrrolidin-2-yl)methyl)sulfonyl)pyridin-4-yl)methanamine (34 mg, 35%) and (2-((((2R,4S)-1-(morpholinosulfonyl)-4-phenylpyrrolidin-2-yl)methyl)sulfonyl)pyridin-4-yl)methanamine (30.4 mg, 31.3%) as a yellow solid.

PH-AOV-0195A: $^1$H NMR (400 MHz, MeOD-$d_4$) δ 8.72 (d, J=5.2 Hz, 1H), 8.17 (d, J=0.8 Hz, 1H), 7.70 (dt, J=5.2, 0.8 Hz, 1H), 7.38-7.24 (m, 5H), 4.33-4.24 (m, 1H), 4.19 (dd, J=14.4, 2.8 Hz, 1H), 3.99 (s, 2H), 3.96-3.64 (m, 6H), 3.31-3.14 (m, 6H), 2.77-2.66 (m, 1H), 2.22-2.10 (m, 1H).

PH-AOV-0195B: $^1$H NMR (400 MHz, MeOD-$d_4$) δ 8.72 (d, J=5.2 Hz, 1H), 8.17 (d, J=0.8 Hz, 1H), 7.70 (dt, J=5.2, 0.8 Hz, 1H), 7.38-7.24 (m, 5H), 4.33-4.24 (m, 1H), 4.19 (dd, J=14.4, 2.8 Hz, 1H), 3.99 (s, 2H), 3.96-3.64 (m, 6H), 3.31-3.14 (m, 6H), 2.77-2.66 (m, 1H), 2.22-2.10 (m, 1H).

Examples in Table 18 below were prepared using similar conditions as described in PH-AOV-0195 from appropriate starting materials.

TABLE 15

| Example | Structure | Name | Data | Prep Info |
|---|---|---|---|---|
| AOV-0196 | 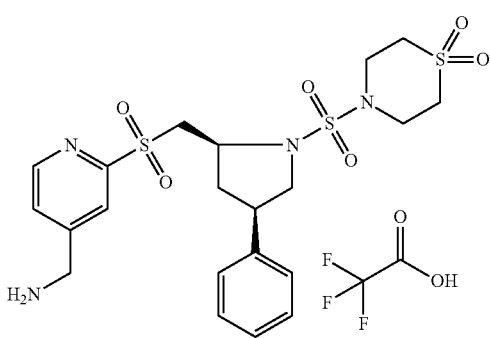 cis racemic | cis-4-((2-(((4-(Aminomethyl)pyridin-2-yl)sulfonyl)methyl)-4-phenylpyrrolidin-1-yl)sulfonyl)thiomorpholine 1,1-dioxide 2,2,2-trifluoroacetate | MS-ESI: 529 (M + 1) | Xselect CSH C18 OBD Column 30 * 150 mm 5 μm, n; Water (0.05% TFA) and ACN (19% ACN to 31% ACN in 7 min) |
| AOV-0196A | 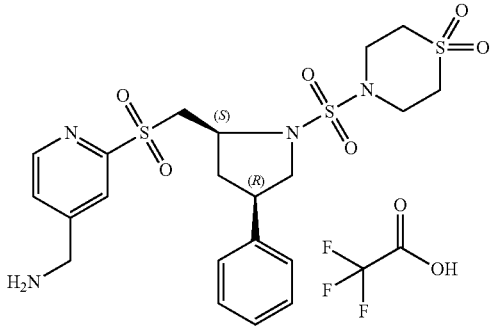 unconfirmed | 4-(((2S,4R)-2-(((4-(aminomethyl)pyridin-2-yl)sulfonyl)methyl)-4-phenylpyrrolidin-1-yl)sulfonyl)thiomorpholine 1,1-dioxide 2,2,2-trifluoroacetate | MS-ESI: 529 (M + 1) | CHIRALPAK IG, 2 * 25 cm, 5 μm; Hex (0.5% 2M NH$_3$—MeOH) and EtOH: DCM = 1:1 (60% B to 60% B in 30 min) |

TABLE 15-continued

| Example | Structure | Name | Data | Prep Info |
|---|---|---|---|---|
| AOV-0196B | *(unconfirmed)* | 4-(((2R,4S)-2-(((4-(aminomethyl)pyridin-2-yl)sulfonyl)methyl)-4-phenylpyrrolidin-1-yl)sulfonyl)thiomorpholine 1,1-dioxide 2,2,2-trifluoroacetate | MS-ESI: 529 (M + 1) | CHIRALPAK IG, 2 * 25 cm, 5 µm; Hex (0.5% 2M NH₃—MeOH) and EtOH: DCM = 1:1 (60% B to 60% B in 30 min) |
| AOV-0203 | *cis racemic* | cis-(2-(((4-(2-fluorophenyl)-1-(morpholinosulfonyl)pyrrolidin-2-yl)methyl)sulfonyl)pyridin-4-yl)methanamine 2,2,2-trifluoroacetate | MS-ESI: 499 (M + 1) | Xselect CSH C18 OBD Column 30 * 150 mm 5 µm, n; Water (0.05% TFA) and ACN (20% B to 32% B in 7 min) |
| AOV-0207 | *cis racemic* | cis-(5-(((4-(2-Fluorophenyl)-1-(morpholinosulfonyl)pyrrolidin-2-yl)methyl)sulfonyl)thiophen-2-yl)methanamine 2,2,2-trifluoroacetate | MS-ESI: 504 (M + 1) | Xselect CSH C18 OBD Column 30 * 150 mm 5 µm, Water (0.05% TFA) and ACN (23% B to 35% B in 7 min) |
| AOV-0204 | 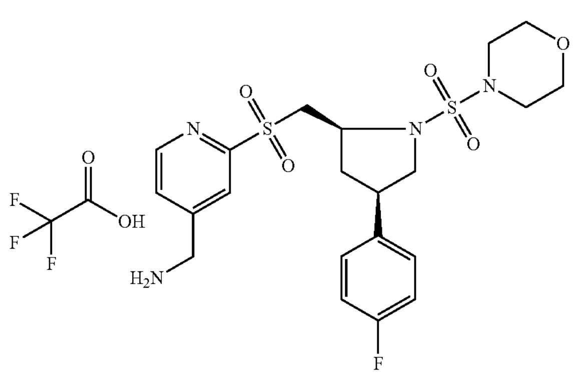 | cis-(2-(((4-(4-fluorophenyl)-1-(morpholinosulfonyl)pyrrolidin-2-yl)methyl)sulfonyl)pyridin-4-yl)methanamine 2,2,2-trifluoroacetate | MS-ESI: 499 (M + 1) | Xselect CSH C18 OBD Column 30 * 150 mm 5 µm; Water (0.05% TFA), ACN (22% B to 36% B in 7 min) |

TABLE 15-continued

| Example | Structure | Name | Data | Prep Info |
|---|---|---|---|---|
| AOV-0205 | 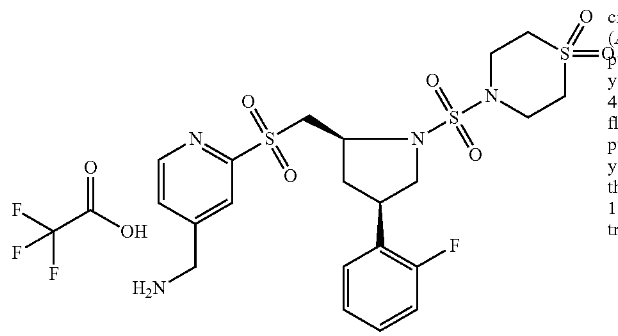 | cis- 4-((2-(((4-(Aminomethyl)pyridin-2-yl)sulfonyl)methyl)-4-(2-fluorophenyl)pyrrolidin-1-yl)sulfonyl)thiomorpholine 1,1-dioxide 2,2,2-trifluoroacetate | MS-ESI: 547 (M + 1) | Xselect CSH C18 OBD Column 30*150 mm 5 µm; Water (0.05% TFA) and ACN (21% ACN to 32% ACN in 7 min) |
| AOV-0209 | 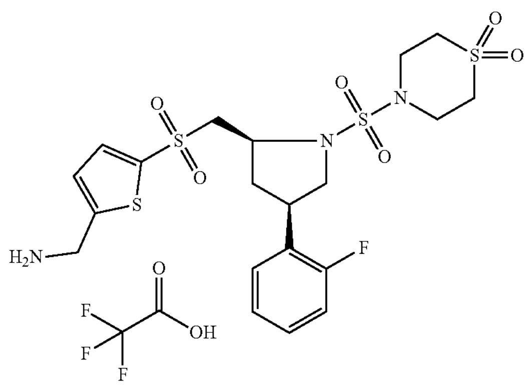 | cis-4-((2-(((5-(Aminomethyl)thiophen-2-yl)sulfonyl)methyl)-4-(2-fluorophenyl)pyrrolidin-1-yl)sulfonyl)thiomorpholine 1,1-dioxide 2,2,2-trifluoroacetate | MS-ESI: 552 (M + 1) | Xselect CSH C18 OBD Column 30 * 150 mm 5 µm; Water (0.05% TFA) and ACN (22% ACN to 36% ACN in 7 min) |
| AOV-0208 | 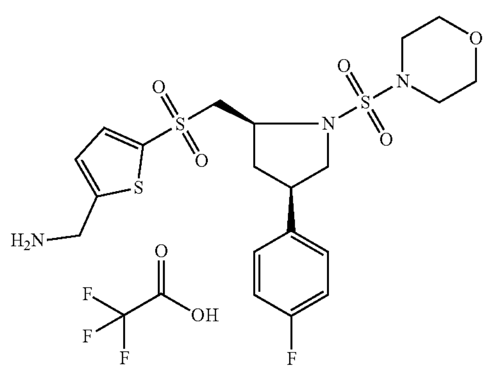 | cis- (5-(((4-(4-Fluorophenyl)-1-(morpholinosulfonyl)pyrrolidin-2-yl)methyl)sulfonyl)thiophen-2-yl)methanamine 2,2,2-trifluoroacetate | MS-ESI: 504 (M + 1) | Xselect CSH C18 OBD Column 30 * 150 mm 5 µm; Water (0.05% TFA) and ACN (25% ACN to 35% ACN in 7 min) |
| AOV-0223 | 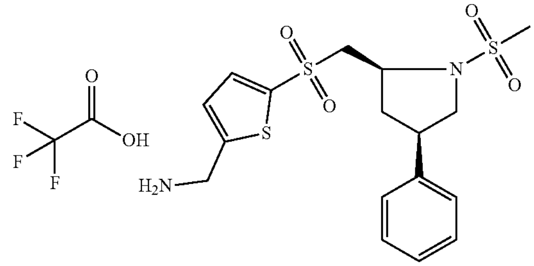 | cis- (5-(((1-(Methylsulfonyl)-4-phenylpyrrolidin-2-yl)methyl)sulfonyl)thiophen-2-yl)methanamine 2,2,2-trifluoroacetate | MS-ESI: 415 (M + 1) | Xselect CSH C18 OBD Column 30 * 150 mm 5 µm; Water (0.05% TFA) and ACN (17% ACN to 27% ACN in 9 min) |

TABLE 15-continued

| Example | Structure | Name | Data | Prep Info |
|---|---|---|---|---|
| AOV-0223T | 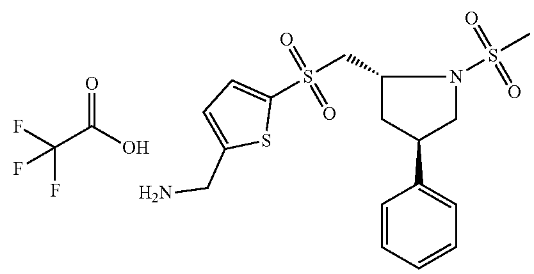 | trans- (5-(((1-(Methylsulfonyl)-4-phenylpyrrolidin-2-yl)methyl)sulfonyl)thiophen-2-yl)methanamine 2,2,2-trifluoroacetate | MS-ESI: 415 (M + 1) | Xselect CSH C18 OBD Column 30 * 150 mm 5 μm; Water (0.05% TFA) and ACN (17% ACN to 27% ACN in 9 min) |
| AOV-0206 | 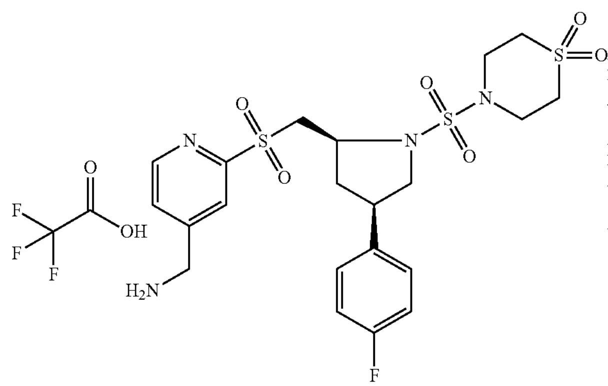 | cis-4-((2-(((4-(Aminomethyl)pyridin-2-yl)sulfonyl)methyl)-4-(4-fluorophenyl)pyrrolidin-1-yl)sulfonyl)thiomorpholine 1,1-dioxide 2,2,2-trifluoroacetate | MS-ESI: 547 (M + 1) | Xselect CSH C18 OBD Column 30 * 150 mm 5 μm; Water (0.05% TFA) and ACN (21% ACN to 33% ACN in 7 min) |
| AOV-0210 | 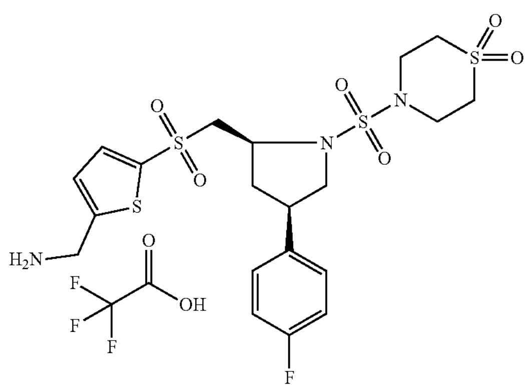 | cis-4-((2-(((5-(Aminomethyl)thiophen-2-yl)sulfonyl)methyl)-4-(4-fluorophenyl)pyrrolidin-1-yl)sulfonyl)thiomorpholine 1,1-dioxide 2,2,2-trifluoroacetate | MS-ESI: 552 (M + 1) | Xselect CSH C18 OBD Column 30 * 150 mm 5 μm; Water (0.05% TFA) and ACN (22% ACN to 35% ACN in 7 min) |
| AOV-0219 | 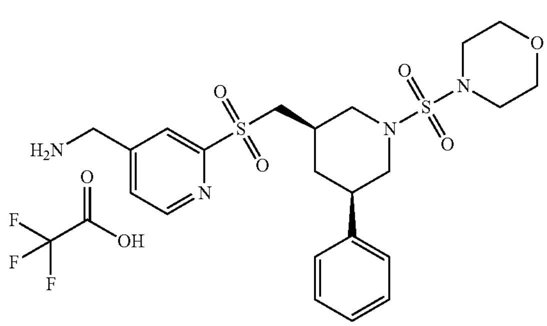 | cis- (2-(((1-(Morpholinosulfonyl)-5-phenylpiperidin-3-yl)methyl)sulfonyl)pyridin-4-yl)methanamine 2,2,2-trifluoroacetate | MS-ESI: 495 (M + 1) | Xselect CSH C18 OBD Column 30 * 150 mm 5 μm; Water (0.05% TFA) and ACN (20% ACN to 31% ACN in 8 min) |

TABLE 15-continued

| Example | Structure | Name | Data | Prep Info |
|---|---|---|---|---|
| AOV-0219T | 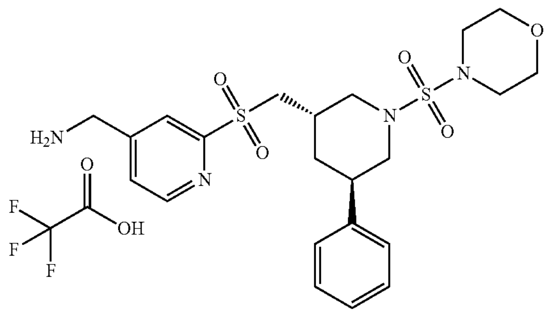 | trans- (2-(((1-(Morpholinosulfonyl)-5-phenylpiperidin-3-yl)methyl)sulfonyl)pyridin-4-yl)methanamine 2,2,2-trifluoroacetate | MS-ESI: 495 (M + 1) | Xselect CSH C18 OBD Column 30 * 150 mm 5 µm; Water (0.05% TFA) and ACN (21% ACN to 31% ACN in 7 min) |
| AOV-0222 | 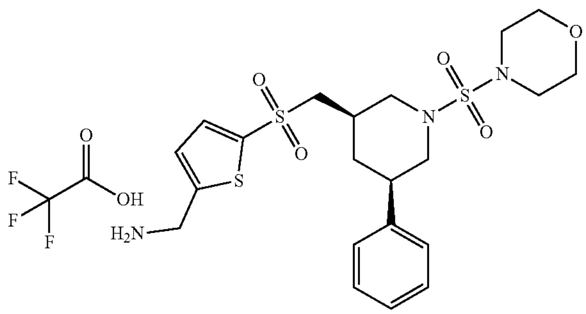 | cis-(5-(((1-(Morpholinosulfonyl)-5-phenylpiperidin-3-yl)methyl)sulfonyl)thiophen-2-yl)methanamine 2,2,2-trifluoroacetate | MS-ESI: 500 (M + 1) | Xselect CSH C18 OBD Column 30 * 150 mm 5 µm; Water (0.05% TFA) and ACN (22% ACN to 35% ACN in 7 min) |
| AOV-0222T | 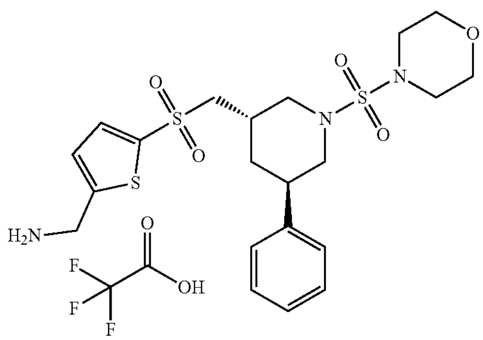 | trans- (5-(((1-(Morpholinosulfonyl)-5-phenylpiperidin-3-yl)methyl)sulfonyl)thiophen-2-yl)methanamine 2,2,2-trifluoroacetate | MS-ESI: 500 (M + 1) | Xselect CSH C18 OBD Column 30 * 150 mm 5 µm; Water (0.05% TFA) and ACN (22% ACN to 35% ACN in 7 min) |
| AOV-0230 | 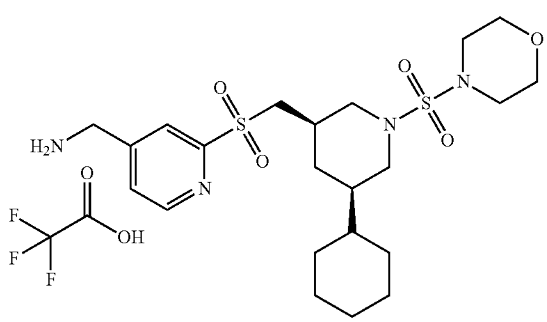 | cis- (2-(((5-Cyclohexyl-1-(morpholinosulfonyl)piperidin-3-yl)methyl)sulfonyl)pyridin-4-yl)methanamine 2,2,2-trifluoroacetate | MS-ESI: 501 (M + 1) | Xselect CSH C18 OBD Column 30 * 150 mm 5 µm; Water (0.05% TFA) and ACN (22% ACN to 35% ACN in 10 min) |
| AOV-0230T | 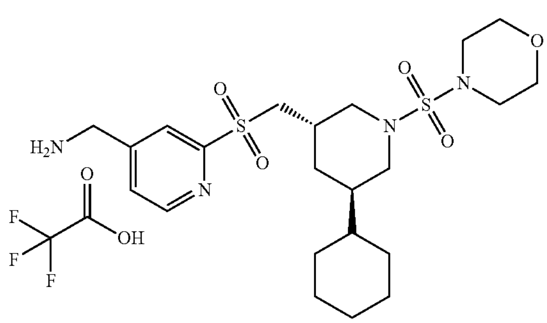 | trans- (2-(((5-Cyclohexyl-1-(morpholinosulfonyl)piperidin-3-yl)methyl)sulfonyl)pyridin-4-yl)methanamine 2,2,2-trifluoroacetate | MS-ESI: 501 (M + 1) | Xselect CSH C18 OBD Column 30 * 150 mm 5 µm; Water (0.05% TFA) and ACN (22% ACN to 35% ACN in 10 min) |

TABLE 15-continued

| Example | Structure | Name | Data | Prep Info |
|---|---|---|---|---|
| AOV-0234 | 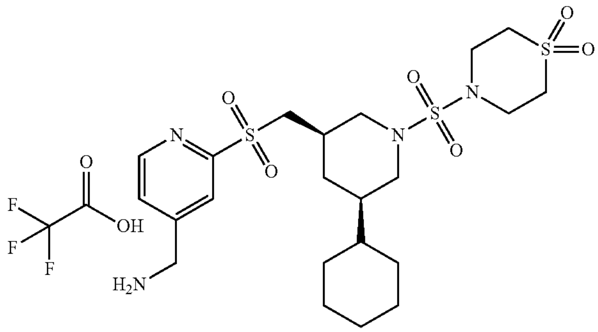 | cis-4-((3-(((4-(Aminomethyl)pyridin-2-yl)sulfonyl)methyl)-5-cyclohexylpiperidin-1-yl)sulfonyl)thiomorpholine 1,1-dioxide 2,2,2-trifluoroacetate | MS-ESI: 549 (M + 1) | Sunfire prep C18 column, 30 * 150 mm, 5 μm; Water (0.05% TFA) and ACN (15% ACN to 45% ACN in 7 min) |
| AOV-0234T | 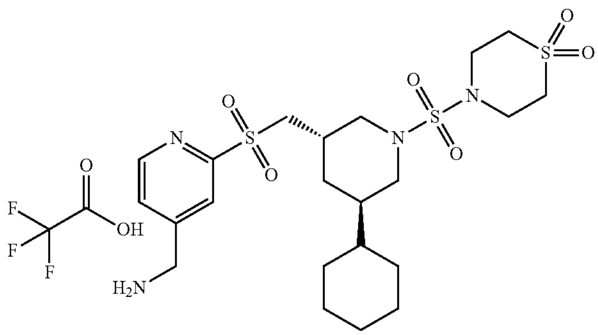 | trans-4-((3-(((4-(Aminomethyl)pyridin-2-yl)sulfonyl)methyl)-5-cyclohexylpiperidin-1-yl)sulfonyl)thiomorpholine 1,1-dioxide 2,2,2-trifluoroacetate | MS-ESI: 549 (M + 1) | Sunfire prep C18 column, 30 * 150 mm, 5 μm; Water (0.05% TFA) and ACN (15% ACN to 45% ACN in 7 min) |
| AOV-0260 | 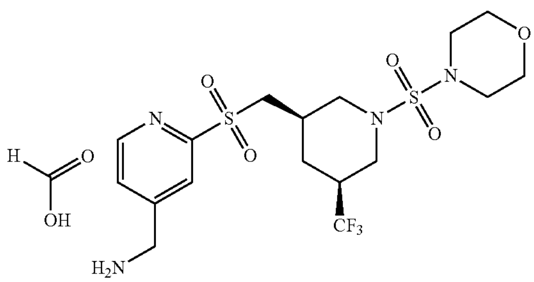 | cis- (2-(((1-(Morpholinosulfonyl)-5-(trifluoromethyl)piperidin-3-yl)methyl)sulfonyl)pyridin-4-yl)methanamine formate | MS-ESI: 487 (M + 1) | SunFire Prep C18 OBD Column, 19 * 150 mm, 5 μm; Water (0.1% FA) and ACN (23% ACN to 50% ACN in 6 min) |
| AOV-0260T | 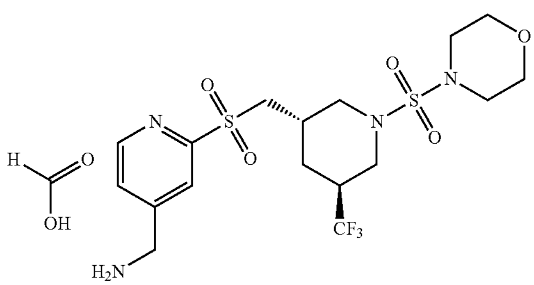 | trans- (2-(((1-(Morpholinosulfonyl)-5-(trifluoromethyl)piperidin-3-yl)methyl)sulfonyl)pyridin-4-yl)methanamine formate | MS-ESI: 487 (M + 1) | SunFire Prep C18 OBD Column, 19 * 150 mm, 5 μm; Water (0.1% FA) and ACN (23% ACN to 50% ACN in 6 min) |
| AOV-0238RAC | 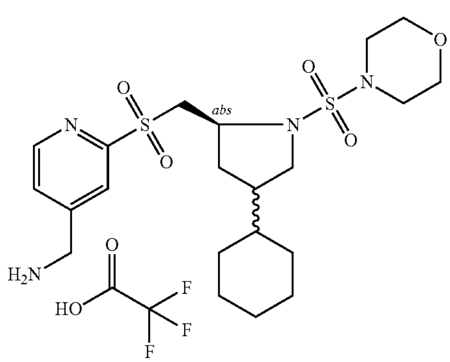 | (2-((((2S)-4-Cyclohexyl-1-(morpholinosulfonyl)pyrrolidin-2-yl)methyl)sulfonyl)pyridin-4-yl)methanamine 2,2,2-trifluoroacetate | MS-ESI: 487 (M + 1) | SunFire Prep C18 OBD Column, 19 * 150 mm, 5 μm; Water (0.05% TFA) and ACN (20% ACN to 40% ACN in 7 min) |

TABLE 15-continued

| Example | Structure | Name | Data | Prep Info |
|---|---|---|---|---|
| AOV-0238 | 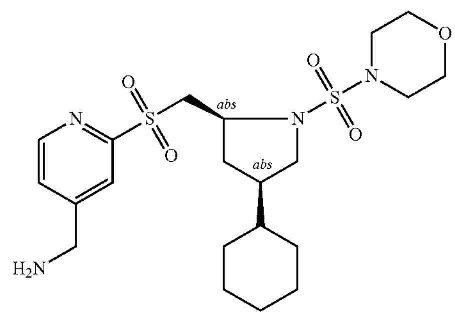 [SMILES: NCc1ccnc(S(=O)(=O)C[C@@H]2C[C@H](C3CCCCC3)CN2S(=O)(=O)N2CCOCC2)c1] | cis- (2-(((4-Cyclohexyl-1-(morpholinosulfonyl)pyrrolidin-2-yl)methyl)sulfonyl)pyridin-4-yl)methanamine | MS-ESI: 487 (M + 1) | Column: CHIRAL-Amylose-SB 20 * 250 mm, 5 μm; Mobile Phase A: EtOH, Mobile Phase B: Hex: DCM = 3:1 (0.5% 2M NH$_3$—MeOH); Gradient: 80% B to 80% B in 24.5 min. |
| AOV-0238T | 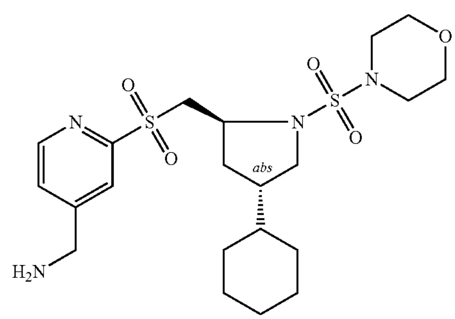 [SMILES: NCc1ccnc(S(=O)(=O)C[C@@H]2C[C@@H](C3CCCCC3)CN2S(=O)(=O)N2CCOCC2)c1] | trans- (2-(((4-Cyclohexyl-1-(morpholinosulfonyl)pyrrolidin-2-yl)methyl)sulfonyl)pyridin-4-yl)methanamine | MS-ESI: 487 (M + 1) | Column: CHIRAL-Amylose-SB 20 * 250 mm, 5 μm; Mobile Phase A: EtOH, Mobile Phase B: Hex: DCM = 3:1 (0.5% 2M NH$_3$—MeOH); Gradient: 80% B to 80% B in 24.5 min. |
| AOV-0262 | 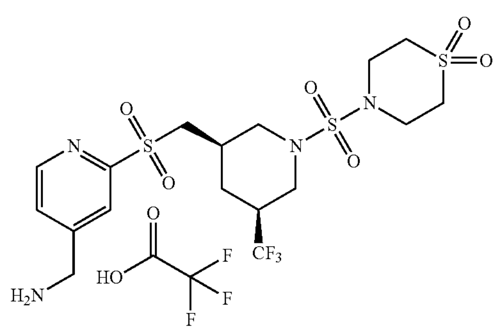 | cis-4-((3-(((4-(Aminomethyl)pyridin-2-yl)sulfonyl)methyl)-5-(trifluoromethyl)piperidin-1-yl)sulfonyl)thiomorpholine 1,1-dioxide 2,2,2-trifluoroacetate | MS-ESI: 535 (M + 1) | SunFire Prep OBD C18 Column, 30 * 150 mm, 5 μm; Water (0.05% TFA), ACN (Gradient: 30% B to 50% B in 7 min). |
| AOV-0242RAC | | 4-(((2S)-2-(((4-(aminomethyl)pyridin-2-yl)sulfonyl)methyl)-4-cyclohexylpyrrolidin-1-yl)sulfonyl)thiomorpholine 1,1-dioxide formate | MS-ESI: 535 (M + 1) | SunFire Prep C18 OBD Column, 19 * 150 mm, 5 μm; Water (0.1% FA) and ACN (20% ACN to 55% ACN in 8 min) | h. Synthesis of pH-AOV-0215 (Method B)

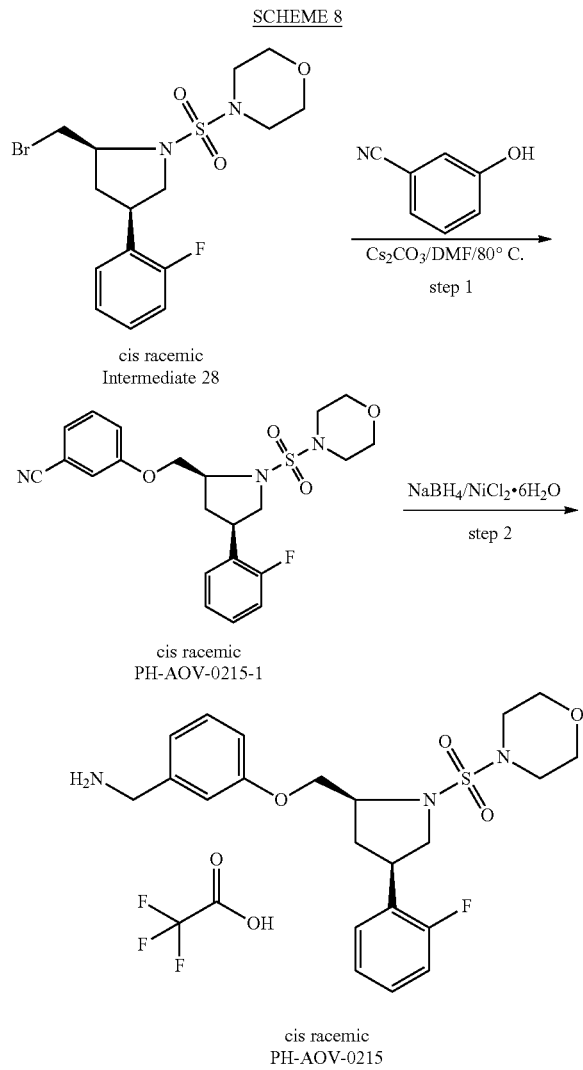

SCHEME 8 cis racemic
Intermediate 28 cis racemic
PH-AOV-0215-1 cis racemic
PH-AOV-0215

Step 1: cis-3-((4-(2-Fluorophenyl)-1-(morpholinosulfonyl)pyrrolidin-2-yl)methoxy)benzonitrile. To a stirred solution 4-((2-(bromomethyl)-4-(2-fluorophenyl)pyrrolidin-1-yl)sulfonyl)morpholine (500 mg, 1.23 mmol, 1.0 equiv) in DMF (5 mL) were added 3-hydroxybenzonitrile (146 mg, 1.23 mmol, 1.0 equiv) and $Cs_2CO_3$ (800 mg, 2.46 mmol, 2.0 equiv). The mixture was stirred overnight at 80° C. The reaction mixture was quenched with $H_2O$ (10 mL) and extracted with EtOAc (3×50 mL). The organic layers were dried over anhydrous $Na_2SO_4$ and concentrated under vacuum. The residue was eluted from silica gel with PE/EtOAc (4:1) to afford the title compound as colorless oil. MS-ESI: 446 (M+1).

Step 2: cis-(3-((4-(2-Fluorophenyl)-1-(morpholinosulfonyl)pyrrolidin-2-2,2,2-trifluoroacetate. To a stirred solution of cis-3-((4-(2-Fluorophenyl)-1-(morpholinosulfonyl)pyrrolidin-2-yl)methoxy)benzonitrile (170 mg, 0.38 mmol, 1.0 equiv) in MeOH (10 mL) were added $NaBH_4$ (28.9 mg, 0.76 mmol, 2.00 equiv) and $NiCl_2 \cdot 6H_2O$ (181 mg, 0.76 mmol, 2.0 equiv). The reaction mixture was stirred overnight at room temperature. The reaction was quenched with sat. $NH_4C_1$ (aq.) and extracted with EtOAc (3×50 mL). The residue was purified by Prep-TLC (PE/EtOAc: 2:1) and Prep-HPLC with the following conditions: Xselect CSH C18 OBD Column 30*150 mm 5um, mobile phase, Water (0.05% TFA) and ACN (26% ACN up to 36% in 7 min); Detector, UV 220/254 nm. This resulted in 7 mg (4.07%) of the title compound as a white solid. MS-ESI: 450 (M+1). $^1$H NMR (400 MHz, MeOD-$d_4$) δ 8.14 (br s, 2H), 7.45 (t, J=7.0 Hz, 1H), 7.40-7.30 (m, 2H), 7.26-7.17 (m, 2H), 7.13-7.08 (m, 1H), 7.07-6.97 (m, 2H), 4.33-4.24 (m, 1H), 4.23-4.17 (m, 1H), 4.16-4.10 (m, 1H), 4.06-3.98 (m, 2H), 3.91-3.83 (m, 1H), 3.60 (t, J=4.6 Hz, 4H), 3.58-3.50 (m, 1H), 3.31-3.23 (m, 1H), 3.14 (t, J=4.4H, 4H), 2.69-2.57 (m, 1H), 2.18-2.06 (m, 1H).

Examples in Table 19 were prepared using similar conditions as described in PH-AOV-0215 from appropriate starting materials.

TABLE 16

| Example | Structure | Name | Data | Prep Info |
|---|---|---|---|---|
| AOV-0216 | 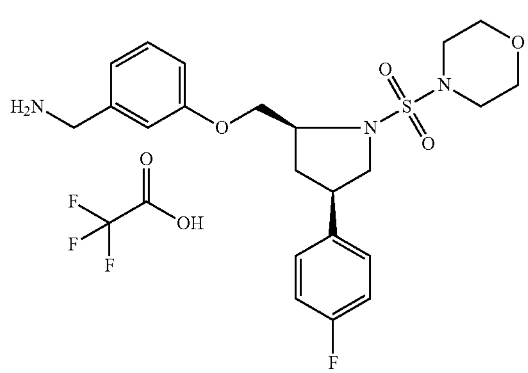 | cis-(3-((4-(4-Fluorophenyl)-1-(morpholinosulfonyl)pyrrolidin-2-yl)methoxy)phenyl)methanamine 2,2,2-trifluoroacetate | MS-ESI: 450 (M + 1) | Xselect CSH C18 OBD Column 30 * 150 mm 5 µm; Mobile Phase A: Water (0.05% TFA) and ACN (26% ACN to 36% ACN in 7 min) |

TABLE 16-continued

| Example | Structure | Name | Data | Prep Info |
| --- | --- | --- | --- | --- |
| AOV-0217 | 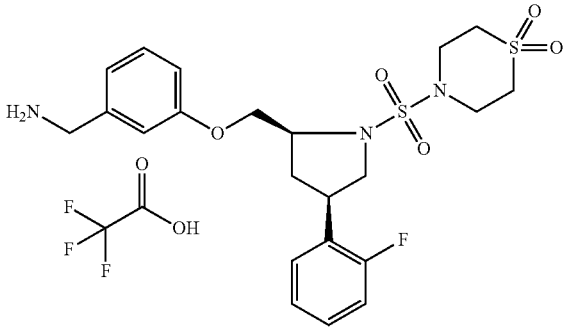 | cis- 4-((2-((3-(Aminomethyl)phenoxy)methyl)-4-(2-fluorophenyl)pyrrolidin-1-yl)sulfonyl)thiomorpholine 1,1-dioxide 2,2,2-trifluoroacetate | MS-ESI: 498 (M + 1) | Xselect CSH C18 OBD Column 30 * 150 mm 5 μm; Water (0.05% TFA) and ACN (25% ACN to 36% ACN in 7 min) |
| AOV-0218 | 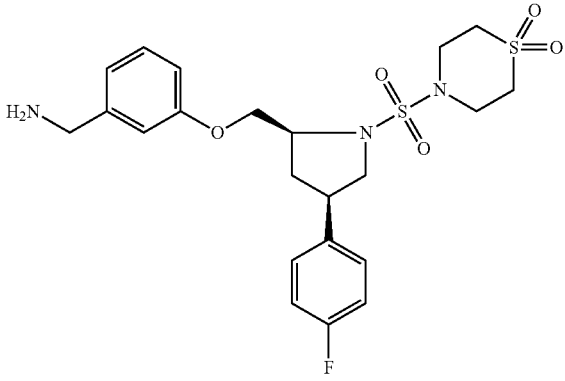 [SMILES: NCc1cccc(OC[C@@H]2C[C@H](c3ccc(F)cc3)CN2S(=O)(=O)N2CCS(=O)(=O)CC2)c1] | cis-4-((2-((3-(Aminomethyl)phenoxy)methyl)-4-(4-fluorophenyl)pyrrolidin-1-yl)sulfonyl)thiomorpholine 1,1-dioxide | MS-ESI: 498 (M + 1) | XBridge Prep OBD C18 Column, 30 * 150 mm, 5 μm; Water (10 mmol/L NH$_4$HCO$_3$) and CAN (25% ACN to 55% ACN in 7 min) |
| AOV-0221 | 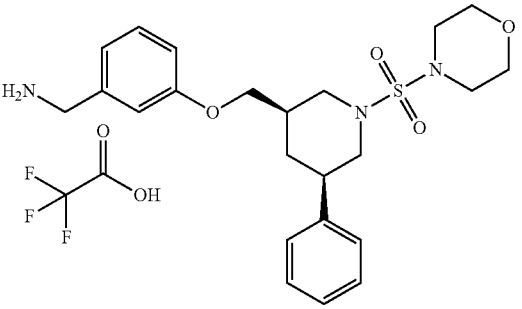 | cis- (3-((1-(Morpholinosulfonyl)-5-phenylpiperidin-3-yl)methoxy)phenyl)methanamine 2,2,2-trifluoroacetate | MS-ESI: 446 (M + 1) | Xselect CSH C18 OBD Column 30*150 mm 5 μm; Water (0.05% TFA) and ACN (28% ACN to 38% ACN in 7 min) |
| AOV-0221T | 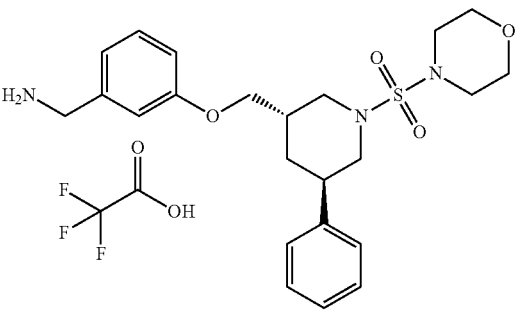 | trans-(3-((1-(Morpholinosulfonyl)-5-phenylpiperidin-3-yl)methoxy)phenyl)methanamine 2,2,2-trifluoroacetate | MS-ESI: 446 (M + 1) | Xselect CSH C18 OBD Column 30 * 150 mm 5 μm; Water (0.05% TFA) and ACN (25% ACN to 40% ACN in 7 min) |

TABLE 16-continued

| Example | Structure | Name | Data | Prep Info |
|---|---|---|---|---|
| AOV-0231 | 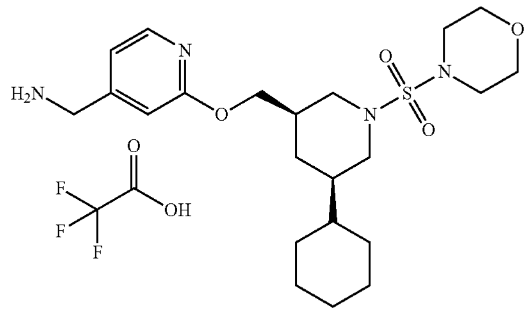 | cis- (2-((5-Cyclohexyl-1-(morpholinosulfonyl)piperidin-3-yl)methoxy)pyridin-4-yl)methanamine 2,2,2-trifluoroacetate | MS-ESI: 453 (M + 1) | Sunfire prep C18 column, 30 * 150 mm, 5 μm; Water (0.05% TFA) and ACN (30% ACN to 40% ACN in 8 min) |
| AOV-0231T | 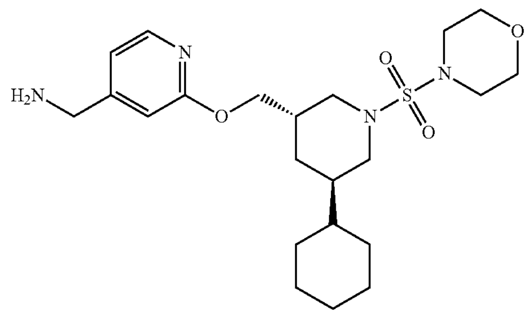 [SMILES: NCc1ccnc(OC[C@H]2C[C@H](C3CCCCC3)CN(S(=O)(=O)N3CCOCC3)C2)c1] | trans- (2-(((3S,5R)-5-cyclohexyl-1-(morpholinosulfonyl)piperidin-3-yl)methoxy)pyridin-4-yl)methanamine | MS-ESI: 453 (M + 1) | Sunfire prep C18 column, 30 * 150 mm, 5 μm; Water (10 Mm $NH_4HCO_3$) and ACN (30% ACN to 40% ACN in 8 min) |
| AOV-0235 | 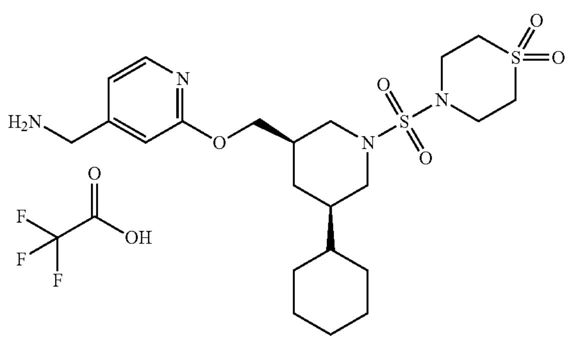 | cis-4-((3-(((4-(Aminomethyl)pyridin-2-yl)oxy)methyl)-5-cyclohexylpiperidin-1-yl)sulfonyl)thiomorpholine 1,1-dioxide 2,2,2-trifluoroacetate | MS-ESI: 501 (M + 1) | SunFire Prep C18 OBD Column, 19 * 150 mm, 5 μm; Water (0.05% TFA) and ACN (35% ACN to 55% ACN in 5.32 min) |
| AOV-0235T | 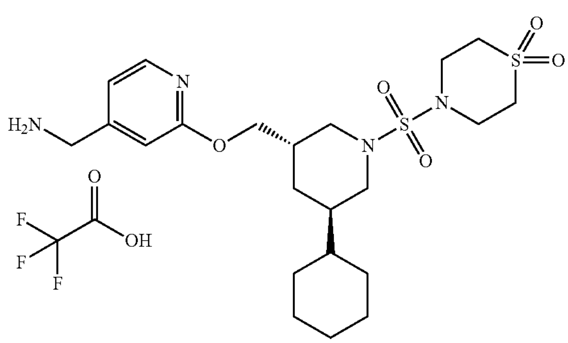 | trans-4-((3-(((4-(Aminomethyl)pyridin-2-yl)oxy)methyl)-5-cyclohexylpiperidin-1-yl)sulfonyl)thiomorpholine 1,1-dioxide 2,2,2-trifluoroacetate | MS-ESI: 501 (M + 1) | SunFire Prep C18 OBD Column, 19 * 150 mm, 5 μm; Water (0.05% TFA) and ACN (62% ACN to 80% ACN in 6 min) |
| AOV-0261 | 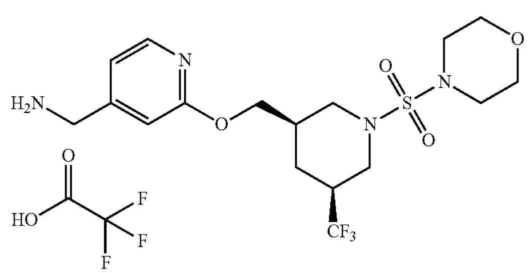 | cis- (2-((-1-(Morpholinosulfonyl)-5-(trifluoromethyl)piperidin-3-yl)methoxy)pyridin-4-yl)methanamine | MS-ESI: 439 (M + 1) | SunFire Prep C18 OBD Column, 19 * 150 mm, 5 μm; Water (0.05% TFA), ACN (20% ACN to 40% ACN in 6 min) |

TABLE 16-continued

| Example | Structure | Name | Data | Prep Info |
|---|---|---|---|---|
| AOV-0261T | 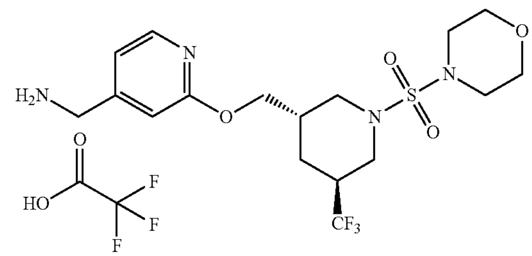 | trans-(2-((-1-(Morpholinosulfonyl)-5-(trifluoromethyl)piperidin-3-yl)methoxy)pyridin-4-yl)methanamine 2,2,2-trifluoroacetate | MS-ESI: 439 (M + 1) | SunFire Prep C18 OBD Column, 19 * 150 mm, 5 μm; Water (0.05% TFA) and ACN (20% ACN to 40% ACN in 6 min) |
| AOV-0263 | 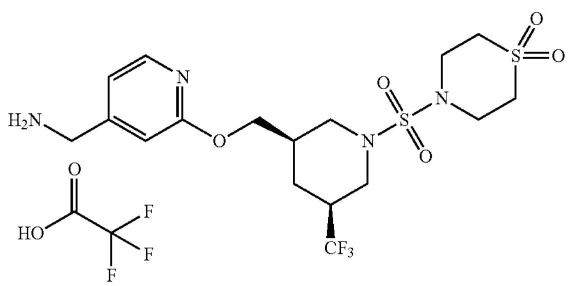 | cis-4-((3-(((4-(Aminomethyl)pyridin-2-yl)oxy)methyl)-5-(trifluoromethyl)piperidin-1-yl)sulfonyl)thiomorpholine 1,1-dioxide 2,2,2-trifluoroacetate | MS-ESI: 487 (M + 1) | SunFire Prep C18 OBD Column, 19 * 150 mm, 5 μm; Water (0.05% TFA) and ACN (23% ACN to 23% ACN in 6.6 min) |
| AOV-0263T | 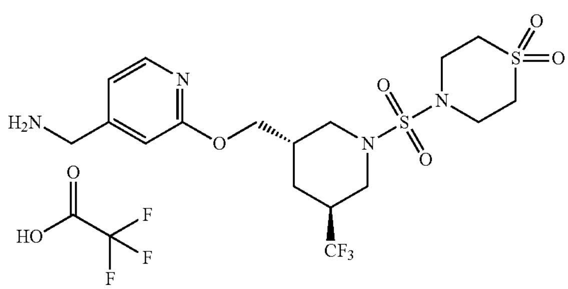 | trans-4-((3-(((4-(Aminomethyl)pyridin-2-yl)oxy)methyl)-5-(trifluoromethyl)piperidin-1-yl)sulfonyl)thiomorpholine 1,1-dioxide 2,2,2-trifluoroacetate | MS-ESI: 487 (M + 1) | SunFire Prep C18 OBD Column, 19 * 150 mm, 5 μm; Water (0.05% TFA) and ACN (23% ACN to 23% ACN in 6.6 min) |
| AOV-0239RAC | 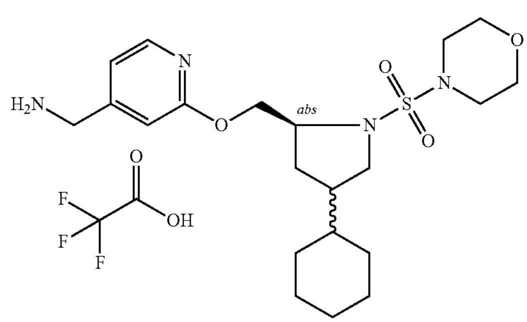 | (2-(((2S)-4-Cyclohexyl-1-(morpholinosulfonyl)pyrrolidin-2-yl)methoxy)pyridin-4-yl)methanamine 2,2,2-trifluoroacetate | MS-ESI: 439 (M + 1) | SunFire Prep C18 OBD Column, 19 * 150 mm, 5 μm; Water (0.05% TFA) and ACN (24% ACN to 45% ACN in 5.8 min) |
| AOV-0239 | 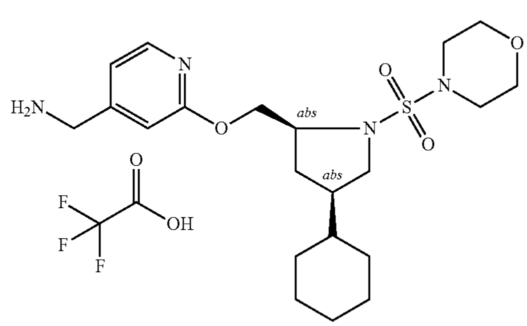 | cis-(2-((4-Cyclohexyl-1-(morpholinosulfonyl)pyrrolidin-2-yl)methoxy)pyridin-4-yl)methanamine 2,2,2-trifluoroacetate | MS-ESI: 439 (M + 1) | Column: CHIRAL-Amylose-SA 20 * 250 mm, 5 μm; Mobile Phase A: EtOH, Mobile Phase B: Hex (0.5% 2M NH$_3$—MeOH); Gradient: 60% B to 60% B in 20 min. |

TABLE 16-continued

| Example | Structure | Name | Data | Prep Info |
| --- | --- | --- | --- | --- |
| AOV-0239T | 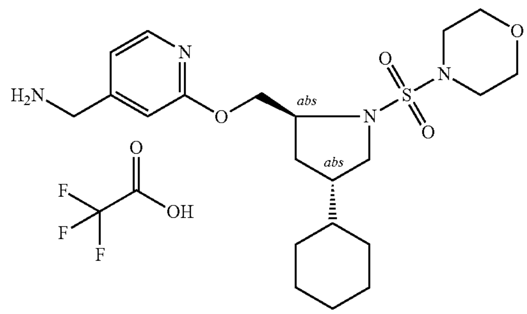 | trans- (2-((4-Cyclohexyl-1-(morpholinosulfonyl) pyrrolidin-2-yl)methoxy) pyridin-4-yl)methanamine 2,2,2-trifluoroacetate | MS-ESI: 439 (M + 1) | CHIRAL-Amylose-SA 20 * 250 mm, 5 μm; Mobile Phase A: EtOH, Mobile Phase B: Hex (0.5% 2M NH₃—MeOH); Flow rate: 20 mL/min; Gradient: 60% B to 60% B in 20 min; |
| AOV-0243RAC | 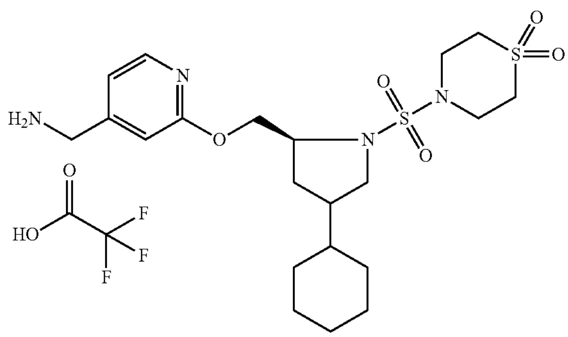 | 4-(((2S)-2-(((4-(aminomethyl) pyridin-2-yl)oxy)methyl)-4-cyclohexylpyrrolidin-1-yl)sulfonyl) thiomorpholine 1,1-dioxide 2,2,2-trifluoroacetate | MS-ESI: 487 (M + 1) | Sun-Fire Prep OBD C18 Column, 30 * 150 mm, 5 μm; Water (0.05% TFA) and ACN; (30% B to 50% B in 7 min) |
| AOV-0243 | 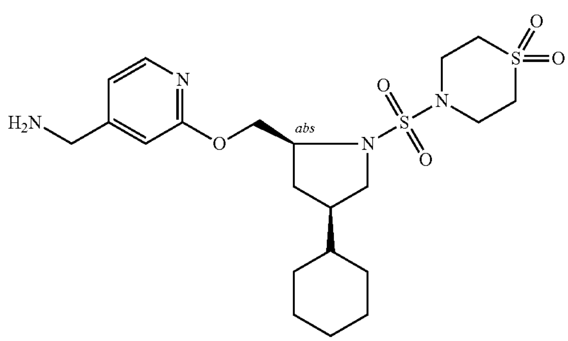 [SMILES: NCc1ccnc(OC[C@@H]2C[C@H](C3CCCCC3)CN2S(=O)(=O)N2CCS(=O)(=O)CC2)c1] | 4-(((2S,4R)-2-(((4-(aminomethyl) pyridin-2-yl)oxy)methyl)-4-cyclohexylpyrrolidin-1-yl)sulfonyl) thiomorpholine 1,1-dioxide | MS-ESI: 487 (M + 1) | CHIRAL ART Cellulose-SB, 20 * 250 mm, 5 μm; Mobile Phase A: EtOH, Mobile Phase B: Hex (0.5% 2M NH₃—MeOH); Gradient: 55% B to 55% B in 35 min |
| AOV-0243T | | -(((2S,4S)-2-(((4-(aminomethyl) pyridin-2-yl)oxy)methyl)-4-cyclohexylpyrrolidin-1-yl)sulfonyl) thiomorpholine 1,1-dioxide | MS-ESI: 487 (M + 1) | CHIRAL ART Cellulose-SB, 20 * 250 mm, 5 μm; Mobile Phase A: EtOH, Mobile Phase B: Hex (0.5% 2M NH₃—MeOH); Gradient: 55% B to 55% B in 35 min | i. Synthesis of pH-AOV-0211 (Method C)

SCHEME 9

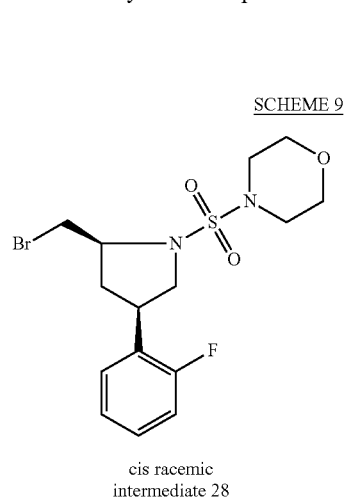

cis racemic
intermediate 28

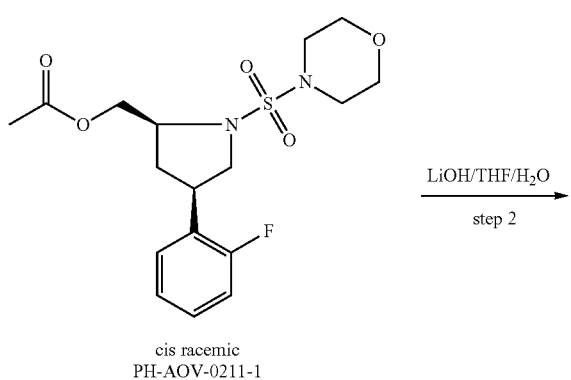

cis racemic
PH-AOV-0211-1

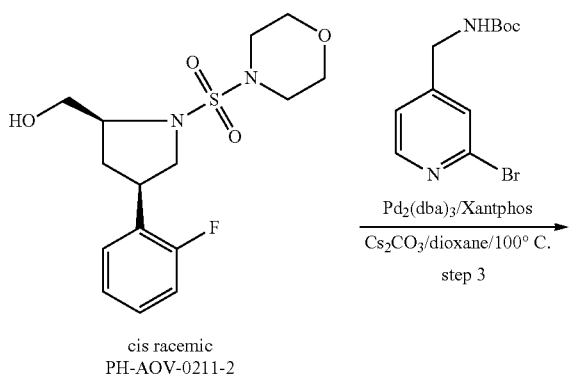

cis racemic
PH-AOV-0211-2

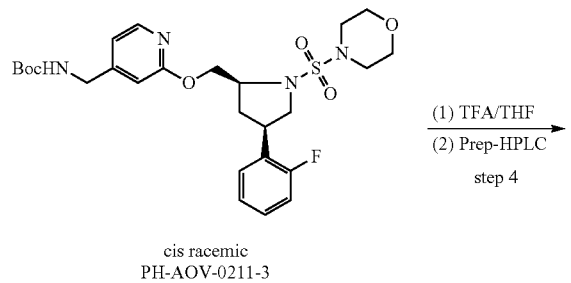

cis racemic
PH-AOV-0211-3

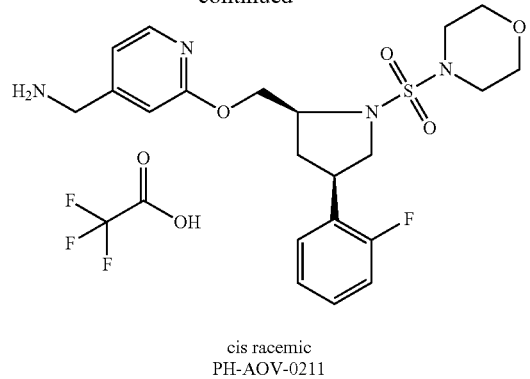

cis racemic
PH-AOV-0211

Step 1: cis-(4-(2-Fluorophenyl)-1-(morpholinosulfonyl) pyrrolidin-2-acetate. To a stirred solution of cis-4-((2-(bromomethyl)-4-(2-fluorophenyl)pyrrolidin-1-yl)sulfonyl) morpholine (500 mg, 1.23 mmol, 1 equiv) in DMF (5 mL) were added potassium acetate (301 mg, 3.07 mmol, 2.5 equiv) in portions at room temperature. The resulting mixture was stirred for 2 h at 100° C. The mixture was allowed to cool down to room temperature. The resulting mixture was diluted with water (50 mL) and extracted with EtOAc (2×50 mL). The combined organic layers were dried over anhydrous $Na_2SO_4$. After filtration, the filtrate was concentrated under vacuum to afford the title compound (400 mg, crude) as brown oil. MS-ESI: 387 (M+1).

Step 2: cis-(4-(2-Fluorophenyl)-1-(morpholinosulfonyl) pyrrolidin-2-yl)methanol. To a stirred solution of cis-(4-(2-fluorophenyl)-1-(morpholinosulfonyl)pyrrolidin-2-yl) methyl acetate (400 mg, crude) in THF (10 mL) and $H_2O$ (2 mL) was added LiOH (49.6 mg, 2.07 mmol, 2 equiv). The resulting mixture was stirred for 2 h at room temperature. The resulting mixture was extracted with EtOAc (2×50 mL). The combined organic layers were washed with $H_2O$ (2×50 mL) and dried over anhydrous $Na_2SO_4$. After filtration, the filtrate was concentrated under vacuum. The residue was purified by Prep-TLC (PE/EtOAc 1:2) to afford the title compound (399 mg, 94%, over two steps) as colorless oil. MS-ESI: 345 (M+1).

Step 3: cis-Tert-butyl ((2-(((4-(2-fluorophenyl)-1-(morpholinosulfonyl)pyrrolidin-2-yl)methoxy)pyridin-4-yl) methul)carbamate. To a stirred solution of cis-(4-(2-fluorophenyl)-1-(morpholinosulfonyl)pyrrolidin-2-yl)methanol (280 mg, mmol, 1 equiv) and tert-butyl ((2-bromopyridin-4-yl)methyl)carbamate (350 mg, 1.22 mmol, 1.5 equiv) in dioxane (7 mL) were added $Pd_2(dba)_3$ (74.5 mg, 0.081 mmol, 0.1 equiv), XantPhos (47 mg, 0.081 mmol, 0.1 equiv) and $Cs_2CO_3$ (530 mg, 1.63 mmol, 2 equiv) in portions at room temperature under nitrogen atmosphere. The resulting mixture was stirred overnight at 100° C. under nitrogen atmosphere. The mixture was allowed to cool down to room temperature. The resulting mixture was filtered and the filter cake was washed with DCM (2×20 mL). The filtrate was concentrated under vacuum. The residue was purified by Prep-TLC (PE/EtOAc 1:1) to afford the title compound (90 mg, 19%) as colorless oil. MS-ESI: 551 (M+1).

Step 4: cis-(2-((4-(2-Fluorophenyl)-1-(morpholinosulfonyl)pyrrolidin-2-yl)methoxy)pyridin-4-yl)methanamine; trifluoroacetic acid. A mixture of cis-Tert-butyl ((2-((4-(2-fluorophenyl)-1-(morpholinosulfonyl)pyrrolidin-2-yl) methoxy)pyridin-4-yl)methyl)carbamate (90 mg, 0.163 mmol, 1 equiv) and TFA (4 mL, 53.9 mmol, 329 equiv) in THF (5 mL) was stirred for 2 h at room temperature. The resulting mixture was concentrated under vacuum. The crude product (37 mg) was purified by Prep-HPLC with the following conditions (Column, Xselect CSH C18 OBD Column 30*150 mm 5 um; mobile phase, Water (0.05% TFA) and ACN (21% ACN up to 31% in 8 min)) to afford the title compound (9.4 mg, 10%) as a white solid. MS-ESI: 451 (M+1).

¹H NMR (400 MHz, DMSO-d6) δ 8.27 (s, 3H), 8.21 (d, J=5.2 Hz, 1H), 7.46-7.42 (m, 1H), 7.35-7.31 (m, 1H), 7.23-7.18 (m, 2H), 7.07-7.16 (m, 1H), 6.94 (s, 1H), 4.49 (dd, J=10.8, 4.4 Hz, 1H), 4.41 (dd, J=10.8, 5.6 Hz, 1H), 4.32-4.30 (m, 1H), 4.07 (q, J=5.2 Hz, 2H), 3.85 (dd, J=10.8, 7.6 Hz, 1H), 3.62-3.56 (m, 4H), 3.28 (t, J=10.8 Hz, 1H), 3.14-3.12 (m, 4H), 2.59-2.33 (m, 2H), 2.11-2.06 (m, 1H).

Examples in Table 20 below were prepared using similar conditions as described in PH-AOV-0211 from appropriate starting materials.

TABLE 17

| Ex | Structure | Name | Data | Prep Info |
|---|---|---|---|---|
| AOV-0212 | 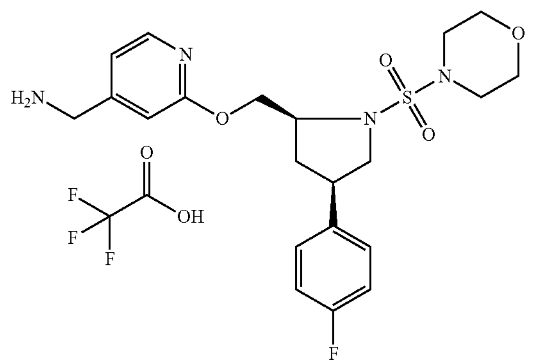 | cis-(2-((4-(4-Fluorophenyl)-1-(morpholinosulfonyl)pyrrolidin-2-yl)methoxy)pyridin-4-yl)methanamine 2,2,2-trifluoroacetate | MS-ESI: 451 (M + 1) | Xselect CSH C18 OBD Column 30 * 150 mm 5 μm; Water (0.05% TFA) and ACN (20% ACN to 34% ACN in 7 min) |
| AOV-0213 | 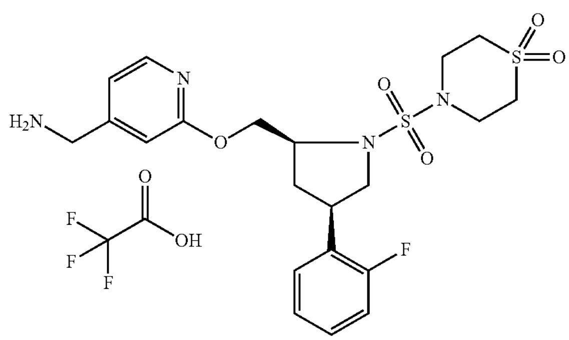 | cis-4-((2-(((4-(Aminomethyl)pyridin-2-yl)oxy)methyl)-4-(2-fluorophenyl)pyrrolidin-1-yl)sulfonyl)thiomorpholine 1,1-dioxide 2,2,2-trifluoroacetate | MS-ESI: 499 (M + 1) | Xselect CSH C18 OBD Column 30 * 150 mm 5 μm; Water (0.05% TFA) and ACN (20% ACN to 30% ACN in 9 min) |
| AOV-0214 | 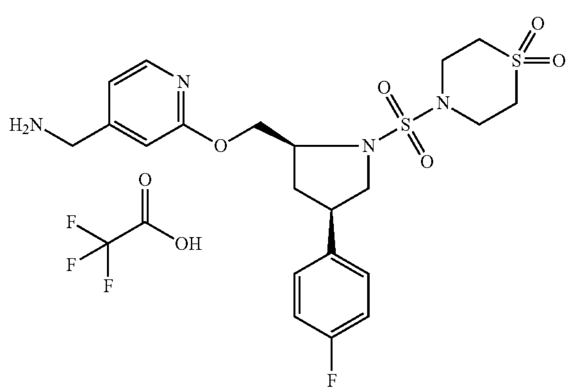 | cis-((2-(((4-(Aminomethyl)pyridin-2-yl)oxy)methyl)-4-(4-fluorophenyl)pyrrolidin-1-yl)sulfonyl)thiomorpholine 1,1-dioxide 2,2,2-trifluoroacetate | MS-ESI: 499 (M + 1) | Xselect CSH C18 OBD Column 30 * 150 mm 5 μm; Water (0.05% TFA) and ACN (22% ACN to 33% ACN in 7 min) |

TABLE 17-continued

| Ex | Structure | Name | Data | Prep Info |
|---|---|---|---|---|
| AOV-0220 | 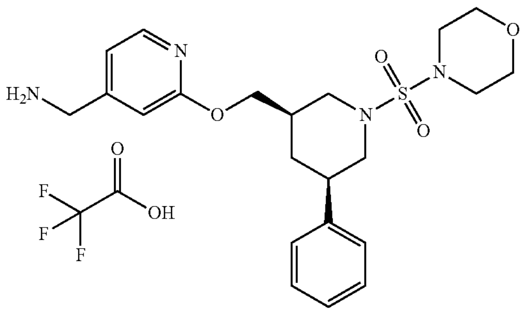 | cis- (2-((1-(Morpholinosulfonyl)-5-phenylpiperidin-3-yl)methoxy)pyridin-4-yl)methanamine 2,2,2-trifluoroacetate | MS-ESI: 447 (M + 1) | Xselect CSH C18 OBD Column 30 * 150 mm 5 µm; Water (0.05% TFA) and ACN (22% ACN to 35% ACN in 7 min) |
| AOV-0220T | | trans-(2-((1-(Morpholinosulfonyl)-5-phenylpiperidin-3-yl)methoxy)pyridin-4-yl)methanamine 2,2,2-trifluoroacetate | MS-ESI: 447 (M + 1) | Xselect CSH C18 OBD Column 30 * 150 mm 5 µm; Water (0.05% TFA) and ACN (22% ACN to 35% ACN in 7 min) | j. Synthesis of pH-AOV-0026 (Method D)

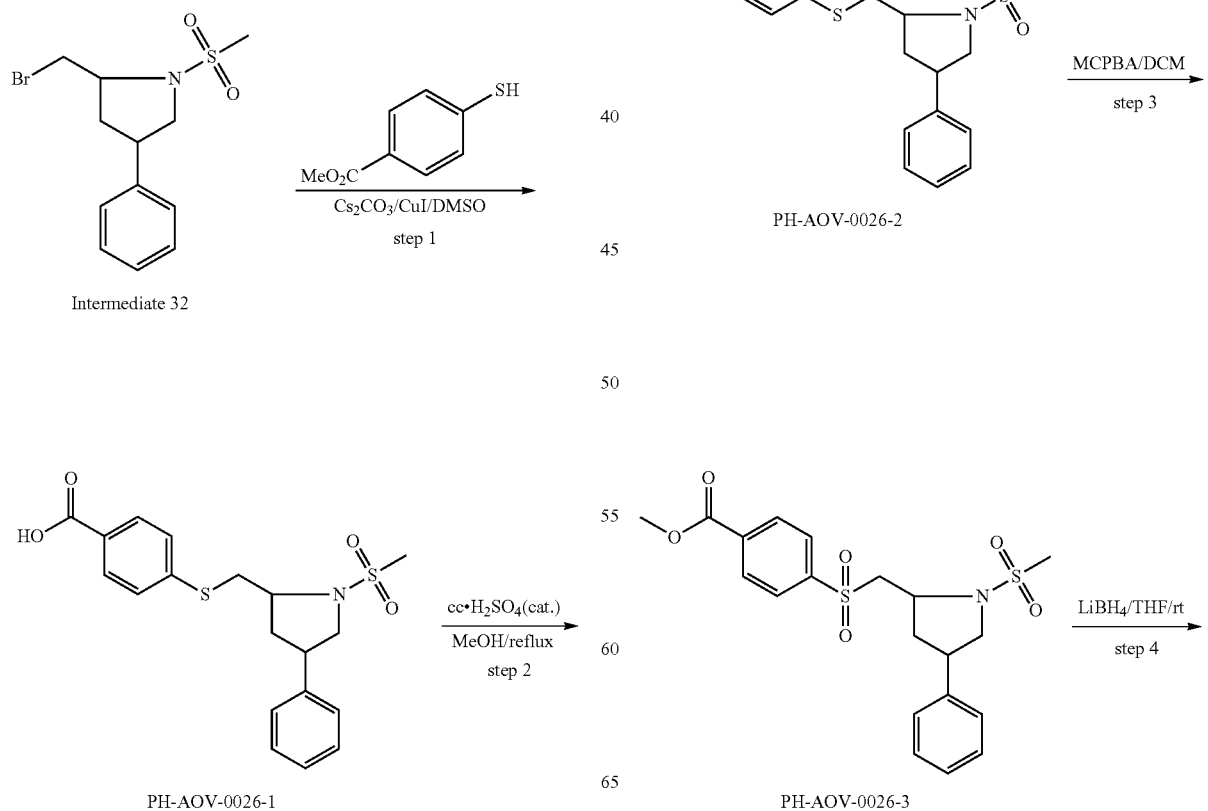

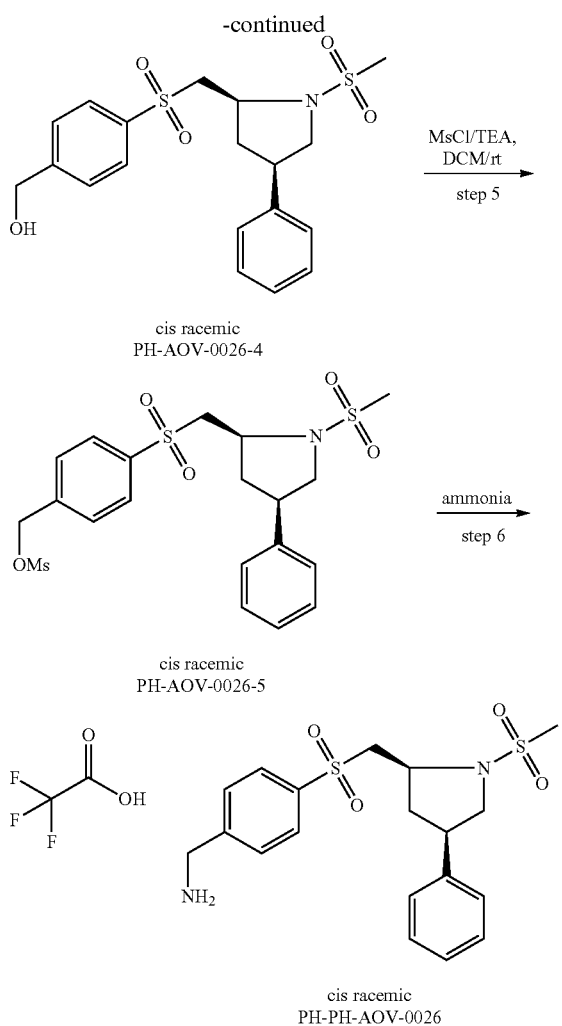

cis racemic
PH-AOV-0026-4 cis racemic
PH-AOV-0026-5 cis racemic
PH-PH-AOV-0026

Step 1: 4-(((1-(Methylsulfonyl)-4-phenylpyrrolidin-2-yl)methyl)thio)benzoic acid. To a solution of 2-(bromomethyl)-1-(methylsulfonyl)-4-phenylpyrrolidine (2.5 g, 7.86 mmol, 1.00 equiv) in DMSO (30 mL) under nitrogen were added methyl 4-mercaptobenzoate (1.59 g, 9.43 mmol, 1.20 equiv), 2,2,6,6-tetramethylheptane-3,5-dione (434 mg, 2.36 mmol, equiv), $Cs_2CO_3$ (7.68 g, 23.6 mmol, 3.00 equiv) and CuI (299 mg, 1.57 mmol, 0.20 equiv). The reaction mixture was stirred for 5 h at 130° C. The reaction was quenched with $H_2O$ (50 mL). The mixture was extracted with EtOAc (3×50 mL). The combined organic layers were dried over anhydrous $Na_2SO_4$ and concentrated under vacuum. This resulted in 3.0 g (crude) of the title compound as dark brown oil. MS-ESI: 392 (M+1).

Step 2: Methyl 4-(((1-(methylsulfonyl)-4-phenylpyrrolidin-2-yl)methyl)thio)benzoate. To a stirred solution of 4-(((1-(methylsulfonyl)-4-phenylpyrrolidin-2-yl)methyl)thio)benzoic acid (3.0 g, crude) in MeOH (40 mL) was added $H_2SO_4$ (98% wt., 1 mL). The reaction solution was stirred for 5 h at 80° C. The reaction was quenched with $H_2O$ (40 mL). The mixture was extracted with EtOAc (3×30 mL). The combined organic layers were dried over anhydrous $Na_2SO_4$ and concentrated under vacuum. The residue was eluted from silica gel with EtOAc/PE (1:1). This resulted in 2.6 g (81.5%, over two steps) of the title compound as yellow oil. MS-ESI: 406 (M+1).

Step 3: Methyl 4-(((1-(methylsulfonyl)-4-phenylpyrrolidin-2-yl)methyl)sulfonyl)benzoate. To a stirred solution of methyl 4-(((1-(methylsulfonyl)-4-phenylpyrrolidin-2-yl)methyl)thio)benzoate (2.6 g, 6.41 mmol, 1.00 equiv) in DCM (4.3 mL) was added m-CPBA (3.32 g, 19.2 mmol, 3.00 equiv) in portions at 0° C. The reaction mixture was stirred for 2 h at 0° C. The reaction was quenched with sat. $Na_2S_2O_3$ aq. (10 mL). The mixture was extracted with DCM (3×20 mL). The combined organic layers were dried over anhydrous $Na_2SO_4$ and concentrated under vacuum. The residue was eluted from silica gel with EtOAc/PE (1:1). This resulted in 2.2 g (78.4%) of the title compound as a yellow solid. MS-ESI: 438 (M+1).

Step 4: cis-(4-O-(Methylsulfonyl)-5-phenylpiperidin-3-yl)sulfonyl)phenyl)methanol. To a solution of methyl 4-((1-(methylsulfonyl)-5-phenylpiperidin-3-yl)sulfonyl)benzoate (500 mg, 1.14 mmol, 1.00 equiv) in THF (15 mL) under nitrogen was added $LiBH_4$ (149 mg, 6.86 mmol, 6.00 equiv) in portions at 0° C. The reaction mixture was stirred for 5 h at rt. The reaction was quenched with MeOH (10 mL). The resulting mixture was concentrated under vacuum. The residue was eluted from silica gel column dichloromethane/methanol (10:1). This resulted in 320 mg (68.4%) of the title compound as a yellow solid. MS-ESI: 410 (M+1).

Step 5: cis-4-O-(Methylsulfonyl)-5-phenylpiperidin-3-yl)sulfonyl)benzyl methanesulfonate. To a solution of cis-(4-((1-(methylsulfonyl)-5-phenylpiperidin-3-yl)sulfonyl)phenyl)methanol (200 mg, 0.49 mmol) in DCM (10 mL) under nitrogen were added methanesulfonyl chloride (62 mg, 0.54 mmol, 1.10 equiv) and TEA (59.3 mg, 0.59 mmol, 1.20 equiv). The reaction solution was stirred for 0.5 h at 0° C. The resulting solution was stirred for additional 2 h at rt. The reaction was quenched with 10 mL of sat. $NH_4C_1$. The mixture was extracted with 3×10 mL of dichloromethane. The organic layers were combined and dried over anhydrous sodium sulfate and concentrated under vacuum. This resulted in 200 mg (crude) of the title compound as a yellow solid. MS-ESI: 488 (M+1).

Step 6: cis-(4-((1-(Methylsulfonyl)-5-phenylpiperidin-3-yl)sulfonyl)phenyl)methanamine 2,2,2-trifluoroacetate. A solution of cis-4-((1-(methylsulfonyl)-5-phenylpiperidin-3-yl)sulfonyl)benzyl methanesulfonate (150.00 mg) in $NH_3H_2O$ (20 mL) was stirred for 16 h at rt. The mixture was concentrated under vacuum. The crude product was purified by Prep-HPLC with the following conditions: Column: Sunfire prep C18 column, 30*150, 5um; Mobile Phase A: Water (0.05% TFA), Mobile Phase B: ACN; Flow rate: 60 mL/min; Gradient: 17% B to 34% B over 7 min; Detector: 254/210 nm; RT1:5.82. This resulted in 94.5 mg of the title compound as a white solid. MS-ESI: 409 (M+1)

1H NMR (400 MHz, DMSO-d6) δ 8.34 (br s, 2H), 8.00 (d, J=8.0 Hz, 2H), 7.74 (d, J=8.0 Hz, 2H), 7.39-7.30 (m, 4H), 7.29-7.23 (m, 1H), 4.21 (s, 2H), 4.16-4.06 (m, 1H), 3.98-3.67 (m, 3H), 3.36-3.26 (m, 1H), 3.25-3.11 (m, 1H), 3.01 (s, 3H), 2.67-2.56 (m, 1H), 2.15-2.05 (m, 1H).

k. Synthesis of pH-AOV-0027 (Method E)

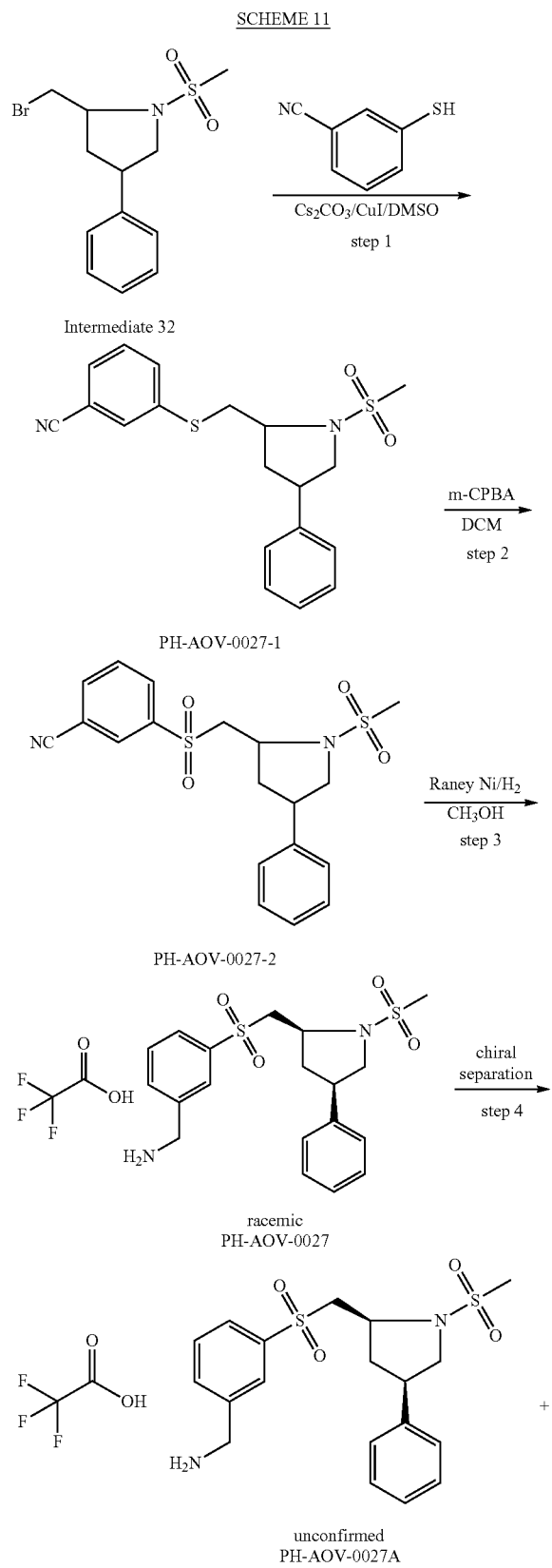

SCHEME 11

Intermediate 32

PH-AOV-0027-1

PH-AOV-0027-2 racemic
PH-AOV-0027 unconfirmed
PH-AOV-0027A

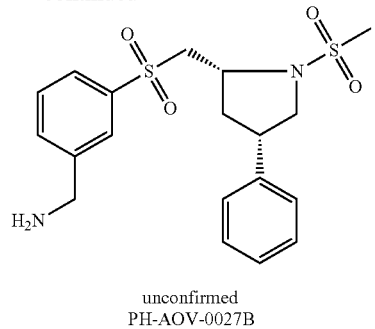

unconfirmed
PH-AOV-0027B

Step 1: 3-(((1-(Methylsulfonyl)-4-phenylpyrrolidin-2-yl)sulfonyl)phenyl)methanol. To a stirred solution of 2-(bromomethyl)-1-(methylsulfonyl)-4-phenylpyrrolidine (1.5 g, 4.71 mmol, 1.00 equiv) in DMSO (20 mL) under nitrogen were added 3-mercaptobenzonitrile (765 mg, 5.66 mmol, 1.20 equiv), 2,2,6,6-tetramethylheptane-3,5-dione (261 mg, 1.41 mmol, 0.30 equiv), CuI (180 mg, 0.94 mmol, 0.20 equiv) and $Cs_2CO_3$ (4.61 g, 14.1 mmol, 3.00 equiv). The reaction mixture was stirred for 5 h at 130° C. The reaction was quenched with $H_2O$ (20 mL). The mixture was extracted with EtOAc (3×20 mL). The combined organic layers were dried over anhydrous $Na_2SO_4$ and concentrated under vacuum. The residue was eluted from silica gel with EtOAc/PE (1:1). This resulted in 800 mg (45.6%) of the title compound as a yellow solid. MS-ESI: 373 (M+1).

Step 2: 3-(((1-(Methylsulfonyl)-4-phenylpyrrolidin-2-yl)sulfonyl)phenyl)methanol. To a stirred solution of 3-(((1-(methylsulfonyl)-4-phenylpyrrolidin-2-yl)methyl)thio)benzonitrile (300 mg, 0.81 mmol, 1.00 equiv) in DCM (0.54 mL) was added m-CPBA (417 mg, 2.42 mmol, 3.00 equiv) in portions at 0° C. The reaction mixture was stirred for 2 h at room temperature. The reaction was quenched with sat. $Na_2S_2O_3$ aq. (10 mL). The mixture was extracted with DCM (3×10 mL). The combined organic layers were dried over anhydrous $Na_2SO_4$ and concentrated under vacuum. The residue was eluted from silica gel with EtOAc/PE (1:1). This resulted in 200 mg (61.4%) of the title compound as a yellow solid. MS-ESI: 405 (M+1).

Step 3: cis-(34(1-(Methylsulfonyl)-4-phenylpyrrolidin-2-2,2,2-trifluoroacetate. To a stirred solution of 3-(((1-(methylsulfonyl)-4-phenylpyrrolidin-2-yl)methyl)sulfonyl)benzonitrile (200 mg, 0.49 mmol, 1.00 equiv) in MeOH (10 mL) under nitrogen was added Raney Ni (30 mg, 0.35 mmol, 0.71 equiv). The mixture was evacuated and refilled three times with hydrogen. The mixture was stirred for 16 h at rt. The solids were filtered out. The filtrate was concentrated under vacuum. The crude product was purified by Prep-HPLC with the following conditions: Column: Sunfire prep C18, 30*150, 5um; Mobile Phase A: water (0.05% TFA), Mobile Phase B: ACN; Flow rate: 60 mL/min; Gradient: 16% B to 28% B over 10 min; Detector, UV 254/210 nm; RT1:9.62. This resulted in 82.8 mg (41%) of the title compound a white solid. MS-ESI: 409 (M+1).

Step 4: (3-((((2S,4R)-1-(methylsulfonyl)-4-phenylpyrrolidin-2-yl)methyl)sulfonyl)phenyl)methanamine 2,2,2-trifluoroacetate and (3-((((2R,4S)-1-(methylsulfonyl)-4-phenylpyrrolidin-2-yl)methyl)sulfonyl)phenyl)methanamine 2,2,2-trifluoroacetate. (3-((((2S,4R)-1-(methylsulfonyl)-4-phenylpyrrolidin-2-yl)methyl)sulfonyl)phenyl)methanamine 2,2,2-trifluoroacetate (70 mg) was separated by Chiral-Prep-HPLC with the following conditions: Column: CHIRALPAK IE, 2*25 cm, 5 um; Mobile Phase A: MTBE (10 mM NH$_3$-MeOH), Mobile Phase B: EtOH; Flow rate:15 mL/min; Gradient: 50% B to 50% B in 12 min; Detector UV: 220/254 nm; RT1:9.43, RT2: 15.48. This resulted in 10.9 mg of (3-(4(2S,4R)-1-(methylsulfonyl)-4-phenylpyrrolidin-2-yl)methyl)sulfonyl)phenyl)methanamine 2,2,2-trifluoroacetate as a white solid and 7.5 mg of (3-((((2R,4S)-1-(methylsulfonyl)-4-phenylpyrrolidin-2-yl)methyl)sulfonyl) phenyl)methanamine 2,2,2-trifluoroacetate as a white solid. MS-ESI: 409 (M+1).

PH-AOV-0027A: $^1$H NMR (400 MHz, DMSO-d$_6$) δ 8.23 (br s, 2H), 8.09 (t, J=1.8 Hz, 1H), 7.96 (dt, J=8.0 Hz, 1.4 Hz, 1H), 7.84 (dt, J=8.0 Hz, 1.4 Hz, 1H), 7.75 (t, J=7.7 Hz, 1H), 7.38-7.24 (m, 5H), 4.24-4.09 (m, 3H), 3.89-3.72 (m, 3H), 3.36-3.26 (m, 1H), 3.21 (t, J=11.2 Hz, 1H), 3.02 (s, 3H), 2.70-2.62 (m, 1H), 2.16-2.06 (m, 1H).

PH-AOV-0027B: $^1$H NMR (400 MHz, DMSO-d$_6$) δ 8.24 (br s, 2H), 8.09 (t, J=1.8 Hz, 1H), 7.96 (dt, J=8.0 Hz, 1.4 Hz, 1H), 7.84 (dt, J=8.0 Hz, 1.4 Hz, 1H), 7.75 (t, J=7.7 Hz, 1H), 7.38-7.30 (m, 4H), 7.29-7.24 (m, 1H), 4.24-4.16 (m, 2H), 4.15-4.08 (m, 1H), 3.91-3.82 (m, 1H), 3.86-3.79 (m, 1H), 3.75 (dd, J=13.7 Hz, 3.0 Hz, 1H), 3.73-3.26 (m, 1H), 3.21 (t, J=11.2 Hz, 1H), 3.02 (s, 3H), 2.69-2.62 (m, 1H), 2.16-2.06 (m, 1H).

6. In Vitro Characterization of Exemplary Lox Enzyme-Inhibiting Compounds a. Permeability Study Caco-2 cell suspensions are dispensed into the inserts of the 96-well HTS Transwell plate and cultivated for 14-18 days. Transepithelial electrical resistance (TEER) across the monolayer is measured using Millicell Epithelial Volt-Ohm measuring system. The Caco-2 plate is then washed twice with pre-warmed HBSS (pH 7.4) and incubated at 37° C. for 30 minutes. To determine the rate of drug transport in the apical to basolateral direction. 5 μM test compound is added to the Transwell insert and the wells in the receiver plate are filled with HBSS (pH 7.4). To determine the rate of drug transport in the basolateral to apical direction, 5 μM test compound is added to the receiver plate wells and then the Transwell inserts were filled with HBSS (pH 7.4). The plates are incubated at 37° C. for 2 hours. 50 μL samples from donor sides and receiver sides are transferred to wells of a new 96-well plate followed by the addition of 4 volume of cold methanol containing internal standards (IS). Samples are centrifuged and the supernatant is used for LC-MS/MS analysis. After the incubation, residue solutions are removed from the Transwell plates, and Lucifer yellow (100 μM) solution is added to each Transwell insert, followed by filling the receiver wells with HBSS. The plates are incubated at 37° C. for 30 minutes. 80 μL samples are removed from the apical and basolateral wells and the fluorescence of Lucifer yellow is measured in a microplate reader with 485 nM excitation and 530 nM emission.

b. Microsome Stability Study

Pooled CD-1 mouse liver microsomes at 0.5 mg/mL are pre-incubated in phosphate buffer (100 mM, pH 7.4) containing 1 mM NADPH and 3 mM MgCl$_2$ in a 96-well plate for 5 minutes at 37° C. Ultra-pure water is added instead of NADPH in the negative control group to exclude the misleading factor that resulted from instability of chemical itself. The reaction is initiated by adding test compound at the final concentration of 2 μM and incubated at 37° C. Aliquots are taken from the incubation at 0, 15, 30, 45, and 60 minutes followed by the addition of 4 volume of cold acetonitrile containing internal standards. Samples are centrifuged and supernatant is used for LC-MS/MS analysis.

7. In Vivo Characterization of Exemplary Lox Enzyme-Inhibiting Compounds a. PK/PD Study, Experimental Design The objective of this study is to determine the pharmacokinetic (PK) profile of LOX enzyme inhibiting compounds following IV and PO administrations in male CD1 mice. Dosing information is shown in Table 18.

TABLE 18

| Group | Dose Level (mg/kg) | Dose Volume (mL/kg) | Conc. (mg/mL) | Administration Route | No. of Animals |
|---|---|---|---|---|---|
| 1 | 10 | 5 | 2 | IV | 3 |
| 2 | 50 | 10 | 5 | PO | 3 |

Male CD1 mice from a qualified provider are used for all studies. Mice are 6-8 weeks old at the time of the experiment (~20-30 g body weight). All animals for IV & PO administration are fasted overnight and fed after 4 hours collection. The dose formulation is kept at room temperature no more than 2 hours.

Dose formulations are prepared fresh on the day of dosing and stored at ambient temperature.

Blood samples are collected from the dorsal metatarsal vein. Circa 0.03 mL are collected per time point and 0.3 mL at final time point via heart puncture. The blood samples are centrifuged at 4000 g for 5 minutes at 4° C. to obtain plasma and samples are immediately frozen in the upright position and stored at −75±15° C. prior to analysis. Blood samples are collected at time points outlined in Table 22.

TABLE 22

| Group | PK Time Points |
|---|---|
| IV | 5, 15, 30 min, 1, 2, 4, 8, 24 hours post dose |
| PO | 15, 30 min, 1, 2, 4, 8, 24 hours post dose |

Acceptable time ranges for blood collection are as following: 5 min and 15 min: within ±0.25 minute, 30 min, 1 hour, and 2 hours: within ±2 minutes; 4 hours, 6 hours, 8 hours, and 24 hours: within ±10 minutes.

During In-Life Phase, all mice are evaluated twice daily via cage side observation. A detailed clinical observation was performed once prior to dosing on Day 1, including measuring the body weight to dosing.

b. Analysis

Concentrations of LOX enzyme inhibiting compounds in the plasma are analyzed using a LC-MS/MS method. WinNonlin (Phoenix™, version 8.2) software is used for pharmacokinetic calculations. The following pharmacokinetic parameters are calculated, whenever possible from the plasma concentration versus time data:

IV administration: $T_{1/2}$, $C_0$, $AUC_{last}$, $AUC_{inf}$, $MRT_{inf}$, Cl, $V_{SS}$, Number of Points for Regression.

PO administration: $T_{1/2}$, $C_{max}$, $T_{max}$, $AUC_{last}$, $AUC_{inf}$ and F. Number of Points for Regression.

The pharmacokinetic data are described using descriptive statistics such as mean, standard deviation.

G. SYNTHESIS
The disclosed compounds can be prepared according to the following reactions.
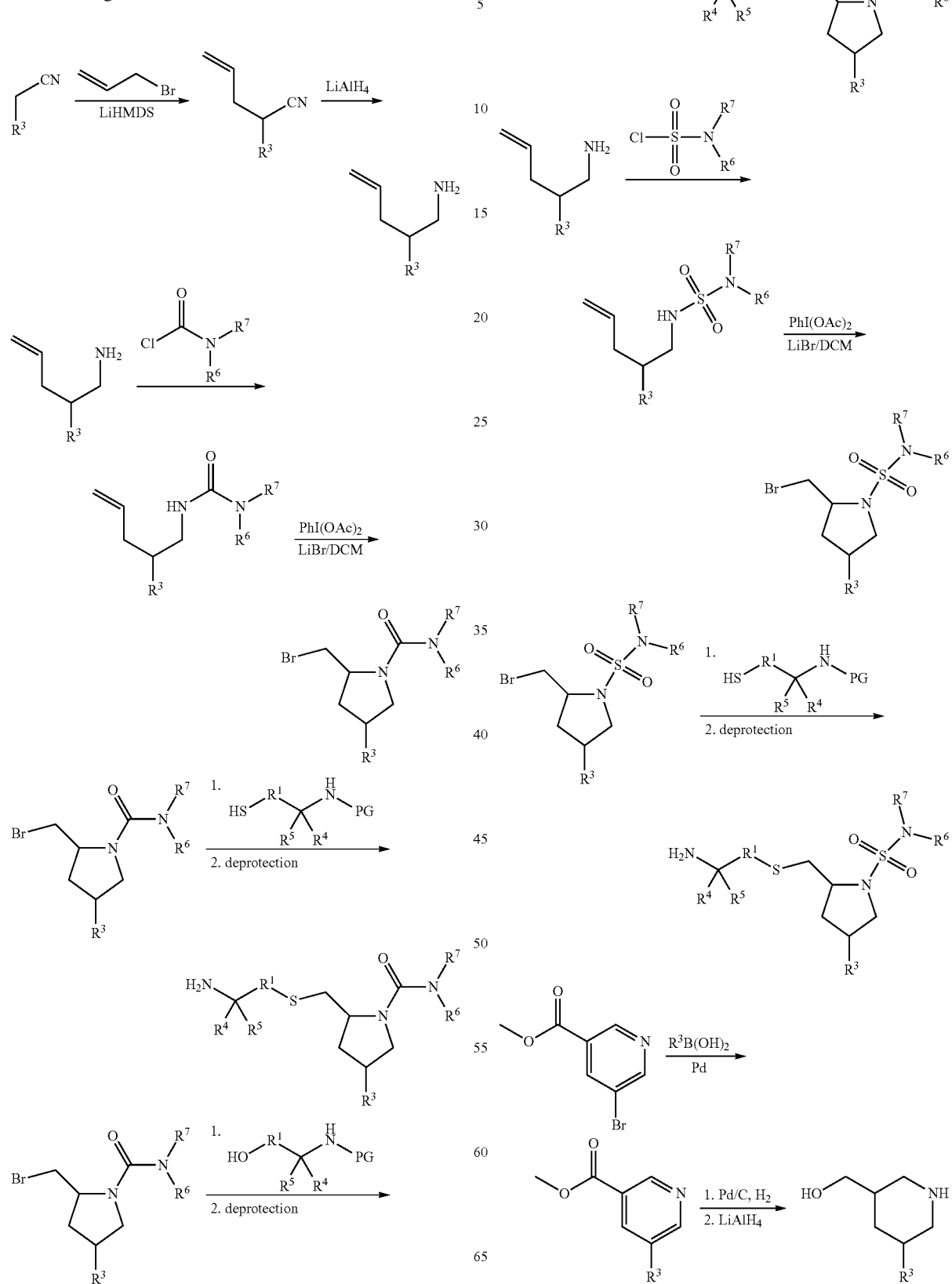

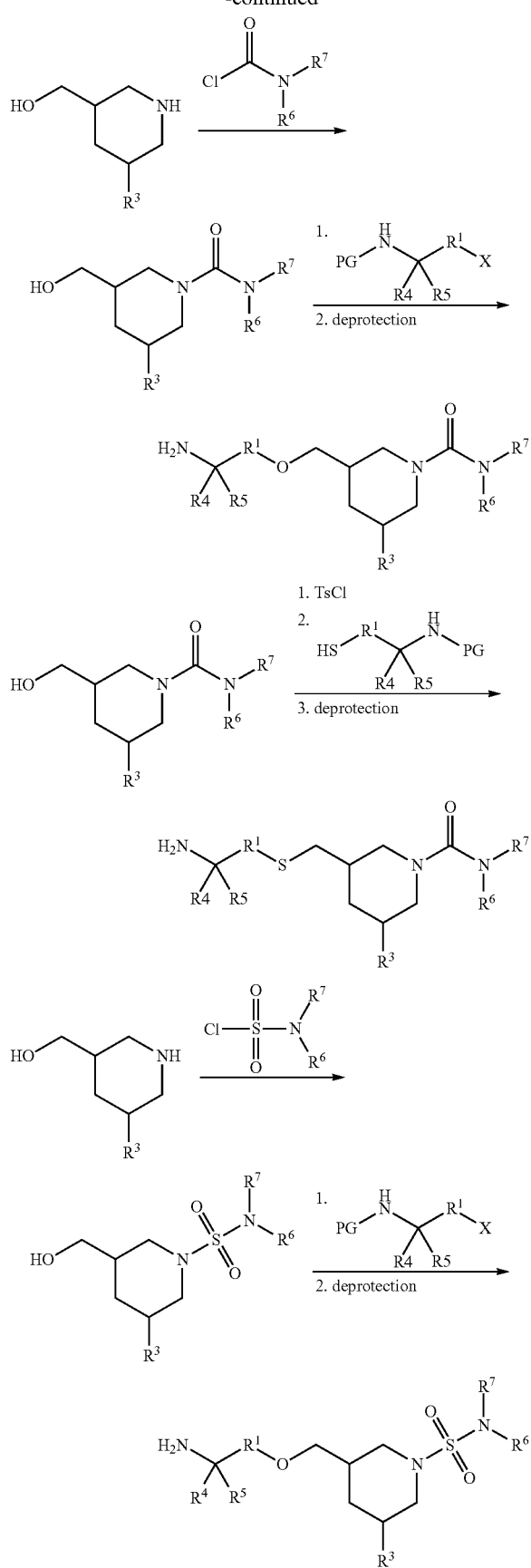
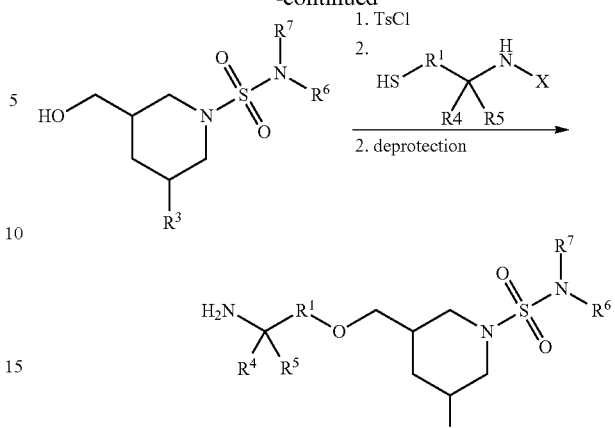

H. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

The discussion herein provides a better understanding of the nature of the problems confronting the art and should not be construed in any way as an admission as to prior art nor should the citation of any reference herein be construed as an admission that such reference constitutes "prior art" to the instant application.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

I. REFERENCES

Abbonante, V., et al. (2017). "Upregulation of lysyl oxidase and adhesion to collagen of human megakaryocytes and platelets in primary myelofibrosis." *Blood* 130(6): 829-831.

Abourbih, D. A., et al. (2010). "Lysyl oxidase expression and inhibition in uveal melanoma." *Melanoma Res* 20(2): 97-106.

Al-U'datt, D., et al. (2019). "Role of the lysyl oxidase enzyme family in cardiac function and disease." *Cardiovasc Res* 115(13): 1820-1837.

Albinger-Hegyi, A., et al. (2010). "Lysyl oxidase expression is an independent marker of prognosis and a predictor of lymph node metastasis in oral and oropharyngeal squamous cell carcinoma (OSCC)." *Int J Cancer* 126(11): 2653-2662.

Almassian, B., et al. (1991). "Induction of lung lysyl oxidase activity and lysyl oxidase protein by exposure of rats to cadmium chloride: properties of the induced enzyme." *Connect Tissue Res* 25(3-4): 197-208.

Amendola, P. G., et al. (2019). "Interplay Between LOX Enzymes and Integrins in the Tumor Microenvironment." *Cancers (Basel)* 11(5).

Aumiller, V., et al. (2017). "Comparative analysis of lysyl oxidase (like) family members in pulmonary fibrosis." *Sci Rep* 7(1): 149.

Baker, A. M., et al. (2013). "Lysyl oxidase enzymatic function increases stiffness to drive colorectal cancer progression through FAK." *Oncogene* 32(14): 1863-1868.

Barker, H. E., et al. (2012). "The rationale for targeting the LOX family in cancer." *Nat Rev Cancer* 12(8): 540-552.

Borel, A., et al. (2001). "Lysyl oxidase-like protein from bovine aorta. Isolation and maturation to an active form by bone morphogenetic protein-1." *J Biol Chem* 276(52): 48944-48949.

Burke, A. A., et al. (2017). "Comparing hydrazine-derived reactive groups as inhibitors of quinone-dependent amine oxidases." *J Enzyme Inhib Med Chem* 32(1): 496-503.

Carter, E. A., et al. (1982). "Lysyl oxidase and collagenase in experimental acute and chronic liver injury." *Gastroenterology* 82(3): 526-534.

Chang, J., et al. (2017). "Pre-clinical evaluation of small molecule LOXL2 inhibitors in breast cancer." *Oncotarget* 8(16): 26066-26078.

Cheng, T., et al. (2014). "Lysyl oxidase promotes bleomycin-induced lung fibrosis through modulating inflammation." *J Mol Cell Biol* 6(6): 506-515.

Cheon, D. J., et al. (2014). "A collagen-remodeling gene signature regulated by TGF-beta signaling is associated with metastasis and poor survival in serous ovarian cancer." *Clin Cancer Res* 20(3): 711-723.

Chou, T. F., et al. (2007). "Engineered monomeric human histidine triad nucleotide-binding protein 1 hydrolyzes fluorogenic acyl-adenylate and lysyl-tRNA synthetase-generated lysyl-adenylate." *J Biol Chem* 282(20): 15137-15147.

Cosgrove, D., et al. (2018). "Lysyl oxidase like-2 contributes to renal fibrosis in Col4alpha3/Alport mice." *Kidney Int* 94(2): 303-314.

Counts, D. F., et al. (1981). "Collagen lysyl oxidase activity in the lung increases during bleomycin-induced lung fibrosis." *J Pharmacol Exp Ther* 219(3): 675-678.

de Bruyn, J. R., et al. (2018). "Fibrostenotic Phenotype of Myofibroblasts in Crohn's Disease is Dependent on Tissue Stiffness and Reversed by LOX Inhibition." *J Crohns Colitis* 12(7): 849-859.

Dentillo, D. B., et al. (2010). "Deregulation of LOXL1 and HTRA1 gene expression in endometriosis." *Reprod Sci* 17(11): 1016-1023.

Erler, J. T., et al. (2006). "Lysyl oxidase is essential for hypoxia-induced metastasis." *Nature* 440(7088): 1222-1226.

Gilad, G. M., et al. (2001). "Lysyl oxidase, the extracellular matrix-forming enzyme, in rat brain injury sites." *Neurosci Lett* 310(1): 45-48.

Gilad, G. M., et al. (2005). "Evidence for increased lysyl oxidase, the extracellular matrix-forming enzyme, in Alzheimer's disease brain." *Neurosci Lett* 376(3): 210-214.

Gorogh, T., et al. (2015). "Characterisation of seven newly established head and neck squamous cell carcinoma cell lines." *Eur Arch Otorhinolaryngol* 272(5): 1251-1258.

Goto, Y., et al. (2005). "Transforming growth factor-beta1 mediated up-regulation of lysyl oxidase in the kidneys of hereditary nephrotic mouse with chronic renal fibrosis." *Virchows Arch* 447(5): 859-868.

Hajdu, I., et al. (2018). "Inhibition of the LOX enzyme family members with old and new ligands. Selectivity analysis revisited." *Bioorg Med Chem Lett* 28(18): 3113-3118.

Halberg, N., et al. (2009). "Hypoxia-inducible factor 1alpha induces fibrosis and insulin resistance in white adipose tissue." *Mol Cell Biol* 29(16): 4467-4483.

Hase, H., et al. (2014). "LOXL2 status correlates with tumor stage and regulates integrin levels to promote tumor progression in ccRCC." *Mol Cancer Res* 12(12): 1807-1817.

Hutchinson, J. H., et al. (2017). "Small Molecule Lysyl Oxidase-like 2 (LOXL2) Inhibitors: The Identification of an Inhibitor Selective for LOXL2 over LOX." *ACS Med Chem Lett* 8(4): 423-427.

Kagan, H. M. and W. Li (2003). "Lysyl oxidase: properties, specificity, and biological roles inside and outside of the cell." *J Cell Biochem* 88(4): 660-672.

Kagan, H. M., et al. (1981). "Changes in aortic lysyl oxidase activity in diet-induced atherosclerosis in the rabbit." *Arteriosclerosis* 1(4): 287-291.

Kagan, H. M., et al. (1979). "Purification and properties of four species of lysyl oxidase from bovine aorta." *Biochem J* 177(1): 203-214.

Kim, D., et al. (2015). "Impaired osteogenesis in Menkes disease-derived induced pluripotent stem cells." *Stem Cell Res Ther* 6: 160.

Kim, Y., et al. (2009). "Differential expression of the LOX family genes in human colorectal adenocarcinomas." *Oncol Rep* 22(4): 799-804

Kirschmann, D. A., et al. (2002). "A molecular role for lysyl oxidase in breast cancer invasion." *Cancer Res* 62(15): 4478-4483.

Kumar, P., et al. (2018). "Periostin promotes liver fibrogenesis by activating lysyl oxidase in hepatic stellate cells." *J Biol Chem* 293(33): 12781-12792.

Lapointe, J., et al. (2004). "Gene expression profiling identifies clinically relevant subtypes of prostate cancer." *Proc Natl Acad Sci USA* 101(3): 811-816.

Le, Q. T., et al. (2009). "Validation of lysyl oxidase as a prognostic marker for metastasis and survival in head and neck squamous cell carcinoma: Radiation Therapy Oncology Group trial 90-03." *J Clin Oncol* 27(26): 4281-4286.

Leiva, O., et al. (2019). "Novel lysyl oxidase inhibitors attenuate hallmarks of primary myelofibrosis in mice." *Int J Hematol* 110(6): 699-708.

Li, P. A., et al. (2004). "Up-regulation and altered distribution of lysyl oxidase in the central nervous system of mutant SOD1 transgenic mouse model of amyotrophic lateral sclerosis." *Brain Res Mol Brain Res* 120(2): 115-122.

Li, W., et al. (2003). "Lysyl oxidase oxidizes basic fibroblast growth factor and inactivates its mitogenic potential." *J Cell Biochem* 88(1): 152-164.

Liu, N., et al. (2017). "Nuclear expression of lysyl oxidase enzyme is an independent prognostic factor in rectal cancer patients." *Oncotarget* 8(36): 60015-60024.

Liu, S. B., et al. (2016). "Lysyl oxidase activity contributes to collagen stabilization during liver fibrosis progression and limits spontaneous fibrosis reversal in mice." *FASEB J* 30(4): 1599-1609

Lopez, B., et al. (2009). "Impact of treatment on myocardial lysyl oxidase expression and collagen cross-linking in patients with heart failure." *Hypertension* 53(2): 236-242.

Lu, J., et al. (2018). "Hypoxia-inducible factor-1alpha regulates epithelial-to-mesenchymal transition in paraquat-induced pulmonary fibrosis by activating lysyl oxidase." *Exp Ther Med* 15(3): 2287-2294.

Lu, M., et al. (2019). "Induction of LOX by TGF-beta1/Smad/AP-1 signaling aggravates rat myocardial fibrosis and heart failure." *IUBMB Life* 71(11): 1729-1739.

Lucero, H. A. and H. M. Kagan (2006). "Lysyl oxidase: an oxidative enzyme and effector of cell function." *Cell Mol Life Sci* 63(19-20): 2304-2316.

Lucero, H. A., et al. (2008). "Lysyl oxidase oxidizes cell membrane proteins and enhances the chemotactic response of vascular smooth muscle cells." *J Biol Chem* 283(35): 24103-24117.

Mambetsariev, I., et al. (2014). "Stiffness-activated GEF-$H_1$ expression exacerbates LPS-induced lung inflammation." *PLoS One* 9(4): e92670.

Martin, A., et al. (2015). "Lysyl oxidase-like 2 represses Notch1 expression in the skin to promote squamous cell carcinoma progression." *EMBO J* 34(8): 1090-1109.

Mesarwi, O. A., et al. (2015). "Lysyl Oxidase as a Serum Biomarker of Liver Fibrosis in Patients with Severe Obesity and Obstructive Sleep Apnea." *Sleep* 38(10): 1583-1591.

Miana, M., et al. (2015). "The lysyl oxidase inhibitor beta-aminopropionitrile reduces body weight gain and improves the metabolic profile in diet-induced obesity in rats." *Dis Model Mech* 8(6): 543-551.

Miller, B. W., et al. (2015). "Targeting the LOX/hypoxia axis reverses many of the features that make pancreatic cancer deadly: inhibition of LOX abrogates metastasis and enhances drug efficacy." *EMBO Mol Med* 7(8): 1063-1076.

Min, C., et al. (2007). "The tumor suppressor activity of the lysyl oxidase propeptide
reverses the invasive phenotype of Her-2/neu-driven breast cancer." *Cancer Res* 67(3):1105-1112.

Murawaki, Y., et al. (1991). "Serum lysyl oxidase activity in chronic liver disease in comparison with serum levels of prolyl hydroxylase and laminin." *Hepatology* 14(6): 1167-1173.

Ovchinnikova, O. A., et al. (2014). "The collagen cross-linking enzyme lysyl oxidase is associated with the healing of human atherosclerotic lesions." *J Intern Med* 276(5): 525-536.

Papadantonakis, N., et al. (2012). "Megakaryocyte pathology and bone marrow fibrosis: the lysyl oxidase connection." *Blood* 120(9): 1774-1781.

Rivera, A. D. and A. M. Butt (2019). "Astrocytes are direct cellular targets of lithium treatment: novel roles for lysyl oxidase and peroxisome-proliferator activated receptor-gamma as astroglial targets of lithium." *Transl Psychiatry* 9(1): 211.

Rowbottom, M. W., et al. (2017). "Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2)." *J Med Chem* 60(10): 4403-4423.

Rowbottom, M. W. et al. (2016a). "Preparation of substituted pyridinylmethylamine compounds as lysyl oxidase-like 2 inhibitors". WO2016144702

Rowbottom, M. W. et al. (2016b). "Preparation of fluorinated pyridine derivatives as lysyl oxidase-like 2 inhibitors and uses thereof." WO2016144703

Rowbottom, M. W.; Hutchinson, J. H. (2017a). "Preparation of pyrimidine derivatives as Lysyl oxidase-like 2 inhibitors useful for the treatment of fibrosis." WO2017003862

Rowbottom, M. W.; Hutchinson, J. H. (2017b). "Lysyl oxidase-like 2 inhibitors and uses thereof." WO2017015221

Ruiz, L. A., et al. (2011). "Single-nucleotide polymorphisms in the lysyl oxidase-like protein 4 and complement component 3 genes are associated with increased risk for endometriosis and endometriosis-associated infertility." *Fertil Steril* 96(2): 512-515.

Ryner, L., et al. (2015). "Upregulation of Periostin and Reactive Stroma Is Associated with Primary Chemoresistance and Predicts Clinical Outcomes in Epithelial Ovarian Cancer." *Clin Cancer Res* 21(13): 2941-2951.

Saifi, M. A. and C. Godugu (2020). "Inhibition of lysyl oxidase ameliorates renal injury by inhibiting CD44-mediated pericyte detachment and loss of peritubular capillaries." *Life Sci* 243: 117294.

Salvador, F., et al. (2017). "Lysyl Oxidase-like Protein LOXL2 Promotes Lung Metastasis of Breast Cancer." *Cancer Res* 77(21): 5846-5859.

Sasaki, T., et al. (2016). "Loss of fibulin-4 results in abnormal collagen fibril assembly in bone, caused by impaired lysyl oxidase processing and collagen cross-linking." *Matrix Biol* 50: 53-66.

Sato, S., et al. (2011). "The Ras signaling inhibitor LOX-PP interacts with Hsp70 and c-Raf to reduce Erk activation and transformed phenotype of breast cancer cells." *Mol Cell Biol* 31(13): 2683-2695.

Schilter, H., et al. (2019). "The lysyl oxidase like 2/3 enzymatic inhibitor, PXS-5153A, reduces crosslinks and ameliorates fibrosis." *J Cell Mol Med* 23(3): 1759-1770.

Siegel, R. C., et al. (1978). "Biochemical and immunochemical study of lysyl oxidase in experimental hepatic fibrosis in the rat." *Proc Natl Acad Sci USA* 75(6): 2945-2949.

Smithen, D. A., et al. (2020). "2-Aminomethylene-5-sulfonylthiazole Inhibitors of Lysyl Oxidase (LOX) and LOXL2 Show Significant Efficacy in Delaying Tumor Growth." *J Med Chem* 63(5): 2308-2324.

Springer, C et. al. (2017). "Methylamine derivatives as lysyl oxidase inhibitors for the treatment of cancer." WO2017141049

Stangenberg, S., et al. (2018). "Lysyl oxidase-like 2 inhibition ameliorates glomerulosclerosis and albuminuria in diabetic nephropathy." *Sci Rep* 8(1): 9423.

Tadmor, T., et al. (2013). "The expression of lysyl-oxidase gene family members in myeloproliferative neoplasms." *Am J Hematol* 88(5): 355-358.

Tang, H., et al. (2017). "Lysyl oxidase drives tumour progression by trapping EGF receptors at the cell surface." *Nat Commun* 8: 14909.

Tjin, G., et al. (2017). "Lysyl oxidases regulate fibrillar collagen remodelling in idiopathic pulmonary fibrosis." *Dis Model Mech* 10(11): 1301-1312.

Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." *J Biol Chem* 276(25): 22537-22543.

Van Bergen, T., et al. (2015). "The Role of LOX and LOXL2 in the Pathogenesis of an Experimental Model of Choroidal Neovascularization." *Invest Ophthalmol Vis Sci* 56(9): 5280-5289.

Virani, S. S., et al. (2020). "Heart Disease and Stroke Statistics-2020 Update: A Report From the American Heart Association." *Circulation* 141(9): e139-e596.

Vulpe, C., et al. (1993). "Isolation of a candidate gene for Menkes disease and evidence that it encodes a copper-transporting ATPase." *Nat Genet* 3(1): 7-13.

Wakasaki, H. and A. Ooshima (1990). "Synthesis of lysyl oxidase in experimental hepatic fibrosis." *Biochem Biophys Res Commun* 166(3): 1201-1204.

Wilhelmus, M. M., et al. (2013). "Extracellular matrix modulator lysyl oxidase colocalizes with amyloid-beta pathology in Alzheimer's disease and hereditary cerebral hemorrhage with amyloidosis—Dutch type." *Exp Gerontol* 48(2): 109-114.

Yang, J., et al. (2016). "Targeting LOXL2 for cardiac interstitial fibrosis and heart failure treatment." *Nat Commun* 7: 13710.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A LOX enzyme-inhibiting compound in accordance with Formula I or Formula II, or a pharmaceutically acceptable salt or hydrate thereof:

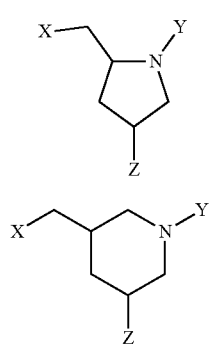

wherein:
X is independently selected from $-OR^1$, $-SO_2R^1$, and $-C(=O)R^1$;
Y is independently selected from $-SO_2R^2$ and $-C(=O)R^2$;
Z is independently selected from $-R^3$, $-CH_2-R^3$, $-SO_2R^3$, $-C(=O)R^3$, and $-OR^3$;
$R^1$ is phenyl or heteroaryl containing 1 to 2 heteroatom(s) each independently selected from N, O, and S, wherein said phenyl or heteroaryl is substituted with $-CR^4R^5NH_2$, and optionally, halogen or lower alkyl,
where $R^4$ and $R^5$ are independently H or lower alkyl or $R^4$ and $R^5$ form a ($C_3$-$C_8$) cycloalkyl or ($C_1$-$C_8$) hetero-cycloalkyl;
$R^2$ is substituted or unsubstituted phenyl, substituted or unsubstituted benzyl, substituted or unsubstituted heteroaryl containing 1 to 2 heteroatom(s) each independently selected from N, O, and S, ($C_1$-$C_8$) alkyl, ($C_3$-$C_8$) cycloalkyl mono-, di-, or trihalo($C_1$-$C_4$)alkyl, or $-NR^6R^7$, wherein said substituted phenyl, benzyl, or heteroaryl has at least one substituent being halogen, mono-, di-, or trihalo($C_1$-$C_4$)alkyl, $-SO_2R^8$, or $-OR^8$,
where $R^6$ and $R^7$ are independently selected from H and lower alkyl or where $R^6$, $R^7$, and N together form a ($C_3$-$C_6$) hetero-cycloalkyl, wherein the ($C_3$-$C_6$) hetero-cycloalkyl optionally contains besides the N one additional heteroatom selected from N, O, and S, wherein the additional N is optionally substituted with lower alkyl, $-SO_2R^8$, or $-OR^8$, and wherein S is unsubstituted or forms sulfonyl,
where $R^8$ is lower alkyl, cyano, lower alkyl, or $-SO_2NR^9R^{10}$, and
where $R^9$ and $R^{10}$ are independently selected from H and lower alkyl;
$R^3$ is unsubstituted or substituted phenyl, substituted or unsubstituted benzyl, substituted or unsubstituted heteroaryl containing 1 to 2 heteroatom(s) each independently selected from N, O, and S, mono-, di-, or trihalo($C_1$-$C_4$)alkyl, ($C_3$-$C_8$) cycloalkyl ($C_1$-$C_8$) alkyl, or $-NR^{11}R^{12}$, wherein said substituted phenyl, benzyl, or heteroaryl has at least one substituent being halogen, mono-, di-, or trihalo($C_1$-$C_4$)alkyl, $-SO_2R^{14}$, or $-OR^{14}$,
where $R^{11}$ and $R^{12}$ are independently selected from H and lower alkyl or where $R^{11}$, $R^{12}$, and N together form a ($C_3$-$C_6$) hetero-cycloalkyl, wherein the ($C_3$-$C_6$) hetero-cycloalkyl optionally contains besides the N one additional heteroatom selected from N, O, and S, wherein the additional N is optionally substituted with lower alkyl, $-SO_2R^{13}$, or $-OR^{13}$, and wherein S is unsubstituted or forms sulfonyl,
where $R^{14}$ is lower alkyl, cyano, lower alkyl, or $-SO_2NR^{15}R^{16}$, and
where $R^{15}$ and $R^{16}$ are independently selected from H and lower alkyl, or a tautomer or stereoisomer thereof.

2. The compound according to claim 1, wherein the compound is one of:
cis-4-((2-(((4-(Aminomethyl)pyridin-2-yl)sulfonyl)methyl)-4-phenylpyrrolidin-1-yl)sulfonyl)thiomorpholine 1,1-dioxide;
4-(((2S,4R)-2-(((4-(aminomethyl)pyridin-2-yl)sulfonyl)methyl)-4-phenylpyrrolidin-1-yl)sulfonyl)thiomorpholine 1,1-dioxide;
4-(((2R,4S)-2-(((4-(aminomethyl)pyridin-2-yl)sulfonyl)methyl)-4-phenylpyrrolidin-1-yl)sulfonyl)thiomorpholine 1,1-dioxide;

cis-(2-(((4-(2-fluorophenyl)-1-(morpholinosulfonyl)pyr-rolidin-2-yl)methyl)sulfonyl)pyridin-4-yl)meth-anamine;
cis-(4-(((1-(Methylsulfonyl)-4-phenylpyrrolidin-2-yl)methyl)sulfonyl)phenyl)methanamine;
cis-(3-(((1-(Methylsulfonyl)-4-phenylpyrrolidin-2-yl)methyl)sulfonyl)phenyl)methanamine;
cis-(2-(((4-(2-Fluorophenyl)-1-(morpholinosulfonyl)pyr-rolidin-2-yl)methyl)sulfonyl)pyridin-4-yl)meth-anamine;
cis-(2-(((4-(4-Fluorophenyl)-1-(morpholinosulfonyl)pyr-rolidin-2-yl)methyl)sulfonyl)pyridin-4-yl)meth-anamine;
cis-4-((2-(((4-(Aminomethyl)pyridin-2-yl)sulfonyl)methyl)-4-(2-fluorophenyl)pyrrolidin-1-yl)sulfonyl)thiomorpholine 1,1-dioxide;
cis-4-((2-(((4-(Aminomethyl)pyridin-2-yl)sulfonyl)methyl)-4-(4-fluorophenyl)pyrrolidin-1-yl)sulfonyl)thiomorpholine 1,1-dioxide;
cis-(5-(((4-(2-Fluorophenyl)-1-(morpholinosulfonyl)pyr-rolidin-2-yl)methyl)sulfonyl)thiophen-2-yl)meth-anamine;
cis-(5-(((4-(4-Fluorophenyl)-1-(morpholinosulfonyl)pyr-rolidin-2-yl)methyl)sulfonyl)thiophen-2-yl)meth-anamine;
cis-4-((2-(((5-(Aminomethyl)thiophen-2-yl)sulfonyl)methyl)-4-(2-fluorophenyl)pyrrolidin-1-yl)sulfonyl)thiomorpholine 1,1-dioxide;
cis-4-((2-(((5-(Aminomethyl)thiophen-2-yl)sulfonyl)methyl)-4-(4-fluorophenyl)pyrrolidin-1-yl)sulfonyl)thiomorpholine 1,1-dioxide;
cis-(2-((4-(2-Fluorophenyl)-1-(morpholinosulfonyl)pyr-rolidin-2-yl)methoxy)pyridin-4-yl)methanamine;
cis-(2-((4-(4-Fluorophenyl)-1-(morpholinosulfonyl)pyr-rolidin-2-yl)methoxy)pyridin-4-yl)methanamine;
cis-4-((2-(((4-(Aminomethyl)pyridin-2-yl)oxy)methyl)-4-(2-fluorophenyl)pyrrolidin-1-yl)sulfonyl)thiomor-pholine 1,1-dioxide;
cis-4-((2-(((4-(Aminomethyl)pyridin-2-yl)oxy)methyl)-4-(4-fluorophenyl)pyrrolidin-1-yl)sulfonyl)thiomor-pholine 1,1-dioxide;
cis-(3-((4-(2-Fluorophenyl)-1-(morpholinosulfonyl)pyr-rolidin-2-yl)methoxy)phenyl)methanamine;
cis-(3-((4-(4-Fluorophenyl)-1-(morpholinosulfonyl)pyr-rolidin-2-yl)methoxy)phenyl)methanamine;
cis-4-((2-((3-(Aminomethyl)phenoxy)methyl)-4-(2-fluorophenyl)pyrrolidin-1-yl)sulfonyl)thiomorpholine 1,1-dioxide;
cis-4-((2-((3-(Aminomethyl)phenoxy)methyl)-4-(4-fluorophenyl)pyrrolidin-1-yl)sulfonyl)thiomorpholine 1,1-dioxide;
(3-((((2S,4R)-1-(methylsulfonyl)-4-phenylpyrrolidin-2-yl)methyl)sulfonyl)phenyl)methanamine;
(3-((((2R,4S)-1-(methylsulfonyl)-4-phenylpyrrolidin-2-yl)methyl)sulfonyl)phenyl)methanamine;
cis-(2-(((1-(Morpholinosulfonyl)-5-phenylpiperidin-3-yl)methyl)sulfonyl)pyridin-4-yl)methanamine;
cis-(2-((1-(Morpholinosulfonyl)-5-phenylpiperidin-3-yl)methoxy)pyridin-4-yl)methanamine;
cis-(3-((1-(Morpholinosulfonyl)-5-phenylpiperidin-3-yl)methoxy)phenyl)methanamine; and
cis-(5-(((1-(Morpholinosulfonyl)-5-phenylpiperidin-3-yl)methyl)sulfonyl)thiophen-2-yl)methanamine,
or a pharmaceutically acceptable salt or hydrate thereof or stereoisomer or racemic mixture thereof.

3. The compound according to claim 1, wherein the compound has a structure represented by a formula:

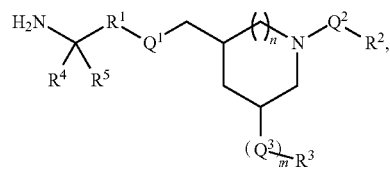

wherein:
n is 0 or 1;
m is 0 or 1;
$Q^1$ is selected from —O—, —SO$_2$—, and —C(O)—;
$Q^2$ is selected from —SO$_2$— and —C(O)—;
$Q^3$, when present, is selected from —CH$_2$—, —SO$_2$—, —C(O)—, and —O—;
$R^1$ is selected from phenyl and heteroaryl containing 1 to 2 heteroatoms independently selected from N, O, and S, and is substituted with 0, 1, 2, or 3 additional groups independently selected from halogen and C1-C4 alkyl;
$R^2$ is selected from C1-C4 alkyl, C1-C4 haloalkyl, and —NR$^6$R$^7$;
$R^6$ and $R^7$ are covalently bonded and, together with the intermediate atoms, form a C3-C6 heterocycloalkyl containing 0 or 1 additional heteroatom selected from N, O, and S;
wherein the additional N, when present, is unsubstituted or substituted with C1-C4 alkyl or —SO$_2$R$^8$;
wherein $R^8$, when present, is C1-C4 alkyl; and
wherein the additional S, when present, is unsubstituted or forms a sulfonyl group;
$R^3$ is selected from C1-C4 haloalkyl, C3-C8 cycloalkyl, phenyl and heteroaryl containing 1 to 2 heteroatoms independently selected from N, O, and S, and wherein the phenyl and heteroaryl, when present, are either unsubstituted or substituted with ROM 1, 2, or 3 groups independently selected from halogen, C1-C4 haloalkyl, C1-C4 alkoxy, and —SO$_2$R$^{14}$;
wherein $R^{14}$, when present, is C1-C4 alkyl;
wherein $R^{15}$ and $R^{16}$, when present, are independently selected from H and C1-C4 alkyl; and
$R^4$ and $R^5$ are independently selected from H and C1-C4 alkyl,
or a pharmaceutically acceptable salt thereof.

4. The compound according to claim 3, wherein m is 0.
5. The compound according to claim 3, wherein $Q^1$ is selected from —O— and —SO$_2$—.
6. The compound according to claim 3, wherein $Q^2$ is —SO$_2$—.
7. The compound according to claim 3, wherein $R^6$ and $R^7$ are covalently bonded and, together with the intermediate atoms, form a C3-C6 heterocycloalkyl having a structure selected from:

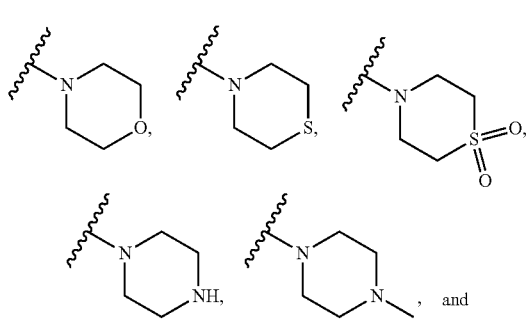

-continued

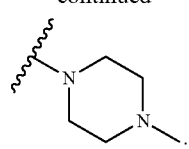

8. The compound according to claim 3, wherein the compound has a structure represented by a formula:

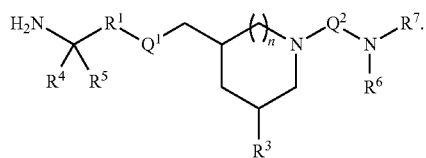

9. The compound according to claim 3, wherein the compound has a structure represented by a formula:

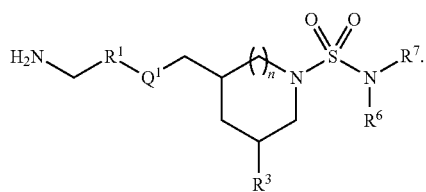

10. The compound according to claim 3, wherein the compound has a structure represented by a formula:

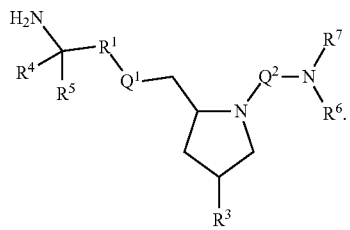

11. The compound according to claim 3, wherein the compound has a structure represented by a formula:

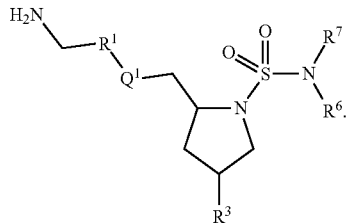

12. The compound according to claim 3, wherein the compound is selected from:

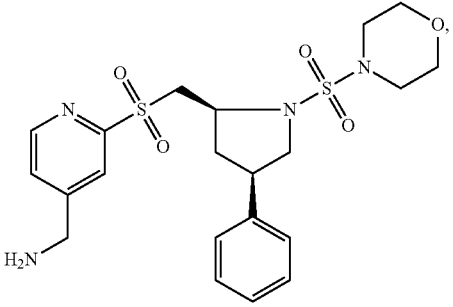

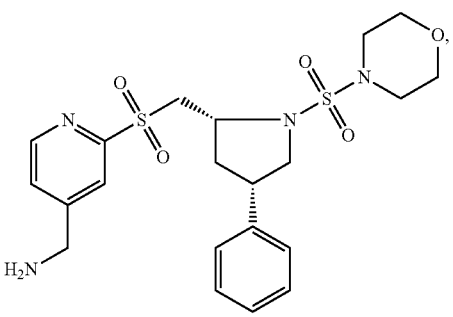

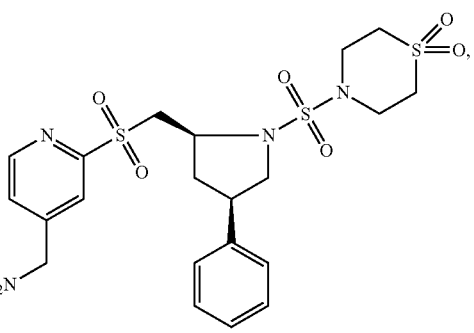

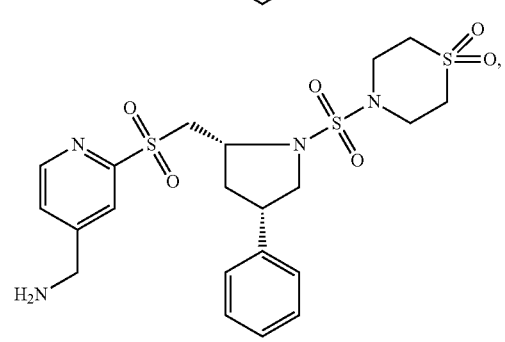

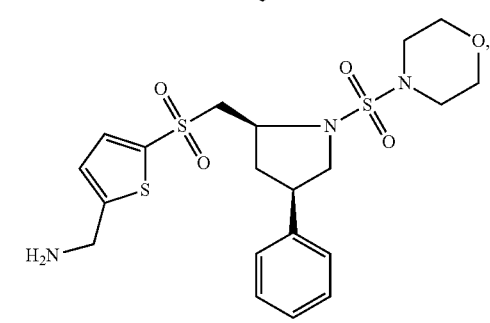

173
-continued
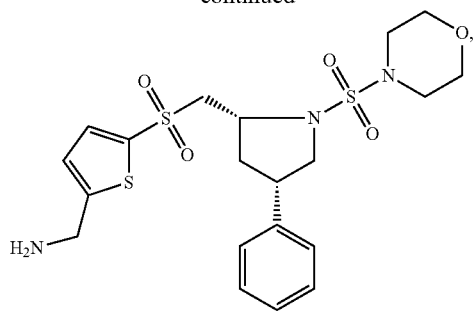
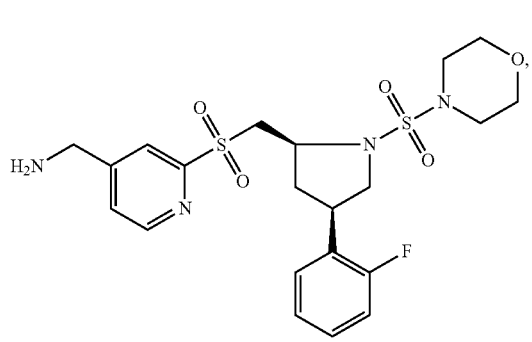
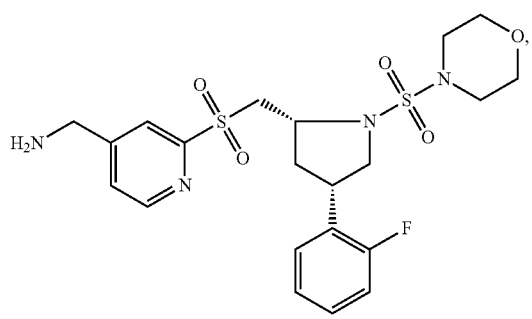
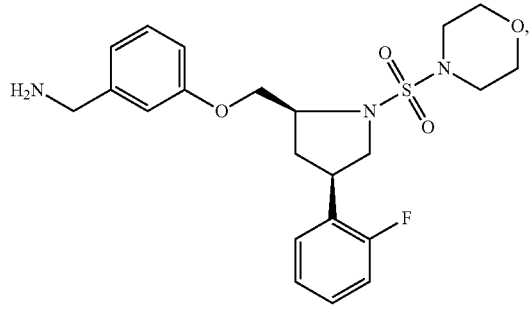
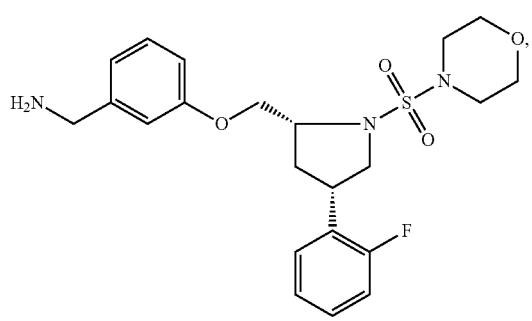
174
-continued
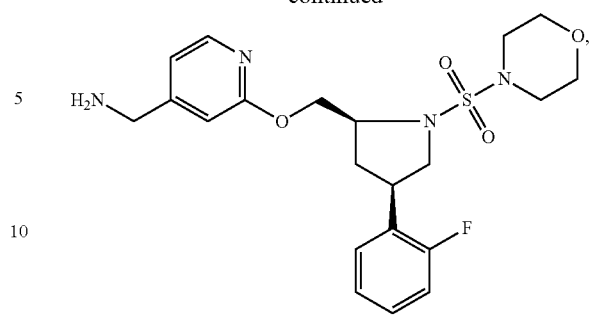
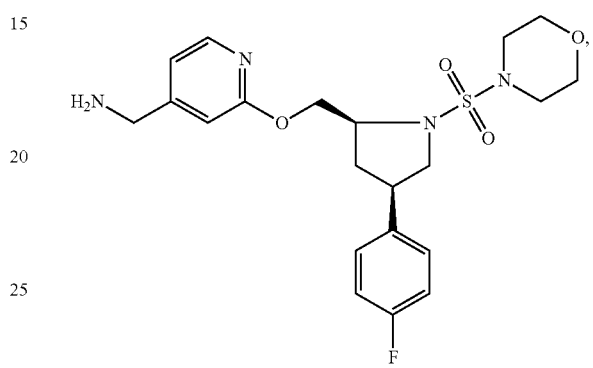
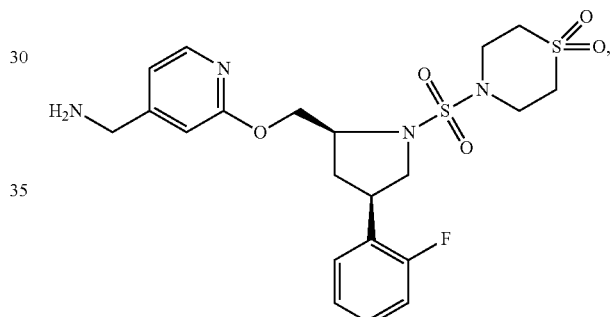
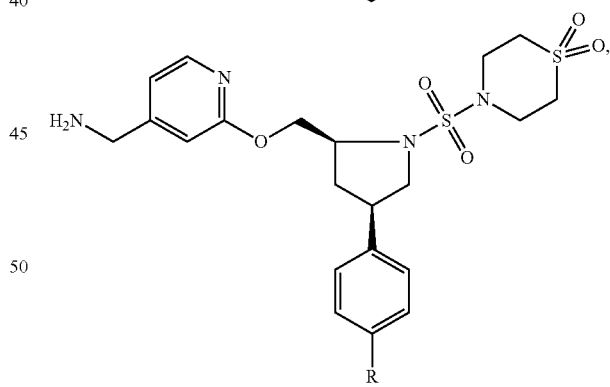
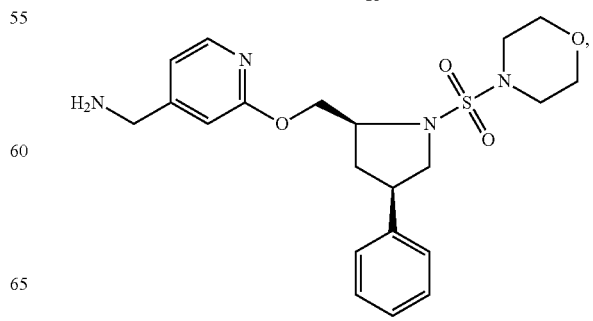

175
-continued
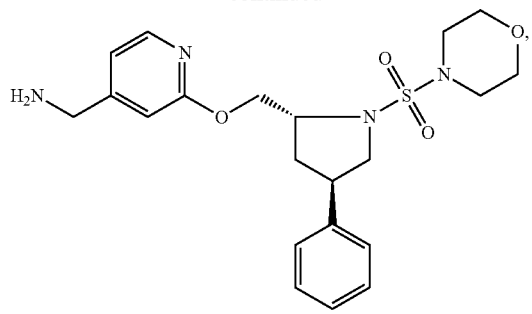
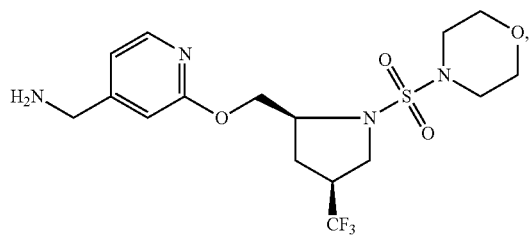
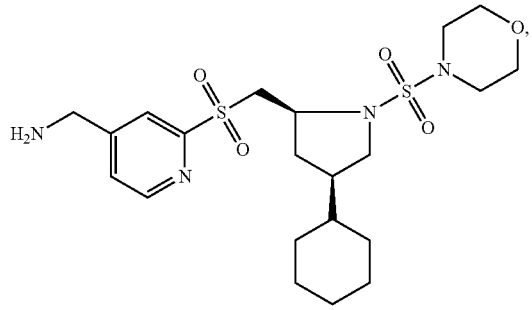
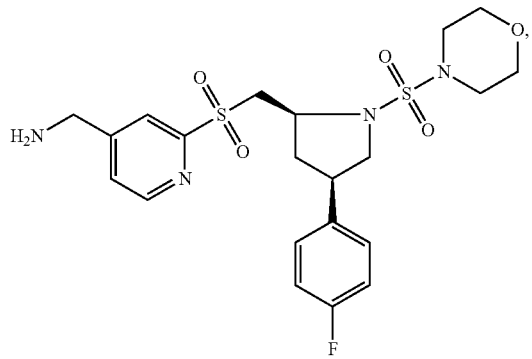
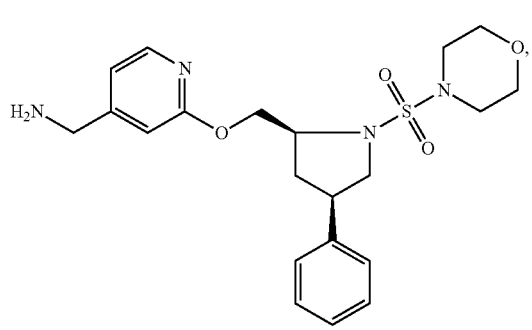
176
-continued
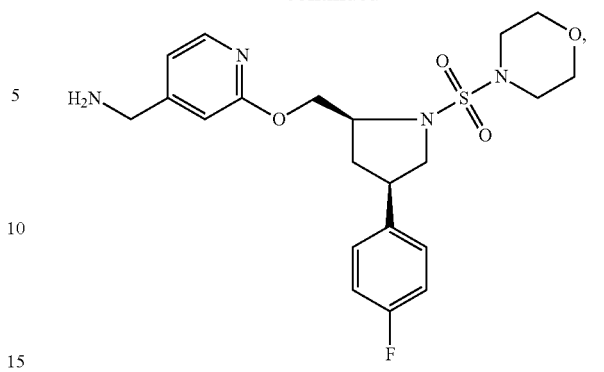
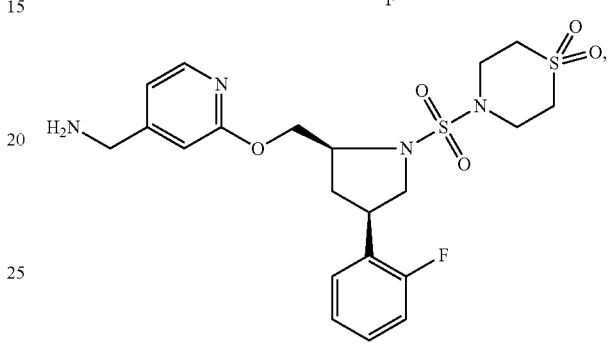
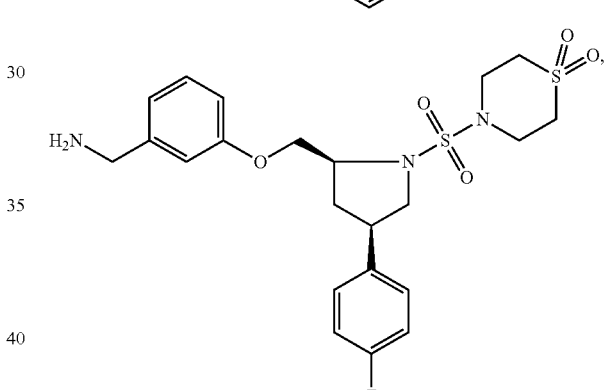
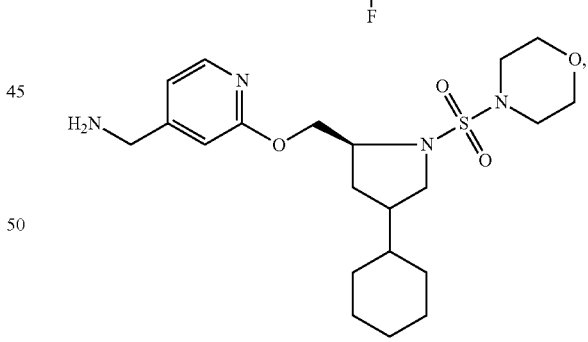
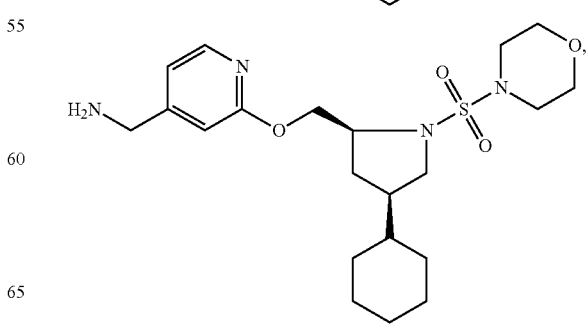

177
-continued
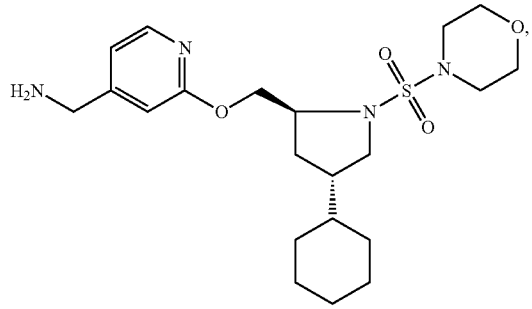
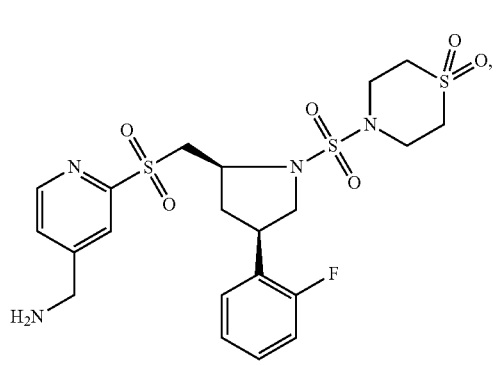
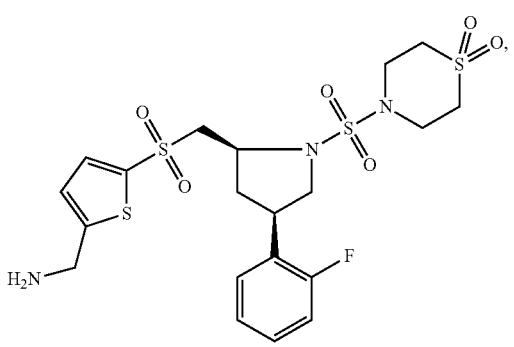
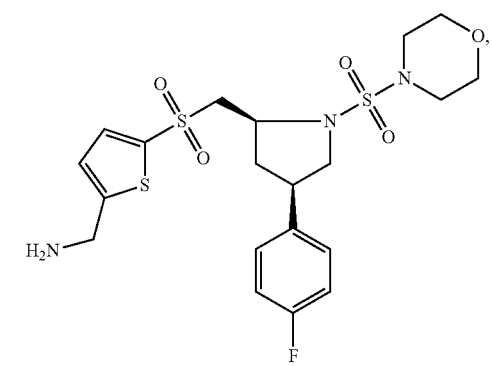
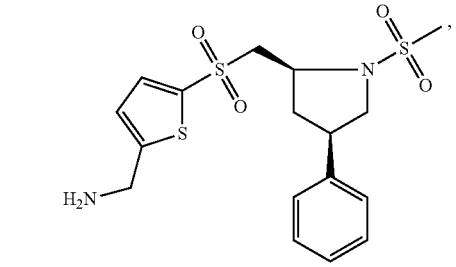
178
-continued
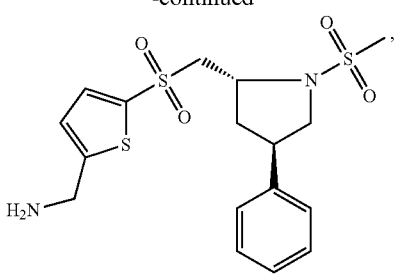
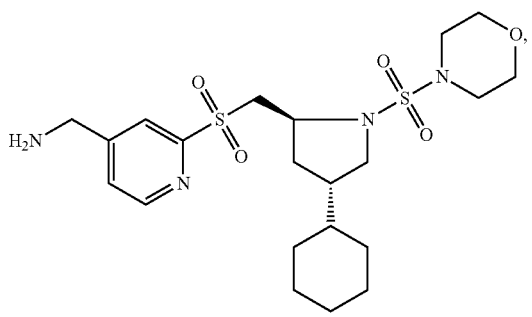 [SMILES: NCc1ccnc(S(=O)(=O)C[C@@H]2CC(C3CCCCC3)CN2S(=O)(=O)N2CCOCC2)c1]
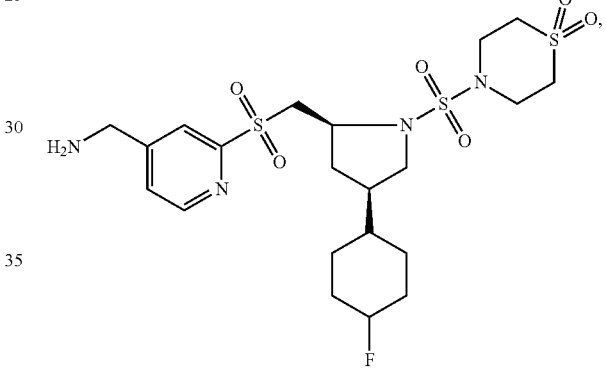
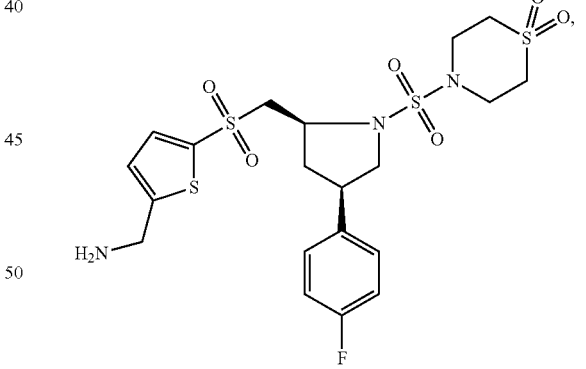
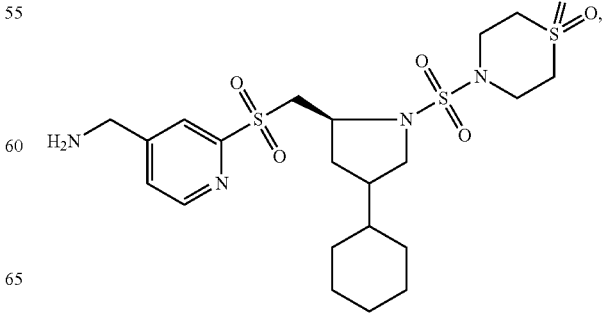

-continued
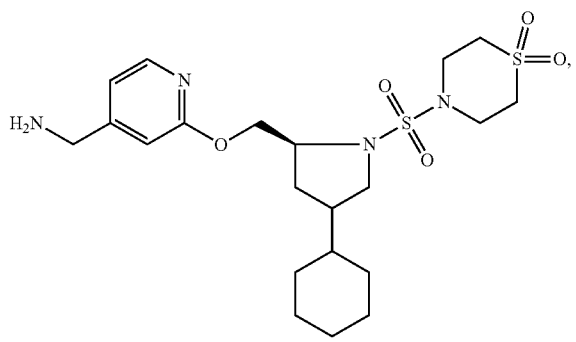
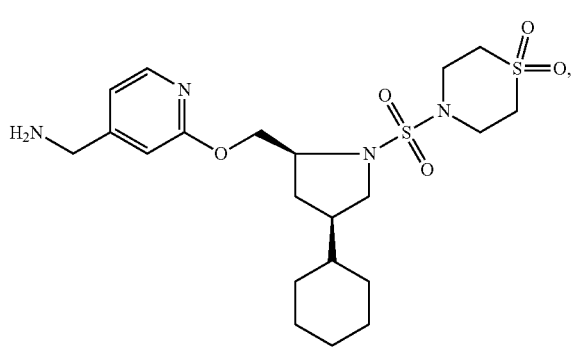
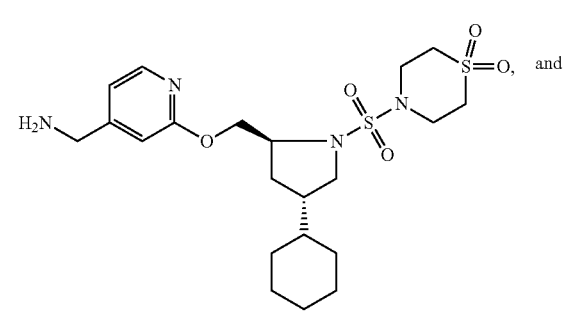
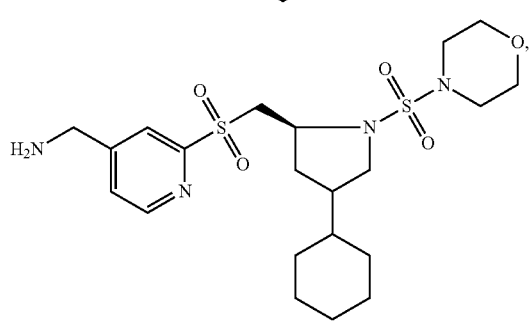
or a pharmaceutically acceptable salt thereof.
13. The compound according to claim 3, wherein the compound has a structure represented by a formula:
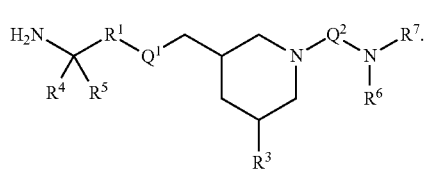
14. The compound according to claim 3, wherein the compound has a structure represented by a formula:
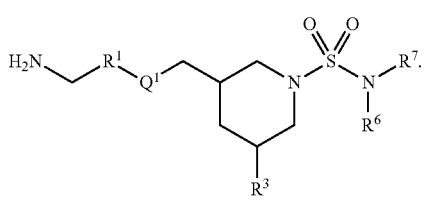
15. The compound according to claim 13, wherein the compound is selected from:
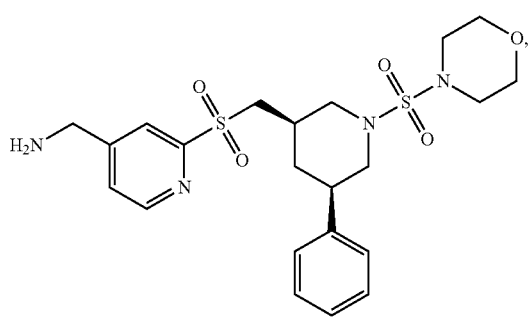
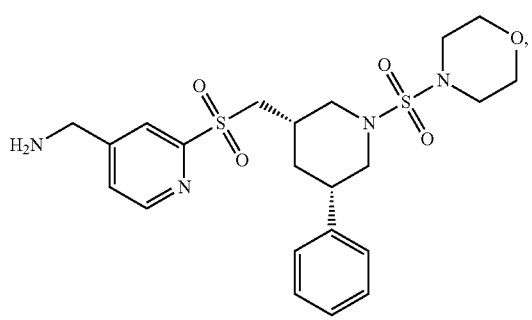
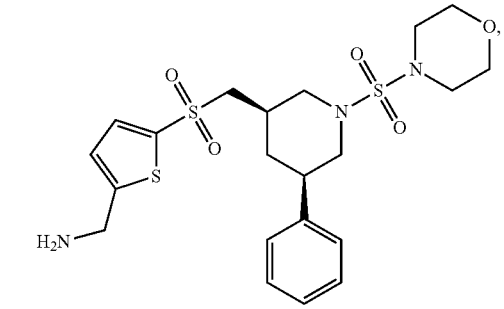
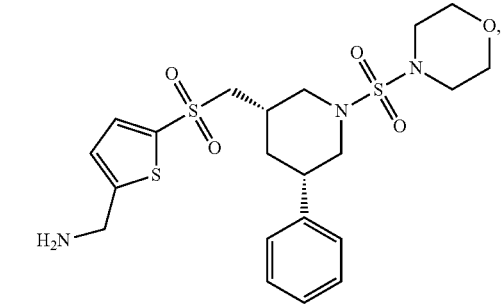

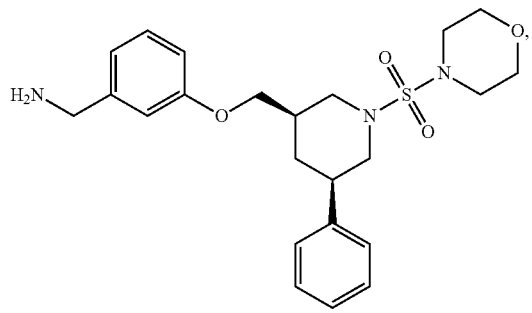
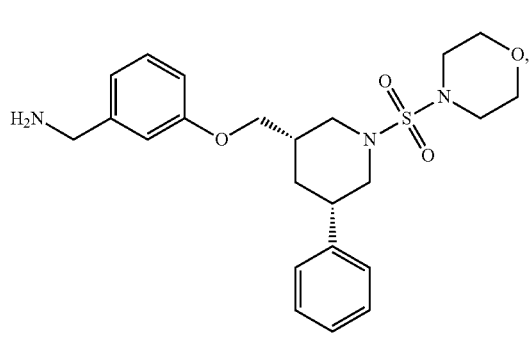
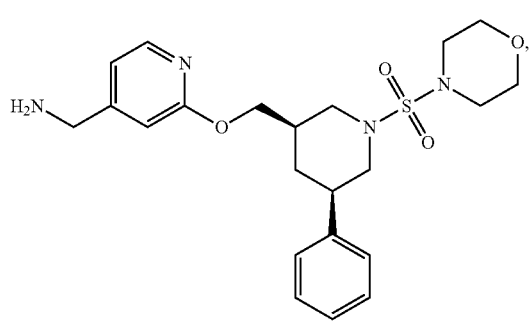
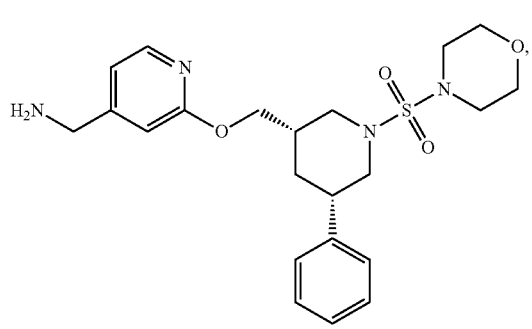
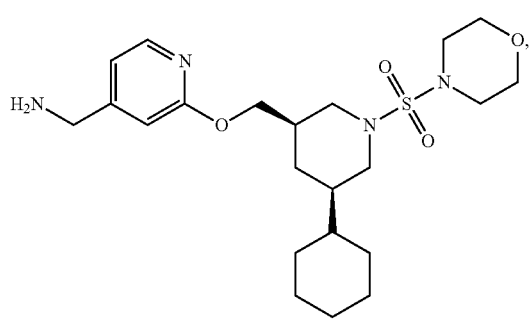
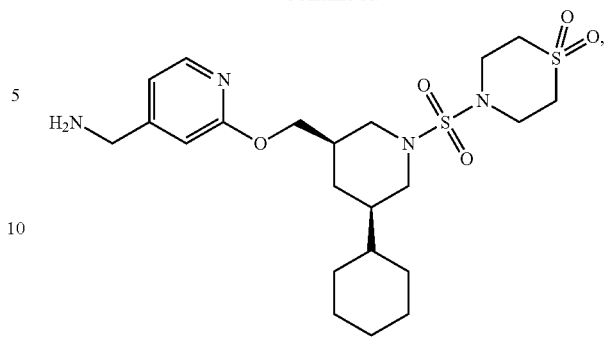
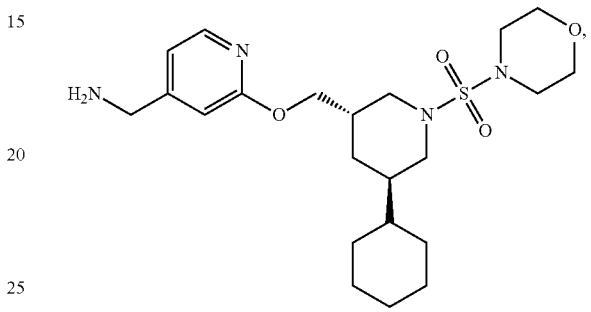
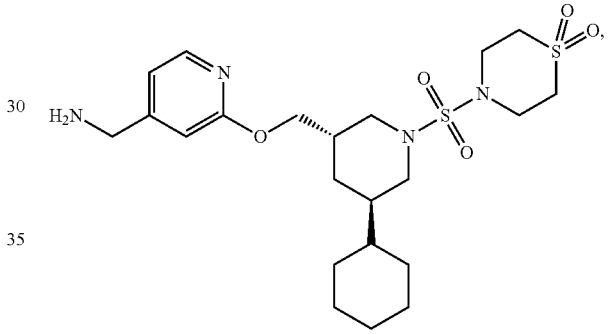
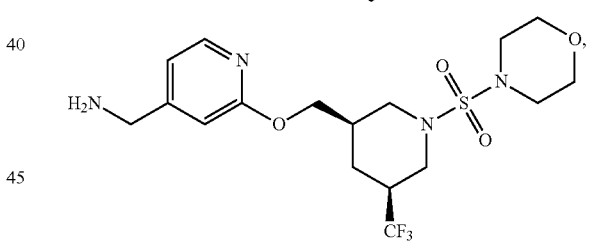
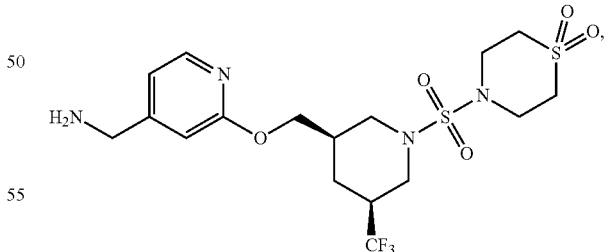
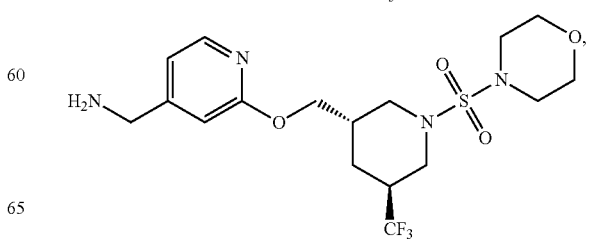

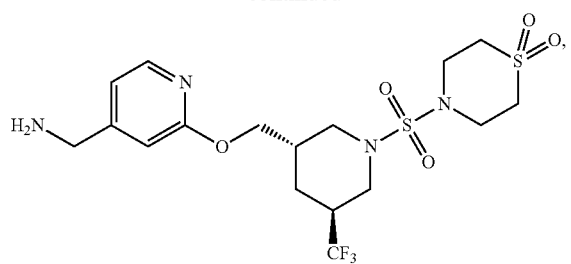
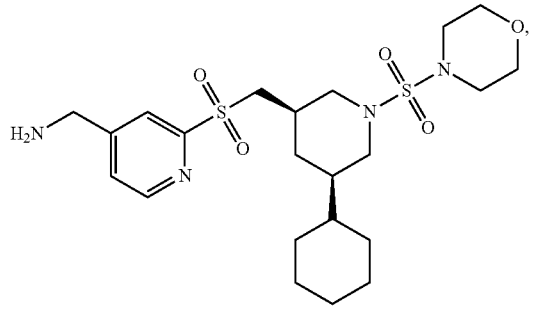
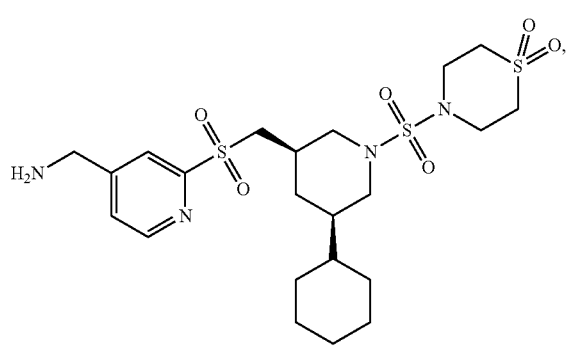
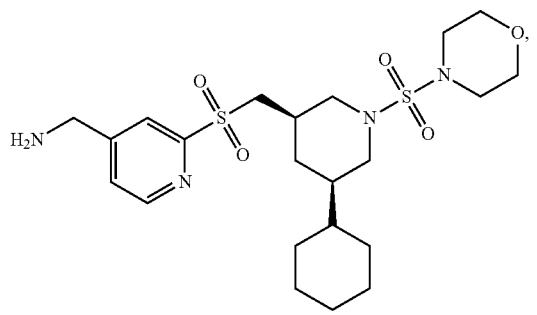
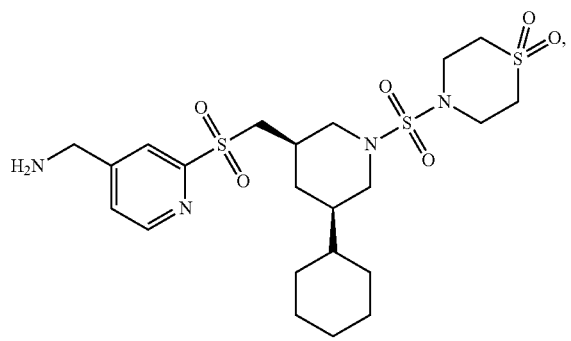
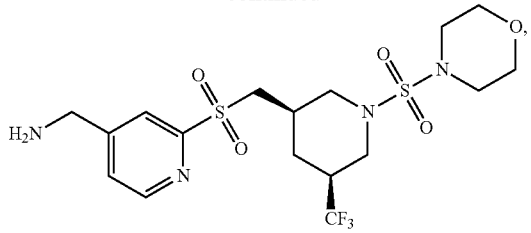
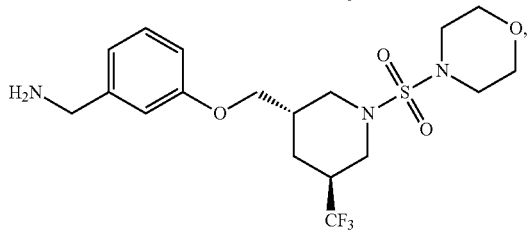
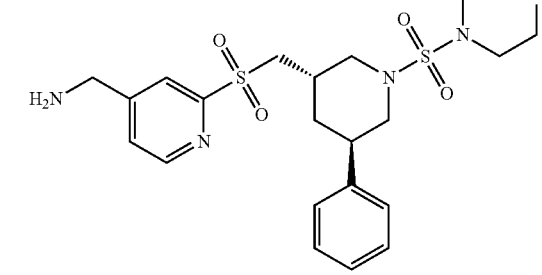
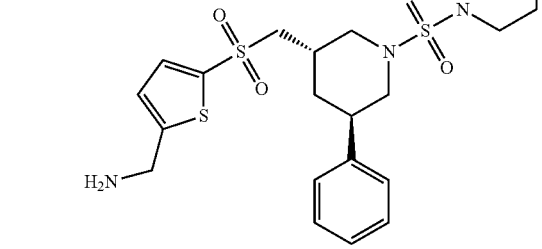
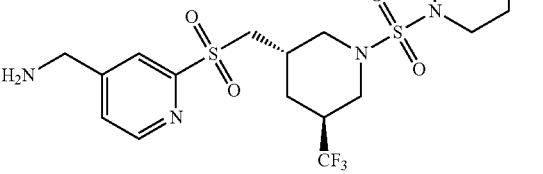
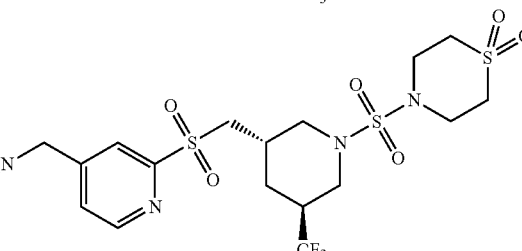
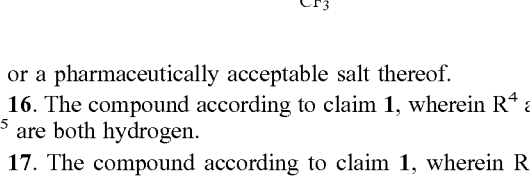
or a pharmaceutically acceptable salt thereof.
16. The compound according to claim 1, wherein $R^4$ and $R^5$ are both hydrogen.
17. The compound according to claim 1, wherein R' is phenyl, thiophen-2-yl, pyridin-4-yl, pyridin-2-yl, thiazol-2- yl, or pyrimidin-2-yl, wherein said phenyl, thiophen-2-yl, pyridin-4-yl, pyridin-2-yl, thiazol-2-yl, or pyrimidin-2-yl is substituted with —$CR^4R^5NH_2$, and optionally, halogen or lower alkyl, and wherein $R^4$ and $R^5$ are independently H or lower alkyl or $R^4$ and $R^5$ form a ($C_3$-$C_8$) cycloalkyl or ($C_1$-$C_8$) hetero-cycloalkyl.

18. The compound according to claim 1, wherein X is independently selected from —$OR^1$ and —$SO_2R^1$, wherein $R^1$ is phenyl, where said phenyl is substituted with —$CR^4R^5NH_2$, and optionally, halogen or lower alkyl, and wherein $R^4$ and $R^5$ are independently H or lower alkyl or $R^4$ and $R^5$ form a ($C_3$-$C_8$) cycloalkyl or a ($C_1$-$C_8$) hetero-cycloalkyl.

19. The compound according to claim 1, wherein Y is —$SO_2R^2$, and wherein $R^2$ is selected from:

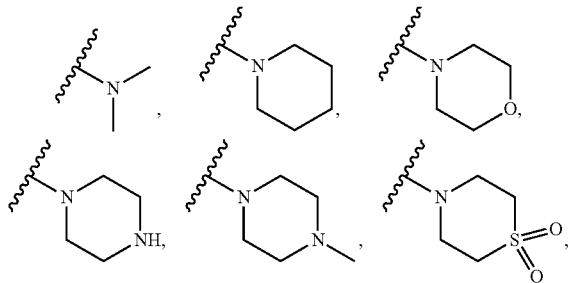

-continued

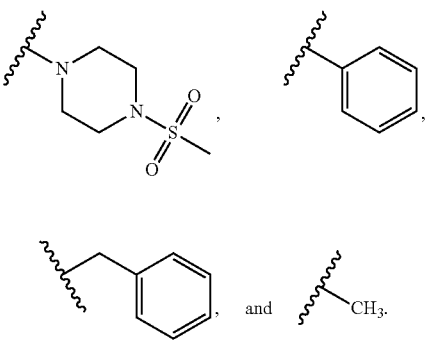

20. The compound according to claim 1, wherein X is independently selected from —$OR^1$ and —$SO_2R^1$, wherein $R^1$ is phenyl, wherein said phenyl is substituted with —$CR^4R^5NH_2$, and optionally, halogen or lower alkyl, and wherein $R^4$ and $R^5$ are independently H or lower alkyl or $R^4$ and $R^5$ form a ($C_3$-$C_8$) cycloalkyl or a ($C_1$-$C_8$) hetero-cycloalkyl.

* * * * *